United States Patent
Zank et al.

(10) Patent No.: US 8,344,205 B2
(45) Date of Patent: Jan. 1, 2013

(54) PLANTS WITH INCREASED YIELD

(75) Inventors: Thorsten Zank, Mannheim (DE); Oliver Oswald, Lautertal (DE); Jörg Bauer, Limburgerhof (DE); Rita Maria Zrenner, Potsdam Golm (DE); Silke Koslowsky, Potsdam (DE)

(73) Assignees: BASF Plant Science GmbH (DE); Max-Planck-Gesellschaft zur Förderung der Wissenschaften e.V. (DE)

( * ) Notice: Subject to any disclaimer, the term of this patent is extended or adjusted under 35 U.S.C. 154(b) by 562 days.

(21) Appl. No.: 12/444,728

(22) PCT Filed: Oct. 12, 2007

(86) PCT No.: PCT/EP2007/060912
§ 371 (c)(1),
(2), (4) Date: Apr. 8, 2009

(87) PCT Pub. No.: WO2008/043849
PCT Pub. Date: Apr. 17, 2008

(65) Prior Publication Data
US 2010/0037350 A1    Feb. 11, 2010

(30) Foreign Application Priority Data
Oct. 13, 2006    (EP) .................... 06122225

(51) Int. Cl.
*A01H 1/00* (2006.01)
*A01H 5/00* (2006.01)
*C12N 15/00* (2006.01)

(52) U.S. Cl. ........ 800/278; 800/281; 800/298; 435/410; 435/419

(58) Field of Classification Search ........................ None
See application file for complete search history.

(56) References Cited

U.S. PATENT DOCUMENTS

| | | | |
|---|---|---|---|
| 6,376,216 B1 | 4/2002 | Doval et al. | |
| 6,391,603 B1 | 5/2002 | Pompejus et al. | |
| 6,717,034 B2 * | 4/2004 | Jiang .................... | 800/290 |
| 6,878,536 B2 | 4/2005 | Pompejus et al. | |
| 7,579,517 B2 | 8/2009 | Renz et al. | |
| 7,807,870 B2 | 10/2010 | Geigenberger et al. | |
| 2002/0137169 A1 | 9/2002 | Bastuck et al. | |
| 2003/0233675 A1 | 12/2003 | Cao et al. | |
| 2004/0034888 A1 | 2/2004 | Liu et al. | |
| 2005/0176033 A1 | 8/2005 | Klyachko et al. | |
| 2006/0123505 A1 | 6/2006 | Kikuchi et al. | |
| 2006/0141495 A1 | 6/2006 | Wu | |

FOREIGN PATENT DOCUMENTS

| | | |
|---|---|---|
| CA | 2263186 A1 | 2/1998 |
| EP | 0927761 A2 | 7/1999 |
| JP | 2005 185101 A | 7/2005 |
| WO | WO-98/06831 A1 | 2/1998 |
| WO | WO-02/079403 A2 | 10/2002 |
| WO | WO-03/095655 A2 | 11/2003 |
| WO | WO-2004/035798 A2 | 4/2004 |
| WO | WO-2004/039946 A2 | 5/2004 |
| WO | WO-2004/057946 A2 | 7/2004 |

OTHER PUBLICATIONS

Koslowsky and Zrenner, Abstract Titled "Manipulating Phosphoribosyl-Pyrophosphate Synthase Acitivity in *Arabidopsis thaliana*" presented at the poster session for the annual meeting of the American Society of Plant Biologists, Seattle, Washington, Poster Session #56—Metabolism, Abstract No. 573, Jul. 17, 2005.*
Koslowsky et al, Plant Biotechnology Journal (2008), vol. 6, pp. 281-294.*
Accession No. NP_987037, created May 6, 2004, Blast of SEQ ID No. 2.*
EPO Application No. 07 821 279.2-1212 Office Action dated Dec. 2, 2009.
Töpfer, R., et al., "Modification of Plant Lipid Synthesis", Science, vol. 268, (1995), pp. 681-685.
European Search Report EP 11 19 2632 mailed Aug. 1, 2012.

* cited by examiner

*Primary Examiner* — Eileen B O Hara
(74) *Attorney, Agent, or Firm* — Connolly Bove Lodge & Hutz LLP

(57) ABSTRACT

This invention relates generally to plant cells and/or plants with increased yield as compared to a corresponding non-transformed wild type plant cell by increasing or generating one or more activities of polypeptides associated with the intermediate phosphoribosylpyrophosphate (PRPP) in plants. In particular, this invention relates to plant cells and/or plants with increased yield as compared to a corresponding non-transformed wild type plant cell by increasing or generating one or more activities of phosphoribosyl pyrophosphate synthases (PRPP synthetase, PRS) The invention also deals with methods of producing and screening for and breeding such plant cells and/or plants.

17 Claims, 10 Drawing Sheets

PLANTS WITH INCREASED YIELD

RELATED APPLICATIONS

This application is a national stage application (under 35 U.S.C. §371) of PCT/EP2007/060912, filed Oct. 12, 2007, which claims benefit of European application 06122225.3, filed Oct. 13, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List_13311_00053_US. The size of the text file is 114 KB, and the text file was created on Apr. 7, 2009.

This invention relates generally to plant cells and/or plants with increased yield as compared to a corresponding non-transformed wild type plant cell by increasing or generating one or more activities of polypeptides associated with the intermediate phosphoribosylpyrophosphate (PRPP) in plants. In particular, this invention relates to plant cells and/or plants with increased yield as compared to a corresponding non-transformed wild type plant cell by increasing or generating one or more activities of phosphoribosyl pyrophosphate synthases (PRPP synthetase, PRS) The invention also deals with methods of producing and screening for and breeding such plant cells and/or plants.

Plants are photoautotrophic organisms that are able to produce all organic compounds needed for development and growth. Over the last years, many factors that influence cell and organ growth of plants have been identified, and molecular functions of growth related proteins are beginning to be elucidated. Considering that developmental processes together with metabolic pathways use a common resource pool and both processes respond to changes in environmental energy and resource supplies it might be evident that resource availability may have a direct influence on cell proliferation and growth. Such a close interrelation has recently been demonstrated by Baldet and co-workers (J. Exp. Bot. 57, 961-970, 2006) showing that fruit load reduction of tomato plants resulted in an increased photoassimilate availability and increased growth rates in all other plant organs including roots, stems, leaves, flowers, and other fruits.

On the other hand it was shown in previous experiments that with decreased nucleotide de novo synthesis growth of potato and tobacco plants was reduced without further pleiotropic effects (Schröder et al., Plant Physiol. 138, 1926-1938, 2005).

The targeted modulation of plant metabolic pathways, preferably by recombinant methods, allows the modification of the plant metabolism in an advantageous manner which, when using traditional breeding methods, could only be achieved after a complicated procedure or not at all. Thus, unusual fatty acids, for example specific polyunsaturated fatty acids, are only synthesized in certain plants or not at all in plants and can therefore only be produced by expressing the relevant enzyme in transgenic plants (for example Millar et al. Trends Plant Sci 5:95-101, 2000).

Triacylgylcerides and other lipids are synthesized from fatty acids. Fatty acid biosynthesis and triacylglyceride biosynthesis can be considered as separate biosynthetic pathways owing to the compartmentalization, but as a single biosynthetic pathway in view of the end product. Lipid synthesis can be divided into two part-mechanisms, one which might be termed "prokaryotic" and another which may be termed "eukaryotic" (Browse et al. Biochemical J 235:25-31, 1986; Ohlrogge & Browse Plant Cell 7:957-970, 1995). The prokaryotic mechanism of the synthesis is localized in the plastids and encompasses the biosynthesis of the free fatty acids which are exported into the cytosol, where they enter the eukaryotic mechanism in the form of fatty acid acyl-CoA esters and are esterified with glycerol-3-phosphate (G3P) to give phosphatidic acid (PA). PA is the starting point for the synthesis of neutral and polar lipids. The neutral lipids are synthesized on the endoplasmic reticulum via, inter alia, the Kennedy pathway (Voelker Genetic Engineering, Setlow (ed.) 18:111-113, 1996; Shankline & Cahoon, Annu Rev Plant Physiol Plant Mol Biol 49:611-649, 1998; Frentzen et al., Lipids 100:161-166, 1998). Besides the biosynthesis of triacylglycerides, G3P also plays a role in glycerol synthesis.

G3P, which is essential for the synthesis, is synthesized here by the reduction of dihydroxyacetone phosphate (DHAP) by means of glycerol-3-phosphate dehydrogenase (G3PDH), also termed dihydroxyacetone phosphate reductase. As a rule, NADH acts as reducing cosubstrate (EC 1.1.1.8). A further class of glycerol-3-phosphate dehydrogenases (EC 1.1.99.5) utilizes FAD as cosubstrate. The enzymes of this class catalyze the reaction of DHAP to G3PDH. In eukaryotic cells, the two classes of enzymes are distributed in different compartments, those which are NAD-dependent being localized in the cytosol and those which are FAD-dependent being localized in the mitochondria (for *Saccharomyces cerevisiae*, see, for example, Larsson et al., Yeast 14:347-357, 1998).

Increasing the total oil content in transgenic plants by expression of glycerol-3-phosphate dehydrogenases (G3PDH) from yeasts is known from WO 2003/095655.

Furthermore, WO 2004/039946 discloses a method for increasing the oil content in plants based on changing the concentration of the FAD2 mRNA or the FAD2 protein.

WO2004/057946 describes a process for changing the content of storage substances in plants by use of leghemoglobin- and/or hemoglobin-expressing transformed plants.

The enzyme phosphoribosyl pyrophosphate synthase (PRS; EC 2.7.6.1) catalyzes the formation of 5-phosphoribosyl α-1-pyrophosphate (PRPP) in which a pyrophosphyl transfer from ATP to ribose 5-phosphate (R5P) takes place (Kronberg et al., 1955). The reaction proceeds via a nucleophilic attack of the C1-OH group of R5P at the β-phosphoryl group of ATP. For its part, 5-phosphoribosyl α-1-pyrophosphate (PRPP) is required as a central compound for the synthesis of all nucleotides, both in the de novo synthesis and in the salvage pathway—the recycling—, and it is thus an important intermediate in the entire cellular metabolism. Owing to this central role in the metabolism, it is not surprising that all life-forms have at least one copy of the PRS gene coding for PRS (Krath et al., 1999). PRS has already been characterized in various organisms on a molecular and biochemical level; inter alia in *Homo sapiens* (Fox & Kelly, 1971), *Escherichia coli* (Hove-Jensen et al., 1986), *Bacillus subtilis* (Arnvig et al., 1990), *Saccharomyces cervisiae* (Carter et al., 1994) and *A. thaliana* (Krath et al., 1999). Whereas prokaryotic organisms have only one copy of the PRS gene, eukaryotic organisms contain a plurality of isoforms. Rats and humans have two and three PRS genes, respectively (Taira et al., 1987), four isoforms could be identified in spinach (Krath & Hove-Jensen, 1999), five isoforms in *A. thaliana* and even six isoforms in the poplar tree (*Populus trichocarpa*). Two of the four isoforms of spinach were localized in organelles, a third in the cytosol (Krath et al., 1999).

The PRS proteins can be divided into two classes. Class I, the "classic" PRS, represents, for example, the enzymes of *E. coli, Bacillus subtilis,* mammals and also some isoforms of plants. In contrast, the second class appears to be specific for plants and comprises, for example, the PRS of isoforms 3 and 4 of spinach (Krath et al., 1999). The two classes are distinguished on the basis of their enzymatic properties. Activity and stability of the PRS of class I depends on the supply of Pi, whereas the activity of the enzymes of class II is independent thereof. In contrast to the PRS of the second class, the "classic" enzymes of the first class are inhibited allosterically by ADP (adenosine 5'-diphosphate). A difference in substrate specificity is also found: the "classic" enzymes use in particular ATP (adenosine 5'-triphosphate) and in certain cases also dATP as substrate, whereas those of class II have a broader substrate spectrum. In addition to ATP and dATP, they also accept GTP, CTP and UTP. These big differences in the enzymatic properties of the two classes are also reflected in the low similarity of their amino acid sequences (Krath et al., 1999; Krath & Hove-Jensen, 1999; 2001).

The use of a feedback-resistant mutant of phosphoribosyl pyrophosphate synthase (PRPP synthase) from *E. coli* for preparing L-histidine is known from the US application 20050176033. 5-Phosphoribosyl alpha-1-pyrophosphate (PRPP) and adenosine 5'-triphosphate (ATP) are the starting materials for the histidine biosynthesis.

Also known is the overexpression of a PRS gene coding for a PRPP synthase (AC-CESSION No. U76387), from the US application 20020137169. Here, the PRS gene is overexpressed together with the nadC gene coding for the nicotinate nucleotide pyrophosphorylase protein for preparing nicotinic acid and derivatives thereof.

Hitherto, there are no findings on the significance of the availability of nucleotides on lipid synthesis.

As mentioned above, there are also poor significant findings about the relation between growth and production of compounds for defense or storage products in plants.

But from the present knowledge base it can be assumed that a tight regulation of the distribution of metabolites between growth, production of defense compounds and storage products takes place in plants.

For example, the increase of the root/shoot dry weight ratio is mostly due to a relative reduction in shoot dry weight. The ratio of seed yield to above-ground dry weight is relatively stable under many environmental conditions and so a robust correlation between plant size and grain yield can often be obtained. These processes are intrinsically linked because the majority of grain biomass is dependent on current stored photosynthetic productivity by the leaves and stem of the plant.

There is a need to identify genes expressed in plants that have the capacity to confer increased yield. It is a object of this invention to identify new methods to confer increased yield in plants or plant cells.

A further object of the present invention is to put at disposal a biotechnological approach to increase plant yield as an alternative renewable energy source.

There is still a great need for increasing the yield of cultivatable plants, preferably in the seeds of these plants. In addition to a increased yield of the plants, preferably a high harvest yield from the plant organisms used, rapidly and robustly growing seedlings or progeny should be cultivatable from the seed. Furthermore, except for changes in the desired features, such as, for example, an increased yield, preferably biomass or total oil content and a more rapid growth of seedlings from seeds generated in a method according to the invention, such a method should not imply any other undesired or negative properties of the plant organisms. Accordingly, for example, to increase the total oil content in transgenic plants, as few genes as possible should be introduced into the plant. Furthermore, the method should be simple and economical.

Accordingly, in a first embodiment, the present invention provides a method for producing a transgenic plant cell or plant with increased yield as compared to a corresponding (non-transformed) wild type or starting plant cell by increasing or generating one or more activities selected from the group consisting of phosphoribosyl pyrophosphate synthases.

DETAILED DESCRIPTION

Figure 1:
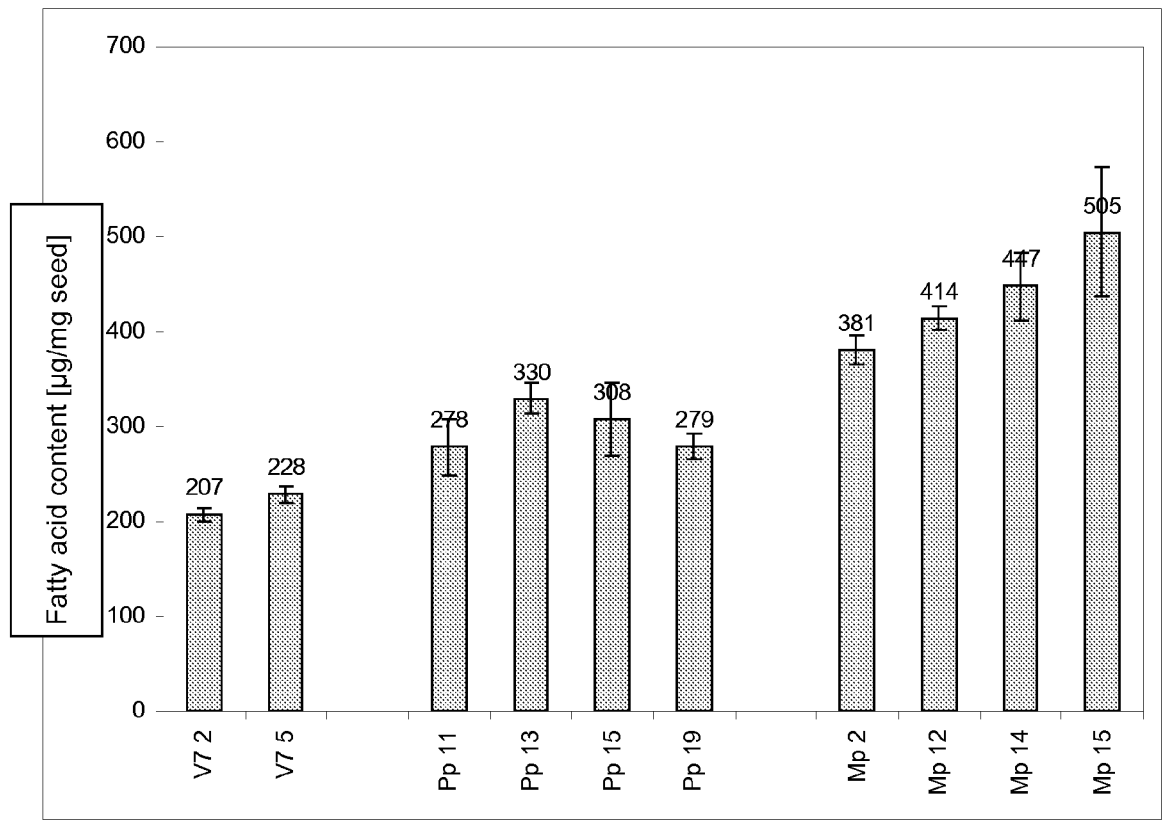
FIG. 1 shows, in an exemplary manner, the results for the quantitative determination of the oil contents (based on the seed weight in T3 seeds of 4 independent transgenic Arabidopsis lines (Mp2, Mp12, Mp14 and Mp15 and also Pp11, Pp13, Pp15 and Pp19) which had been transformed with the expression constructs pBIN19-PRSM and pBIN-PRS, respectively. Also listed are the seed weights of the control plants V72 and V75.

For the purposes of the description of the present invention, enhanced or increased "yield" refers to one or more yield parameters selected from the group consisting of biomass yield, dry biomass yield, aerial dry biomass yield, underground dry biomass yield, freshweight biomass yield, aerial freshweight biomass yield, underground freshweight biomass yield; enhanced yield of harvestable parts, either dry or freshweight or both, either aerial or underground or both; enhanced yield of crop fruit, either dry or freshweight or both, either aerial or underground or both; and preferably enhanced yield of seeds, either dry or freshweight or both, either aerial or underground or both, fresh weight accumulation of seedlings, rosette fresh weight, plant height, total amino acid content, total nucleotide content, total oil content, total lipid content.

The meaning of "yield" is, mainly, dependent on the crop of interest, and it is understood, that the skilled person will understand in each particular case what is meat from the circumstances of the description.

In one embodiment, the activity is increased by increasing the amount and/or activity of one or more proteins having an activity selected from the group consisting of: phosphoribosyl pyrophosphate synthases and the polypeptides comprising a polypeptide selected from the group consisting of SEQ ID NOs: 2, 4, 13, 51, 52, 53, 54, 55, 56, 57, 58, 59, 60, 61, 62, 63, 51, 52, 53, 54, 55, 56, 57, 58, 59, 60, 61, 62, 63, 7, 8, 9, 10, 11, 14, 15, 16, 17, 18.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced biomass yield as compared to a corresponding (non-transformed) wild type or starting photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced dry biomass yield as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced aerial dry biomass yield as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced underground dry bio-mass yield as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced fresh weight biomass yield as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced aerial fresh weight biomass yield as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced underground fresh weight biomass yield as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of harvestable parts of a plant as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of dry harvestable parts of a plant as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of dry aerial harvestable parts of a plant as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of underground dry harvestable parts of a plant as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of fresh weight harvestable parts of a plant as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of aerial fresh weight harvestable parts of a plant as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of underground fresh weight harvestable parts of a plant as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of the crop fruit as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of the fresh crop fruit as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of the dry crop fruit as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced grain dry weight as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of seeds as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of fresh weight seeds as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of dry seeds as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of fresh weight of seedlings as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of rosette fresh weight, for example in the case of *Arabidopsis*, as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced plant height, as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of total amino acid content as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of total nucleotide content as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of total oil content as compared to a corresponding non-transformed wild type photosynthetic active organism.

In an embodiment, a transgenic plant cell, plant or part thereof with increased yield as compared to a corresponding (non-transformed) wild type or starting plant cell by increasing or generating one or more activities selected from the group consisting of phosphoribosyl pyrophosphate synthases, exhibits an enhanced yield of total lipid content as compared to a corresponding non-transformed wild type photosynthetic active organism.

The photosynthetic active organism in the sense of the invention include plant cells, plants and parts thereof, starting plant cell and certain tissues, organs and parts of plants, propagation material (such as seeds, tubers and fruits) or seed of plants, and also plants in all their manifestations, such as anthers, fibers, root hairs, stems, leaves, embryos, calli, cotyledons, petioles, shoots, seedlings, harvested material, plant tissue, reproductive tissue and cell cultures which is/are derived from the actual transgenic plant and/or can be used to produce the transgenic plant. Also included are mature plants. Mature plants are to be understood as plants of any development stage older than the seedling. The seedling is a young immature plant in an early development stage.

In an embodiment thereof, the term "increased yield" means that the photosynthetic active organism, especially a plant, exhibits an increased growth rate compared to the corresponding wild-type photosynthetic active organism. An increased growth rate may be reflected inter alia by an increased biomass production of the whole plant, or by an increased biomass production of the aerial parts of a plant, or by an increased biomass production of the underground parts of a plant, or by an increased biomass production of parts of a plant, like stems, leaves, blossoms, fruits, and/or seeds.

In an embodiment thereof, increased yield includes higher fruit yields, higher seed yields, higher fresh matter production, and/or higher dry matter production.

In another embodiment this invention fulfills the need to identify new, unique genes capable of conferring an increase of yield to photosynthetic active organism, preferably plants, upon expression or over-expression of endogenous and/or exogenous genes.

In another embodiment thereof this invention fulfills the need to identify new, unique genes capable of conferring an increase of yield to photosynthetic active organism, preferably plants, upon expression or over-expression of endogenous genes.

In another embodiment thereof this invention fulfills the need to identify new, unique genes capable of conferring an increase of yield to photosynthetic active organism, preferably plants, upon expression or over-expression of exogenous genes.

In one embodiment the present invention relates to a method for producing a transgenic photosynthetic active organism or a part thereof, preferably a plant cell, a plant or a part thereof, with increased yield as compared to a corresponding non-transformed wild type photosynthetic active organism or a part thereof, preferably a plant cell, a plant or a part thereof, which comprises
(a) increasing or generating one or more activities selected from the group consisting of phosphoribosyl pyrophosphate synthases in a photosynthetic active organism or a part thereof, preferably a plant cell, a plant or a part thereof, and
(b) growing the photosynthetic active organism or a part thereof, preferably a plant cell, a plant or a part thereof under conditions which permit the development of a photosynthetic active organism or a part thereof, preferably a plant cell, a plant or a part thereof, with increased yield as compared to a corresponding non-transformed wild type photosynthetic active organism or a part thereof, preferably a plant cell, a plant or a part thereof.

In one embodiment the present invention relates to a method for producing a transgenic photosynthetic active organism or a part thereof, preferably a plant cell, a plant or a part thereof, with increased yield as compared to a corresponding non-transformed wild type photosynthetic active organism or a part thereof, preferably a plant cell, a plant or a part thereof, which comprises
(a) increasing or generating one or more activities selected from the group consisting of phosphoribosyl pyrophosphate synthases in the plastid of a cell of a photosynthetic active organism, and
(b) growing the photosynthetic active organism or a part thereof, preferably a plant cell, a plant or a part thereof under conditions which permit the development of a photosynthetic active organism or a part thereof, preferably a plant cell, a plant or a part thereof, with increased yield as compared to a corresponding non-transformed wild type photosynthetic active organism or a part thereof, preferably a plant cell, a plant or a part thereof.

In one embodiment the present invention relates to a method for producing a transgenic photosynthetic active organism or a part thereof, preferably a plant cell, a plant or a part thereof, with increased yield as compared to a corresponding non-transformed wild type photosynthetic active organism or a part thereof, preferably a plant cell, a plant or a part thereof, which comprises
(a) increasing or generating one or more activities selected from the group consisting of phosphoribosyl pyrophosphate synthases in the cytoplasm of a cell of a photosynthetic active organism, and
(b) growing the photosynthetic active organism or a part thereof, preferably a plant cell, a plant or a part thereof under conditions which permit the development of a photosynthetic active organism or a part thereof, preferably a plant cell, a plant or a part thereof, with increased yield as compared to a corresponding non-transformed wild type photosynthetic active organism or a part thereof, preferably a plant cell, a plant or a part thereof.

In one embodiment the present invention relates to a method for producing a transgenic photosynthetic active organism or a part thereof, preferably a plant cell, a plant or a part thereof with increased yield as compared to a corresponding non-transformed wild type photosynthetic active organism or a part thereof, preferably a plant cell, a plant or a part thereof, which comprises
(a) increasing or generating the activity of a protein selected from the group consisting of SEQ ID NOs: 2, 4, 13, 51, 52, 53, 54, 55, 56, 57, 58, 59, 60, 61, 62, 63, 51, 52, 53, 54, 55, 56, 57, 58, 59, 60, 61, 62, 63 or homologs thereof, in photosynthetic active organism or a part thereof, preferably a plant cell, a plant or a part thereof, and
(b) growing the photosynthetic active organism or a part thereof, preferably a plant cell, a plant or a part thereof under conditions which permit the development of a plant with increased yield as compared to a corresponding non-transformed wild type photosynthetic active organism or a part thereof, preferably a plant.

In one embodiment the present invention relates to a method for producing a transgenic photosynthetic active organism or a part thereof, preferably a plant cell, a plant or a part thereof with increased yield as compared to a corresponding non-transformed wild type photosynthetic active organism or a part thereof, preferably a plant cell, a plant or a part thereof, which comprises
(a) increasing or generating the activity of a protein selected from the group consisting of SEQ ID NOs: 2, 4, 13, 51, 52, 53, 54, 55, 56, 57, 58, 59, 60, 61, 62, 63, 51, 52, 53, 54, 55, 56, 57, 58, 59, 60, 61, 62, 63 or homologs thereof, in the plastid of a cell of a photosynthetic active organism, and
(b) growing the photosynthetic active organism or a part thereof, preferably a plant cell, a plant or a part thereof under conditions which permit the development of a plant with increased yield as compared to a corresponding non-transformed wild type photosynthetic active organism or a part thereof, preferably a plant.

In one embodiment the present invention relates to a method for producing a transgenic photosynthetic active organism or a part thereof, preferably a plant cell, a plant or a part thereof with increased yield as compared to a corresponding non-transformed wild type photosynthetic active organism or a part thereof, preferably a plant cell, a plant or a part thereof, which comprises
(a) increasing or generating the activity of a protein selected from the group consisting of SEQ ID NOs: 2, 4, 13, 51, 52, 53, 54, 55, 56, 57, 58, 59, 60, 61, 62, 63, 51, 52, 53, 54, 55, 56, 57, 58, 59, 60, 61, 62, 63 or homologs thereof, in the cytoplasm of a cell of a photosynthetic active organism, and
(b) growing the photosynthetic active organism or a part thereof, preferably a plant cell, a plant or a part thereof under conditions which permit the development of a plant with increased yield as compared to a corresponding non-transformed wild type photosynthetic active organism or a part thereof, preferably a plant.

Accordingly, the present invention relates to a method for producing a transgenic plant cell, a plant or a part thereof with enhanced tolerance to nutrient limitation and/or increased yield as compared to a corresponding non-transformed wild type plant cell, a plant or a part thereof, which comprises (a) increasing or generating one or more activities selected from the group consisting of phosphoribosyl pyrophosphate synthases in the plastid of a plant cell, and (b) growing the plant cell under conditions which permit the development of a plant with enhanced tolerance to nutrient limitation and/or increased yield as compared to a corresponding non-transformed wild type plant.

In another embodiment the present invention relates to a method for producing a transgenic plant cell, a plant or a part thereof with enhanced tolerance to nutrient limitation and/or increased yield as compared to a corresponding non-transformed wild type plant cell, a plant or a part thereof, which comprises (a) increasing or generating one or more activities selected from the group consisting of phosphoribosyl pyrophosphate synthases in the cytoplasm of a plant cell, and (b) growing the plant cell under conditions which permit the development of a plant with enhanced tolerance to nutrient limitation and/or increased yield as compared to a corresponding non-transformed wild type plant.

In one embodiment the present invention relates to a method for producing a transgenic plant cell, a plant or a part thereof with enhanced tolerance to nutrient limitation and/or increased yield as compared to a corresponding non-transformed wild type plant cell, a plant or a part thereof, which comprises (a) increasing or generating the activity of a protein selected from the group consisting of SEQ ID NOs: 2, 4, 13, 51, 52, 53, 54, 55, 56, 57, 58, 59, 60, 61, 62, 63, 51, 52, 53, 54, 55, 56, 57, 58, 59, 60, 61, 62, 63 or homologs thereof, in the plastid of a plant cell, and (b) growing the plant cell under conditions which permit the development of a plant with enhanced tolerance to nutrient limitation and/or increased yield as compared to a corresponding non-transformed wild type plant.

In one embodiment the present invention relates to a method for producing a transgenic plant cell, a plant or a part thereof with enhanced tolerance to nutrient limitation and/or increased yield as compared to a corresponding non-transformed wild type plant cell, a plant or a part thereof, which comprises (a) increasing or generating the activity of a protein selected from the group consisting of SEQ ID NOs: 2, 4, 13, 51, 52, 53, 54, 55, 56, 57, 58, 59, 60, 61, 62, 63, 51, 52, 53, 54, 55, 56, 57, 58, 59, 60, 61, 62, 63 or homologs thereof, in the cytoplasm of a plant cell, and (b) growing the plant cell under conditions which permit the development of a plant with enhanced tolerance to nutrient limitation and/or increased yield as compared to a corresponding non-transformed wild type plant.

In another embodiment the present invention is related to a method for producing a transgenic plant cell, a plant or a part thereof with increased yield as compared to a corresponding non-transformed wild type plant cell, a plant or a part thereof, which comprises (a) increasing or generating one or more activities selected from the group consisting of phosphoribosyl pyrophosphate synthases in an organelle of a plant cell or (b) increasing or generating the activity of a protein selected from the group consisting of SEQ ID NOs: 2, 4, 13, 51, 52, 53, 54, 55, 56, 57, 58, 59, 60, 61, 62, 63 or homologs thereof encoded by the nucleic acid sequences selected from the group consisting of SEQ ID NOs: 1, 3, 12, 38, 39, 40, 41, 42, 43, 44, 45, 46, 47, 48, 49, 50 or homologs thereof, which are joined to a nucleic acid sequence encoding a transit peptide in a plant cell; or (c) increasing or generating the activity of a protein selected from the group consisting of SEQ ID NOs: 2, 4, 13, 51, 52, 53, 54, 55, 56, 57, 58, 59, 60, 61, 62, 63 or homologs thereof encoded by the nucleic acid sequences selected from the group consisting of SEQ ID NOs: 1, 3, 12, 38, 39, 40, 41, 42, 43, 44, 45, 46, 47, 48, 49, 50 or homologs thereof, which are joined to a nucleic acid sequence encoding chloroplast localization sequence, in a plant cell, and (d) growing the plant cell under conditions which permit the development of a plant with increased yield as compared to a corresponding non-transformed wild type plant.

In another embodiment, the present invention relates to a method for producing a transgenic plant cell, a plant or a part thereof with increased yield as compared to a corresponding non-transformed wild type plant cell, a plant or a part thereof, which comprises (a) increasing or generating the activity of a protein selected from the group consisting of SEQ ID NOs: 2, 4, 13, 51, 52, 53, 54, 55, 56, 57, 58, 59, 60, 61, 62, 63 or homologs thereof encoded by the nucleic acid sequences selected from the group consisting of SEQ ID NOs: 1, 3, 12, 38, 39, 40, 41, 42, 43, 44, 45, 46, 47, 48, 49, 50 or homologs thereof, in an organelle of a plant through the transformation of the organelle, or (b) increasing or generating the activity of a protein selected from the group consisting of SEQ ID NOs: 2, 4, 13, 51, 52, 53, 54, 55, 56, 57, 58, 59, 60, 61, 62, 63 or homologs thereof encoded by the nucleic acid sequences selected from the group consisting of SEQ ID NOs: 1, 3, 12, 38, 39, 40, 41, 42, 43, 44, 45, 46, 47, 48, 49, 50 or homologs thereof in the plastid of a plant, or in one or more parts thereof through the transformation of the plastids; and (c) growing the plant cell under conditions which permit the development of a plant with increased yield as compared to a corresponding non-transformed wild type plant.

In principle the nucleic acid sequence encoding a transit peptide can be isolated from every organism such as microorganisms such as algae or plants containing plastids preferably chloroplasts. A "transit peptide" is an amino acid sequence, whose encoding nucleic acid sequence is translated together with the corresponding structural gene. That means the transit peptide is an integral part of the translated protein and forms an amino terminal extension of the protein. Both are translated as so called "preprotein". In general the transit peptide is cleaved off from the preprotein during or just after import of the protein into the correct cell organelle such as a plastid to yield the mature protein. The transit peptide ensures correct localization of the mature protein by facilitating the transport of proteins through intracellular membranes.

Preferred nucleic acid sequences encoding a transit peptide are derived from a nucleic acid sequence encoding a protein finally resided in the plastid and stemming from an organism selected from the group consisting of the genera *Acetabularia, Arabidopsis, Brassica, Capsicum, Chlamydomonas, Cururbita, Dunaliella, Euglena, Flayeria, Glycine, Helianthus, Hordeum, Lemna, Lolium, Lycopersion, Malus, Medicago, Mesembryanthemum, Nicotiana, Oenotherea, Oryza, Petunia, Phaseolus, Physcomitrella, Pinus, Pisum, Raphanus, Silene, Sinapis, Solanum, Spinacea, Stevia, Synechococcus, Triticum* and *Zea*.

Advantageously such transit peptides, which are beneficially used in the inventive process, are derived from the nucleic acid sequence encoding a protein selected from the group consisting of ribulose bisphosphate carboxylase/oxygenase, 5-enolpyruvyl-shikimate-3-phosphate synthase, acetolactate synthase, chloroplast ribosomal protein CS17, Cs protein, ferredoxin, plastocyanin, ribulose bisphosphate carboxylase activase, tryptophan synthase, acyl carrier protein, plastid chaperonin-60, cytochrome C552, 22-kDA heat shock protein, 33-kDa Oxygen-evolving enhancer protein 1, ATP synthase γ subunit, ATP synthase δ subunit, chlorophyII-a/b-binding proteinII-1, Oxygen-evolving enhancer protein 2, Oxygen-evolving enhancer protein 3, photosystem I: P21, photosystem I: P28, photosystem I: P30, photosystem I: P35, photosystem I: P37, glycerol-3-phosphate acyltransferases, chlorophyll a/b binding protein, CAB2 protein, hydroxymethyl-bilane synthase, pyruvate-orthophosphate dikinase, CAB3 protein, plastid ferritin, ferritin, early light-inducible protein, glutamate-1-semialdehyde aminotransferase, protochlorophyllide reductase, starch-granule-bound amylase synthase, light-harvesting chlorophyll a/b-binding protein of photosystem II, major pollen allergen Lol p 5a, plastid ClpB ATP-dependent protease, superoxide dismutase, ferredoxin NADP oxidoreductase, 28-kDa ribonucleoprotein, 31-kDa ribonucleoprotein, 33-kDa ribonucleoprotein, acetolactate synthase, ATP synthase $CF_0$ subunit 1, ATP synthase $CF_0$ subunit 2, ATP synthase $CF_0$ subunit 3, ATP synthase $CF_0$ subunit 4, cytochrome f, ADP-glucose pyrophosphorylase, glutamine synthase, glutamine synthase 2, carbonic anhydrase, GapA protein, heat-shock-protein hsp21, phosphate translocator, plastid ClpA ATP-dependent protease, plastid ribosomal protein CL24, plastid ribosomal protein CL9, plastid ribosomal protein PsCL18, plastid ribosomal protein PsCL25, DAHP synthase, starch phosphorylase, root acyl carrier protein II, betainealdehyde dehydrogenase, GapB protein, glutamine synthetase 2, phosphoribulokinase, nitrite reductase, ribosomal protein L12, ribosomal protein L13, ribosomal protein L21, ribosomal protein L35, ribosomal protein L40, triose phosphate-3-phosphoglyeratephosphate translocator, ferredoxin-dependent glutamate synthase, glyceraldehyde-3-phosphate dehydrogenase, NADP-dependent malic enzyme and NADP-malate dehydrogenase.

More preferred the nucleic acid sequence encoding a transit peptide is derived from a nucleic acid sequence encoding a protein finally resided in the plastid and stemming from an organism selected from the group consisting of the species *Acetabularia mediterranea, Arabidopsis thaliana, Brassica campestris, Brassica napus, Capsicum annuum, Chlamydomonas reinhardtii, Cururbita moschata, Dunaliella salina, Dunaliella tertiolecta, Euglena gracilis, Flayeria trinervia, Glycine max, Helianthus annuus, Hordeum vulgare, Lemna gibba, Lolium perenne, Lycopersion esculentum, Malus domestica, Medicago falcata, Medicago sativa, Mesembryanthemum crystallinum, Nicotiana plumbaginifolia, Nicotiana sylvestris, Nicotiana tabacum, Oenotherea hookeri, Oryza sativa, Petunia hybrida, Phaseolus vulgaris, Physcomitrella patens, Pinus tunbergii, Pisum sativum, Raphanus sativus, Silene pratensis, Sinapis alba, Solanum tuberosum, Spinacea oleracea, Stevia rebaudiana, Synechococcus, Synechocystis, Triticum aestivum* and *Zea mays*.

Even more preferred nucleic acid sequences are encoding transit peptides as disclosed by von Heijne et al. (Plant Molecular Biology Reporter, 9 (2), 104, (1991)), which are hereby incorparated by reference. Table V shows some examples of the transit peptide sequences disclosed by von Heijne et al. According to the disclosure of the invention especially in the examples the skilled worker is able to link other nucleic acid sequences disclosed by von Heijne et al. to the nucleic acid sequences shown in table I, columns 5 and 7.

Most preferred nucleic acid sequences encoding transit peptides are derived from the genus *Spinacia* such as chloroplast 30S ribosomal protein PSrp-1, root acyl carrier protein II, acyl carrier protein, ATP synthase: γ subunit, ATP synthase: δ subunit, cytochrom f, ferredoxin I, ferredoxin NADP oxidoreductase (=FNR), nitrite reductase, phosphoribulokinase, plastocyanin or carbonic anhydrase. The skilled worker will recognize that various other nucleic acid sequences encoding transit peptides can easily isolated from plastid-localized proteins, which are expressed from nuclear genes as precursors and are then targeted to plastids. Such transit peptides encoding sequences can be used for the construction of other expression constructs. The transit peptides advantageously used in the inventive process and which are part of the inventive nucleic acid sequences and proteins are typically 20 to 120 amino acids, preferably 25 to 110, 30 to 100 or 35 to 90 amino acids, more preferably 40 to 85 amino acids and most preferably 45 to 80 amino acids in length and functions post-translationally to direct the protein to the plastid preferably to the chloroplast. The nucleic acid sequences encoding such transit peptides are localized upstream of nucleic acid sequence encoding the mature protein. For the correct molecular joining of the transit peptide encoding nucleic acid and the nucleic acid encoding the protein to be targeted it is sometimes necessary to introduce additional base pairs at the joining position, which forms restriction enzyme recognition sequences useful for the molecular joining of the different nucleic acid molecules. This procedure might lead to very few additional amino acids at the N-terminal of the mature imported protein, which usually and preferably do not interfer with the protein function. In any case, the additional base pairs at the joining position which forms restriction enzyme recognition sequences have to be chosen with care, in order to avoid the formation of stop codons or codons which encode amino acids with a strong influence on protein folding, like e.g. proline. It is preferred that such additional codons encode small structural flexible amino acids such as glycine or alanine.

As mentioned above the nucleic acid sequences coding for the proteins selected from the group consisting of SEQ ID NOs: 2, 4, 13, 51, 52, 53, 54, 55, 56, 57, 58, 59, 60, 61, 62, 63 or homologs thereof encoded by the nucleic acid sequences selected from the group consisting of SEQ ID NOs: 1, 3, 12, 38, 39, 40, 41, 42, 43, 44, 45, 46, 47, 48, 49, 50 or homologs thereof can be joined to a nucleic acid sequence encoding a transit peptide. This nucleic acid sequence encoding a transit peptide ensures transport of the protein to the plastid. The nucleic acid sequence of the gene to be expressed and the nucleic acid sequence encoding the transit peptide are operably linked. Therefore the transit peptide is fused in frame to the nucleic acid sequence coding for proteins selected from the group consisting of SEQ ID NOs: 2, 4, 13, 51, 52, 53, 54, 55, 56, 57, 58, 59, 60, 61, 62, 63 or homologs thereof encoded by the nucleic acid sequences selected from the group consisting of SEQ ID NOs: 1, 3, 12, 38, 39, 40, 41, 42, 43, 44, 45, 46, 47, 48, 49, 50 or homologs thereof.

The term "organelle" according to the invention shall mean for example "mitochondria" or preferably "plastid" (throughout the specification the "plural" shall comprise the "singular" and vice versa). The term "plastid" according to the invention are intended to include various forms of plastids including proplastids, chloroplasts, chromoplasts, gerontoplasts, leucoplasts, amyloplasts, elaioplasts and etioplasts, preferably chloroplasts. They all have as a common ancestor the aforementioned proplasts.

Other transit peptides are disclosed by Schmidt et al. (J. Biol. Chem. 268 (36), 27447 (1993)), Della-Cioppa et al. (Plant. Physiol. 84, 965 (1987)), de Castro Silva Filho et al. (Plant Mol. Biol. 30, 769 (1996)), Zhao et al. (J. Biol. Chem.

270 (11), 6081 (1995)), Römer et al. (Biochem. Biophys. Res. Commun. 196 (3), 1414 (1993)), Keegstra et al. (Annu. Rev. Plant Physiol. Plant Mol. Biol. 40, 471 (1989)), Lubben et al. (Photosynthesis Res. 17, 173 (1988)) and Lawrence et al. (J. Biol. Chem. 272 (33), 20357 (1997)). A general review about targeting is disclosed by Kermode Allison R. in Critical Reviews in Plant Science 15 (4), 285 (1996) under the title "Mechanisms of Intracellular Protein Transport and Targeting in Plant Cells."

Favored transit peptide sequences, which are used in the inventive process and which form part of the inventive nucleic acid sequences are generally enriched in hydroxylated amino acid residues (serine and threonine), with these two residues generally constituting 20 to 35% of the total. They often have an amino-terminal region empty of Gly, Pro, and charged residues. Furthermore they have a number of small hydrophobic amino acids such as valine and alanine and generally acidic amino acids are lacking. In addition they generally have a middle region rich in Ser, Thr, Lys and Arg. Overall they have very often a net positive charge.

Alternatively, nucleic acid sequences coding for the transit peptides may be chemically synthesized either in part or wholly according to structure of transit peptide sequences disclosed in the prior art. Said natural or chemically synthesized sequences can be directly linked to the sequences encoding the mature protein or via a linker nucleic acid sequence, which may be typically less than 500 base pairs, preferably less than 450, 400, 350, 300, 250 or 200 base pairs, more preferably less than 150, 100, 90, 80, 70, 60, 50, 40 or 30 base pairs and most preferably less than 25, 20, 15, 12, 9, 6 or 3 base pairs in length and are in frame to the coding sequence. Furthermore favorable nucleic acid sequences encoding transit peptides may comprise sequences derived from more than one biological and/or chemical source and may include a nucleic acid sequence derived from the amino-terminal region of the mature protein, which in its native state is linked to the transit peptide. In a preferred embodiment of the invention said amino-terminal region of the mature protein is typically less than 150 amino acids, preferably less than 140, 130, 120, 110, 100 or 90 amino acids, more preferably less than 80, 70, 60, 50, 40, 35, 30, 25 or 20 amino acids and most preferably less than 19, 18, 17, 16, 15, 14, 13, 12, 11 or 10 amino acids in length. But even shorter or longer stretches are also possible. In addition target sequences, which facilitate the transport of proteins to other cell compartments such as the vacuole, endoplasmic reticulum, golgi complex, glyoxysomes, peroxisomes or mitochondria may be also part of the inventive nucleic acid sequence. The proteins translated from said inventive nucleic acid sequences are a kind of fusion proteins that means the nucleic acid sequences encoding the transit peptide for example the ones shown in table I, preferably the last one of the table are joint to the nucleic acid sequences selected from the group consisting of SEQ ID NOs: 1, 3, 12, 38, 39, 40, 41, 42, 43, 44, 45, 46, 47, 48, 49, 50 or homologs thereof. The person skilled in the art is able to join said sequences in a functional manner. Advantageously the transit peptide part is cleaved off from the protein part selected from the group consisting of SEQ ID NOs: 2, 4, 13, 51, 52, 53, 54, 55, 56, 57, 58, 59, 60, 61, 62, 63 or homologs thereof during the transport preferably into the plastids. All products of the cleavage of the preferred transit peptide shown in the last line of table I have preferably the N-terminal amino acid sequences QIA CSS or QIA EFQLTT in front of the start methionine of the protein selected from the group consisting of SEQ ID NOs: 2, 4, 13, 51, 52, 53, 54, 55, 56, 57, 58, 59, 60, 61, 62, 63 or homologs thereof. Other short amino acid sequences of an range of 1 to 20 amino acids preferable 2 to 15 amino acids, more preferable 3 to 10 amino acids most preferably 4 to 8 amino acids are also possible in front of the start methionine of the protein selected from the group consisting of SEQ ID NOs: 2, 4, 13, 51, 52, 53, 54, 55, 56, 57, 58, 59, 60, 61, 62, 63 or homologs thereof. In case of the amino acid sequence QIA CSS the three amino acids in front of the start methionine are stemming from the LIC (=ligatation independent cloning) cassette. Said short amino acid sequence is preferred in the case of the expression of E. coli genes. In case of the amino acid sequence QIA EFQLTT the six amino acids in front of the start methionine are stemming from the LIC cassette. Said short amino acid sequence is preferred in the case of the expression of S. cerevisiae genes. The skilled worker knows that other short sequences are also useful in the expression of the genes selected from the group consisting of SEQ ID NOs: 1, 3, 12, 38, 39, 40, 41, 42, 43, 44, 45, 46, 47, 48, 49, 50 or homologs thereof. Furthermore the skilled worker is aware of the fact that there is not a need for such short sequences in the expression of the genes.

TABLE I

Examples of transit peptides disclosed by von Heijne et al.

| Trans Pep | Organism | Transit Peptide | SEQ ID NO: | Reference |
|---|---|---|---|---|
| 1 | Acetabularia mediterranea | MASIMMNKSVVLSKECAKPLATPK VTLNKRGFATTIATKNREMMVWQP FNNKMFETFSFLPP | 19 | Mol. Gen. Genet. 218, 445 (1989) |
| 2 | Arabidopsis thaliana | MAASLQSTATFLQSAKIATAPSRG SSHLRSTQAVGKSFGLETSSARLT CSFQSDFKDFTGKCSDAVKIAGFA LATSALVVSGASAEGAPK | 20 | EMBO J. 8, 3187 (1989) |
| 3 | Arabidopsis thaliana | MAQVSRICNGVQNPSLICNLSKSS QRKSPLSVSLKTQQHPRAYPISSS WGLKKSGMTLIGSELRPLKVMSSV STAEKASEIVLQPIREISGLIKLP | 21 | Mol. Gen. Genet. 210, 437 (1987) |
| 4 | Arabidopsis thaliana | MAAATTTTTTSSSISFSTKPSPSS SKSPLPISRFSLPFSLNPNKSSSS SRRRGIKSSSPSSISAVLNTTTNV TTTPSPTKPTKPETFISRFAPDQP RKGA | 22 | Plant Physiol. 85, 1110 (1987) |

TABLE I-continued

Examples of transit peptides disclosed by von Heijne et al.

| Trans Pep | Organism | Transit Peptide | SEQ ID NO: | Reference |
|---|---|---|---|---|
| 5 | Arabidopsis thaliana | MITSSLTCSLQALKLSSPFAHGST PLSSLSKPNSFPNHRMPALVPV | 23 | J. Biol. Chem. 265, 2763 (1990) |
| 6 | Arabidopsis thaliana | MASLLGTSSSAI-WASPSLSSPSSKPSSSPICFRPGK LFGSKLNAGIQI RPKKNRSRYHVSVMNVATEINSTE QVVGKFDSKKSARPVYPFAAI | 24 | EMBO J. 9, 1337 (1990) |
| 7 | Arabidopsis thaliana | MASTALSSAIVGTSFIRRSPAPISL RSLPSANTQSLFGLKSGTARGGRVV AM | 25 | Plant Physiol. 93, 572 (1990) |
| 8 | Arabidopsis thaliana | MAASTMALSSPAFAGKAVNLSPAA SEVLGSGRVTNRKTV | 26 | Nucl. Acids Res. 14, 4051 (1986) |
| 9 | Arabidopsis thaliana | MAAITSATVTIPSFTGLKLAVSSK PKTLSTISRSSSATRAPPKLALKS SLKDFGVIAVATAASIVLAGNAMA MEVLLGSDDGSLAFVPSEFT | 27 | Gene 65, 59 (1988) |
| 10 | Arabidopsis thaliana | MAAAVSTVGAINRAPLSLNGSGSG AVSAPASTFLGKKVVTVSRFAQSN KKSNGSFKVLAVKEDKQTDGDRWR GLAYDTSDDQIDI | 28 | Nucl. Acids Res. 17, 2871 (1989) |
| 11 | Arabidopsis thaliana | MKSSMLSSTAWTSPAQATMVAPFT GLKSSASFPVTRKANNDITSITSN GGRVSC | 29 | Plant Mol. Biol. 11, 745 (1988) |
| 12 | Arabidopsis thaliana | MAASGTSATFRASVSSAPSSSSQL THLKSPFKAVKYTPLPSSRSKSSS FSVSCTIAKDPPVLMAAGSDPALW QRPDSFGRFGKFGGKYVPE | 30 | Proc. Natl. Acad. Sci. USA, 86, 4604 (1989) |
| 13 | Brassica campestris | MSTTFCSSVCMQATSLAATTRISF QKPALVSTTNLSFNLRRSIPTRFS ISCAAKPETVEKVSKIVKKQLSLK DDQKVVAE | 31 | Nucl. Acids Res. 15, 7197 (1987) |
| 14 | Brassica napus | MATTFSASVSMQATSLATTTRISF QKPVLVSNHGRTNLSFNLSRTRLS ISC | 32 | Eur. J. Bio chem. 174, 287 (1988) |
| 15 | Chlamydomonas reinhardtii | MQALSSRVNIAAKPQRAQRLVVRA EEVKAAPKKEVGPKRGSLVK | 33 | Plant Mol. Biol. 12, 463 (1989) |
| 16 | Cucurbita moschata | MAELIQDKESAQSAATAAAASSGY ERRNEPAHSRKFLEVRSEEELL-SCIKK | 34 | FEBS Lett. 238, 424 (1988) |
| 17 | Spinacea oleracea | MSTINGCLTSISPSRTQLKNTSTL RPTFIANSRVNPSSSVPPSLIRNQ PVFAAPAPIITPTL | 35 | J. Biol. Chem. 265, (10) 5414 (1990) |
| 18 | Spinacea oleracea | MTTAVTAAVSFPSTKTTSLSARCS SVISPDKISYKKVPLYYRNVSATG KMGPIRAQIASDVEAPPPAPAK-VEKMS | 36 | Curr. Genet. 13, 517 (1988) |
| 19 | Spinacea oleracea | MTTAVTAAVSFPSTKTTSLSARSS SVISPDKISYKKVPLYYRNVSATG KMGPIRA | 37 | |

Alternatively to the targeting of the sequences selected from the group consisting of SEQ ID NOs: 2, 4, 13, 51, 52, 53, 54, 55, 56, 57, 58, 59, 60, 61, 62, 63 or homologs thereof preferably of sequences in general encoded in the nucleus with the aid of the targeting sequences mentioned for example in table I alone or in combination with other targeting sequences preferably into the plastids, the nucleic acids of the invention can directly be introduced into the plastidal genome. Therefore in a preferred embodiment the nucleic acid sequences selected from the group consisting of SEQ ID NOs: 1, 3, 12, 38, 39, 40, 41, 42, 43, 44, 45, 46, 47, 48, 49, 50 or homologs thereof are directly introduced and expressed in plastids.

The term "introduced" in the context of this specification shall mean the insertion of a nucleic acid sequence into the organism by means of a "transfection", "transduction" or preferably by "transformation".

A plastid, such as a chloroplast, has been "transformed" by an exogenous (preferably foreign) nucleic acid sequence if nucleic acid sequence has been introduced into the plastid that means that this sequence has crossed the membrane or the membranes of the plastid. The foreign DNA may be integrated (covalently linked) into plastid DNA making up the genome of the plastid, or it may remain unintegrated (e.g., by including a chloroplast origin of replication). "Stably" integrated DNA sequences are those, which are inherited through plastid replication, thereby transferring new plastids, with the features of the integrated DNA sequence to the progeny.

For expression a person skilled in the art is familiar with different methods to introduce the nucleic acid sequences into different organelles such as the preferred plastids. Such methods are for example disclosed by Maiga P. (Annu. Rev. Plant Biol. 55, 289 (2004)), Evans T. (WO 2004/040973), McBride K. E. et al. (U.S. Pat. No. 5,455,818), Daniell H. et al. (U.S. Pat. No. 5,932,479 and U.S. Pat. No. 5,693,507) and Straub J. M. et al. (U.S. Pat. No. 6,781,033). A preferred method is the transformation of microspore-derived hypocotyl or cotyledonary tissue (which are green and thus contain numerous plastids) leaf tissue and afterwards the regeneration of shoots from said transformed plant material on selective medium. As methods for the transformation bombarding of the plant material or the use of independently replicating shuttle vectors are well known by the skilled worker. But also a PEG-mediated transformation of the plastids or *Agrobacterium* transformation with binary vectors is possible. Useful markers for the transformation of plastids are positive selection markers for example the chloramphenicol-, streptomycin-, kanamycin-, neomycin-, amikamycin-, spectinomycin-, triazine- and/or lincomycin-tolerance genes. As additional markers named in the literature often as secondary markers, genes coding for the tolerance against herbicides such as phosphinothricin (=glufosinate, BASTA™, Liberty™, encoded by the bar gene), glyphosate (=N-(phosphonomethyl)glycine, Roundup™, encoded by the 5-enolpyruvylshikimate-3-phosphate synthase gene=epsps), sulfonylureas (like Staple™, encoded by the ace-tolactate synthase (ALS) gene), imidazolinones [=IMI, like imazethapyr, imazamox, Clearfield™, encoded by the acetohydroxyacid synthase (AHAS) gene, also known as acetolactate synthase (ALS) gene] or bromoxynil (=Buctril™, encoded by the oxy gene) or genes coding for antibiotics such as hygromycin or G418 are useful for further selection. Such secondary markers are useful in the case when most genome copies are transformed. In addition negative selection markers such as the bacterial cytosine deaminase (encoded by the codA gene) are also useful for the transformation of plastids.

To increase the possibility of identification of transformants it is also desirable to use reporter genes other then the aforementioned tolerance genes or in addition to said genes. Reporter genes are for example β-galactosidase-, β-glucuronidase-(GUS), alkaline phosphatase- and/or green-fluorescent protein-genes (GFP).

For the inventive process it is of great advantage that by transforming the plastids the intraspecies specific transgene flow is blocked, because a lot of species such as corn, cotton and rice have a strict maternal inheritance of plastids. By placing the genes selected from the group consisting of SEQ ID NOs: 1, 3, 12, 38, 39, 40, 41, 42, 43, 44, 45, 46, 47, 48, 49, 50 or homologs thereof or active fragments thereof in the plastids of plants, these genes will not be present in the pollen of said plants.

A further preferred embodiment of the invention relates to the use of so called "chloroplast localization sequences", in which a first RNA sequence or molecule is capable of transporting or "chaperoning" a second RNA sequence, such as a RNA sequence transcribed from the sequences selected from the group consisting of SEQ ID NOs: 1, 3, 12, 38, 39, 40, 41, 42, 43, 44, 45, 46, 47, 48, 49, 50 or homologs thereof or a sequence encoding a protein selected from the group consisting of SEQ ID NOs: 2, 4, 13, 51, 52, 53, 54, 55, 56, 57, 58, 59, 60, 61, 62, 63 or homologs thereof, from an external environment inside a cell or outside a plastid into a chloroplast. In one embodiment the chloroplast localization signal is substantially similar or complementary to a complete or intact viroid sequence. The chloroplast localization signal may be encoded by a DNA sequence, which is transcribed into the chloroplast localization RNA. The term "viroid" refers to a naturally occurring single stranded RNA molecule (Flores, C. R. Acad Sci Ill. 324 (10), 943 (2001)). Viroids usually contain about 200-500 nucleotides and generally exist as circular molecules. Examples of viroids that contain chloroplast localization signals include but are not limeted to ASBVd, PLMVd, CChMVd and ELVd. The viroid sequence or a functional part of it can be fused to the sequences selected from the group consisting of SEQ ID NOs: 1, 3, 12, 38, 39, 40, 41, 42, 43, 44, 45, 46, 47, 48, 49, 50 or homologs thereof or a sequence encoding a protein, selected from the group consisting of SEQ ID NOs: 2, 4, 13, 51, 52, 53, 54, 55, 56, 57, 58, 59, 60, 61, 62, 63 or homologs thereof in such a manner that the viroid sequence transports a sequence transcribed from a sequence selected from the group consisting of SEQ ID NOs: 1, 3, 12, 38, 39, 40, 41, 42, 43, 44, 45, 46, 47, 48, 49, 50 or homologs thereof or a sequence encoding a protein selected from the group consisting of SEQ ID NOs: 2, 4, 13, 51, 52, 53, 54, 55, 56, 57, 58, 59, 60, 61, 62, 63 or homologs thereof into the chloroplasts. A preferred embodiment uses a modified ASBVd (Navarro et al., Virology. 268 (1), 218 (2000)).

In a further specific embodiment the protein to be expressed in the plastids such as the proteins selected from the group consisting of SEQ ID NOs: 2, 4, 13, 51, 52, 53, 54, 55, 56, 57, 58, 59, 60, 61, 62, 63 or homologs thereof are encoded by different nucleic acids. Such a method is disclosed in WO 2004/040973, which shall be incorporated by reference. WO 2004/040973 teaches a method, which relates to the translocation of an RNA corresponding to a gene or gene fragment into the chloroplast by means of a chloroplast localization sequence. The genes, which should be expressed in the plant or plants cells, are split into nucleic acid fragments, which are introduced into different compartments in the plant e.g. the nucleus, the plastids and/or mitochondria. Additionally plant cells are described in which the chloroplast contains a ribozyme fused at one end to an RNA encoding a fragment of a protein used in the inventive process such that the ribozyme can trans-splice the translocated fusion RNA to the RNA encoding the gene fragment to form and as the case may be reunite the nucleic acid fragments to an intact mRNA encoding a functional protein for example selected from the group consisting of SEQ ID NOs: 2, 4, 13, 51, 52, 53, 54, 55, 56, 57, 58, 59, 60, 61, 62, 63 or homologs thereof.

In a preferred embodiment of the invention the nucleic acid sequences selected from the group consisting of SEQ ID NOs: 2, 4, 13, 51, 52, 53, 54, 55, 56, 57, 58, 59, 60, 61, 62, 63 or homologs thereof used in the inventive process are transformed into plastids, which are metabolical active. Those plastids should preferably maintain at a high copy number in the plant or plant tissue of interest, most preferably the chloroplasts found in green plant tissues, such as leaves or cotyledons or in seeds.

For a good expression in the plastids the nucleic acid sequences selected from the group consisting of SEQ ID NOs: 2, 4, 13, 51, 52, 53, 54, 55, 56, 57, 58, 59, 60, 61, 62, 63 are introduced into an expression cassette using a preferably a promoter and terminator, which are active in plastids preferably a chloroplast promoter. Examples of such promoters include the psbA promoter from the gene from spinach or pea, the rbcL promoter, and the atpB promoter from corn.

Comprises/comprising and grammatical variations thereof when used in this specification are to be taken to specify the presence of stated features, integers, steps or components or groups thereof, but not to preclude the presence or addition of one or more other features, integers, steps, components or groups thereof.

In accordance with the invention, the term "plant cell" or the term "organism" as understood herein relates always to a plant cell or a organelle thereof, preferably a plastid, more preferably chloroplast.

As used herein, "plant" is meant to include not only a whole plant but also a part thereof i.e., one or more cells, and tissues, including for example, leaves, stems, shoots, roots, flowers, fruits and seeds.

In an embodiment, the nucleic acid sequence coding for the phosphoribosyl pyrophosphate synthase originates and/or is isolated from a fungus selected from the group of the ascomycetes, the filamentous fungi, preferably fungi from the genera *Aspergillus, Trichoderma, Ashbya, Eremothecium, Neurospora, Fusarium, Beauveria, Mortierella, Saprolegnia, Pythium.*

In an embodiment, the nucleic acid sequence coding for the phosphoribosyl pyrophosphate synthase originates and/or is isolated from a organism selected from the group consisting of *Ashbya gossypii, Aspergillus fumigatus, Aspergillus niger, Candida glabrata, Coccidioides immitis, Debaryomyces hansenii, Kluyveromyces lactis, Lodderomyces elongisporus, Neosartorya fischeri, Pichia stipitis, Saccharomyces cerevisiae, Sclerotinia sclerotiorum* and *Vanderwaltozyma polyspora.*

In an embodiment, the nucleic acid sequence coding for the phosphoribosyl pyrophosphate synthase originates and/or is isolated from a fungus of the species *Ashbya gossypii.*

In a further variant of the present invention, the method is characterized in that the gene encoding for the phosphoribosyl pyrophosphate synthase contains at least one point mutation in the area of the ADP binding site. The point mutation within the ADP binding site should, if possible, prevent a negative allosteric regulation of the enzyme activity.

In a preferred embodiment, a nucleic acid sequence according to SEQ ID NO 3 or functional equivalents thereof is used for this purpose. Preferably, the following point mutations are found: Leu133Ile and His196Glu.

In an embodiment, the nucleic acid sequence coding for the phosphoribosyl pyrophosphate synthase originates and/or is isolated from the group consisting of corn (maize), wheat, rye, oat, triticale, rice, barley, soybean, peanut, cotton, oil seed rape, including canola and winter oil seed rape, manihot, pepper, sunflower, flax, borage, safflower, linseed, primrose, rapeseed, turnip rape, tagetes, solanaceous plants comprising potato, tobacco, eggplant, tomato; *Vicia* species, pea, alfalfa, coffee, cacao, tea, *Salix* species, oil palm, coconut, perennial grass, forage crops and *Arabidopsis thaliana*, preferably *Zea mais.*

Surprisingly it was found, that the transgenic expression of the *Ashbya gossypii* protein as shown SEQ ID NO: 2, and/or the transgenic expression of the mutated *Ashbya gossypii* protein as shown SEQ ID NO: 4 in a plant such as *Arabidopsis thaliana* or *Nicotiana tabacum* for example, conferred increased yield to the transgenic plant cell, plant or a part thereof as compared to a corresponding non-transformed wild type plant cell, a plant or a part thereof.

Accordingly, in one embodiment, in case the activity of the Ashbya gossypii nucleic acid molecule or a polypeptide comprising the nucleic acid SEQ ID NO. 1 or polypeptide SEQ ID NO. 2, respectively is increased or generated, e.g. if the activity of a nucleic acid molecule or a polypeptide comprising the nucleic acid or polypeptide or the polypeptide motif of the ADP binding site selected from the group consisting of SEQ ID NOs: 7, 8, 9, 10, 11, or comprising a polypeptide according to the motif selected from the group consisting of SEQ ID No. 64, 65, 66, 67, 68, 69, 70, 71, 72, 73 respectively is increased or generated in an plant cell, plant or part thereof, preferable in the cytoplasm of a cell, an increase of yield as compared to a corresponding non-transformed wild type plant cell, a plant or a part thereof is conferred.

Accordingly, in one embodiment, in case the activity of the Ashbya gossypii nucleic acid molecule or a polypeptide comprising the nucleic acid SEQ ID NO. 3 or polypeptide SEQ ID NO. 4, respectively is increased or generated, e.g. if the activity of a nucleic acid molecule or a polypeptide comprising the nucleic acid or polypeptide or the polypeptide motif of the ADP binding site selected from the group consisting of SEQ ID NOs: 14, 15, 16, 17, 18, or comprising a polypeptide according to the motif selected from the group consisting of SEQ ID No. 64, 65, 66, 67, 68, 69, 70, 71, 72, 73 respectively is increased or generated in an plant cell, plant or part thereof, preferable in the cytoplasm of a cell, an increase of yield as compared to a corresponding non-transformed wild type plant cell, a plant or a part thereof is conferred.

Accordingly, in one embodiment, in case the activity of the Ashbya gossypii nucleic acid molecule or a polypeptide comprising the nucleic acid SEQ ID NO. 1 or polypeptide SEQ ID NO. 2, respectively is increased or generated, e.g. if the activity of a nucleic acid molecule or a polypeptide comprising the nucleic acid or polypeptide or the polypeptide motif of the ADP binding site selected from the group consisting of SEQ ID NOs: 7, 8, 9, 10, 11, or comprising a polypeptide according to the motif selected from the group consisting of SEQ ID No. 64, 65, 66, 67, 68, 69, 70, 71, 72, 73 respectively is increased or generated in an plant cell, plant or part thereof, preferable in the plastid of a cell, an increase of yield as compared to a corresponding non-transformed wild type plant cell, a plant or a part thereof is conferred.

Accordingly, in one embodiment, in case the activity of the Ashbya gossypii nucleic acid molecule or a polypeptide comprising the nucleic acid SEQ ID NO. 3 or polypeptide SEQ ID NO. 4, respectively is increased or generated, e.g. if the activity of a nucleic acid molecule or a polypeptide comprising the nucleic acid or polypeptide or the polypeptide motif of the ADP binding site selected from the group consisting of SEQ ID NOs: 14, 15, 16, 17, 18, or comprising a polypeptide according to the motif selected from the group consisting of SEQ ID No. 64, 65, 66, 67, 68, 69, 70, 71, 72, 73 respectively is increased or generated in an plant cell, plant or part thereof, preferable in the plastid of a cell, an increase of yield as compared to a corresponding non-transformed wild type plant cell, a plant or a part thereof is conferred.

For the purposes of the invention, as a rule the plural is intended to encompass the singular and vice versa.

Unless otherwise specified, the terms "polynucleotides", "nucleic acid" and "nucleic acid molecule" are interchangeably in the present context. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or deoxyribonucleotides. The terms refer only to the primary structure of the molecule.

Thus, the terms "gene(s)", "polynucleotide", "nucleic acid sequence", "nucleotide sequence", or "nucleic acid molecule(s)" as used herein include double- and single-stranded DNA and/or RNA. They also include known types of modifications, for example, methylation, "caps", substitutions of one or more of the naturally occurring nucleotides with an analog. Preferably, the DNA or RNA sequence comprises a coding sequence encoding the herein defined polypeptide.

A "coding sequence" is a nucleotide sequence, which is transcribed into an RNA, e.g. a regulatory RNA, such as a miRNA, a ta-siRNA, cosuppression molecule, an RNAi, a ribozyme, etc. or into a mRNA which is translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

As used in the present context a nucleic acid molecule may also encompass the untranslated sequence located at the 3' and at the 5' end of the coding gene region, for example at least 500, preferably 200, especially preferably 100, nucleotides of the sequence upstream of the 5' end of the coding region and at least 100, preferably 50, especially preferably 20, nucleotides of the sequence downstream of the 3' end of the coding gene region. In the event for example the antisense, RNAi, snRNA, dsRNA, siRNA, miRNA, ta-siRNA, cosuppression molecule, ribozyme etc. technology is used coding regions as well as the 5'- and/or 3'-regions can advantageously be used.

However, it is often advantageous only to choose the coding region for cloning and expression purposes.

"Polypeptide" refers to a polymer of amino acid (amino acid sequence) and does not refer to a specific length of the molecule. Thus, peptides and oligopeptides are included within the definition of polypeptide. This term does also refer to or include posttranslational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The terms "comprise" or "comprising" and grammatical variations thereof when used in this specification are to be taken to specify the presence of stated features, integers, steps or components or groups thereof, but not to preclude the presence or addition of one or more other features, integers, steps, components or groups thereof.

In accordance with the invention, a protein or polypeptide has the "activity of an protein selected from the group consisting of SEQ ID NOs: 2, 4, 13, 51, 52, 53, 54, 55, 56, 57, 58, 59, 60, 61, 62, 63 or homologs thereof" if its de novo activity, or its increased expression directly or indirectly leads to and confers an increased yield as compared to a corresponding non-transformed wild type plant cell, plant or part thereof and the protein has the above mentioned activities of a phosphoribosyl pyrophosphate synthases. Throughout the specification the activity or preferably the biological activity of such a protein or polypeptide or an nucleic acid molecule or sequence encoding such protein or polypeptide is identical or similar if it still has the biological or enzymatic activity of a protein selected from the group consisting of SEQ ID NOs: 2, 4, 13, 51, 52, 53, 54, 55, 56, 57, 58, 59, 60, 61, 62, 63 or homologs thereof, or which has at least 10% of the original enzymatic activity, preferably 20%, 30%, 40%, 50%, particularly preferably 60%, 70%, 80% most particularly preferably 90%, 95%, 98%, 99% in comparison to a phosphoribosyl pyrophosphate synthases of *Ashbya Gossypii*.

The terms "increased", "rised", "extended", "enhanced", "improved" or "amplified" relate to a corresponding change of a property in a plant, an organism, a part of an organism such as a tissue, seed, root, leave, flower etc. or in a cell and are interchangeable. Preferably, the overall activity in the volume is increased or enhanced in cases if the increase or enhancement is related to the increase or enhancement of an activity of a gene product, independent whether the amount of gene product or the specific activity of the gene product or both is increased or enhanced or whether the amount, stability or translation efficacy of the nucleic acid sequence or gene encoding for the gene product is increased or enhanced.

The terms "increase" relate to a corresponding change of a property an organism or in a part of a plant, an organism, such as a tissue, seed, root, leave, flower etc. or in a cell. Preferably, the overall activity in the volume is increased in cases the increase relates to the increase of an activity of a gene product, independent whether the amount of gene product or the specific activity of the gene product or both is increased or generated or whether the amount, stability or translation efficacy of the nucleic acid sequence or gene encoding for the gene product is increased.

Under "change of a property" it is understood that the activity, expression level or amount of a gene product or the metabolite content is changed in a specific volume relative to a corresponding volume of a control, reference or wild type, including the de novo creation of the activity or expression.

The terms "increase" include the change of said property in only parts of the subject of the present invention, for example, the modification can be found in compartment of a cell, like a organelle, or in a part of a plant, like tissue, seed, root, leave, flower etc. but is not detectable if the overall subject, i.e. complete cell or plant, is tested.

Accordingly, the term "increase" means that the specific activity of an enzyme as well as the amount of a compound or metabolite, e.g. of a polypeptide, a nucleic acid molecule of the invention or an encoding mRNA or DNA, can be increased in a volume.

By means of the method, the yield of the plant organisms is increased by at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% by weight, advantageously by at least 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80% by weight, particularly advantageously by at least 81, 82, 83, 84, 85, 86, 87, 88, 89, 90, 91, 92, 93, 94, 95, 96, 97, 98, 99 or 100% by weight, very particularly advantageously by at least 101, 102, 103, 104, 105, 106, 107, 108, 109, 110, 111, 112, 113, 114, 115,116, 117, 118, 119, 120, 121, 122, 123, 124, 125, 126, 127, 128, 129, 130, 131, 132, 133, 134, 135, 136,137, 138, 139, 140, 145, 150, 160, 170, 180, 190 or 200, 300, 400 or 500% by weight.

In one embodiment the increase of yield of a transgenic plant cell, plant or part thereof, is an significant increase of yield dterminated by t-test or unpaired two-tailed t-test as compared to a corresponding non-transformed wild type plant cell, a plant or a part thereof.

The term "activity" describes the ability of an enzyme to convert a substrate into a product. The activity can be determined in a so-called activity test via the increase of the product, the decrease of the substrate (or starting material) or the decrease of a specific cofactor or via a combination of at least two of the parameters mentioned above as a function of time.

According to the invention, the activity of the phosphoribosyl pyrophosphate synthase is the catalytic conversion of ribose 5-phosphate (R5P) into 5-phosphoribosyl α-1-pyrophosphate (PRPP), preferably an enzyme as defined under the IUPAC name EC 2.7.6.1.

According to the invention, the increase or decrease in the activity, the production or the concentration, the increase and decrease in substances, products, starting materials or substrates refers to the comparison with the wild-type which does not have the increase in the EC 2.7.6.1. enzyme activity according to the invention in a comparative experiment under identical conditions.

The terms "wild type", "control" or "reference" are exchangeable and can be a cell or a part of organisms such as an organelle like a chloroplast or a tissue, or an organism, in particular a plant, which was not modified or treated according to the herein described process according to the invention. Accordingly, the cell or a part of organisms such as an organelle like a chloroplast or a tissue, or an organism, in particular a plant used as wild typ, control or reference corresponds to the cell, organism, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property.

Preferably, any comparison is carried out under analogous conditions. The term "analogous conditions" means that all conditions such as, for example, culture or growing conditions, soil, nutrient, water content of the soil, temperature, humidity or surrounding air or soil, assay conditions (such as buffer composition, temperature, substrates, pathogen strain, concentrations and the like) are kept identical between the experiments to be compared.

Plants grown with limiting nutrients were grown with a content of salt, N, $P_2O_5$, $K_2O$ which amounts 50, 49, 48, 47, 46, 45, 44, 43, 42, 41, 40% of the content of salt used for normal growth conditions.

The "reference", "control", or "wild type" is preferably a subject, e.g. an organelle, a cell, a tissue, an organism, in particular a plant, which was not modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-"-organelle, -cell, -tissue or -organism, in particular plant, relates to an organelle, cell, tissue or organism, in particular plant, which is nearly genetically identical to the organelle, cell, tissue or organism, in particular plant, of the present invention or a part thereof preferably 95%, more preferred are 98%, even more preferred are 99.00%, in particular 99.10%, 99.30%, 99.50%, 99.70%, 99.90%, 99.99%, 99.999% or more. Most preferable the "reference", "control", or "wild type" is a subject, e.g. an organelle, a cell, a tissue, an organism, in particular a plant, which is genetically identical to the organism, in particular plant, cell, a tissue or organelle used according to the process of the invention except that the responsible or activity conferring nucleic acid molecules or the gene product encoded by them are amended, manipulated, exchanged or introduced according to the inventive process.

In case, a control, reference or wild type differing from the subject of the present invention only by not being subject of the process of the invention can not be provided, a control, reference or wild type can be an organism in which the cause for the modulation of an activity conferring the increased yield as compared to a corresponding non-transformed wild type plant cell, plant or part thereof or expression of the nucleic acid molecule of the invention as described herein has been switched back or off, e.g. by knocking out the expression of responsible gene product, e.g. by antisense inhibition, by inactivation of an activator or agonist, by activation of an inhibitor or antagonist, by inhibition through adding inhibitory antibodies, by adding active compounds as e.g. hormones, by introducing negative dominant mutants, etc. A gene production can for example be knocked out by introducing inactivating point mutations, which lead to an enzymatic activity inhibition or a destabilization or an inhibition of the ability to bind to cofactors etc.

Accordingly, preferred reference subject is the starting subject of the present process of the invention. Preferably, the reference and the subject matter of the invention are compared after standardization and normalization, e.g. to the amount of total RNA, DNA, or Protein or activity or expression of reference genes, like housekeeping genes, such as ubiquitin, actin or ribosomal proteins.

The increase or modulation according to this invention can be constitutive, e.g. due to a stable permanent transgenic expression or to a stable mutation in the corresponding endogenous gene encoding the nucleic acid molecule of the invention or to a modulation of the expression or of the behavior of a gene conferring the expression of the polypeptide of the invention, or transient, e.g. due to an transient transformation or temporary addition of a modulator such as a agonist or antagonist or inducible, e.g. after transformation with a inducible construct carrying the nucleic acid molecule of the invention under control of a inducible promoter and adding the inducer, e.g. tetracycline or as described herein below.

The increase in activity of the polypeptide amounts in a cell, a tissue, an organelle, an organ or an organism, preferably a plant, or a part thereof preferably to at least 5%, preferably to at least 20% or at to least 50%, especially preferably to at least 70%, 80%, 90% or more, very especially preferably are to at least 100%, 150% or 200%, most preferably are to at least 250% or more in comparison to the control, reference or wild type.

In one embodiment the term increase means the increase in amount in relation to the weight of the organism or part thereof (w/w).

In one embodiments the increase in activity of the polypeptide amounts in an organelle such as a plastid.

In another embodiment the increase in activity of the polypeptide amounts in the cytoplasm.

The specific activity of a polypeptide encoded by a nucleic acid molecule of the present invention or of the polypeptide of the present invention can be tested as described in the examples. In particular, the expression of a protein in question in a cell, e.g. a plant cell in comparison to a control is an easy test and can be performed as described in the state of the art.

The term "increase" includes, that a compound or an activity, especially an activity, is introduced into a cell, the cytoplasm or a subcellular compartment or organelle de novo or that the compound or the activity, especially an activity, has not been detected before, in other words it is "generated".

Accordingly, in the following, the term "increasing" also comprises the term "generating" or "stimulating". The increased activity manifests itself in an increased yield as compared to a corresponding non-transformed wild type plant cell, plant or part thereof.

Surprisingly, it was observed that an increasing or generating of at least one gene conferring an activity of the Ashbya gossypii nucleic acid molecule or a polypeptide comprising the nucleic acid SEQ ID NO. 1 or polypeptide SEQ ID NO. 2, respectively, in the cytoplasm of a cell, preferably in *Arabidopsis thaliana*, conferred an increase of yield, preferably of seedling fresh weight of 1.1-fold to 1.3-fold or more as compared to a corresponding non-transformed wild type plant cell, a plant or a part thereof.

Surprisingly, it was observed that an increasing or generating of at least one gene conferring an activity of the Ashbya gossypii nucleic acid molecule or a polypeptide comprising the nucleic acid SEQ ID NO. 1 or polypeptide SEQ ID NO. 2, respectively, in the cytoplasm of a cell, preferably in *Nicotiana tabacum*, conferred an increase of yield, preferably of seedling fresh weight of 1.1-fold to 1.25-fold or more as compared to a corresponding non-transformed wild type plant cell, a plant or a part thereof.

Surprisingly, it was observed that an increasing or generating of at least one gene conferring an activity of the mutated Ashbya gossypii nucleic acid molecule or a polypeptide comprising the nucleic acid SEQ ID NO. 3 or polypeptide SEQ ID NO. 4, respectively, in the cytoplasm of a cell, preferably in *Arabidopsis thaliana*, conferred an increase of yield, preferably of seedling fresh weight of 1.1-fold to 1.6-fold or more as compared to a corresponding non-transformed wild type plant cell, a plant or a part thereof.

Surprisingly, it was observed that an increasing or generating of at least one gene conferring an activity of the mutated Ashbya gossypii nucleic acid molecule or a polypeptide comprising the nucleic acid SEQ ID NO. 3 or polypeptide SEQ ID NO. 4, respectively, in the cytoplasm of a cell, preferably in *Nicotiana tabacum*, conferred an increase of yield, preferably of seedling fresh weight of 1.1-fold to 1.5-fold or more as compared to a corresponding non-transformed wild type plant cell, a plant or a part thereof.

Surprisingly, it was observed that an increasing or generating of at least one gene conferring an activity of the Ashbya gossypii nucleic acid molecule or a polypeptide comprising the nucleic acid SEQ ID NO. 1 or polypeptide SEQ ID NO. 2, respectively, in the cytoplasm of a cell, preferably in *Arabidopsis thaliana*, conferred an increase of yield, preferably of total nucleotides of 1.1-fold to 1.15-fold or more as compared to a corresponding non-transformed wild type plant cell, a plant or a part thereof.

Surprisingly, it was observed that an increasing or generating of at least one gene conferring an activity of the mutated Ashbya gossypii nucleic acid molecule or a polypeptide comprising the nucleic acid SEQ ID NO. 3 or polypeptide SEQ ID NO. 4, respectively, in the cytoplasm of a cell, preferably in *Arabidopsis thaliana*, conferred an increase of yield, preferably of total nucleotides of 1.1-fold to 1.15-fold or more as compared to a corresponding non-transformed wild type plant cell, a plant or a part thereof.

Surprisingly, it was observed that an increasing or generating of at least one gene conferring an activity of the Ashbya gossypii nucleic acid molecule or a polypeptide comprising the nucleic acid SEQ ID NO. 1 or polypeptide SEQ ID NO. 2, respectively, in the cytoplasm of a cell, preferably in *Arabidopsis thaliana*, conferred an increase of yield, preferably of total amino acids of 1.1-fold to 1.15-fold or more as compared to a corresponding non-transformed wild type plant cell, a plant or a part thereof.

Surprisingly, it was observed that an increasing or generating of at least one gene conferring an activity of the mutated Ashbya gossypii nucleic acid molecule or a polypeptide comprising the nucleic acid SEQ ID NO. 3 or polypeptide SEQ ID NO. 4, respectively, in the cytoplasm of a cell, preferably in *Arabidopsis thaliana*, conferred an increase of yield, preferably of total amino acids of 1.1-fold to 1.15-fold or more as compared to a corresponding non-transformed wild type plant cell, a plant or a part thereof.

Surprisingly, it was observed that an increasing or generating of at least one gene conferring an activity of the Ashbya gossypii nucleic acid molecule or a polypeptide comprising the nucleic acid SEQ ID NO. 1 or polypeptide SEQ ID NO. 2, respectively, in the cytoplasm of a cell, preferably in *Arabidopsis thaliana*, conferred an increase of yield, preferably of rosette fresh weight of 1.1-fold to 1.2-fold or more as compared to a corresponding non-transformed wild type plant cell, a plant or a part thereof.

Surprisingly, it was observed that an increasing or generating of at least one gene conferring an activity of the mutated *Ashbya gossypii* nucleic acid molecule or a polypeptide comprising the nucleic acid SEQ ID NO. 3 or polypeptide SEQ ID NO. 4, respectively, in the cytoplasm of a cell, preferably in *Arabidopsis thaliana*, conferred an increase of yield, preferably of rosette fresh weight of 1.1-fold to 1.2 fold or more as compared to a corresponding non-transformed wild type plant cell, a plant or a part thereof.

Surprisingly, it was observed that an increasing or generating of at least one gene conferring an activity of the mutated *Ashbya gossypii* nucleic acid molecule or a polypeptide comprising the nucleic acid SEQ ID NO. 3 or polypeptide SEQ ID NO. 4, respectively, in the cytoplasm of a cell, preferably in *Nicotiana tabacum*, conferred an increase of yield, preferably of plant height of 1.1-fold to 1.2 fold or more as compared to a corresponding non-transformed wild type plant cell, a plant or a part thereof.

Surprisingly, it was observed that an increasing or generating of at least one gene conferring an activity of the mutated *Ashbya gossypii* nucleic acid molecule or a polypeptide comprising the nucleic acid SEQ ID NO. 3 or polypeptide SEQ ID NO. 4, respectively, in the cytoplasm of a cell, preferably in *Nicotiana tabacum*, conferred an increase of yield, preferably of fresh weight, of 1.1-fold to 1.2 fold or more as compared to a corresponding non-transformed wild type plant cell, a plant or a part thereof.

Surprisingly, it was observed that an increasing or generating of at least one gene conferring an activity of the *Ashbya gossypii* nucleic acid molecule or a polypeptide comprising the nucleic acid SEQ ID NO. 1 or polypeptide SEQ ID NO. 2, respectively, in the plastid of a cell, preferably in *Arabidopsis thaliana*, conferred an increase of yield, preferably of seed total lipid content of 1.1-fold to 1.3-fold or more as compared to a corresponding non-transformed wild type plant cell, a plant or a part thereof.

Surprisingly, it was observed that an increasing or generating of at least one gene conferring an activity of the mutated *Ashbya gossypii* nucleic acid molecule or a polypeptide comprising the nucleic acid SEQ ID NO. 3 or polypeptide SEQ ID NO. 4, respectively, in the cytoplasm of a cell, preferably in *Arabidopsis thaliana*, conferred an increase of yield, preferably of seed total lipid content of 1.1-fold to 1.5-fold or more as compared to a corresponding non-transformed wild type plant cell, a plant or a part thereof.

Surprisingly, it was observed that an increasing or generating of at least one gene conferring an activity of the *Ashbya gossypii* nucleic acid molecule or a polypeptide comprising the nucleic acid SEQ ID NO. 1 or polypeptide SEQ ID NO. 2, respectively, in the plastid of a cell, preferably in *Arabidopsis thaliana*, conferred an increase of yield, preferably of seed total oil content of 1.1-fold to 1.5-fold or more as compared to a corresponding non-transformed wild type plant cell, a plant or a part thereof.

Surprisingly, it was observed that an increasing or generating of at least one gene conferring an activity of the mutated *Ashbya gossypii* nucleic acid molecule or a polypeptide comprising the nucleic acid SEQ ID NO. 3 or polypeptide SEQ ID NO. 4, respectively, in the cytoplasm of a cell, preferably in *Arabidopsis thaliana*, conferred an increase of yield, preferably of seed total oil content of 1.1-fold to 2.3-fold or more as compared to a corresponding non-transformed wild type plant cell, a plant or a part thereof.

Surprisingly, it was observed that an increasing or generating of at least one gene conferring an activity of the *Ashbya gossypii* nucleic acid molecule or a polypeptide comprising the nucleic acid SEQ ID NO. 1 or polypeptide SEQ ID NO. 2, respectively, in the cytoplasm of a cell, preferably in *Arabidopsis thaliana*, grown with limiting nutrients conferred an increase of yield, preferably of rosette fresh weight of 1.1-fold to 1.15-fold or more as compared to a corresponding non-transformed wild type plant cell, a plant or a part thereof.

Surprisingly, it was observed that an increasing or generating of at least one gene conferring an activity of the mutated *Ashbya gossypii* nucleic acid molecule or a polypeptide comprising the nucleic acid SEQ ID NO. 3 or polypeptide SEQ ID NO. 4, respectively, in the cytoplasm of a cell, preferably in *Arabidopsis thaliana*, grown with limiting nutrients conferred an increase of yield, preferably of rosette fresh weight of 1.1-fold to 1.2 fold or more as compared to a corresponding non-transformed wild type plant cell, a plant or a part thereof.

Advantageous plants used in the method have a high harvest yield of oil per hectare. This oil harvest yield is at least 100, 110, 120, 130, 140 or 150 kg of oil/ha, advantageously at least 250, 300, 350, 400, 450 or 500 kg of oil/ha, preferably at least 550, 600, 650, 700, 750, 800, 850, 900 or 950 kg of oil/ha, particularly preferably at least 1000 kg of oil/ha or more.

In a further variant, the plants are transformed such that they express the phosphoribosyl pyrophosphate synthase specifically in storage organs.

In one embodiment the method according to the invention increases the total oil content in the seed of the plants. Particularly preferably, the seed of the plant is harvested after cultivation and the oil contained in the seed is, if appropriate, isolated.

In the present method, the heterologous expression of the PRS gene (PRS) from *Ashbya gossypii* in *Arabidopsis thaliana* leads especially in seed to a significant increase in the oil content as described above. Here, the oil content is increased preferably by about 20-60%, particularly preferably by 25-55%, especially by 28-52%, based on the weight of the seeds compared to the wild type control plants (FIG. 1).

In the present method, the heterologous expression of the mutated PRS gene (PRSM: Leu133Ile, His196Glu) from *Ashbya gossypii* in *Arabidopsis thaliana* leads especially in the seed to a significant increase in the oil content as described above. Here, the oil content is increased preferably by about 60-150%, particularly preferably by 70-140%, especially by 75-132%, based on the weight of the seed compared to the wild-type control plants (FIG. 1). Advantageously, the transgenic expression of the phosphoribosyl pyrophosphate synthase had no disadvantageous effects on growth or other properties of the transformed plants.

In one embodiment the plants produced by the methods according to the invention which have an increased oil content can be marketed directly without isolation of the synthesized oil. In the method according to the invention, plants are to be understood as meaning whole plants and also all plant parts, plant organs or plant parts such as leaf, stalk, seeds, roots, tubers, anthers, fibers, root hairs, stems, embryos, calli, cotyledons, petioles, harvested material, plant tissue, reproductive tissue, cell cultures derived from the transgenic plant and/or which can be used to produce the transgenic plant. Here, the seed includes all parts of seeds, such as seed coats, epidermal cells and seed cells, endosperm or embryo tissue. However, the oils produced by the process according to the invention can also be isolated from the plants in the form of their oils, fat, lipids and/or free fatty acids. Oils produced by the method can be obtained by harvesting the plants either from the culture in which they grow or from the field. This can be carried out by pressing or extracting the plant parts, preferably the plant seeds. Here, the oils can be obtained by "cold beating or cold pressing" without input of heat by pressing. So that the plant parts, especially the seeds, can be digested more easily, they are comminuted, steam-treated or roasted beforehand. The seeds pretreated in this manner can then be pressed or be extracted with solvents, such as warm hexane. The solvent is then removed again. In this manner, more than 96% of the oils produced by the method can be isolated. The products obtained in this manner are then processed further, i.e. refined. Here, initially, the plant mucillage and the turbidity-causing solids, for example, are removed initially. The mucos removal can be carried out enzymatically or, for example, chemically/physically by addition of acid, such as phosphoric acid. The free fatty-acids can then be removed by treatment with a base, for example aqueous sodium hydroxide solution. To remove the base still present in the product, the product obtained is washed thoroughly with water and dried. To remove the dyes still present in the product, the products are subjected to bleaching using, for example, bleaching earth or activated carbon. At the end, the product is also deodorized using, for example, steam.

One embodiment according to the invention is the use of oils prepared by the method according to the invention or obtained by mixing these oils with animal, microbial or vegetable oils, lipids or fatty acids in feedstuff, foodstuff, cosmetics or pharmaceuticals. The oils prepared by the method according to the invention can be used in a manner known to the person skilled in the art for mixing with other oils, lipids, fatty acids or fatty acid mixtures of animal origin, such as, for example, fish oils. The fatty acids present in the oils prepared according to the invention, which were released from the oils by treatment with base, can also be added in customary amounts directly or after mixing with other oils, lipids, fatty acids or fatty acid mixtures of animal origin, such as, for example, fish oils, to feedstuff, foodstuff, cosmetics and/or pharmaceuticals.

The oils prepared in the method comprise compounds such as sphingolipids, phosphoglycerides, lipids, glycolipids, phospholipids, monoacylglycerides, diacylglycerides, triacylglycerides or other fatty esters, preferably triacylglycerides (see table 1).

From the oils thus prepared by the method according to the invention, the saturated and unsaturated fatty acids comprised therein can be released, for example, by treatment with alkali, for example with aqueous KOH or NaOH, or acidic hydrolysis, advantageously in the presence of an alcohol, such as methanol or ethanol, or by enzymatic cleavage, and isolated, for example, by phase separation and subsequent acidification using, for example, $H_2SO_4$. The fatty acids can also be released directly, without the work-up described above.

The term "oil" is to be understood also to include "lipids" or "fats" or "fatty acid mixtures" which comprise unsaturated, saturated, preferably esterified, fatty acid(s), advantageously attached to triglycerides. It is preferred for the oil. The oil may comprise various other saturated or unsaturated fatty acids, such as, for example, palmitic acid, palmitoleic acid, stearic acid, oleic acid, linoleic acid or a-linolenic acid, etc. In particular, depending on the original plant, the content of the various fatty acids in the oil may vary.

"Total oil content" refers to the sum of all oils, lipids, fats or fatty acid mixtures, preferably to the sum of all triacylglycerides.

"Oils" encompasses neutral and/or polar lipids and mixtures of these. Those mentioned in Table II may be mentioned by way of example, but not by limitation.

TABLE II

| Classes of plant lipids | |
| --- | --- |
| Neutral lipids | Triacylglycerol (TAG) |
| | Diacylglycerol (DAG) |
| | Monoacylglycerol (MAG) |
| Polar lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

Neutral lipids preferably refers to triacylglycerides. Both neutral and polar lipids may comprise a wide range of various fatty acids. The fatty acids mentioned in Table 2 may be mentioned by way of example, but not by limitation.

TABLE III

| Overview over various fatty acids (selection) | |
| --- | --- |
| Nomenclature[1] | Name |
| 14:0 | Myristic acid |
| 16:0 | Palmitic acid |
| 16:1 | Palmitoleic acid |
| 16:3 | Roughanic acid |
| 18:0 | Stearic acid |
| 18:1 | Oleic acid |
| 18:2 | Linoleic acid |
| α-18:3 | Linolenic acid |
| γ-18:3 | Gamma-linolenic acid[+] |
| 20:0 | Arachidic acid |
| 20:1 | Eicosgenic acid |
| 22:6 | Docosahexanoic acid (DHA)[*] |
| 20:2 | Eicosadienoic acid |
| 20:4 | Arachidonic acid (AA)[+] |
| 20:5 | Eicosapentaenoic acid (EPA)[+] |
| 22:1 | Erucic acid |

[1]Chain length: number of double bonds
[+]occurring only in very few plant genera
[*]not naturally occurring in plants The term "oil" therefore refers, according to the invention, to one of the above-mentioned triacylglycerides, lipids, fatty acids, fats and/or fatty acid esters as such, or to mixtures of two, three, four, five, six, seven, eight, nine or ten or more of these compounds.

Oils preferably relates to seed oils.

The term "expression" refers to the transcription and/or translation of a codogenic gene segment or gene. As a rule, the resulting product is an mRNA or a protein. However, expression products can also include functional RNAs such as, for example, antisense, nucleic acids, tRNAs, snRNAs, rRNAs, RNAi, siRNA, ribozymes etc. Expression may be systemic, local or temporal, for example limited to certain cell types, tissues organs or organelles or time periods.

In one embodiment, the process of the present invention comprises one or more of the following steps (a) stabilizing a protein conferring the increased expression of a protein encoded by the nucleic acid molecule of the invention or of the polypeptid of the invention having the herein-mentioned activity selected from the group consisting of phosphoribosyl pyrophosphate synthases and conferring an increased yield as compared to a corresponding non-transformed wild type plant cell, plant or part thereof;

(b) stabilizing a mRNA conferring the increased expression of a protein encoded by the nucleic acid molecule of the invention or its homologs or of a mRNA encoding the polypeptide of the present invention having the herein-mentioned activity selected from the group consisting of phosphoribosyl pyrophosphate synthases and confering an increased yield as compared to a corresponding non-transformed wild type plant cell, plant or part thereof;

(c) increasing the specific activity of a protein conferring the increased expression of a protein encoded by the nucleic acid molecule of the invention or of the polypeptide of the present invention or decreasing the inhibitory regulation of the polypeptide of the invention;

(d) generating or increasing the expression of an endogenous or artificial transcription factor mediating the expression of a protein conferring the increased expression of a protein encoded by the nucleic acid molecule of the invention or of the polypeptide of the invention having the herein-mentioned activity selected from the group consisting of phosphoribosyl pyrophosphate synthases and conferring an increased yield as compared to a corresponding non-transformed wild type plant cell, plant or part thereof;

(e) stimulating activity of a protein conferring the increased expression of a protein encoded by the nucleic acid molecule of the present invention or a polypeptide of the present invention having the herein-mentioned activity selected from the group consisting of phosphoribosyl pyrophosphate synthases and conferring an increased yield as compared to a corresponding non-transformed wild type plant cell, plant or part thereof by adding one or more exogenous inducing factors to the organisms or parts thereof;

(f) expressing a transgenic gene encoding a protein conferring the increased expression of a polypeptide encoded by the nucleic acid molecule of the present invention or a polypeptide of the present invention, having the herein-mentioned activity selected from the group consisting of phosphoribosyl pyrophosphate synthases and conferring an increased yield as compared to a corresponding non-transformed wild type plant cell, plant or part thereof; and/or (g) increasing the copy number of a gene conferring the increased expression of a nucleic acid molecule encoding a polypeptide encoded by the nucleic acid molecule of the invention or the polypeptide of the invention having the herein-mentioned activity selected from the group consisting of phosphoribosyl pyrophosphate synthases and conferring an increased yield as compared to a corresponding non-transformed wild type plant cell, plant or part thereof;
(h) increasing the expression of the endogenous gene encoding the polypeptide of the invention or its homologs by adding positive expression or removing negative expression elements, e.g. homologous recombination can be used to either introduce positive regulatory elements like for plants the 35S enhancer into the promoter or to remove repressor elements form regulatory regions. Further gene conversion methods can be used to disrupt repressor elements or to enhance to activity of positive elements-positive elements can be randomly introduced in plants by T-DNA or transposon mutagenesis and lines can be identified in which the positive elements have been integrated near to a gene of the invention, the expression of which is thereby enhanced; and/or
(i) modulating growth conditions of the plant in such a manner, that the expression or activity of the gene encoding the protein of the invention or the protein itself is enhanced;
(j) selecting of organisms with especially high activity of the proteins of the invention from natural or from mutagenized resources and breeding them into the target organisms, e.g. the elite crops.

Preferably, said mRNA is the nucleic acid molecule of the present invention and/or the protein conferring the increased expression of a protein encoded by the nucleic acid molecule of the present invention alone or linked to a transit nucleic acid sequence or transit peptide encoding nucleic acid sequence or the polypeptide having the herein mentioned activity, e.g. conferring an increased yield as compared to a corresponding non-transformed wild type plant cell, plant or part thereof after increasing the expression or activity of the encoded polypeptide or having the activity of a polypeptide having an activity as the protein selected from the group consisting of SEQ ID NOs: 2, 4, 13, 51, 52, 53, 54, 55, 56, 57, 58, 59, 60, 61, 62, 63 or its homologs.

In general, the amount of mRNA or polypeptide in a cell or a compartment of an organism correlates with the amount of encoded protein and thus with the overall activity of the encoded protein in said volume. Said correlation is not always linear, the activity in the volume is dependent on the stability of the molecules or the presence of activating or inhibiting co-factors. Further, product and educt inhibitions of enzymes are well known and described in textbooks, e.g. Stryer, Biochemistry.

In general, the amount of mRNA, polynucleotide or nucleic acid molecule in a cell or a compartment of an organism correlates with the amount of encoded protein and thus with the overall activity of the encoded protein in said volume. Said correlation is not always linear, the activity in the volume is dependent on the stability of the molecules, the degradation of the molecules or the presence of activating or inhibiting co-factors. Further, product and educt inhibitions of enzymes are well known, e.g. Zinser et al. "Enzyminhibitoren"/Enzyme inhibitors".

The activity of the abovementioned proteins and/or polypeptides encoded by the nucleic acid molecule of the present invention can be increased in various ways. For example, the activity in an organism or in a part thereof, like a cell, is increased via increasing the gene product number, e.g. by increasing the expression rate, like introducing a stronger promoter, or by increasing the stability of the mRNA expressed, thus increasing the translation rate, and/or increasing the stability of the gene product, thus reducing the proteins decayed. Further, the activity or turnover of enzymes can be influenced in such a way that a reduction or increase of the reaction rate or a modification (reduction or increase) of the affinity to the substrate results, is reached. A mutation in the catalytic center of an polypeptide of the invention, e.g. as enzyme, can modulate the turn over rate of the enzyme, e.g. a knock out of an essential amino acid can lead to a reduced or completely knock out activity of the enzyme, or the deletion or mutation of regulator binding sites can reduce a negative regulation like a feedback inhibition (or a substrate inhibition, if the substrate level is also increased). The specific activity of an enzyme of the present invention can be increased such that the turn over rate is increased or the binding of a co-factor is improved. Improving the stability of the encoding mRNA or the protein can also increase the activity of a gene product. The stimulation of the activity is also under the scope of the term "increased activity".

Moreover, the regulation of the abovementioned nucleic acid sequences may be modified so that gene expression is increased. This can be achieved advantageously by means of heterologous regulatory sequences or by modifying, for example mutating, the natural regulatory sequences which are present. The advantageous methods may also be combined with each other.

In general, an activity of a gene product in an organism or part thereof, in particular in a plant cell or organelle of a plant cell, a plant, or a plant tissue or a part thereof or in a microorganism can be increased by increasing the amount of the specific encoding mRNA or the corresponding protein in said organism or part thereof. "Amount of protein or mRNA" is understood as meaning the molecule number of polypeptides or mRNA molecules in an organism, especially a plant, a tissue, a cell or a cell compartment. "Increase" in the amount of a protein means the quantitative increase of the molecule number of said protein in an organism, especially a plant, a tissue, a cell or a cell compartment such as an organelle like a plastid or mitochondria or part thereof—for example by one of the methods described herein below—in comparison to a wild type, control or reference.

The increase in molecule number amounts preferably to at least 1%, preferably to more than 10%, more preferably to 30% or more, especially preferably to 50%, 70% or more, very especially preferably to 100%, most preferably to 500% or more. However, a de novo expression is also regarded as subject of the present invention.

A modification, i.e. an increase, can be caused by endogenous or exogenous factors. For example, an increase in activity in an organism or a part thereof can be caused by adding a gene product or a precursor or an activator or an agonist to the media or nutrition or can be caused by introducing said subjects into a organism, transient or stable. Furthermore such an increase can be reached by the introduction of the inventive nucleic acid sequence or the encoded protein in the correct cell compartment for example into the nucleus or cytoplasm respectively or into plastids either by transformation and/or targeting. For the purposes of the description of the present invention, the term "cytoplasmic" shall indicate, that the nucleic acid of the invention is expressed without the addition of an non-natural transit peptide encoding sequence. A non-natural transient peptide encoding sequence is a sequence which is not a natural part of a nucleic acid of the invention but is rather added by molecular manipulation steps as for example described in the example under "plastid targeted expression". Therefore the term "cytoplasmic" shall not exclude a targeted localisation to any cell compartment for the products of the inventive nucleic acid sequences by their naturally occurring sequence properties.

In one embodiment the enhancement of yield as compared to a corresponding non-transformed wild type plant cell in the plant or a part thereof, e.g. in a cell, a tissue, a organ, an organelle, the cytoplasm etc., is achieved by increasing the endogenous level of the polypeptide of the invention. Accordingly, in an embodiment of the present invention, the present invention relates to a process wherein the gene copy number of a gene encoding the polynucleotide or nucleic acid molecule of the invention is increased. Further, the endogenous level of the polypeptide of the invention can for example be increased by modifying the transcriptional or translational regulation of the polypeptide.

In one embodiment the increased yield of the plant or part thereof can be altered by targeted or random mutagenesis of the endogenous genes of the invention. For example homologous recombination can be used to either introduce positive regulatory elements like for plants the 35S enhancer into the promoter or to remove repressor elements form regulatory regions. In addition gene conversion like methods described by Kochevenko and Willmitzer (Plant Physiol. 132 (1), 174 (2003)) and citations therein can be used to disrupt repressor elements or to enhance to activity of positive regulatory elements.

Furthermore positive elements can be randomly introduced in (plant) genomes by T-DNA or transposon mutagenesis and lines can be screened for, in which the positive elements have been integrated near to a gene of the invention, the expression of which is thereby enhanced. The activation of plant genes by random integrations of enhancer elements has been described by Hayashi et al. (Science 258, 1350 (1992)) or Weigel et al. (Plant Physiol. 122, 1003 (2000)) and others cited therein.

Reverse genetic strategies to identify insertions (which eventually carrying the activation elements) near in genes of interest have been described for various cases e.g. Krysan et al. (Plant Cell 11, 2283 (1999)); Sessions et al. (Plant Cell 14, 2985 (2002)); Young et al. (Plant Physiol. 125, 513 (2001)); Koprek et al. (Plant J. 24, 253 (2000)); Jeon et al. (Plant J. 22, 561 (2000)); Tissier et al. (Plant Cell 11, 1841 (1999)); Speulmann et al. (Plant Cell 11, 1853 (1999)). Briefly material from all plants of a large T-DNA or transposon mutagenized plant population is harvested and genomic DNA prepared. Then the genomic DNA is pooled following specific architectures as described for example in Krysan et al. (Plant Cell 11, 2283 (1999)). Pools of genomics DNAs are then screened by specific multiplex PCR reactions detecting the combination of the insertional mutagen (eg T-DNA or Transposon) and the gene of interest. Therefore PCR reactions are run on the DNA pools with specific combinations of T-DNA or transposon border primers and gene specific primers. General rules for primer design can again be taken from Krysan et al. (Plant Cell 11, 2283 (1999)). Rescreening of lower levels DNA pools lead to the identification of individual plants in which the gene of interest is activated by the insertional mutagen.

The enhancement of positive regulatory elements or the disruption or weakening of negative regulatory elements can also be achieved through common mutagenesis techniques: The production of chemically or radiation mutated populations is a common technique and known to the skilled worker. Methods for plants are described by Koorneef et al. (Mutat Res. Mar. 93 (1) (1982)) and the citations therein and by Lightner and Caspar in "Methods in Molecular Biology" Vol. 82. These techniques usually induce pointmutations that can be identified in any known gene using methods such as TILLING (Colbert et al., Plant Physiol, 126, (2001)).

Accordingly, the expression level can be increased if the endogenous genes encoding a polypeptide conferring an increased expression of the polypeptide of the present invention, in particular genes comprising the nucleic acid molecule of the present invention, are modified via homologous recombination, Tilling approaches or gene conversion. It also possible to add as mentioned herein targeting sequences to the inventive nucleic acid sequences.

Regulatory sequences, if desired, in addition to a target sequence or part thereof can be operatively linked to the coding region of an endogenous protein and control its transcription and translation or the stability or decay of the encoding mRNA or the expressed protein. In order to modify and control the expression, promoter, UTRs, splicing sites, processing signals, polyadenylation sites, terminators, enhancers, repressors, post transcriptional or posttranslational modification sites can be changed, added or amended. For example, the activation of plant genes by random integrations of enhancer elements has been described by Hayashi et al. (Science 258, 1350 (1992)) or Weigel et al. (Plant Physiol. 122, 1003 (2000)) and others cited therein. For example, the expression level of the endogenous protein can be modulated by replacing the endogenous promoter with a stronger transgenic promoter or by replacing the endogenous 3'UTR with a 3'UTR, which provides more stability without amending the coding region. Further, the transcriptional regulation can be modulated by introduction of an artificial transcription factor as described in the examples. Alternative promoters, terminators and UTR are described below.

The activation of an endogenous polypeptide having above-mentioned activity, e.g. having the activity of a protein as shown in table II, column 3 or of the polypeptide of the invention, e.g. conferring the increased yield as compared to a corresponding non-transformed wild type plant cell, plant or part thereof after increase of expression or activity in the cytoplasm and/or in an organelle like a plastid, can also be increased by introducing a synthetic transcription factor, which binds close to the coding region of the gene encoding the protein as shown in table II, column 3 and activates its transcription. A chimeric zinc finger protein can be constructed, which comprises a specific DNA-binding domain and an activation domain as e.g. the VP16 domain of Herpes Simplex virus. The specific binding domain can bind to the regulatory region of the gene encoding the protein as shown in table II, column 3. The expression of the chimeric transcription factor in a organism, in particular in a plant, leads to a specific expression of the protein as shown in table II, column 3. The methods thereto a known to a skilled person and/or disclosed e.g. in WO01/52620, Oriz, Proc. Natl. Acad. Sci. USA, 99, 13290 (2002) or Guan, Proc. Natl. Acad. Sci. USA 99, 13296 (2002).

In one further embodiment of the process according to the invention, organisms are used in which one of the abovementioned genes, or one of the above-mentioned nucleic acids, is mutated in a way that the activity of the encoded gene products is less influenced by cellular factors, or not at all, in comparison with the unmutated proteins. For example, well known regulation mechanism of enzymic activity are substrate inhibition or feed back regulation mechanisms. Ways and techniques for the introduction of substitution, deletions and additions of one or more bases, nucleotides or amino acids of a corresponding sequence are described herein below in the corresponding paragraphs and the references listed there, e.g. in Sambrook et al., Molecular Cloning, Cold Spring Habour, N.Y., 1989. The person skilled in the art will be able to identify regulation domains and binding sites of regulators by comparing the sequence of the nucleic acid molecule of the present invention or the expression product thereof with the state of the art by computer software means which comprise algorithms for the identifying of binding sites and regulation domains or by introducing into a nucleic acid molecule or in a protein systematically mutations and assaying for those mutations which will lead to an increased specific activity or an increased activity per volume, in particular per cell.

It can therefore be advantageous to express in an organism a nucleic acid molecule of the invention or a polypeptide of the invention derived from a evolutionary distantly related organism, as e.g. using a prokaryotic gene in a eukaryotic host, as in these cases the regulation mechanism of the host cell may not weaken the activity (cellular or specific) of the gene or its expression product.

The mutation is introduced in such a way that the yield increase are not adversely affected.

Less influence on the regulation of a gene or its gene product is understood as meaning a reduced regulation of the enzymatic activity leading to an increased specific or cellular activity of the gene or its product. An increase of the enzymatic activity is understood as meaning an enzymatic activity, which is increased by at least 10%, advantageously at least 20, 30 or 40%, especially advantageously by at least 50, 60 or 70% in comparison with the starting organism. This leads to an increased yield as compared to a corresponding non-transformed wild type plant cell, plant or part thereof.

The invention provides that the above methods can be performed such that the yield is increased.

The invention is not limited to specific nucleic acids, specific polypeptides, specific cell types, specific host cells, specific conditions or specific methods etc. as such, but may vary and numerous modifications and variations therein will be apparent to those skilled in the art. It is also to be understood that the terminology used herein is for the purpose of describing specific embodiments only and is not intended to be limiting.

The present invention also relates to isolated nucleic acids comprising a nucleic acid molecule selected from the group consisting of:

(a) a nucleic acid molecule encoding the polypeptide selected from the group consisting of SEQ ID NOs: 2, 4, 13, 51, 52, 53, 54, 55, 56, 57, 58, 59, 60, 61, 62, 63;

(b) a nucleic acid molecule selected from the group consisting of SEQ ID NOs: 1, 3, 12, 38, 39, 40, 41, 42, 43, 44, 45, 46, 47, 48, 49, 50;

(c) a nucleic acid molecule, which, as a result of the degeneracy of the genetic code, can be derived from a polypeptide sequence selected from the group consisting of SEQ ID NOs: 2, 4, 13, 51, 52, 53, 54, 55, 56, 57, 58, 59, 60, 61, 62, 63, and confers an increased yield as compared to a corresponding non-transformed wild type plant cell, a plant or a part thereof;

(d) a nucleic acid molecule having at least 30% identity, preferably at least 40%, 50%, 60%, 70%, 75%, 80%, 85%, 90%, 95%, 96%, 97%, 98%, 99%, 99.5%, with the nucleic acid molecule sequence of a polynucleotide comprising the nucleic acid molecule selected from the group consisting of SEQ ID NOs: 1, 3, 12, 38, 39, 40, 41, 42, 43, 44, 45, 46, 47, 48, 49, 50, and confers an increased yield as compared to a corresponding non-transformed wild type plant cell, a plant or a part thereof;

(e) a nucleic acid molecule encoding a polypeptide having at least 30% identity, preferably at least 40%, 50%, 60%, 70%, 75%, 80%, 85%, 90%, 95%, 96%, 97%, 98%, 99%, 99.5%, with the amino acid sequence of the polypeptide encoded by the nucleic acid molecule of (a), (b), (c) or (d) and having the activity represented by a nucleic acid molecule comprising a polynucleotide selected from the group consisting of SEQ ID NOs: 1, 3, 12, 38, 39, 40, 41, 42, 43, 44, 45, 46, 47, 48, 49, 50, and confers an increased yield as compared to a corresponding non-transformed wild type plant cell, a plant or a part thereof;

(f) nucleic acid molecule which hybridizes with a nucleic acid molecule of (a), (b), (c), (d) or (e) under stringent hybridization conditions and confers an increased yield as compared to a corresponding non-transformed wild type plant cell, a plant or a part thereof;

(g) a nucleic acid molecule encoding a polypeptide which can be isolated with the aid of monoclonal or polyclonal antibodies made against a polypeptide encoded by one of the nucleic acid molecules of (a), (b), (c), (d), (e) or (f) and having the activity represented by the nucleic acid molecule comprising a polynucleotide selected from the group consisting of SEQ ID NOs: 1, 3, 12, 38, 39, 40, 41, 42, 43, 44, 45, 46, 47, 48, 49, 50;

(h) a nucleic acid molecule encoding a polypeptide comprising the polypeptide motif of the ADP selected from the group consisting of SEQ ID NOs: 7, 8, 9, 10, 11, 14, 15, 16, 17, 18, or a polypeptide comprising a polypeptide according to the motif selected from the group consisting of SEQ ID No. 64, 65, 66, 67, 68, 69, 70, 71, 72, 73 and preferably having the activity represented by a nucleic acid molecule comprising a polynucleotide selected from the group consisting of SEQ ID NOs: 1, 3, 12, 38, 39, 40, 41, 42, 43, 44, 45, 46, 47, 48, 49, 50;

(i) a nucleic acid molecule encoding a polypeptide having the activity represented by a protein selected from the group consisting of SEQ ID NOs: 2, 4, 13, 51, 52, 53, 54, 55, 56, 57, 58, 59, 60, 61, 62, 63, and confers an increased yield as compared to a corresponding non-transformed wild type plant cell, a plant or a part thereof;

(j) nucleic acid molecule which comprises a polynucleotide, which is obtained by amplifying a cDNA library or a genomic library using the primers selected from the group consisting of SEQ ID NOs: 5, 6, which do not start at their 5'-end with the nucleotides ATA and preferably having the activity represented by a nucleic acid molecule comprising a polynucleotide selected from the group consisting of SEQ ID NOs: 1, 3, 12, 38, 39, 40, 41, 42, 43, 44, 45, 46, 47, 48, 49, 50; and (k) a nucleic acid molecule which is obtainable by screening a suitable nucleic acid library, especially a cDNA library and/or a genomic library, under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt, 500 nt, 750 nt or 1000 nt of a nucleic acid molecule complementary to a nucleic acid molecule sequence characterized in (a) to (e) and encoding a polypeptide having the activity represented by a protein comprising a polypeptide selected from the group consisting of SEQ ID NOs: 2, 4, 13, 51, 52, 53, 54, 55, 56, 57, 58, 59, 60, 61, 62, 63;

whereby the nucleic acid molecule according to (a), (b), (c), (d), (e), (f), (g), (h), (i), (j) and (k) is at least in one or more nucleotides different from the sequence selected from the group consisting of SEQ ID NOs: 1, 3, 12, 38, 39, 40, 41, 42, 43, 44, 45, 46, 47, 48, 49, 50, and preferably which encodes a protein which differs at least in one or more amino acids from the protein sequences selected from the group consisting of SEQ ID NOs: 2, 4, 13, 51, 52, 53, 54, 55, 56, 57, 58, 59, 60, 61, 62, 63.

In one embodiment the invention relates to homologs of the aforementioned sequences, which can be isolated advantageously from yeast, fungi, viruses, algae, bacteria, such as *Acetobacter* (subgen. *Acetobacter*) aceti; *Acidithiobacillus* ferrooxidans; Acinetobacter sp.; Actinobacillus sp; Aeromonas salmonicida; Agrobacterium tumefaciens; Aquifex aeolicus; Arcanobacterium pyogenes; Aster yellows phytoplasma; Bacillus sp.; Bifidobacterium sp.; Borrelia burgdorferi; Brevibacterium linens; Brucella melitensis; Buchnera sp.; Butyrivibrio fibrisolvens; Campylobacter jejuni; Caulobacter crescentus; Chlamydia sp.; Chlamydophila sp.; Chlorobium limicola; Citrobacter rodentium; Clostridium sp.; Comamonas testosteroni; Corynebacterium sp.; Coxiella burnetii; Deinococcus radiodurans; Dichelobacter nodosus; Edwardsiella ictaluri; Enterobacter sp.; Erysipelothrix rhusiopathiae; Escherichia coli; Flavobacterium sp.; Francisella tularensis; Frankia sp. Cpl1; Fusobacterium nucleatum; Geobacillus stearothermophilus; Gluconobacter oxydans; Haemophilus sp.; Helicobacter pylori; Klebsiella pneumoniae; Lactobacillus sp.; Lactococcus lactis; Listeria sp.; Mannheimia haemolytica; Mesorhizobium loti; Methylophaga thalassica; Microcystis aeruginosa; Microscilla sp. PREL; Moraxella sp. TA144; Mycobacterium sp.; Mycoplasma sp.; Neisseria sp.; Nitrosomonas sp.; Nostoc sp. PCC 7120; Novosphingobium aromaticivorans; Oenococcus oeni; Pantoea citrea; Pasteurella multocida; Pediococcus pentosaceus; Phormidium foveolarum; Phytoplasma sp.; Plectonema boryanum; Prevotella ruminicola; Propionibacterium sp.; Proteus vulgaris; Pseudomonas sp.; Ralstonia sp.; Rhizobium sp.; Rhodococcus equi; Rhodothermus marinus; Rickettsia sp.; Riemerella anatipestifer; Ruminococcus flavefaciens; Salmonella sp.; Selenomonas ruminantium; Serratia entomophila; Shigella sp.; Sinorhizobium meliloti; Staphylococcus sp.; Streptococcus sp.; Streptomyces sp.; Synechococcus sp.; Synechocystis sp. PCC 6803; Thermotoga maritima; Treponema sp.; Ureaplasma urealyticum; Vibrio cholerae; Vibrio parahaemolyticus; Xylella fastidiosa; Yersinia sp.; Zymomonas mobilis, preferably Salmonella sp. or Escherichia coli or plants, preferably from yeasts such as from the genera Saccharomyces, Pichia, Candida, Hansenula, Torulopsis or Schizosaccharomyces or plants such as Arabidopsis thaliana, maize, wheat, rye, oat, triticale, rice, barley, soybean, peanut, cotton, borage, sunflower, linseed, primrose, rapeseed, canola and turnip rape, manihot, pepper, sunflower, tagetes, solanaceous plant such as potato, tobacco, eggplant and tomato, Vicia species, pea, alfalfa, bushy plants such as coffee, cacao, tea, Salix species, trees such as oil palm, coconut, perennial grass, such as ryegrass and fescue, and forage crops, such as alfalfa and clover and from spruce, pine or fir for example. More preferably homologs of aforementioned sequences can be isolated from Saccharomyces cerevisiae, E. coli or Synechocystis sp. or plants, preferably Brassica napus, Glycine max, Zea mays, cotton or Oryza sativa.

The proteins of the present invention are preferably produced by recombinant DNA techniques. For example, a nucleic acid molecule encoding the protein is cloned into an expression vector, for example in to a binary vector, the expression vector is introduced into a host cell, for example the Arabidopsis thaliana wild type NASC N906 or any other plant cell as described in the examples see below, and the protein is expressed in said host cell. Examples for binary vectors are pBIN19, pBI101, pBinAR, pGPTV, pCAMBIA, pBIB-HYG, pBecks, pGreen or pPZP (Hajukiewicz, P. et al., Plant Mol. Biol. 25, 989 (1994), and Hellens et al, Trends in Plant Science 5, 446 (2000)).

In one embodiment the protein of the present invention is preferably produced in a compartment of the cell, more preferably in the plastids. Ways of introducing nucleic acids into plastids and producing proteins in this compartment are known to the person skilled in the art have been also described in this application.

In another embodiment the protein of the present invention is preferably produced in the cytoplasm of the cell. Ways of producing proteins in the cytoplasm are known to the person skilled in the art.

Advantageously, the nucleic acid sequences according to the invention or the gene construct together with at least one reporter gene are cloned into an expression cassette, which is introduced into the organism via a vector or directly into the genome. This reporter gene should allow easy detection via a growth, fluorescence, chemical, bioluminescence or tolerance assay or via a photometric measurement. Examples of reporter genes which may be mentioned are antibiotic- or herbicidetolerance genes, hydrolase genes, fluorescence protein genes, bioluminescence genes, sugar or nucleotide metabolic genes or biosynthesis genes such as the Ura3 gene, the Ilv2 gene, the luciferase gene, the β-galactosidase gene, the gfp gene, the 2-desoxyglucose-6-phosphate phosphatase gene, the β-glucuronidase gene, β-lactamase gene, the neomycin phosphotransferase gene, the hygromycin phosphotransferase gene, a mutated acetohydroxyacid synthase (AHAS) gene (also known as acetolactate synthase (ALS) gene), a gene for a D-amino acid metabolizing enzyme or the BASTA (=gluphosinate-tolerance) gene. These genes permit easy measurement and quantification of the transcription activity and hence of the expression of the genes. In this way genome positions may be identified which exhibit differing productivity.

In a preferred embodiment a nucleic acid construct, for example an expression cassette, comprises upstream, i.e. at the 5' end of the encoding sequence, a promoter and downstream, i.e. at the 3' end, a polyadenylation signal and optionally other regulatory elements which are operably linked to the intervening encoding sequence selected from the group consisting of SEQ ID NOs: 1, 3, 12, 38, 39, 40, 41, 42, 43, 44, 45, 46, 47, 48, 49, 50. By an operable linkage is meant the sequential arrangement of promoter, encoding sequence, terminator and optionally other regulatory elements in such a way that each of the regulatory elements can fulfill its function in the expression of the encoding sequence in due manner. In one embodiment the sequences preferred for operable linkage are targeting sequences for ensuring subcellular localization in plastids. However, targeting sequences for ensuring subcellular localization in the mitochondrium, in the endoplasmic reticulum (=ER), in the nucleus, in oil corpuscles or other compartments may also be employed as well as translation promoters such as the 5' lead sequence in tobacco mosaic virus (Gallie et al., Nucl. Acids Res. 15 8693 (1987)).

A nucleic acid construct, for example an expression cassette may, for example, contain a constitutive promoter or a tissue-specific promoter (preferably the USP or napin promoter) the gene to be expressed and the ER retention signal. For the ER retention signal the KDEL amino acid sequence (lysine, aspartic acid, glutamic acid, leucine) or the KKX amino acid sequence (lysine-lysine-X-stop, wherein X means every other known amino acid) is preferably employed.

For expression in a host organism, for example a plant, the expression cassette is advantageously inserted into a vector such as by way of example a plasmid, a phage or other DNA which allows optimal expression of the genes in the host organism. Examples of suitable plasmids are: in E. coli pLG338, pACYC184, pBR series such as e.g. pBR322, pUC series such as pUC18 or pUC19, M113 mp series, pKC30, pRep4, pHS1, pHS2, pPLc236, pMBL24, pLG200, pUR290, pIN-III$^{113}$-B1, λgt11 or pBdCl; in Streptomyces plJ101, plJ364, plJ702 or plJ361; in Bacillus pUB110, pC194 or pBD214; in Corynebacterium pSA77 or pAJ667; in fungi pALS1, plL2 or pBB116; other advantageous fungal vectors are described by Romanos M. A. et al., Yeast 8, 423 (1992) and by van den Hondel, C. A. M. J. J. et al. [(1991) "Heterologous gene expression in filamentous fungi"] as well as in "More Gene Manipulations" in "Fungi" in Bennet J. W. & Lasure L. L., eds., pp. 396-428, Academic Press, San Diego, and in "Gene transfer systems and vector development for filamentous fungi" [van den Hondel, C. A. M. J. J. & Punt, P. J. (1991) in: Applied Molecular Genetics of Fungi, Peberdy, J. F. et al., eds., pp. 1-28, Cambridge University Press: Cambridge]. Examples of advantageous yeast promoters are 2 µM, pAG-1, YEp6, YEp13 or pEMBLYe23. Examples of algal or plant promoters are pLGV23, pGHlac$^+$, pBIN19, pAK2004, pVKH or pDH51 (see Schmidt, R. and Willmitzer, L., Plant Cell Rep. 7, 583 (1988))). The vectors identified above or derivatives of the vectors identified above are a small selection of the possible plasmids. Further plasmids are well known to those skilled in the art and may be found, for example, in "Cloning Vectors" (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press, Ch. 6/7, pp. 71-119). Advantageous vectors are known as shuttle vectors or binary vectors which replicate in *E. coli* and *Agrobacterium*.

By vectors is meant with the exception of plasmids all other vectors known to those skilled in the art such as by way of example phages, viruses such as SV40, CMV, baculovirus, adenovirus, transposons, IS elements, phasmids, phagemids, cosmids, linear or circular DNA. These vectors can be replicated autonomously in the host organism or be chromosomally replicated, chromosomal replication being preferred.

In a further embodiment of the vector the expression cassette according to the invention may also advantageously be introduced into the organisms in the form of a linear DNA and be integrated into the genome of the host organism by way of heterologous or homologous recombination. This linear DNA may be composed of a linearized plasmid or only of the expression cassette as vector or the nucleic acid sequences according to the invention.

In a further advantageous embodiment the nucleic acid sequence according to the invention can also be introduced into an organism on its own.

If in addition to the nucleic acid sequence according to the invention further genes are to be introduced into the organism, all together with a reporter gene in a single vector or each single gene with a reporter gene in a vector in each case can be introduced into the organism, whereby the different vectors can be introduced simultaneously or successively.

The vector advantageously contains at least one copy of the nucleic acid sequences according to the invention and/or the expression cassette (=gene construct) according to the invention.

The invention further provides an isolated recombinant expression vector comprising a nucleic acid encoding a polypeptide selected from the group consisting of SEQ ID NOs: 2, 4, 13, 51, 52, 53, 54, 55, 56, 57, 58, 59, 60, 61, 62, 63, wherein expression of the vector in a host cell results in enhanced yield as compared to a wild type variety of the host cell.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) are integrated into the genome of a host cell or a organelle upon introduction into the host cell, and thereby are replicated along with the host or organelle genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g. in an in vitro transcription/translation system or in a host cell when the vector is introduced into the host cell). The term "regulatory sequence" is intended to include promoters, enhancers, and other expression control elements (e.g. polyadenylation signals). Such regulatory sequences are described, for example, in Goeddel, Gene Expression Technology: Methods in Enzymology 185, Academic Press, San Diego, Calif. (1990), and Gruber and Crosby, in: Methods in Plant Molecular Biology and Biotechnology, eds. Glick and Thompson, Chapter 7, 89-108, CRC Press; Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., coding for phosphoribosyl pyrophosphate synthases).

The recombinant expression vectors of the invention can be designed for expression of the polypeptide of the invention in plant cells. For example, PRS genes can be expressed in plant cells (see Schmidt R., and Willmitzer L., Plant Cell Rep. 7 (1988); Plant Molecular Biology and Biotechnology, C Press, Boca Raton, Fla., Chapter 6/7, p. 71-119 (1993); White F. F., Jenes B. et al., Techniques for Gene Transfer, in: Transgenic Plants, Vol. 1, Engineering and Utilization, eds. Kung und Wu R., 128-43, Academic Press: 1993; Potrykus, Annu. Rev. Plant Physiol. Plant Molec. Biol. 42, 205 (1991) and references cited therein). Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

By way of example the plant expression cassette can be installed in the pRT transformation vector ((a) Toepfer et al., Methods Enzymol. 217, 66 (1993), (b) Toepfer et al., Nucl. Acids. Res. 15, 5890 (1987)).

Alternatively, a recombinant vector (=expression vector) can also be transcribed and translated in vitro, e.g. by using the T7 promoter and the T7 RNA polymerase.

Expression vectors employed in prokaryotes frequently make use of inducible systems with and without fusion proteins or fusion oligopeptides, wherein these fusions can ensue in both N-terminal and C-terminal manner or in other useful domains of a protein. Such fusion vectors usually have the following purposes: 1) to increase the RNA expression rate; 2) to increase the achievable protein synthesis rate; 3) to increase the solubility of the protein; 4) or to simplify purification by means of a binding sequence usable for affinity chromatography. Proteolytic cleavage points are also frequently introduced via fusion proteins, which allow cleavage of a portion of the fusion protein and purification. Such recognition sequences for proteases are recognized, e.g. factor Xa, thrombin and enterokinase.

Typical advantageous fusion and expression vectors are pGEX (Pharmacia Biotech Inc; Smith D. B. and Johnson K. S., Gene 67, 31 (1988)), pMAL (New England Biolabs, Beverly, Mass.) and pRIT5 (Pharmacia, Piscataway, N.J.) which contains glutathione S-transferase (GST), maltose binding protein or protein A.

In one embodiment, the coding sequence of the polypeptide of the invention is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant PK PRS unfused to GST can be recovered by cleavage of the fusion polypeptide with thrombin.

Other examples of E. coli expression vectors are pTrc (Amann et al., Gene 69, 301 (1988)) and pET vectors (Studier et al., Gene Expression Technology: Methods in Enzymology 185, Academic Press, San Diego, Calif. (1990) 60-89; Stratagene, Amsterdam, The Netherlands).

Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident I prophage harboring a T7 gn1 gene under the transcriptional control of the lacUV 5 promoter.

In a preferred embodiment of the present invention, the PRSs are expressed in plants and plants cells such as unicellular plant cells (e.g. algae) (see Falciatore et al., Marine Biotechnology 1 (3), 239 (1999) and references therein) and plant cells from higher plants (e.g., the spermatophytes, such as crop plants). A nucleic acid molecule coding for PRS selected from the group consisting of SEQ ID NOs: 1, 3, 12, 38, 39, 40, 41, 42, 43, 44, 45, 46, 47, 48, 49, 50 may be "introduced" into a plant cell by any means, including transfection, transformation or transduction, electroporation, particle bombardment, agroinfection, and the like. One transformation method known to those of skill in the art is the dipping of a flowering plant into an Agrobacteria solution, wherein the Agrobacteria contains the nucleic acid of the invention, followed by breeding of the transformed gametes.

Other suitable methods for transforming or transfecting host cells including plant cells can be found in Sambrook et al., Molecular Cloning: A Laboratory Manual. $2^{nd}$, ed., Cold Spring Harbor Laboratory, Cold Spring Harbor Laboratory Press, Cold Spring Harbor, N.Y., 1989, and other laboratory manuals such as Methods in Molecular Biology, 1995, Vol. 44, Agrobacterium protocols, ed: Gartland and Davey, Humana Press, Totowa, N.J. As increased yield is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. Forage crops include, but are not limited to Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover.

In one embodiment of the present invention, transfection of a nucleic acid molecule coding for PRS selected from the group consisting of SEQ ID NOs: 2, 4, 13, 51, 52, 53, 54, 55, 56, 57, 58, 59, 60, 61, 62, 63 into a plant is achieved by Agrobacterium mediated gene transfer. Agrobacterium mediated plant transformation can be performed using for example the GV3101 (pMP90) (Koncz and Schell, Mol. Gen. Genet. 204, 383 (1986)) or LBA4404 (Clontech) Agrobacterium tumefaciens strain. Transformation can be performed by standard transformation and regeneration techniques (Deblaere et al., Nucl. Acids Res. 13, 4777 (1994), Gelvin, Stanton B. and Schilperoort Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-2731-4; Glick Bernard R., Thompson John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., Plant Cell Report 8, 238 (1989); De Block et al., Plant Physiol. 91, 694 (1989)). Use of antibiotics for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., Plant Cell Report 13, 282 (1994). Additionally, transformation of soybean can be performed using for example a technique described in European Patent No. 424 047, U.S. Pat. No.

5,322,783, European Patent No. 397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

In one embodiment of the invention the nucleic acid sequences used are advantageously introduced into a transgenic expression construct which can ensure a transgenic expression of a phosphoribosyl pyrophospate synthase from Ashbya gossypii, in a plant organism or a tissue, organ, part, cell or propagation material of said plant organism.

In the expression constructs, a nucleic acid molecule encoding a phosphoribosyl pyrophosphate synthase is preferably in operable linkage with at least one genetic control element (for example a promoter and/or terminator) which ensures expression in a plant organism or a tissue, organ, part, cell or propagation material of same.

Operable linkage is understood as meaning, for example, the sequential arrangement of a promoter with the nucleic acid sequence encoding a phosphoribosyl pyrophosphate synthase which is to be expressed (for example the sequence as shown in SEQ ID NO: 1) and, if appropriate, further regulatory elements such as, for example, a terminator in such a way that each of the regulatory elements can fulfil its function when the nucleic acid sequence is expressed recombinantly. Direct linkage in the chemical sense is not necessarily required for this purpose. Genetic control sequences such as, for example, enhancer sequences can also exert their function on the target sequence from positions which are further removed or indeed from other DNA molecules. Preferred arrangements are those in which the nucleic acid sequence to be expressed recombinantly is positioned behind the sequence acting as promoter so that the two sequences are linked covalently to each other. The distance between the promoter sequence and the nucleic acid sequence to be expressed recombinantly is preferably less than 200 base pairs, particularly preferably less than 100 base pairs, very particularly preferably less than 50 base pairs.

Operable linkage and an expression cassette can both be effected by means of conventional recombination and cloning techniques as they are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L und Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or of a signal peptide, may also be positioned between the two sequences. Also, the insertion of sequences may lead to the expression of fusion proteins. Preferably, the expression cassette composed of a promoter linked to a nucleic acid sequence to be expressed can be in a vector-integrated form and can be inserted into a plant genome, for example by transformation.

However, an expression cassette is also understood as meaning those constructs where the nucleic acid sequence encoding a phosphoribosyl pyrophosphate synthase from Ashbya gossypii is placed behind an endogenous promoter in such a way that the latter brings about the expression of the phosphoribosyl pyrophosphate synthase from Ashbya gossypii.

Promoters which are preferably introduced into the transgenic expression cassettes are those which are operable in a plant organism or a tissue, organ, part, cell or propagation material of same. Promoters which are operable in plant organisms is understood as meaning any promoter which is capable of governing the expression of genes, in particular foreign genes, in plants or plant parts, plant cells, plant tissues or plant cultures. In this context, expression may be, for example, constitutive, inducible or development-dependent.

The following are preferred:
a) Constitutive Promoters

"Constitutive" promoters refers to those promoters which ensure expression in a large number of, preferably all, tissues over a substantial period of plant development, preferably at all times during plant development (Benfey et al. (1989) EMBO J. 8:2195-2202). A plant promoter or promoter originating from a plant virus is especially preferably used. The promoter of the CaMV (cauliflower mosaic virus) 35S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J 8:2195-2202) are especially preferred. Another suitable constitutive promoter is the Rubisco small subunit (SSU) promoter (U.S. Pat. No. 4,962,028), the leguminB promoter (GenBank Acc. No. X03677), the promoter of the nopalin synthase from Agrobacterium, the TR dual promoter, the OCS (octopine synthase) promoter from Agrobacterium, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits, the promoter of the Arabidopsis thaliana nitrilase-1 gene (GenBank Acc. No.: U38846, nucleotides 3862 to 5325 or else 5342) or the promoter of a proline-rich protein from wheat (WO 91/13991), and further promoters of genes whose constitutive expression in plants is known to the skilled worker. The CaMV 35S promoter and the Arabidopsis thaliana nitrilase-1 promoter are preferred.

In one embodiment the GOS-2 promoter is used.
b) Tissue-Specific Promoters

Furthermore preferred are promoters with specificities for seeds, such as, for example, the phaseolin promoter (U.S. Pat. No. 5,504,200; Bustos M M et al. (1989) Plant Cell 1 (9):839-53), the promoter of the 2S albumin gene (Joseffson L G et al. (1987) J Biol Chem 262:12196-12201), the legumine promoter (Shirsat A et al. (1989) Mol Gen Genet. 215(2):326-331), the USP (unknown seed protein) promoter (Bäumlein H et al. (1991) Mol Gen Genet 225(3):459-67), the napin gene promoter (U.S. Pat. No. 5,608,152; Stalberg K et al. (1996) L Planta 199:515-519), the promoter of the sucrose binding proteins (WO 00/26388) or the legumin B4 promoter (LeB4; Baumlein H et al. (1991) Mol Gen Genet 225: 121-128; Baumlein et al. (1992) Plant Journal 2(2):233-9; Fiedler U et al. (1995) Biotechnology (NY) 13(10):1090f), the Arabidopsis oleosin promoter (WO 98/45461), and the Brassica Bce4 promoter (WO 91/13980).

Further suitable seed-specific promoters are those of the gene encoding high-molecular weight glutenin (HMWG), gliadin, branching enyzme, ADP glucose pyrophosphatase (AGPase) or starch synthase. Promoters which are furthermore preferred are those which permit a seed-specific expression in monocots such as maize, barley, wheat, rye, rice and the like. The promoter of the lpt2 or lpt1 gene (WO 95/15389, WO 95/23230) or the promoters described in WO 99/16890 (promoters of the hordein gene, the glutelin gene, the oryzin gene, the prolamin gene, the gliadin gene, the glutelin gene, the zein gene, the casirin gene or the secalin gene) can advantageously be employed.

c) Chemically Inducible Promoters

The expression cassettes may also contain a chemically inducible promoter (review article: Gatz et al. (1997) Annu Rev Plant Physiol Plant Mol Biol 48:89-108), by means of which the expression of the exogenous gene in the plant can be controlled at a particular point in time. Such promoters such as, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracyclin-inducible promoter (Gatz et al. (1992) Plant J 2:397-404), an abscisic acid-inducible promoter (EP 0 335 528) or an ethanol-cyclohexanone-inducible promoter (WO 93/21334) can likewise be used. Also suitable is the promoter of the glutathione-S transferase isoform II gene (GST-II-27), which can be activated by exogenously applied safeners such as, for example, N,N-diallyl-2,2-dichloroacetamide (WO 93/01294) and which is operable in a large number of tissues of both monocots and dicots.

Particularly preferred are constitutive promoters, very particularly preferred seed-specific promoters, in particular the napin promoter and the USP promoter.

In addition, further promoters which make possible expression in further plant tissues or in other organisms such as, for example, E. coli bacteria, may be linked operably with the nucleic acid sequence to be expressed. Suitable plant promoters are, in principle, all of the above-described promoters.

The nucleic acid sequences present in the expression cassettes or vectors can be linked operably with further genetic control sequences besides a promoter. The term genetic control sequences is to be understood in the broad sense and refers to all those sequences which have an effect on the establishment or the function of the expression cassette according to the invention. Genetic control sequences modify, for example, transcription and translation in prokaryotic or eukaryotic organisms. The expression cassettes according to the invention preferably encompass a plant-specific promoter 5'-upstream of the nucleic acid sequence to be expressed recombinantly in each case and, as additional genetic control sequence, a terminator sequence 3'-downstream, and, if appropriate, further customary regulatory elements, in each case linked operably with the nucleic acid sequence to be expressed recombinantly.

Genetic control sequences also encompass further promoters, promoter elements or minimal promoters capable of modifying the expression-controlling properties. Thus, genetic control sequences can, for example, bring about tissue-specific expression which is additionally dependent on certain stress factors. Such elements are, for example, described for water stress, abscisic acid (Lam E and Chua N H, J Biol Chem 1991; 266(26): 17131-17135) and thermal stress (Schoffl F et al. (1989) Mol Gen Genetics 217(2-3): 246-53).

Further advantageous control sequences are, for example, in the Gram-positive promoters amy and SPO2, and in the yeast or fungal promotors ADC1, MFa, AC, P-60, CYC1, GAPDH, TEF, rp28, ADH.

In principle all natural promoters with their regulatory sequences like those mentioned above may be used for the method according to the invention. In addition, synthetic promoters may also be used advantageously.

Genetic control sequences further also encompass the 5'-untranslated regions, introns or nonencoding 3'-region of genes, such as, for example, the actin-1 intron, or the Adh1-S intron 1, 2 and 6 (for general reference, see: The Maize Handbook, Chapter 116, Freeling and Walbot, Eds., Springer, New York (1994)). It has been demonstrated that these may play a significant role in regulating gene expression. Thus, it has been demonstrated that 5'-untranslated sequences can enhance the transient expression of heterologous genes. Translation enhancers which may be mentioned by way of example are the tobacco mosaic virus 5' leader sequence (Gallie et al. (1987) Nucl Acids Res 15:8693-8711) and the like. They may furthermore promote tissue specificity (Rouster J et al. (1998) Plant J 15:435-440).

The expression cassette can advantageously contain one or more of what are known as enhancer sequences in operable linkage with the promoter, and these make possible an increased recombinant expression of the nucleic acid sequence. Additional advantageous sequences such as further regulatory elements or terminators may also be inserted at the 3' end of the nucleic acid sequences to be expressed recombinantly. One or more copies of the nucleic acid sequences to be expressed recombinantly may be present in the gene construct.

Polyadenylation signals which are suitable as control sequences are plant polyadenylation signals, preferably those which correspond essentially to Agrobacterium tumefaciens T-DNA polyadenylation signals, in particular those of gene 3 of the T-DNA (octopine synthase) of the Ti plasmid pTiACHS (Gielen et al. (1984) EMBO J 3:835 et seq.) or functional equivalents thereof. Examples of particularly suitable terminator sequences are the OCS (octopin synthase) terminator and the NOS (nopaline synthase) terminator.

Control sequences are furthermore understood as those which make possible homologous recombination or insertion into the genome of a host organism, or removal from the genome. In the case of homologous recombination, for example, the coding sequence of the specific endogenous gene can be exchanged in a directed fashion for a sequence encoding a dsRNA. Methods such as the cre/lox technology permit the tissue-specific, possibly inducible, removal of the expression cassette from the genome of the host organism (Sauer B (1998) Methods. 14(4):381-92). Here, certain flanking sequences are added to the target gene (lox sequences), and these make possible removal by means of cre recombinase at a later point in time.

An expression cassette and the vectors derived from it may comprise further functional elements. The term functional element is to be understood in the broad sense and refers to all those elements which have an effect on generation, replication or function of the expression cassettes, vectors or transgenic organisms according to the invention. Examples which may be mentioned, but not by way of limitation, are:

a) Selection markers which confer resistance to a metabolism inhibitor such as 2-deoxyglucose-6-phosphate (WO 98/45456), antibiotics or biocides, preferably herbicides, such as, for example, kanamycin, G 418, bleomycin, hygromycin, or phosphinothricin and the like. Particularly preferred selection markers are those which confer resistance to herbicides. The following may be mentioned by way of example: DNA sequences which encode phosphinothricin acetyltransferases (PAT) and which inactivate glutamine synthase inhibitors (bar and pat gene), 5-enolpyruvylshikimate-3-phosphate synthase genes (EPSP synthase genes), which confer resistance to Glyphosat® (N(phosphonomethyl)glycine), the gox gene, which encodes Glyphosat®-degrading enzyme (Glyphosate oxidoreductase), the deh gene (encoding a dehalogenase which inactivates dalapon), sulfonylurea- and imidazolinone-inactivating acetolactate synthases, and bxn genes which encode nitrilase enzymes which degrade bromoxynil, the aasa gene, which confers resistance to the antibiotic apectinomycin, the streptomycin phosphotransferase (SPT) gene, which permits resistance to streptomycin, the neomycin phosphotransferase (NPTII) gene, which confers resistance to kanamycin or geneticidin, the hygromycin phosphotransferase (HPT) gene, which confers resistance to hygromycin, the acetolactate synthase gene (ALS), which confers resistance to sulfonylurea herbicides (for example mutated ALS variants with, for example, the S4 and/or Hra mutation).

b) Reporter genes which encode readily quantifiable proteins and which allow the transformation efficacy or the expression site or time to be assessed via their color or enzyme activity. Very particularly preferred in this context are reporter proteins (Schenborn E, Groskreutz D. Mol. Biotechnol. 1999; 13(1):29-44) such as the "green fluorescence protein" (GFP) (Sheen et al. (1995) Plant Journal 8(5):777-784), chloramphenicol transferase, a luciferase (Ow et al. (1986) Science 234:856-859), the aequorin gene (Prasher et al. (1985) Biochem Biophys Res Commun 126(3):1259-1268), β-galactosidase, with β-glucuronidase being very particularly preferred (Jefferson et al. (1987) EMBO J 6:3901-3907).

c) Replication origins which allow replication of the expression cassettes or vectors according to the invention in, for example, E. coli. Examples which may be mentioned are ORI (origin of DNA replication), the pBR322 ori or the P15A ori (Sambrook et al.: Molecular Cloning. A Laboratory Manual, $2^{nd}$ ed. Cold Spring Harbor Laboratory Press, Cold Spring Harbor, N.Y., 1989).

d) Elements which are required for *agrobacterium*-mediated plant transformation such as, for example, the right or left border of the T-DNA, or the vir region.

To select cells which have successfully undergone homologous recombination or else cells which have successfully been transformed, it is generally required additionally to introduce a selectable marker which confers resistance to a biocide (for example a herbicide), a metabolism inhibitor such as 2-deoxyglucose-6-phosphate (WO 98/45456) or an antibiotic to the cells which have successfully undergone recombination. The selection marker permits the selection of the transformed cells from untransformed cells (McCormick et al. (1986) Plant Cell Reports 5:81-84).

In addition, the recombinant expression cassette or expression vectors may comprise further nucleic acid sequences which do not encode a phosphoribosyl pyrophosphate synthase from *Ashbya gossypii* and whose recombinant expression leads to a further increase in fatty acid biosynthesis (as a consequence of proOIL). By way of example, but not by limitation, this proOIL nucleic acid sequence which is additionally expressed recombinantly can be selected from among nucleic acids encoding acetyl-CoA carboxylase (ACCase), glycerol-3-phosphate acyltransferase (GPAT), lysophosphatidate acyltransferase (LPAT), diacylglycerol acyltransferase (DAGAT) and phospholipid:diacylglycerol acyltransferase (PDAT). Such sequences are known to the skilled worker and are readily accessible from databases or suitable cDNA libraries of the respective plants.

An expression cassette according to the invention can advantageously be introduced into an organism or cells, tissues, organs, parts or seeds thereof (preferably into plants or plant cells, tissues, organs, parts or seeds) by using vectors in which the expression cassettes are present. The invention therefore furthermore relates to said recombinant vectors which encompass a recombinant expression cassette for a phosphoribosyl pyrophosphate synthase from *Ashbya gossypii*.

For example, vectors may be plasmids, cosmids, phages, viruses or else *agrobacteria*. The expression cassette can be introduced into the vector (preferably a plasmid vector) via a suitable restriction cleavage site. The resulting vector is first introduced into E. coli. Correctly transformed E. coli are selected, grown, and the recombinant vector is obtained with methods known to the skilled worker. Restriction analysis and sequencing may be used for verifying the cloning step. Preferred vectors are those which make possible stable integration of the expression cassette into the host genome.

Such a transgenic plant organism is generated, for example, by means of transformation or transfection by means of the corresponding proteins or nucleic acids. The generation of a transformed organism (or a transformed cell or tissue) requires introducing the DNA in question (for example the expression vector), RNA or protein into the host cell in question. A multiplicity of methods is available for this procedure, which is termed transformation (or transduction or transfection) (Keown et al. (1990) Methods in Enzymology 185:527-537). Thus, the DNA or RNA can be introduced for example directly by microinjection or by bombardment with DNA-coated microparticles. The cell may also be permeabilized chemically, for example with polyethylene glycol, so that the DNA may reach the cell by diffusion. The DNA can also be carried out by protoplast fusion with other DNA-comprising units such as minicells, cells, lysosomes or liposomes. Electroporation is a further suitable method for introducing DNA; here, the cells are permeabilized reversibly by an electrical pulse. Soaking plant parts in DNA solutions, and pollen or pollen tube transformation, are also possible. Such methods have been described (for example in Bilang et al. (1991) Gene 100:247-250; Scheid et al. (1991) Mol Gen Genet. 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the methods which have been described for transforming and regenerating plants from plant tissues or plant cells are exploited for transient or stable transformation. Suitable methods are, in particular, protoplast transformation by polyethylene glycol-induced DNA uptake, the biolistic method with the gene gun, what is known as the particle bombardment method, electroporation, the incubation of dry embryos in DNA-containing solution, and microinjection.

In addition to these "direct" transformation techniques, transformation may also be effected by bacterial infection by means of *Agrobacterium tumefaciens* or *Agrobacterium rhizogenes* and the transfer of corresponding recombinant Ti plasmids or Ri plasmids by or by infection with transgenic plant viruses. *Agrobacterium*-mediated transformation is best suited to cells of dicotyledonous plants. The methods are described, for example, in Horsch R B et al. (1985) Science 225: 1229f).

When *agrobacteria* are used, the expression cassette is to be integrated into specific plasmids, either into a shuttle vector or into a binary vector. If a Ti or Ri plasmid is to be used for the transformation, at least the right border, but in most cases the right and left border, of the Ti or Ri plasmid T-DNA is linked to the expression cassette to be introduced as flanking region.

Binary vectors are preferably used. Binary vectors are capable of replication both in *E. coli* and in *Agrobacterium*. As a rule, they contain a selection marker gene and a linker or polylinker flanked by the right and left T-DNA border sequence. They can be transformed directly into *Agrobacterium* (Holsters et al. (1978) Mol Gen Genet 163:181-187). The selection marker gene, which is, for example, the nptII gene, which confers resistance to kanamycin, permits a selection of transformed *agrobacteria*. The agrobacterium which acts as host organism in this case should already contain a plasmid with the vir region. The latter is required for transferring the T-DNA to the plant cells. An *agrobacterium* transformed in this way can be used for transforming plant cells. The use of T-DNA for the transformation of plant cells has been studied intensively and described (EP 120 516; Hoekema, In: The Binary Plant Vector System, Offsetdrukkerij Kanters B. V., Alblasserdam, Chapter V; An et al. (1985) EMBO J 4:277-287). Various binary vectors, some of which are commercially available, such as, for example, pBI101.2 or pBIN19 (Clontech Laboratories, Inc. USA), are known.

Further promoters which are suitable for expression in plants have been described (Rogers et al. (1987) Meth in Enzymol 153:253-277; Schardl et al. (1987) Gene 61:1-11; Berger et al. (1989) Proc Natl Acad Sci USA 86:8402-8406).

Direct transformation techniques are suitable for any organism and cell type. In cases where DNA or RNA are injected or electroporated into plant cells, the plasmid used need not meet any particular requirements. Simple plasmids such as those from the pUC series may be used. If intact plants are to be regenerated from the transformed cells, it is necessary for an additional selectable marker gene to be present on the plasmid.

Stably transformed cells, i.e. those which contain the inserted DNA integrated into the DNA of the host cell, can be selected from untransformed cells when a selectable marker is part of the inserted DNA. By way of example, any gene which is capable of conferring resistance to antibiotics or herbicides (such as kanamycin, G 418, bleomycin, hygromycin or phosphinothricin and the like) is capable of acting as marker (see above). Transformed cells which express such a marker gene are capable of surviving in the presence of concentrations of such an antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide Glyphosate. The selection marker permits selection of transformed cells from untransformed cells (McCormick et al. (1986) Plant Cell Reports 5:81-84). The plants obtained can be bred and hybridized in the customary manner. Two or more generations should be grown in order to ensure that the genomic integration is stable and hereditary.

The above-described methods are described, for example, in Jenes B et al. (1993) Techniques for Gene Transfer, in: Transgenic Plants, Vol. 1, Engineering and Utilization, edited by SD Kung and R Wu, Academic Press, pp. 128-143, and in Potrykus (1991) Annu Rev Plant Physiol Plant Molec Biol 42:205-225). The construct to be expressed is preferably cloned into a vector which is suitable for transforming Agrobacterium tumefaciens, for example pBin19 (Bevan et al. (1984) Nucl Acids Res 12:8711f).

Once a transformed plant cell has been generated, an intact plant can be obtained using methods known to the skilled worker. For example, callus cultures are used as starting material. The development of shoot and root can be induced in this as yet undifferentiated cell biomass in the known fashion. The plantlets obtained can be planted out and used for breeding.

The skilled worker is familiar with such methods for regenerating plant parts and intact plants from plant cells. Methods which can be used for this purpose are, for example, those described by Fennell et al. (1992) Plant Cell Rep. 11: 567-570; Stoeger et al (1995) Plant Cell Rep. 14:273-278; Jahne et al. (1994) Theor Appl Genet 89:525-533.

"Transgenic" or "recombinant", for example in the case of a nucleic acid sequence, an expression cassette or a vector comprising said nucleic acid sequence or to an organism transformed with said nucleic acid sequence, expression cassette or vector, refers to all those constructs established by recombinant methods in which either a) the nucleic acid sequence encoding a phosphoribosyl pyrophosphate synthase or b) a genetic control sequence, for example a promoter which is functional in a plant organism, which is linked operably with said nucleic acid sequence under a), or c) (a) and (b)

are not in their natural genetic environment or have been modified by recombinant methods, it being possible for the modification to be, for example, a substitution, addition, deletion, inversion or insertion of one or more nucleotide residues. Natural genetic environment refers to the natural chromosomal locus in the source organism or the presence in a genomic library. In the case of a genomic library, the natural genetic environment of the nucleic acid sequence is preferably retained, at least to some extent. The environment flanks the nucleic acid sequence at least on one side and has a sequence length of at least 50 bp, preferably at least 500 bp, particularly preferably at least 1000 bp, very particularly preferably at least 5000 bp. A naturally occurring expression cassette, for example the naturally occurring combination of the promoter of a gene encoding for a yeast G3PDH, becomes a transgenic expression cassette when the latter is modified by non-natural, synthetic ("artificial") methods such as, for example, a mutagenization. Such methods are described (U.S. Pat. No. 5,565,350; WO 00/15815; see also above).

Host or starting organisms which are preferred as transgenic organisms are, above all, plants in accordance with the above definition. Included for the purposes of the invention are all genera and species of monocotyledonous and dicotyledonous plants of the Plant Kingdom, in particular plants which are used for obtaining oils, such as, for example, oilseed rape, sunflower, sesame, safflower, olive tree, soya, maize and nut species. Furthermore included are the mature plants, seed, shoots and seedlings, and parts, propagation material and cultures, for example cell cultures, derived therefrom. Mature plants refers to plants at any desired developmental stage beyond the seedling stage. Seedling refers to a young, immature plant at an early developmental stage.

The transgenic plants can be generated with the above-described methods for the transformation or transfection of organisms.

According to the present invention, the introduced nucleic acid molecule coding for PRS selected from the group consisting of SEQ ID NOs: 2, 4, 13, 51, 52, 53, 54, 55, 56, 57, 58, 59, 60, 61, 62, 63 may be maintained in the plant cell stably if it is incorporated into a non-chromosomal autonomous replicon or integrated into the plant chromosomes or organelle genome. Alternatively, the introduced PRS may be present on an extra-chromosomal non-replicating vector and be transiently expressed or transiently active.

In one embodiment, a homologous recombinant microorganism can be created wherein the PRS is integrated into a chromosome, a vector is prepared which contains at least a portion of a nucleic acid molecule coding for PRS selected from the group consisting of SEQ ID NOs: 2, 4, 13, 51, 52, 53, 54, 55, 56, 57, 58, 59, 60, 61, 62, 63 into which a deletion, addition, or substitution has been introduced to thereby alter, e.g., functionally disrupt, the gene. Preferably, the PRS gene is a yeast, *E. coli* gene, but it can be a homolog from a related plant or even from a mammalian or insect source. The vector can be designed such that, upon homologous recombination, the endogenous nucleic acid molecule coding for PRS is mutated or otherwise altered but still encodes a functional polypeptide (e.g., the upstream regulatory region can be altered to thereby alter the expression of the endogenous PRS). In a preferred embodiment the biological activity of the protein of the invention is increased upon homologous recombination. To create a point mutation via homologous recombination, DNA-RNA hybrids can be used in a technique known as chimeraplasty (Cole-Strauss et al., Nucleic Acids Research 27 (5), 1323 (1999) and Kmiec, Gene Therapy American Scientist. 87 (3), 240 (1999)). Homologous recombination procedures in *Physcomitrella patens* are also well known in the art and are contemplated for use herein.

Whereas in the homologous recombination vector, the altered portion of the nucleic acid molecule coding for PRS selected from the group consisting of SEQ ID NOs: 2, 4, 13, 51, 52, 53, 54, 55, 56, 57, 58, 59, 60, 61, 62, 63 is flanked at its 5' and 3' ends by an additional nucleic acid molecule of the PRS gene to allow for homologous recombination to occur between the exogenous PRS gene carried by the vector and an endogenous PRS gene, in a microorganism or plant. The additional flanking PRS nucleic acid molecule is of sufficient length for successful homologous recombination with the endogenous gene. Typically, several hundreds of base pairs up to kilobases of flanking DNA (both at the 5' and 3' ends) are included in the vector. See, e.g., Thomas K. R., and Capecchi M. R., Cell 51, 503 (1987) for a description of homologous recombination vectors or Strepp et al., PNAS, 95 (8), 4368 (1998) for cDNA based recombination in *Physcomitrella patens*. The vector is introduced into a microorganism or plant cell (e.g. via polyethylene glycol mediated DNA), and cells in which the introduced PRS gene has homologously recombined with the endogenous PRS gene are selected using art-known techniques.

Whether present in an extra-chromosomal non-replicating vector or a vector that is integrated into a chromosome, the nucleic acid molecule coding for PRS selected from the group consisting of SEQ ID NOs: 2, 4, 13, 51, 52, 53, 54, 55, 56, 57, 58, 59, 60, 61, 62, 63 preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., EMBO J. 3, 835 (1984)) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., Nucl. Acids Research 15, 8693 (1987)). Examples of plant expression vectors include those detailed in: Becker D. et al., Plant Mol. Biol. 20, 1195 (1992); and Bevan M. W., Nucl. Acid. Res. 12, 8711 (1984); and "Vectors for Gene Transfer in Higher Plants" in: Transgenic Plants, Vol. 1, Engineering and Utilization, eds. Kung and Wu R., Academic Press, 1993, S. 15-38.

"Transformation" is defined herein as a process for introducing heterologous DNA into a plant cell, plant tissue, or plant. It may occur under natural or artificial conditions using various methods well known in the art. Transformation may rely on any known method for the insertion of foreign nucleic acid sequences into aprokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time. Transformed plant cells, plant tissue, or plants are understood to encompass not only the end product of a transformation process, but also transgenic progeny thereof.

The terms "transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic" or "non-recombinant" host refers to a wild-type organism, e.g. a bacterium or plant, which does not contain the heterologous nucleic acid molecule.

A "transgenic plant", as used herein, refers to a plant which contains a foreign nucleotide sequence inserted into either its nuclear genome or organellar genome. It encompasses further the offspring generations i.e. the T1-, T2- and consecutively generations or BC1-, BC2- and consecutively generation as well as crossbreeds thereof with non-transgenic or other transgenic plants.

The host organism (=transgenic organism) advantageously contains at least one copy of the nucleic acid according to the invention and/or of the nucleic acid construct according to the invention.

In principle all plants can be used as host organism. Preferred transgenic plants are, for example, selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants such as plants advantageously selected from the group of the genus peanut, oilseed rape, canola, sunflower, safflower, olive, sesame, hazelnut, almond, avocado, bay, pumpkin/squash, linseed, soya, pistachio, borage, maize, wheat, rye, oats, sorghum and millet, triticale, rice, barley, cassava, potato, sugarbeet, egg plant, alfalfa, and perennial grasses and forage plants, oil palm, vegetables (brassicas, root vegetables, tuber vegetables, pod vegetables, fruiting vegetables, onion vegetables, leafy vegetables and stem vegetables), buckwheat, Jerusalem artichoke, broad bean, vetches, lentil, dwarf bean, lupin, clover and Lucerne for mentioning only some of them.

In one embodiment of the invention transgenic plants are selected from the group comprising cereals, soybean, rapeseed (including oil seed rape, especially canola and winter oil seed rape), cotton sugarcane and potato, especially corn, soy, rapeseed (including oil seed rape, especially canola and winter oil seed rape), cotton, wheat and rice.

In another embodiment of the invention the transgenic plant is a gymnosperm plant, especially a spruce, pine or fir.

In one preferred embodiment, the host plant is selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants and in particular plants mentioned herein above as host plants such as the families and genera mentioned above for example preferred the species *Anacardium occidentale, Calendula officinalis, Carthamus tinctorius, Cichorium intybus, Cynara scolymus, Helianthus annus, Tagetes lucida, Tagetes erecta, Tagetes tenuifolia; Daucus carota; Corylus avellana, Corylus colurna, Borago officinalis; Brassica napus, Brassica rapa* ssp., *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis, Brassica oleracea, Arabidopsis thaliana, Anana comosus, Ananas ananas, Bromelia comosa, Carica papaya, Cannabis sative, Ipomoea batatus, Ipomoea pandurata, Convolvulus batatas, Convolvulus tiliaceus, Ipomoea fastigiata, Ipomoea tiliacea, Ipomoea triloba, Convolvulus panduratus, Beta vulgaris, Beta vulgaris* var. *altissima, Beta vulgaris* var. *vulgaris, Beta maritima, Beta vulgaris* var. *perennis, Beta vulgaris* var. *conditiva, Beta vulgaris* var. *esculenta, Cucurbita maxima, Cucurbita mixta, Cucurbita pepo, Cucurbita moschata, Olea europaea, Manihot utilissima, Janipha manihot., Jatropha manihot., Manihot aipil, Manihot dulcis, Manihot manihot, Manihot melanobasis, Manihot esculenta, Ricinus communis, Pisum sativum, Pisum arvense, Pisum humile, Medicago sativa, Medicago falcata, Medicago varia, Glycine max Dolichos soja, Glycine gracilis, Glycine hispida, Phaseolus max, Soja hispida, Soja max, Cocos nucifera, Pelargonium grossularioides, Oleum cocoas, Laurus nobilis, Persea americana, Arachis hypogaea, Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense, Linum trigynum, Punica granatum, Gossypium hirsutum, Gossypium arboreum, Gossypium barbadense, Gossypium herbaceum, Gossypium thurberi, Musa nana, Musa acuminata, Musa paradisiaca, Musa* spp., *Elaeis guineensis, Papaver orientale, Papaver rhoeas, Papaver dubium, Sesamum indicum, Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata, Hordeum vulgare, Hordeum jubatum, Hordeum murinum, Hordeum secalinum, Hordeum distichon Hordeum aegiceras, Hordeum hexastichon., Hordeum hexastichum, Hordeum irregulare, Hordeum sativum, Hordeum secalinum, Avena sativa, Avena fatua, Avena byzantina, Avena fatua* var. *sativa, Avena hybrida, Sorghum* bicolor, *Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum, Zea mays, Triticum aestivum, Triticum durum, Triticum turgidum, Triticum hybernum, Triticum macha, Triticum sativum* or *Triticum vulgare, Cofea* spp., *Coffea arabica, Coffea canephora, Coffea liberica, Capsicum annuum, Capsicum annuum* var. *glabriusculum, Capsicum frutescens, Capsicum annuum, Nicotiana tabacum, Solanum tuberosum, Solanum melongena, Lycopersicon esculentum, Lycopersicon lycopersicum, Lycopersicon pyriforme, Solanum integrifolium, Solanum lycopersicum Theobroma cacao* or *Camellia sinensis*.

Anacardiaceae such as the genera *Pistacia, Mangifera, Anacardium* e.g. the species *Pistacia vera* [pistachios, Pistazie], *Mangifer indica* [Mango] or *Anacardium occidentale* [Cashew]; Asteraceae such as the genera *Calendula, Carthamus, Centaurea, Cichorium, Cynara, Helianthus, Lactuca, Locusta, Tagetes, Valeriana* e.g. the species *Calendula officinalis* [Marigold], *Carthamus tinctorius* [safflower], *Centaurea cyanus* [cornflower], *Cichorium intybus* [blue daisy], *Cynara scolymus* [Artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [lettuce], *Tagetes lucida, Tagetes erecta* or *Tagetes tenuifolia* [Marigold]; Apiaceae such as the genera *Daucus* e.g. the species *Daucus carota* [carrot]; Betulaceae such as the genera *Corylus* e.g. the species *Corylus avellana* or *Corylus colurna* [hazelnut]; Boraginaceae such as the genera *Borago* e.g. the species *Borago officinalis* [borage]; Brassicaceae such as the genera *Brassica, Melanosinapis, Sinapis, Arabadopsis* e.g. the species *Brassica napus, Brassica rapa* ssp. [canola, oilseed rape, turnip rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*; Bromeliaceae such as the genera *Anana, Bromelia* e.g. the species *Anana comosus, Ananas ananas* or *Bromelia comosa* [pineapple]; Caricaceae such as the genera *Carica* e.g. the species *Carica papaya* [papaya]; Cannabaceae such as the genera *Cannabis* e.g. the species *Cannabis* sative [hemp], Convolvulaceae such as the genera *Ipomea, Convolvulus* e.g. the species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, Man of the Earth, wild potato], Chenopodiaceae such as the genera *Beta*, i.e. the species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugar beet]; Cucurbitaceae such as the genera

*Cucubita* e.g. the species *Cucurbita maxima, Cucurbita mixta, Cucurbita pepo* or *Cucurbita moschata* [pumpkin, squash]; Elaeagnaceae such as the genera *Elaeagnus* e.g. the species *Olea europaea* [olive]; Ericaceae such as the genera *Kalmia* e.g. the species *Kalmia latifolia, Kalmia angustifolia, Kalmia microphylla, Kalmia polifolia, Kalmia occidentalis, Cistus chamaerhodendros* or *Kalmia lucida* [American laurel, broad-leafed laurel, calico bush, spoon wood, sheep laurel, alpine laurel, bog laurel, western bog-laurel, swamp-laurel]; Euphorbiaceae such as the genera *Manihot, Janipha, Jatropha, Ricinus* e.g. the species *Manihot utilissima, Janipha manihot, Jatropha manihot, Manihot aipil, Manihot dulcis, Manihot manihot, Manihot melanobasis, Manihot esculenta* [manihot, arrowroot, tapioca, cassaya] or *Ricinus communis* [castor bean, Castor Oil Bush, Castor Oil Plant, Palma Christi, Wonder Tree]; Fabaceae such as the genera *Pisum, Albizia, Cathormion, Feuillea, Inga, Pithecolobium, Acacia, Mimosa, Medicajo, Glycine, Dolichos, Phaseolus, Soja* e.g. the species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [bastard logwood, silk tree, East Indian Walnut], *Medicago sativa, Medicago falcata, Medicago varia* [alfalfa] *Glycine max Dolichos soja, Glycine gracilis, Glycine hispida, Phaseolus max, Soja hispida* or *Soja max* [soybean]; Geraniaceae such as the genera *Pelargonium, Cocos, Oleum* e.g. the species *Cocos nucifera, Pelargonium grossularioides* or *Oleum cocois* [coconut]; Gramineae such as the genera *Saccharum* e.g. the species *Saccharum officinarum*; Juglandaceae such as the genera *Juglans, Wallia* e.g. the species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut, black walnut, common walnut, persian walnut, white walnut, butternut, black walnut]; Lauraceae such as the genera *Persea, Laurus* e.g. the species *laurel Laurus nobilis* [bay, laurel, bay laurel, sweet bay], *Persea americana Persea americana, Persea gratissima* or *Persea persea* [avocado]; Leguminosae such as the genera *Arachis* e.g. the species *Arachis hypogaea* [peanut]; Linaceae such as the genera *Linum, Adenolinum* e.g. the species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [flax, linseed]; Lythrarieae such as the genera *Punica* e.g. the species *Punica granatum* [pomegranate]; Malvaceae such as the genera *Gossypium* e.g. the species *Gossypium hirsutum, Gossypium arboreum, Gossypium barbadense, Gossypium herbaceum* or *Gossypium thurberi* [cotton]; Musaceae such as the genera *Musa* e.g. the species *Musa nana, Musa acuminata, Musa paradisiaca, Musa* spp. [banana]; Onagraceae such as the genera *Camissonia, Oenothera* e.g. the species *Oenothera biennis* or *Camissonia brevipes* [primrose, evening primrose]; Palmae such as the genera *Elacis* e.g. the species *Elaeis guineensis* [oil plam]; Papaveraceae such as the genera *Papaver* e.g. the species *Papaver orientale, Papaver rhoeas, Papaver dubium* [poppy, oriental poppy, corn poppy, field poppy, shirley poppies, field poppy, long-headed poppy, long-pod poppy]; Pedaliaceae such as the genera *Sesamum* e.g. the species *Sesamum indicum* [sesame]; Piperaceae such as the genera *Piper, Artanthe, Peperomia, Steffensia* e.g. the species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata.* [Cayenne pepper, wild pepper]; Poaceae such as the genera *Hordeum, Secale, Avena, Sorghum, Andropogon, Holcus, Panicum, Oryza, Zea, Triticum* e.g. the species *Hordeum vulgare, Hordeum jubatum, Hordeum murinum, Hordeum secalinum, Hordeum distichon Hordeum aegiceras, Hordeum hexastichon, Hordeum hexastichum, Hordeum irregulare, Hordeum sativum, Hordeum secalinum* [barley, pearl barley, foxtail barley, wall barley, meadow barley], *Secale cereale* [rye], *Avena sativa, Avena fatua, Avena byzantina, Avena fatua* var. *sativa, Avena hybrida* [oat], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum* [*Sorghum,* millet], *Oryza sativa, Oryza latifolia* [rice], *Zea mays* [corn, maize] *Triticum aestivum, Triticum durum, Triticum turgidum, Triticum hybernum, Triticum macha, Triticum sativum* or *Triticum vulgare* [wheat, bread wheat, common wheat], Proteaceae such as the genera *Macadamia* e.g. the species *Macadamia intergrifolia* [macadamia]; Rubiaceae such as the genera *Coffea* e.g. the species *Cofea* spp., *Coffea arabica, Coffea canephora* or *Coffea liberica* [coffee]; Scrophulariaceae such as the genera *Verbascum* e.g. the species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein, white moth mullein, nettle-leaved mullein, dense-flowered mullein, silver mullein, long-leaved mullein, white mullein, dark mullein, greek mullein, orange mullein, purple mullein, hoary mullein, great mullein]; Solanaceae such as the genera *Capsicum, Nicotiana, Solanum, Lycopersicon* e.g. the species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant] (*Lycopersicon esculentum, Lycopersicon lycopersicum., Lycopersicon pyriforme, Solanum integrifolium* or *Solanum* lycopersicum [tomato]; Sterculiaceae such as the genera *Theobroma* e.g. the species *Theobroma cacao* [cacao]; Theaceae such as the genera *Camellia* e.g. the species *Camellia sinensis*) [tea].

In one embodiment of the invention host organism are plants, selected in particular from the monocotyledonous crop plants such as, for example, the Poaceae family, such as maize.

In one embodiment of the invention host organism are plants, selected in particular from the group consisting of
    Asteraceae such as sunflower, tagetes or *calendula* and others, Compositae, especially the genus *Lactuca*, very particularly the species sativa (lettuce) and others, BrassicaceaeCruciferae, particularly the genus *Brassica*, very particularly the species napus (oilseed rape), napus var. *napus* or rapa ssp. oleifera (Canola), juncea (sarepta mustard), *Camelina sative* (false flax) and others, Cucurbitaceae such as melon, pumpkin/squash or zucchini and others, Leguminosae, particularly the genus *Glycine*, very particularly the species max (soybean), soya, and alfalfa, pea, beans or peanut and others, and linseed, soybean, cotton or hemp.

Furthermore, plant organisms for the purposes of the invention are further organisms capable of being photosynthetically active such as, for example, algae, cyanobacteria and mosses. Preferred algae are green algae such as, for example, algae from the genus *Haematococcus, Phaedactylum tricornatum, Volvox* or *Dunaliella. Synechocystis* is particularly preferred.

Most preferred are oil crops, i.e. plants whose oil content is already naturally high and/or which can be used for the industrial production of oils. These plants can have a high oil content and/or else a particular fatty acid composition which is of interest industrially. Preferred plants are those with a lipid content of at least 1% by weight. Oil crops encompass by way of example: *Bovago oficinalis* (borage); *Brassica* species such as *B. campestris, B. napus, B. rapa* (mustard or oilseed rape); *Cannabis sativa* (hemp); *Carthamus tinctorius* (safflower); *Cocos nucifera* (coconut); *Crambe abyssinica* (crambe); *Cuphea* species (Cuphea species yield fatty acids of medium chain length, in particular for industrial applications); *Elaeis guinensis* (African oil palm); Elaeis oleifera (American oil palm); *Glycine max* (soybean); *Gossypium hirisfum* (American cotton); *Gossypium barbadense* (Egyptian cotton); *Gossypium herbaceum* (Asian cotton); *Helianthus annuus* (sunflower); *Linum usitatissimum* (linseed or flax); *Oenothera biennis* (evening primrose); *Olea europaea* (olive); *Oryza sativa* (rice); *Ricinus communis* (castor); *Sesamum indicum* (sesame); *Glycine max* (soybean); *Triticum* species (wheat); *Zea mays* (maize), and various nut species such as, for example, walnut or almond.

The introduction of the nucleic acids according to the invention, the expression cassette or the vector into organisms, plants for example, can in principle be done by all of the methods known to those skilled in the art. The introduction of the nucleic acid sequences gives rise to recombinant or transgenic organisms.

Unless otherwise specified, the terms "polynucleotides", "nucleic acid" and "nucleic acid molecule" as used herein are interchangeably. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or deoxyribonucleotides. The terms refer only to the primary structure of the molecule.

Thus, the terms "gene(s)", "polynucleotide", "nucleic acid sequence", "nucleotide sequence", or "nucleic acid molecule(s)" as used herein include double- and single-stranded DNA and RNA. They also include known types of modifications, for example, methylation, "caps", substitutions of one or more of the naturally occurring nucleotides with an analog. Preferably, the DNA or RNA sequence of the invention comprises a coding sequence encoding the herein defined polypeptide.

The genes of the invention, coding for an activity selected from the group consisting of phosphoribosyl pyrophosphate synthases are also called "PRS gene".

A "coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

The transfer of foreign genes into the genome of a plant is called transformation. In doing this the methods described for the transformation and regeneration of plants from plant tissues or plant cells are utilized for transient or stable transformation. Suitable methods are protoplast transformation by poly(ethylene glycol)-induced DNA uptake, the "biolistic" method using the gene cannon—referred to as the particle bombardment method, electroporation, the incubation of dry embryos in DNA solution, microinjection and gene transfer mediated by *Agrobacterium*. Said methods are described by way of example in Jenes B. et al., Techniques for Gene Transfer, in: Transgenic Plants, Vol. 1, Engineering and Utilization, eds. Kung S. D and Wu R., Academic Press (1993) 128-143 and in Potrykus, Annu. Rev. Plant Physiol. Plant Molec. Biol. 42, 205 (1991). The nucleic acids or the construct to be expressed is preferably cloned into a vector which is suitable for transforming *Agrobacterium* tumefaciens, for example pBin19 (Bevan et al., Nucl. Acids Res. 12, 8711 (1984)). Agrobacteria transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. 16, 9877 (1988) or is known inter alia from White F. F., Vectors for Gene Transfer in Higher Plants; in Transgenic Plants, Vol. 1, Engineering and Utilization, eds. Kung S. D. and Wu R., Academic Press, 1993, pp. 15-38.

*Agrobacteria* transformed by an expression vector according to the invention may likewise be used in known manner for the transformation of plants such as test plants like *Arabidopsis* or crop plants such as cereal crops, corn, oats, rye, barley, wheat, soybean, rice, cotton, sugar beet, canola, sunflower, flax, hemp, potatoes, tobacco, tomatoes, carrots, paprika, oilseed rape, tapioca, cassaya, arrowroot, tagetes, alfalfa, lettuce and the various tree, nut and vine species, in particular oil-containing crop plants such as soybean, peanut, castor oil plant, sunflower, corn, cotton, flax, oilseed rape, coconut, oil palm, safflower (*Carthamus tinctorius*) or cocoa bean, or in particular corn, wheat, soybean, rice, cotton and canola, e.g. by bathing bruised leaves or chopped leaves in an agrobacterial solution and then culturing them in suitable media.

The genetically modified plant cells may be regenerated by all of the methods known to those skilled in the art. Appropriate methods can be found in the publications referred to above by Kung S. D. and Wu R., Potrykus or Höfgen and Willmitzer.

Accordingly, a further aspect of the invention relates to transgenic organisms transformed by at least one nucleic acid sequence, expression cassette or vector according to the invention as well as cells, cell cultures, tissue, parts—such as, for example, leaves, roots, etc. in the case of plant organisms—or reproductive material derived from such organisms. The terms "host organism", "host cell", "recombinant (host) organism" and "transgenic (host) cell" are used here interchangeably. Of course these terms relate not only to the particular host organism or the particular target cell but also to the descendants or potential descendants of these organisms or cells. Since, due to mutation or environmental effects certain modifications may arise in successive generations, these descendants need not necessarily be identical with the parental cell but nevertheless are still encompassed by the term as used here.

For the purposes of the invention "transgenic" or "recombinant" means with regard for example to a nucleic acid sequence, an expression cassette (=gene construct, nucleic acid construct) or a vector containing the nucleic acid sequence according to the invention or an organism transformed by the nucleic acid sequences, expression cassette or vector according to the invention all those constructions produced by genetic engineering methods in which either (a) the nucleic acid sequence selected from the group consisting of SEQ ID NOs: 1, 3, 12, 38, 39, 40, 41, 42, 43, 44, 45, 46, 47, 48, 49, 50 or its derivatives or parts thereof; or
(b) a genetic control sequence functionally linked to the nucleic acid sequence described under (a), for example a 3'- and/or 5'-genetic control sequence such as a promoter or terminator, or
(c) (a) and (b);

are not found in their natural, genetic environment or have been modified by genetic engineering methods, wherein the modification may by way of example be a substitution, addition, deletion, inversion or insertion of one or more nucleotide residues. Natural genetic environment means the natural genomic or chromosomal locus in the organism of origin or inside the host organism or presence in a genomic library. In the case of a genomic library the natural genetic environment of the nucleic acid sequence is preferably retained at least in part. The environment borders the nucleic acid sequence at least on one side and has a sequence length of at least 50 bp, preferably at least 500 bp, particularly preferably at least 1,000 bp, most particularly preferably at least 5,000 bp. A naturally occurring expression cassette—for example the naturally occurring combination of the natural promoter of the nucleic acid sequence according to the invention with the corresponding gene—turns into a transgenic expression cassette when the latter is modified by unnatural, synthetic ("artificial") methods such as by way of example a mutagenation. Appropriate methods are described by way of example in U.S. Pat. No. 5,565,350 or WO 00/15815.

Suitable organisms or host organisms for the nucleic acid, expression cassette or vector according to the invention are advantageously in principle all organisms, which are suitable for the expression of recombinant genes as described above. Further examples which may be mentioned are plants such as *Arabidopsis, Asteraceae* such as *Calendula* or crop plants such as soybean, peanut, castor oil plant, sunflower, flax, corn, cotton, flax, oilseed rape, coconut, oil palm, safflower (*Carthamus tinctorius*) or cocoa bean.

In one embodiment of the invention host plants for the nucleic acid, expression cassette or vector according to the invention are selected from the group comprising corn, soy, oil seed rape (including canola and winter oil seed rape), cotton, wheat and rice.

A further object of the invention relates to the use of a nucleic acid construct, e.g. an expression cassette, containing DNA sequences encoding polypeptides selected from the group consisting of SEQ ID NOs: 2, 4, 13, 51, 52, 53, 54, 55, 56, 57, 58, 59, 60, 61, 62, 63 or DNA sequences hybridizing therewith for the transformation of plant cells, tissues or parts of plants.

In doing so, depending on the choice of promoter, the sequences shown in table I can be expressed specifically in the leaves, in the seeds, the nodules, in roots, in the stem or other parts of the plant. Those transgenic plants overproducing sequences as depicted in table I, the reproductive material thereof, together with the plant cells, tissues or parts thereof are a further object of the present invention.

The expression cassette or the nucleic acid sequences or construct according to the invention containing sequences according to the invention can, moreover, also be employed for the transformation of the organisms identified by way of example above such as bacteria, yeasts, filamentous fungi and plants.

Within the framework of the present invention, enhanced yield means, for example, the artificially acquired trait of enhanced yield due to functional over expression of polypeptide sequences of table II encoded by the corresponding nucleic acid molecules selected from the group consisting of SEQ ID NOs: 1, 3, 12, 38, 39, 40, 41, 42, 43, 44, 45, 46, 47, 48, 49, 50 and/or homologs in the organisms according to the invention, advantageously in the transgenic plants according to the invention, by comparison with the nongenetically modified initial plants at least for the duration of at least one plant generation.

A constitutive expression of the polypeptide sequences of table II, encoded by the corresponding nucleic acid molecule selected from the group consisting of SEQ ID NOs: 1, 3, 12, 38, 39, 40, 41, 42, 43, 44, 45, 46, 47, 48, 49, 50 and/or homologs is, moreover, advantageous. On the other hand, however, an inducible expression may also appear desirable. Expression of the polypeptide sequences of the invention can be either direct to the cytoplasm or the organelles, preferably the plastids of the host cells, preferably the plant cells.

The efficiency of the expression of the sequences of the of table II, encoded by the corresponding nucleic acid molecule selected from the group consisting of SEQ ID NOs: 1, 3, 12, 38, 39, 40, 41, 42, 43, 44, 45, 46, 47, 48, 49, 50 and/or homologs can be determined, for example, in vitro by shoot meristem propagation. In addition, an expression of the sequences of table II, encoded by the corresponding nucleic acid molecule selected from the group consisting of SEQ ID NOs: 1, 3, 12, 38, 39, 40, 41, 42, 43, 44, 45, 46, 47, 48, 49, 50 and/or homologs modified in nature and level and its effect on the metabolic pathways performance can be tested on test plants in greenhouse trials.

An additional object of the invention comprises transgenic organisms such as transgenic plants transformed by an expression cassette containing sequences selected from the group consisting of SEQ ID NOs: 1, 3, 12, 38, 39, 40, 41, 42, 43, 44, 45, 46, 47, 48, 49, 50 according to the invention or DNA sequences hybridizing therewith, as well as transgenic cells, tissue, parts and reproduction material of such plants. Particular preference is given in this case to transgenic crop plants such as by way of example barley, wheat, rye, oats, corn, soybean, rice, cotton, sugar beet, oilseed rape and canola, sunflower, flax, hemp, thistle, potatoes, tobacco, tomatoes, tapioca, cassaya, arrowroot, alfalfa, lettuce and the various tree, nut and vine species.

In one embodiment of the invention transgenic plants transformed by an expression cassette containing sequences selected from the group consisting of SEQ ID NOs: 1, 3, 38, 39, 40, 41, 42, 43, 44, 45, 46, 47, 48, 49, 50 according to the invention or DNA sequences hybridizing therewith are selected from the group comprising corn, soy, oil seed rape (including canola and winter oil seed rape), cotton, wheat and rice.

For the purposes of the invention plants are mono- and dicotyledonous plants, mosses or algae, especially plants, preferably monocotyledonous plants, or preferably dicotyledonous plants.

A further refinement according to the invention are transgenic plants as described above which contain a nucleic acid sequence or construct according to the invention or a expression cassette according to the invention.

However, transgenic also means that the nucleic acids according to the invention are located at their natural position in the genome of an organism, but that the sequence has been modified in comparison with the natural sequence and/or that the regulatory sequences of the natural sequences have been modified. Preferably, transgenic/recombinant is to be understood as meaning the transcription of the nucleic acids of the invention, occurs at a non-natural position in the genome, that is to say the expression of the nucleic acids is homologous or, preferably, heterologous. This expression can be transiently or of a sequence integrated stably into the genome.

The term "transgenic plants" used in accordance with the invention also refers to the progeny of a transgenic plant, for example the $T_1$, $T_2$, $T_3$, $T_4$ and subsequent plant generations or the $BC_1$, $BC_2$, $BC_3$ and subsequent plant generations. Thus, the transgenic plants according to the invention can be raised and selfed or crossed with other individuals in order to obtain further transgenic plants according to the invention. Transgenic plants may also be obtained by propagating transgenic plant cells vegetatively. The present invention also relates to transgenic plant material, which can be derived from a transgenic plant population according to the invention. Such material includes plant cells and certain tissues, organs and parts of plants in all their manifestations, such as seeds, leaves, anthers, fibers, tubers, roots, root hairs, stems, embryo, calli, cotelydons, petioles, harvested material, plant tissue, reproductive tissue and cell cultures, which are derived from the actual transgenic plant and/or can be used for bringing about the transgenic plant.

Any transformed plant obtained according to the invention can be used in a conventional breeding scheme or in in vitro plant propagation to produce more transformed plants with the same characteristics and/or can be used to introduce the same characteristic in other varieties of the same or related species. Such plants are also part of the invention. Seeds obtained from the transformed plants genetically also contain the same characteristic and are part of the invention. As mentioned before, the present invention is in principle applicable to any plant and crop that can be transformed with any of the transformation method known to those skilled in the art.

Advantageous inducible plant promoters are by way of example the PRP1 promoter (Ward et al., Plant. Mol. Biol. 22361 (1993)), a promoter inducible by benzenesulfonamide (EP 388 186), a promoter inducible by tetracycline (Gatz et al., Plant J. 2, 397 (1992)), a promoter inducible by salicylic acid (WO 95/19443), a promoter inducible by abscisic acid (EP 335 528) and a promoter inducible by ethanol or cyclohexanone (WO 93/21334). Other examples of plant promoters which can advantageously be used are the promoter of cytoplasmic FBPase from potato, the ST-LSI promoter from potato (Stockhaus et al., EMBO J. 8, 2445 (1989)), the promoter of phosphoribosyl pyrophosphate amidotransferase from *Glycine max* (see also gene bank accession number U87999) or a nodiene-specific promoter as described in EP 249 676. Particular advantageous are those promoters which ensure expression upon onset of low temperature conditions, e.g. at the onset of chilling and/or freezing temperatures as defined hereinabove.

In one embodiment, seed-specific promoters may be used for monocotylodonous or dicotylodonous plants.

In principle all natural promoters with their regulation sequences can be used like those named above for the expression cassette according to the invention and the method according to the invention. Over and above this, synthetic promoters may also advantageously be used.

In the preparation of an expression cassette various DNA fragments can be manipulated in order to obtain a nucleotide sequence, which usefully reads in the correct direction and is equipped with a correct reading frame. To connect the DNA fragments (=nucleic acids according to the invention) to one another adaptors or linkers may be attached to the fragments.

The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be both native or homologous as well as foreign or heterologous to the host organism, for example to the host plant. In the 5'-3' transcription direction the expression cassette contains the promoter, a DNA sequence which shown in table I and a region for transcription termination. Different termination regions can be exchanged for one another in any desired fashion.

As also used herein, the terms "nucleic acid" and "nucleic acid molecule" are intended to include DNA molecules (e.g. cDNA or genomic DNA) and RNA molecules (e.g. mRNA) and analogs of the DNA or RNA generated using nucleotide analogs. This term also encompasses untranslated sequence located at both the 3' and 5' ends of the coding region of the gene—at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one that is substantially separated from other nucleic acid molecules, which are present in the natural source of the nucleic acid. That means other nucleic acid molecules are present in an amount less than 5% based on weight of the amount of the desired nucleic acid, preferably less than 2% by weight, more preferably less than 1% by weight, most preferably less than 0.5% by weight. Preferably, an "isolated" nucleic acid is free of some of the sequences that naturally flank the nucleic acid (i.e., sequences located at the 5' and 3' ends of the nucleic acid) in the genomic DNA of the organism from which the nucleic acid is derived. For example, in various embodiments, the isolated low temperature resistance and/or tolerance related protein encoding nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule encoding an PRS or a portion thereof which confers increased yield in plants, can be isolated using standard molecular biological techniques and the sequence information provided herein. For example, an *Arabidopsis thaliana* PRS encoding cDNA can be isolated from a *A. thaliana* c-DNA library or a *Synechocystis* sp., *Brassica napus, Glycine max, Zea mays* or *Oryza sativa* PRS encoding cDNA can be isolated from a *Synechocystis* sp., *Brassica napus, Glycine max, Zea mays* or *Oryza sativa* cDNA library respectively using all or portion of one of the sequences shown in table I. Moreover, a nucleic acid molecule encompassing all or a portion of one of the sequences of table I can be isolated by the polymerase chain reaction using oligonucleotide primers designed based upon this sequence. For example, mRNA can be isolated from plant cells (e.g., by the guanidinium-thiocyanate extraction procedure of Chirgwin et al., Biochemistry 18, 5294 (1979)) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in table I. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PRS encoding nucleotide sequence can be prepared by standard synthetic techniques, e.g., using an automated DNA synthesizer.

In a preferred embodiment, an isolated nucleic acid molecule of the invention comprises one of the nucleotide sequences shown in table I encoding the PRS (i.e., the "coding region"), as well as 5' untranslated sequences and 3' untranslated sequences.

Moreover, the nucleic acid molecule of the invention can comprise only a portion of the coding region of one of the sequences of the nucleic acid of table I, for example, a fragment which can be used as a probe or primer or a fragment encoding a biologically active portion of a PRS.

Portions of proteins encoded by the PRS encoding nucleic acid molecules of the invention are preferably biologically active portions described herein. As used herein, the term "biologically active portion of" a PRS is intended to include a portion, e.g. a domain/motif, of low temperature resistance and/or tolerance related protein that participates in an enhanced NUE efficiency and/or increased yield in a plant. To determine whether a PRS, or a biologically active portion thereof, results in an enhanced NUE efficiency and/or increased yield in a plant, an analysis of a plant comprising the PRS may be performed. Such analysis methods are well known to those skilled in the art, as detailed in the Examples. More specifically, nucleic acid fragments encoding biologically active portions of a PRS can be prepared by isolating a portion of one of the sequences of the nucleic acid of table I expressing the encoded portion of the PRS or peptide (e.g., by recombinant expression in vitro) and assessing the activity of the encoded portion of the PRS or peptide.

Biologically active portions of a PRS are encompassed by the present invention and include peptides comprising amino acid sequences derived from the amino acid sequence of a PRS encoding gene, or the amino acid sequence of a protein homologous to a PRS, which include fewer amino acids than a full length PRS or the full length protein which is homologous to a PRS, and exhibits at least some enzymatic or biological activity of a PRS. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a PRS. Moreover, other biologically active portions in which other regions of the protein are deleted, can be prepared by recombinant techniques and evaluated for one or more of the activities described herein. Preferably, the biologically active portions of a PRS include one or more selected domains/motifs or portions thereof having biological activity.

The term "biological active portion" or "biological activity" means a polypeptide as depicted in table II, column 3 or a portion of said polypeptide which still has at least 10% or 20%, preferably 30%, 40%, 50% or 60%, especially preferably 70%, 75%, 80%, 90% or 95% of the enzymatic or biological activity of the natural or starting enzyme or protein.

In the process according to the invention nucleic acid sequences can be used, which, if appropriate, contain synthetic, non-natural or modified nucleotide bases, which can be incorporated into DNA or RNA. Said synthetic, non-natural or modified bases can for example increase the stability of the nucleic acid molecule outside or inside a cell. The nucleic acid molecules of the invention can contain the same modifications as aforementioned.

As used in the present context the term "nucleic acid molecule" may also encompass the untranslated sequence located at the 3' and at the 5' end of the coding gene region, for example at least 500, preferably 200, especially preferably 100, nucleotides of the sequence upstream of the 5' end of the coding region and at least 100, preferably 50, especially preferably 20, nucleotides of the sequence downstream of the 3' end of the coding gene region. It is often advantageous only to choose the coding region for cloning and expression purposes.

Preferably, the nucleic acid molecule used in the process according to the invention or the nucleic acid molecule of the invention is an isolated nucleic acid molecule.

An "isolated" polynucleotide or nucleic acid molecule is separated from other polynucleotides or nucleic acid molecules, which are present in the natural source of the nucleic acid molecule. An isolated nucleic acid molecule may be a chromosomal fragment of several kb, or preferably, a molecule only comprising the coding region of the gene. Accordingly, an isolated nucleic acid molecule of the invention may comprise chromosomal regions, which are adjacent 5' and 3' or further adjacent chromosomal regions, but preferably comprises no such sequences which naturally flank the nucleic acid molecule sequence in the genomic or chromosomal context in the or ganism from which the nucleic acid molecule originates (for example sequences which are adjacent to the regions encoding the 5'- and 3'-UTRs of the nucleic acid molecule). In various embodiments, the isolated nucleic acid molecule used in the process according to the invention may, for example comprise less than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid molecule originates.

The nucleic acid molecules used in the process, for example the polynucleotide of the invention or of a part thereof can be isolated using molecularbiological standard techniques and the sequence information provided herein. Also, for example a homologous sequence or homologous, conserved sequence regions at the DNA or amino acid level can be identified with the aid of comparison algorithms. The former can be used as hybridization probes under standard hybridization techniques (for example those described in Sambrook et al., Molecular Cloning: A Laboratory Manual. 2nd Ed., Cold Spring Harbor Laboratory, Cold Spring Harbor Laboratory Press, Cold Spring Harbor, N.Y., 1989) for isolating further nucleic acid sequences useful in this process.

A nucleic acid molecule encompassing a complete sequence of the nucleic acid molecules used in the process, for example the polynucleotide of the invention, or a part thereof may additionally be isolated by polymerase chain reaction, oligonucleotide primers based on this sequence or on parts thereof being used. For example, a nucleic acid molecule comprising the complete sequence or part thereof can be isolated by polymerase chain reaction using oligonucleotide primers which have been generated on the basis of this very sequence. For example, mRNA can be isolated from cells (for example by means of the guanidinium thiocyanate extraction method of Chirgwin et al., Biochemistry 18, 5294 (1979)) and cDNA can be generated by means of reverse transcriptase (for example Moloney MLV reverse transcriptase, available from Gibco/BRL, Bethesda, Md., or AMV reverse transcriptase, obtainable from Seikagaku America, Inc., St. Petersburg, Fla.).

Synthetic oligonucleotide primers for the amplification, e.g. selected from the group consisting of SEQ ID NOs: 5, 6, by means of polymerase chain reaction can be generated on the basis of a sequence shown herein, for example the sequence selected from the group consisting of SEQ ID NOs: 1, 3, 12, 38, 39, 40, 41, 42, 43, 44, 45, 46, 47, 48, 49, 50 or the sequences derived sequences selected from the group consisting of SEQ ID NOs: 2, 4, 13, 51, 52, 53, 54, 55, 56, 57, 58, 59, 60, 61, 62, 63.

Moreover, it is possible to identify conserved protein by carrying out protein sequence alignments with the polypeptide encoded by the nucleic acid molecules of the present invention, in particular with the sequences encoded by the nucleic acid molecule selected from the group consisting of SEQ ID NOs: 1, 3, 12, 38, 39, 40, 41, 42, 43, 44, 45, 46, 47, 48, 49, 50, from which conserved regions, and in turn, degenerate primers can be derived.

Conserved regions are those, which show a very little variation in the amino acid in one particular position of several homologs from different origin. The consensus sequence and polypeptide motifs are derived from said aligments. Moreover, it is possible to identify conserved regions from various organisms by carrying out protein sequence alignments with the polypeptide encoded by the nucleic acid of the present invention, in particular with the sequences encoded by the polypeptide molecule selected from the group consisting of SEQ ID NOs: 2, 4, 13, 51, 52, 53, 54, 55, 56, 57, 58, 59, 60, 61, 62, 63 from which conserved regions, and in turn, degenerate primers can be derived.

In one advantageous embodiment, in the method of the present invention the activity of a polypeptide is increased comprising or consisting of a consensus sequence or a polypeptide motif selected from the group consisting of SEQ ID No. 64, 65, 66, 67, 68, 69, 70, 71, 72, 73 and in one another embodiment, the present invention relates to a polypeptide comprising or consisting of a consensus sequence or a polypeptide motif or comprising a polypeptide according to the motif selected from the group consisting of SEQ ID No. 64, 65, 66, 67, 68, 69, 70, 71, 72, 73 whereby less than 20, preferably less than 15 or 10, preferably less than 9, 8, 7, or 6, more preferred less than 5 or 4, even more preferred less then 3, even more preferred less then 2, even more preferred 0 of the amino acids positions indicated can be replaced by any amino acid. In one embodiment not more than 15%, preferably 10%, even more preferred 5%, 4%, 3%, or 2%, most preferred 1% or 0% of the amino acid position indicated by a letter are/is replaced another amino acid. In one embodiment less than 20, preferably less than 15 or 10, preferably less than 9, 8, 7, or 6, more preferred less than 5 or 4, even more preferred less than 3, even more preferred less than 2, even more preferred 0 amino acids are inserted into a consensus sequence or protein motif.

The consensus sequence was derived from a multiple alignment of the sequences as listed in SEQ ID No. 51 to 63.

Conserved patterns are identified with the software tool MEME version 3.5.1 or manually. MEME was developed by Timothy L. Bailey and Charles Elkan, Dept. of Computer Science and Engeneering, University of California, San Diego, USA and is described by Timothy L. Bailey and Charles Elkan (Fitting a mixture model by expectation maximization to discover motifs in biopolymers, Proceedings of the Second International Conference on Intelligent Systems for Molecular Biology, pp. 28-36, AAAI Press, Menlo Park, Calif., 1994). The source code for the stand-alone program is publicly available from the San Diego Supercomputer center (at meme.sdsc.edu).

For identifying common motifs in all sequences with the software tool MEME, the following settings are used: -maxsize 500000, -nmotifs 15, -evt 0.001, -maxw 60, distance 1e-3, -minsites number of sequences used for the analysis. Input sequences for MEME are non-aligned sequences in Fasta format. Other parameters are used in the default settings in this software version.

Prosite patterns for conserved domains are generated with the software tool Pratt version 2.1 or manually. Pratt was developed by Inge Jonassen, Dept. of Informatics, University of Bergen, Norway and is described by Jonassen et al. (I. Jonassen, J. F. Collins and D. G. Higgins, Finding flexible patterns in unaligned protein sequences, Protein Science 4 (1995), pp. 1587-1595; I. Jonassen, Efficient discovery of conserved patterns using a pattern graph, Submitted to CABIOS Febr. 1997]. The source code (ANSI C) for the stand-alone program is public available, e.g. at established Bioinformatic centers like EBI (European Bioinformatics Institute).

For generating patterns with the software tool Pratt, following settings are used: PL (max Pattern Length): 100, PN (max Nr of Pattern Symbols): 100, PX (max Nr of consecutive x's): 30, FN (max Nr of flexible spacers): 5, FL (max Flexibility): 30, FP (max Flex.Product): 10, ON (max number patterns): 50. Input sequences for Pratt are distinct regions of the protein sequences exhibiting high similarity as identified from software tool MEME. The minimum number of sequences, which have to match the generated patterns (CM, min Nr of Seqs to Match) was set to at least 80% of the provided sequences. Parameters not mentioned here are used in their default settings.

The Prosite patterns of the conserved domains can be used to search for protein sequences matching this pattern. Various established Bioinformatic centers provide public internet portals for using those patterns in database searches (e.g. PIR (Protein Information Resource, located at Georgetown University Medical Center) or ExPASy (Expert Protein Analysis System)). Alternatively, stand-alone software is available, like the program Fuzzpro, which is part of the EMBOSS software package. For example, the program Fuzzpro not only allows to search for an exact pattern-protein match but also allows to set various ambiguities in the performed search.

The alignment is performed with the software ClustalW (version 1.83) and is described by Thompson et al. (Nucleic Acids Research 22, 4673 (1994)). The source code for the stand-alone program is public available from the European Molecular Biology Laboratory; Heidelberg, Germany. The analysis was performed using the default parameters of ClustalW v1.83 (gap open penalty: 10.0; gap extension penalty: 0.2; protein matrix: Gonnet; protein/DNA endgap: −1; protein/DNA gapdist: 4).

Degenerated primers can then be utilized by PCR for the amplification of fragments of novel proteins having abovementioned activity, e.g. conferring the increased yield as compared to a corresponding non-transformed wild type plant cell, plant or part thereof after increasing the expression or activity or having the activity of a protein selected from the group consisting of SEQ ID NOs: 2, 4, 13, 51, 52, 53, 54, 55, 56, 57, 58, 59, 60, 61, 62, 63 or further functional homologs of the polypeptide of the invention from other organisms.

These fragments can then be utilized as hybridization probe for isolating the complete gene sequence. As an alternative, the missing 5' and 3' sequences can be isolated by means of RACE-PCR. A nucleic acid molecule according to the invention can be amplified using cDNA or, as an alternative, genomic DNA as template and suitable oligonucleotide primers, following standard PCR amplification techniques. The nucleic acid molecule amplified thus can be cloned into a suitable vector and characterized by means of DNA sequence analysis. Oligonucleotides, which correspond to one of the nucleic acid molecules used in the process can be generated by standard synthesis methods, for example using an automatic DNA synthesizer.

Nucleic acid molecules which are advantageously for the process according to the invention can be isolated based on their homology to the nucleic acid molecules disclosed herein using the sequences or part thereof as hybridization probe and following standard hybridization techniques under stringent hybridization conditions. In this context, it is possible to use, for example, isolated nucleic acid molecules of at least 15, 20, 25, 30, 35, 40, 50, 60 or more nucleotides, preferably of at least 15, or 25 nucleotides in length which hybridize under stringent conditions with the above-described nucleic acid molecules, in particular with those which encompass a nucleotide sequence of the nucleic acid molecule used in the process of the invention or encoding a protein used in the invention or of the nucleic acid molecule of the invention. Nucleic acid molecules with 30, 50, 100, 250 or more nucleotides may also be used.

The term "homology" means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations. These mutations may occur naturally or may be obtained by mutagenesis techniques. The allelic variations may be naturally occurring allelic variants as well as synthetically produced or genetically engineered variants. Structurally equivalents can, for example, be identified by testing the binding of said polypeptide to antibodies or computer based predictions. Structurally equivalent have the similar immunological characteristic, e.g. comprise similar epitopes.

By "hybridizing" it is meant that such nucleic acid molecules hybridize under conventional hybridization conditions, preferably under stringent conditions such as described by, e.g., Sambrook (Molecular Cloning; A Laboratory Manual, 2$^{nd}$ Edition, Cold Spring Harbor Laboratory Press, Cold Spring Harbor, N.Y. (1989)) or in Current Protocols in Molecular Biology, John Wiley & Sons, N.Y. (1989), 6.3.1-6.3.6.

According to the invention, DNA as well as RNA molecules of the nucleic acid of the invention can be used as probes. Further, as template for the identification of functional homologues Northern blot assays as well as Southern blot assays can be performed. The Northern blot assay advantageously provides further informations about the expressed gene product: e.g. expression pattern, occurrence of processing steps, like splicing and capping, etc. The Southern blot assay provides additional information about the chromosomal localization and organization of the gene encoding the nucleic acid molecule of the invention.

A preferred, nonlimiting example of stringent hybridization conditions are hybridizations in 6× sodium chloride/sodium citrate (=SSC) at approximately 45° C., followed by one or more wash steps in 0.2×SSC, 0.1% SDS at 50 to 65° C., for example at 50° C., 55° C. or 60° C. The skilled worker knows that these hybridization conditions differ as a function of the type of the nucleic acid and, for example when organic solvents are present, with regard to the temperature and concentration of the buffer. The temperature under "standard hybridization conditions" differs for example as a function of the type of the nucleic acid between 42° C. and 58° C., preferably between 45° C. and 50° C. in an aqueous buffer with a concentration of 0.1×, 0.5×, 1×, 2×, 3×, 4× or 5×SSC (pH 7.2). If organic solvent(s) is/are present in the abovementioned buffer, for example 50% formamide, the temperature under standard conditions is approximately 40° C., 42° C. or 45° C. The hybridization conditions for DNA:DNA hybrids are preferably for example 0.1×SSC and 20° C., 25° C., 30° C., 35° C., 40° C. or 45° C., preferably between 30° C. and 45° C. The hybridization conditions for DNA:RNA hybrids are preferably for example 0.1×SSC and 30° C., 35° C., 40° C., 45° C., 50° C. or 55° C., preferably between 45° C. and 55° C. The abovementioned hybridization temperatures are determined for example for a nucleic acid approximately 100 bp (=base pairs) in length and a G+C content of 50% in the absence of formamide. The skilled worker knows to determine the hybridization conditions required with the aid of textbooks, for example the ones mentioned above, or from the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

A further example of one such stringent hybridization condition is hybridization at 4×SSC at 65° C., followed by a washing in 0.1×SSC at 65° C. for one hour. Alternatively, an exemplary stringent hybridization condition is in 50% formamide, 4×SSC at 42° C. Further, the conditions during the wash step can be selected from the range of conditions delimited by low-stringency conditions (approximately 2×SSC at 50° C.) and high-stringency conditions (approximately 0.2× SSC at 50° C., preferably at 65° C.) (20×SSC: 0.3 M sodium citrate, 3 M NaCl, pH 7.0). In addition, the temperature during the wash step can be raised from low-stringency conditions at room temperature, approximately 22° C., to higher-stringency conditions at approximately 65° C. Both of the parameters salt concentration and temperature can be varied simultaneously, or else one of the two parameters can be kept constant while only the other is varied. Denaturants, for example formamide or SDS, may also be employed during the hybridization. In the presence of 50% formamide, hybridization is preferably effected at 42° C. Relevant factors like 1)

length of treatment, 2) salt conditions, 3) detergent conditions, 4) competitor DNAs, 5) temperature and 6) probe selection can be combined case by case so that not all possibilities can be mentioned herein.

Thus, in a preferred embodiment, Northern blots are prehybridized with Rothi-Hybri-Quick buffer (Roth, Karlsruhe) at 68° C. for 2 h. Hybridzation with radioactive labelled probe is done overnight at 68° C. Subsequent washing steps are performed at 68° C. with 1×SSC.

For Southern blot assays the membrane is prehybridized with Rothi-Hybri-Quick buffer (Roth, Karlsruhe) at 68° C. for 2 h. The hybridzation with radioactive labelled probe is conducted over night at 68° C. Subsequently the hybridization buffer is discarded and the filter shortly washed using 2×SSC; 0.1% SDS. After discarding the washing buffer new 2×SSC; 0.1% SDS buffer is added and incubated at 68° C. for 15 minutes. This washing step is performed twice followed by an additional washing step using 1×SSC; 0.1% SDS at 68° C. for 10 min.

Some examples of conditions for DNA hybridization (Southern blot assays) and wash step are shown herein below:
(1) Hybridization conditions can be selected, for example, from the following conditions:
(a) 4×SSC at 65° C.,
(b) 6×SSC at 45° C.,
(c) 6×SSC, 100 mg/ml denatured fragmented fish sperm DNA at 68° C.,
(d) 6×SSC, 0.5% SDS, 100 mg/ml denatured salmon sperm DNA at 68° C.,
(e) 6×SSC, 0.5% SDS, 100 mg/ml denatured fragmented salmon sperm DNA, 50% formamide at 42° C.,
(f) 50% formamide, 4×SSC at 42° C.,
(g) 50% (v/v) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
(h) 2× or 4×SSC at 50° C. (low-stringency condition), or
(i) 30 to 40% formamide, 2× or 4×SSC at 42° C. (low-stringency condition).
(2) Wash steps can be selected, for example, from the following conditions:
(a) 0.015 M NaCl/0.0015 M sodium citrate/0.1% SDS at 50° C.
(b) 0.1×SSC at 65° C.
(c) 0.1×SSC, 0.5% SDS at 68° C.
(d) 0.1×SSC, 0.5% SDS, 50% formamide at 42° C.
(e) 0.2×SSC, 0.1% SDS at 42° C.
(f) 2×SSC at 65° C. (low-stringency condition).

Polypeptides having above-mentioned activity, i.e. conferring increased yield as compared to a corresponding non-transformed wild type plant cell, plant or part thereof, derived from other organisms, can be encoded by other DNA sequences which hybridize to the sequences selected from the group consisting of SEQ ID NOs: 1, 3, 12, 38, 39, 40, 41, 42, 43, 44, 45, 46, 47, 48, 49, 50 under relaxed hybridization conditions and which code on expression for peptides conferring the enhanced cold tolerance, and/or increased yield, as compared to a corresponding non-transformed wild type plant cell, plant or part thereof.

Further, some applications have to be performed at low stringency hybridization conditions, without any consequences for the specificity of the hybridization. For example, a Southern blot analysis of total DNA could be probed with a nucleic acid molecule of the present invention and washed at low stringency (55° C. in 2×SSPE, 0.1% SDS). The hybridization analysis could reveal a simple pattern of only genes encoding polypeptides of the present invention or used in the process of the invention, e.g. having the herein-mentioned activity of increasing the yield as compared to a corresponding non-transformed wild type plant cell, plant or part thereof. A further example of such low-stringent hybridization conditions is 4×SSC at 50° C. or hybridization with 30 to 40% formamide at 42° C. Such molecules comprise those which are fragments, analogues or derivatives of the polypeptide of the invention or used in the process of the invention and differ, for example, by way of amino acid and/or nucleotide deletion(s), insertion(s), substitution (s), addition(s) and/or recombination (s) or any other modification(s) known in the art either alone or in combination from the above-described amino acid sequences or their underlying nucleotide sequence(s). However, it is preferred to use high stringency hybridization conditions.

Hybridization should advantageously be carried out with fragments of at least 5, 10, 15, 20, 25, 30, 35 or 40 bp, advantageously at least 50, 60, 70 or 80 bp, preferably at least 90, 100 or 110 bp. Most preferably are fragments of at least 15, 20, or 30 bp. Preferably are also hybridizations with at least 100 bp or 200, very especially preferably at least 400 bp in length. In an especially preferred embodiment, the hybridization should be carried out with the entire nucleic acid sequence with conditions described above.

The terms "fragment", "fragment of a sequence" or "part of a sequence" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to or hybridizing with the nucleic acid molecule of the invention or used in the process of the invention under stringend conditions, while the maximum size is not critical. In some applications, the maximum size usually is not substantially greater than that required to provide the desired activity and/or function(s) of the original sequence.

Typically, the truncated amino acid sequence will range from about 5 to about 310 amino acids in length. More typically, however, the sequence will be a maximum of about 250 amino acids in length, preferably a maximum of about 200 or 100 amino acids. It is usually desirable to select sequences of at least about 10, 12 or 15 amino acids, up to a maximum of about 20 or 25 amino acids.

The term "epitope" relates to specific immunoreactive sites within an antigen, also known as antigenic determinates. These epitopes can be a linear array of monomers in a polymeric composition—such as amino acids in a protein—or consist of or comprise a more complex secondary or tertiary structure. Those of skill will recognize that immunogens (i.e., substances capable of eliciting an immune response) are antigens; however, some antigen, such as haptens, are not immunogens but may be made immunogenic by coupling to a carrier molecule. The term "antigen" includes references to a substance to which an antibody can be generated and/or to which the antibody is specifically immunoreactive.

In one embodiment the present invention relates to a epitope of the polypeptide of the present invention or used in the process of the present invention and confers an increased yield as compared to a corresponding non-transformed wild type plant cell, plant or part thereof.

The term "one or several amino acids" relates to at least one amino acid but not more than that number of amino acids, which would result in a homology of below 50% identity. Preferably, the identity is more than 70% or 80%, more preferred are 85%, 90%, 91%, 92%, 93%, 94% or 95%, even more preferred are 96%, 97%, 98%, or 99% identity.

Further, the nucleic acid molecule of the invention comprises a nucleic acid molecule, which is a complement of one of the nucleotide sequences of above mentioned nucleic acid molecules or a portion thereof. A nucleic acid molecule which is complementary to one of the nucleotide sequences selected from the group consisting of SEQ ID NOs: 1, 3, 12, 38, 39, 40, 41, 42, 43, 44, 45, 46, 47, 48, 49, 50 is one which is sufficiently complementary to one of the nucleotide sequences selected from the group consisting of SEQ ID NOs: 1, 3, 12, 38, 39, 40, 41, 42, 43, 44, 45, 46, 47, 48, 49, 50 such that it can hybridize to one of the nucleotide sequences selected from the group consisting of SEQ ID NOs: 1, 3, 12, 38, 39, 40, 41, 42, 43, 44, 45, 46, 47, 48, 49, 50, thereby forming a stable duplex. Preferably, the hybridization is performed under stringent hybridization conditions. However, a complement of one of the herein disclosed sequences is preferably a sequence complement thereto according to the base pairing of nucleic acid molecules well known to the skilled person. For example, the bases A and G undergo base pairing with the bases T and U or C, resp. and visa versa. Modifications of the bases can influence the base-pairing partner.

The nucleic acid molecule of the invention comprises a nucleotide sequence which is at least about 30%, 35%, 40% or 45%, preferably at least about 50%, 55%, 60% or 65%, more preferably at least about 70%, 80%, or 90%, and even more preferably at least about 95%, 97%, 98%, 99% or more homologous to a nucleotide sequence selected from the group consisting of SEQ ID NOs: 1, 3, 12, 38, 39, 40, 41, 42, 43, 44, 45, 46, 47, 48, 49, 50, or a portion thereof and preferably has above mentioned activity, in particular having yield increasing activity after increasing the activity or an activity of a gene product selected from the group consisting of SEQ ID NOs: 2, 4, 13, 51, 52, 53, 54, 55, 56, 57, 58, 59, 60, 61, 62, 63 by for example expression either in the cytosol or in an organelle such as a plastid or mitochondria or both, preferably in plastids.

The nucleic acid molecule of the invention comprises a nucleotide sequence which hybridizes, preferably hybridizes under stringent conditions as defined herein, to one of the nucleotide sequences selected from the group consisting of SEQ ID NOs: 1, 3, 12, 38, 39, 40, 41, 42, 43, 44, 45, 46, 47, 48, 49, 50, or a portion thereof and encodes a protein having above-mentioned activity, e.g. conferring an enhanced increased yield as compared to a corresponding non-transformed wild type plant cell, plant or part thereof by for example expression either in the cytosol or in an organelle such as a plastid or mitochondria or both, preferably in plastids, and optionally, the activity selected from the group consisting of phosphoribosyl pyrophosphate synthases.

Moreover, the nucleic acid molecule of the invention can comprise only a portion of the coding region of one of the sequences selected from the group consisting of SEQ ID NOs: 1, 3, 12, 38, 39, 40, 41, 42, 43, 44, 45, 46, 47, 48, 49, 50, for example a fragment which can be used as a probe or primer or a fragment encoding a biologically active portion of the polypeptide of the present invention or of a polypeptide used in the process of the present invention, i.e. having above-mentioned activity, e.g. conferring an enhanced yield as compared to a corresponding non-transformed wild type plant cell, plant or part thereof its activity is increased by for example expression either in the cytosol or in an organelle such as a plastid or mitochondria or both, preferably in plastids. The nucleotide sequences determined from the cloning of the present protein-according-to-the-invention-encoding gene allows for the generation of probes and primers designed for use in identifying and/or cloning its homologues in other cell types and organisms. The probe/primer typically comprises substantially purified oligonucleotide. The oligonucleotide typically comprises a region of nucleotide sequence that hybridizes under stringent conditions to at least about 12, preferably about 20 or 25, more preferably about 40, 50 or 75 consecutive nucleotides of a sense strand of one of the sequences set forth, e.g., selected from the group consisting of SEQ ID NOs: 1, 3, 12, 38, 39, 40, 41, 42, 43, 44, 45, 46, 47, 48, 49, 50, an anti-sense sequence of one of the sequences, e.g., selected from the group consisting of SEQ ID NOs: 1, 3, 12, 38, 39, 40, 41, 42, 43, 44, 45, 46, 47, 48, 49, 50, or naturally occurring mutants thereof. Primers based on a nucleotide of invention can be used in PCR reactions to clone homologues of the polypeptide of the invention or of the polypeptide used in the process of the invention, e.g. as the primers described in the examples of the present invention, e.g. as shown in the examples. A PCR with the primers selected from the group consisting of SEQ ID NOs: 5, 6 will result in a fragment of the gene product selected from the group consisting of SEQ ID NOs: 2, 4, 13, 51, 52, 53, 54, 55, 56, 57, 58, 59, 60, 61, 62, 63.

Primer sets are interchangable. The person skilled in the art knows to combine said primers to result in the desired product, e.g. in a full length clone or a partial sequence. Probes based on the sequences of the nucleic acid molecule of the invention or used in the process of the present invention can be used to detect transcripts or genomic sequences encoding the same or homologous proteins. The probe can further comprise a label group attached thereto, e.g. the label group can be a radioisotope, a fluorescent compound, an enzyme, or an enzyme co-factor. Such probes can be used as a part of a genomic marker test kit for identifying cells which express an polypeptide of the invention or used in the process of the present invention, such as by measuring a level of an encoding nucleic acid molecule in a sample of cells, e.g., detecting mRNA levels or determining, whether a genomic gene comprising the sequence of the polynucleotide of the invention or used in the process of the present invention has been mutated or deleted.

The nucleic acid molecule of the invention encodes a polypeptide or portion thereof which includes an amino acid sequence which is sufficiently homologous to the amino acid sequence selected from the group consisting of SEQ ID NOs: 2, 4, 13, 51, 52, 53, 54, 55, 56, 57, 58, 59, 60, 61, 62, 63 such that the protein or portion thereof maintains the ability to participate in the increase of yield as compared to a corresponding non-transformed wild type plant cell, plant or part thereof, in particular increasing the activity as mentioned above or as described in the examples in plants is comprised.

As used herein, the language "sufficiently homologous" refers to proteins or portions thereof which have amino acid sequences which include a minimum number of identical or equivalent amino acid residues (e.g., an amino acid residue which has a similar side chain as an amino acid residue in one of the sequences of the polypeptide of the present invention) to an amino acid sequence selected from the group consisting of SEQ ID NOs: 2, 4, 13, 51, 52, 53, 54, 55, 56, 57, 58, 59, 60, 61, 62, 63 such that the protein or portion thereof is able to participate in the increase of yield as compared to a corresponding non-transformed wild type plant cell, plant or part thereof. For examples having the activity of a phosphoribosyl pyrophosphate synthase as described herein.

In one embodiment, the nucleic acid molecule of the present invention comprises a nucleic acid that encodes a portion of the protein of the present invention. The protein is at least about 30%, 35%, 40%, 45% or 50%, preferably at least about 55%, 60%, 65% or 70%, and more preferably at least about 75%, 80%, 85%, 90%, 91%, 92%, 93% or 94% and most preferably at least about 95%, 97%, 98%, 99% or more homologous to an entire amino acid sequence selected from the group consisting of SEQ ID NOs: 2, 4, 13, 51, 52, 53, 54, 55, 56, 57, 58, 59, 60, 61, 62, 63 and having above-mentioned activity, e.g. conferring an increased yield as compared to a corresponding non-transformed wild type plant cell, plant or part thereof by for example expression either in the cytsol or in an organelle such as a plastid or mitochondria or both, preferably in plastids.

Portions of proteins encoded by the nucleic acid molecule of the invention are preferably biologically active, preferably having above-mentioned annotated activity, e.g. conferring an increase in yield as compared to a corresponding non-transformed wild type plant cell, plant or part thereof after increase of activity.

As mentioned herein, the term "biologically active portion" is intended to include a portion, e.g., a domain/motif, that confers an increase in yield as compared to a corresponding non-transformed wild type plant cell, plant or part thereof or has an immunological activity such that it is binds to an antibody binding specifically to the polypeptide of the present invention or a polypeptide used in the process of the present invention for an increased yield as compared to a corresponding non-transformed wild type plant cell, plant or part thereof.

The invention further relates to nucleic acid molecules that differ from one of the nucleotide sequences selected from the group consisting of SEQ ID NOs: 1, 3, 12, 38, 39, 40, 41, 42, 43, 44, 45, 46, 47, 48, 49, 50 (and portions thereof) due to degeneracy of the genetic code and thus encode a polypeptide of the present invention, in particular a polypeptide having above mentioned activity, e.g. as that polypeptides selected from the group consisting of SEQ ID NOs: 2, 4, 13, 51, 52, 53, 54, 55, 56, 57, 58, 59, 60, 61, 62, 63 or the functional homologues. Advantageously, the nucleic acid molecule of the invention comprises, or in an other embodiment has, a nucleotide sequence encoding a protein comprising, or in an other embodiment having, an amino acid sequence selected from the group consisting of SEQ ID NOs: 2, 4, 13, 51, 52, 53, 54, 55, 56, 57, 58, 59, 60, 61, 62, 63 or the functional homologues. In a still further embodiment, the nucleic acid molecule of the invention encodes a full length protein which is substantially homologous to an amino acid sequence selected from the group consisting of SEQ ID NOs: 2, 4, 13, 51, 52, 53, 54, 55, 56, 57, 58, 59, 60, 61, 62, 63 or the functional homologues. However, in a preferred embodiment, the nucleic acid molecule of the present invention does not consist of the sequence selected from the group consisting of SEQ ID NOs: 1, 3, 12, 38, 39, 40, 41, 42, 43, 44, 45, 46, 47, 48, 49, 50.

In addition, it will be appreciated by those skilled in the art that DNA sequence polymorphisms that lead to changes in the amino acid sequences may exist within a population. Such genetic polymorphism in the gene encoding the polypeptide of the invention or comprising the nucleic acid molecule of the invention may exist among individuals within a population due to natural variation.

As used herein, the terms "gene" and "recombinant gene" refer to nucleic acid molecules comprising an open reading frame encoding the polypeptide of the invention or comprising the nucleic acid molecule of the invention or encoding the polypeptide used in the process of the present invention, preferably from a crop plant or from a microorganism useful for the method of the invention. Such natural variations can typically result in 1 to 5% variance in the nucleotide sequence of the gene. Any and all such nucleotide variations and resulting amino acid polymorphisms in genes encoding a polypeptide of the invention or comprising a the nucleic acid molecule of the invention that are the result of natural variation and that do not alter the functional activity as described are intended to be within the scope of the invention.

Nucleic acid molecules corresponding to natural variants homologues of a nucleic acid molecule of the invention, which can also be a cDNA, can be isolated based on their homology to the nucleic acid molecules disclosed herein using the nucleic acid molecule of the invention, or a portion thereof, as a hybridization probe according to standard hybridization techniques under stringent hybridization conditions.

Accordingly, in another embodiment, a nucleic acid molecule of the invention is at least 15, 20, 25 or 30 nucleotides in length. Preferably, it hybridizes under stringent conditions to a nucleic acid molecule comprising a nucleotide sequence of the nucleic acid molecule of the present invention or used in the process of the present invention, e.g. comprising the sequence selected from the group consisting of SEQ ID NOs: 1, 3, 12, 38, 39, 40, 41, 42, 43, 44, 45, 46, 47, 48, 49, 50. The nucleic acid molecule is preferably at least 20, 30, 50, 100, 250 or more nucleotides in length.

The term "hybridizes under stringent conditions" is defined above. In one embodiment, the term "hybridizes under stringent conditions" is intended to describe conditions for hybridization and washing under which nucleotide sequences at least 30%, 40%, 50% or 65% identical to each other typically remain hybridized to each other. Preferably, the conditions are such that sequences at least about 70%, more preferably at least about 75% or 80%, and even more preferably at least about 85%, 90% or 95% or more identical to each other typically remain hybridized to each other.

Preferably, nucleic acid molecule of the invention that hybridizes under stringent conditions to a sequence selected from the group consisting of SEQ ID NOs: 1, 3, 12, 38, 39, 40, 41, 42, 43, 44, 45, 46, 47, 48, 49, 50 corresponds to a naturally-occurring nucleic acid molecule of the invention. As used herein, a "naturally-occurring" nucleic acid molecule refers to an RNA or DNA molecule having a nucleotide sequence that occurs in nature (e.g., encodes a natural protein). Preferably, the nucleic acid molecule encodes a natural protein having above-mentioned activity, e.g. conferring increased yield after increasing the expression or activity thereof or the activity of a protein of the invention or used in the process of the invention by for example expression the nucleic acid sequence of the gene product in the cytsol and/or in an organelle such as a plastid or mitochondria, preferably in plastids.

In addition to naturally-occurring variants of the sequences of the polypeptide or nucleic acid molecule of the invention as well as of the polypeptide or nucleic acid molecule used in the process of the invention that may exist in the population, the skilled artisan will further appreciate that changes can be introduced by mutation into a nucleotide sequence of the nucleic acid molecule encoding the polypeptide of the invention or used in the process of the present invention, thereby leading to changes in the amino acid sequence of the encoded said polypeptide, without altering the functional ability of the polypeptide, preferably not decreasing said activity.

For example, nucleotide substitutions leading to amino acid substitutions at "non-essential" amino acid residues can be made in a sequence of the nucleic acid molecule of the invention or used in the process of the invention, e.g. selected from the group consisting of SEQ ID NOs: 1, 3, 12, 38, 39, 40, 41, 42, 43, 44, 45, 46, 47, 48, 49, 50.

A "non-essential" amino acid residue is a residue that can be altered from the wild-type sequence of one without altering the activity of said polypeptide, whereas an "essential" amino acid residue is required for an activity as mentioned above, e.g. leading to an increase of yield as compared to a corresponding non-transformed wild type plant cell, plant or part thereof in an organism after an increase of activity of the polypeptide. Other amino acid residues, however, (e.g., those that are not conserved or only semi-conserved in the domain having said activity) may not be essential for activity and thus are likely to be amenable to alteration without altering said activity.

Further, a person skilled in the art knows that the codon usage between organisms can differ. Therefore, he may adapt the codon usage in the nucleic acid molecule of the present invention to the usage of the organism or the cell compartment for example of the plastid or mitochondria in which the polynucleotide or polypeptide is expressed.

Accordingly, the invention relates to nucleic acid molecules encoding a polypeptide having above-mentioned activity, in an organisms or parts thereof by for example expression either in the cytsol or in an organelle such as a plastid or mitochondria or both, preferably in plastids that contain changes in amino acid residues that are not essential for said activity. Such polypeptides differ in amino acid sequence from a sequence contained in the sequences selected from the group consisting of SEQ ID NOs: 2, 4, 13, 51, 52, 53, 54, 55, 56, 57, 58, 59, 60, 61, 62, 63 yet retain said activity described herein. The nucleic acid molecule can comprise a nucleotide sequence encoding a polypeptide, wherein the polypeptide comprises an amino acid sequence at least about 50% identical to an amino acid sequence selected from the group consisting of SEQ ID NOs: 2, 4, 13, 51, 52, 53, 54, 55, 56, 57, 58, 59, 60, 61, 62, 63 and is capable of participation in the increase of yield as compared to a corresponding non-transformed wild type plant cell, plant or part thereof after increasing its activity, e.g. its expression by for example expression either in the cytsol or in an organelle such as a plastid or mitochondria or both, preferably in plastids. Preferably, the protein encoded by the nucleic acid molecule is at least about 60% identical to the sequence selected from the group consisting of SEQ ID NOs: 2, 4, 13, 51, 52, 53, 54, 55, 56, 57, 58, 59, 60, 61, 62, 63, more preferably at least about 70% identical to one of the sequences selected from the group consisting of SEQ ID NOs: 2, 4, 13, 51, 52, 53, 54, 55, 56, 57, 58, 59, 60, 61, 62, 63, even more preferably at least about 80%, 90%, 95% homologous to the sequence shown in table II, columns 5 and 7, and most preferably at least about 96%, 97%, 98%, or 99% identical to the sequence selected from the group consisting of SEQ ID NOs: 2, 4, 13, 51, 52, 53, 54, 55, 56, 57, 58, 59, 60, 61, 62, 63.

To determine the percentage homology (=identity, herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage homology between the two sequences is a function of the number of identical positions shared by the sequences (i.e. % homology=number of identical positions/total number of positions ×100). The terms "homology" and "identity" are thus to be considered as synonyms.

For the determination of the percentage homology (=identity) of two or more amino acids or of two or more nucleotide sequences several computer software programs have been developed. The homology of two or more sequences can be calculated with for example the software fasta, which presently has been used in the version fasta 3 (W. R. Pearson and D. J. Lipman, PNAS 85, 2444 (1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of homologies of different sequences is the standard blast program, which is included in the Biomax pedant software (Biomax, Munich, Federal Republic of Germany). This leads unfortunately sometimes to suboptimal results since blast does not always include complete sequences of the subject and the querry. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast[nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; —l Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25

[Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence homology are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which has 80% homology with sequence SEQ ID NO: 1 at the nucleic acid level is understood as meaning a sequence which, upon comparison with the sequence SEQ ID NO: 1 by the above program "Needle" with the above parameter set, has a 80% homology.

Homology between two polypeptides is understood as meaning the identity of the amino acid sequence over in each case the entire sequence length which is calculated by comparison with the aid of the above program "Needle" using Matrix: EBLOSUM62, Gap_penalty: 8.0, Extend_penalty: 2.0.

For example a sequence which has a 80% homology with sequence SEQ ID NO: 2 at the protein level is understood as meaning a sequence which, upon comparison with the sequence SEQ ID NO: 2 by the above program "Needle" with the above parameter set, has a 80% homology.

Functional equivalents derived from the nucleic acid sequence selected from the group consisting of SEQ ID NOs: 1, 3, 12, 38, 39, 40, 41, 42, 43, 44, 45, 46, 47, 48, 49, 50 according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides selected from the group consisting of SEQ ID NOs: 2, 4, 13, 51, 52, 53, 54, 55, 56, 57, 58, 59, 60, 61, 62, 63 according to the invention and encode polypeptides having essentially the same properties as the polypeptide selected from the group consisting of SEQ ID NOs: 2, 4, 13, 51, 52, 53, 54, 55, 56, 57, 58, 59, 60, 61, 62, 63.

Functional equivalents derived from one of the polypeptides selected from the group consisting of SEQ ID NOs: 2, 4, 13, 51, 52, 53, 54, 55, 56, 57, 58, 59, 60, 61, 62, 63 according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides selected from the group consisting of SEQ ID NOs: 2, 4, 13, 51, 52, 53, 54, 55, 56, 57, 58, 59, 60, 61, 62, 63 according to the invention and having essentially the same properties as the polypeptide selected from the group consisting of SEQ ID NOs: 2, 4, 13, 51, 52, 53, 54, 55, 56, 57, 58, 59, 60, 61, 62, 63.

"Essentially the same properties" of a functional equivalent is above all understood as meaning that the functional equivalent has above mentioned activity, by for example expression either in the cytsol or in an organelle such as a plastid or mitochondria or both, preferably in plastids while increasing the amount of protein, activity or function of said functional equivalent in an organism, e.g. a microorganism, a plant or plant tissue or animal tissue, plant or animal cells or a part of the same.

A nucleic acid molecule encoding an homologous to a protein sequence selected from the group consisting of SEQ ID NOs: 2, 4, 13, 51, 52, 53, 54, 55, 56, 57, 58, 59, 60, 61, 62, 63 can be created by introducing one or more nucleotide substitutions, additions or deletions into a nucleotide sequence of the nucleic acid molecule of the present invention, in particular selected from the group consisting of SEQ ID NOs: 1, 3, 12, 38, 39, 40, 41, 42, 43, 44, 45, 46, 47, 48, 49, 50 such that one or more amino acid substitutions, additions or deletions are introduced into the encoded protein. Mutations can be introduced into the encoding sequences selected from the group consisting of SEQ ID NOs: 1, 3, 12, 38, 39, 40, 41, 42, 43, 44, 45, 46, 47, 48, 49, 50 by standard techniques, such as site-directed mutagenesis and PCR-mediated mutagenesis.

Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophane), beta-branched side chains (e.g., threonine, valine, isoleucine) and aromatic side chains (e.g., tyrosine, phenylalanine, tryptophane, histidine).

Thus, a predicted nonessential amino acid residue in a polypeptide of the invention or a polypeptide used in the process of the invention is preferably replaced with another amino acid residue from the same family. Alternatively, in another embodiment, mutations can be introduced randomly along all or part of a coding sequence of a nucleic acid molecule of the invention or used in the process of the invention, such as by saturation mutagenesis, and the resultant mutants can be screened for activity described herein to identify mutants that retain or even have increased above mentioned activity, e.g. conferring an increased yield as compared to a corresponding non-transformed wild type plant cell, plant or part thereof.

Following mutagenesis of one of the sequences as shown herein, the encoded protein can be expressed recombinantly and the activity of the protein can be determined using, for example, assays described herein (see Examples).

The highest homology of the nucleic acid molecule used in the process according to the invention was found for the following database entries by Gap search.

Homologues of the nucleic acid sequences used, with the sequence selected from the group consisting of SEQ ID NOs: 1, 3, 12, 38, 39, 40, 41, 42, 43, 44, 45, 46, 47, 48, 49, 50, comprise also allelic variants with at least approximately 30%, 35%, 40% or 45% homology, by preference at least approximately 50%, 60% or 70%, more preferably at least approximately 90%, 91%, 92%, 93%, 94% or 95% and even more preferably at least approximately 96%, 97%, 98%, 99% or more homology with one of the nucleotide sequences shown or the abovementioned derived nucleic acid sequences or their homologues, derivatives or analogues or parts of these. Allelic variants encompass in particular functional variants which can be obtained by deletion, insertion or substitution of nucleotides from the sequences shown, preferably selected from the group consisting of SEQ ID NOs: 1, 3, 12, 38, 39, 40, 41, 42, 43, 44, 45, 46, 47, 48, 49, 50, or from the derived nucleic acid sequences, the intention being, however, that the enzyme activity or the biological activity of the resulting proteins synthesized is advantageously retained or increased.

In one embodiment of the present invention, the nucleic acid molecule of the invention or used in the process of the invention comprises the sequences selected from the group consisting of SEQ ID NOs: 1, 3, 12, 38, 39, 40, 41, 42, 43, 44, 45, 46, 47, 48, 49, 50. It is preferred that the nucleic acid molecule comprises as little as possible other nucleotides not shown in any sequence selected from the group consisting of SEQ ID NOs: 1, 3, 12, 38, 39, 40, 41, 42, 43, 44, 45, 46, 47, 48, 49, 50. In one embodiment, the nucleic acid molecule comprises less than 500, 400, 300, 200, 100, 90, 80, 70, 60, 50 or 40 further nucleotides. In a further embodiment, the nucleic acid molecule comprises less than 30, 20 or 10 further nucleotides. In one embodiment, the nucleic acid molecule use in the process of the invention is identical to the sequences selected from the group consisting of SEQ ID NOs: 1, 3, 12, 38, 39, 40, 41, 42, 43, 44, 45, 46, 47, 48, 49, 50.

Also preferred is that the nucleic acid molecule used in the process of the invention encodes a polypeptide comprising the sequence selected from the group consisting of SEQ ID NOs: 2, 4, 13, 51, 52, 53, 54, 55, 56, 57, 58, 59, 60, 61, 62, 63. In one embodiment, the nucleic acid molecule encodes less than 150, 130, 100, 80, 60, 50, 40 or 30 further amino acids. In a further embodiment, the encoded polypeptide comprises less than 20, 15, 10, 9, 8, 7, 6 or 5 further amino acids. In one embodiment used in the inventive process, the encoded polypeptide is identical to the sequences selected from the group consisting of SEQ ID NOs: 2, 4, 13, 51, 52, 53, 54, 55, 56, 57, 58, 59, 60, 61, 62, 63.

In one embodiment, the nucleic acid molecule of the invention or used in the process encodes a polypeptide comprising the sequence selected from the group consisting of SEQ ID NOs: 2, 4, 13, 51, 52, 53, 54, 55, 56, 57, 58, 59, 60, 61, 62, 63 comprises less than 100 further nucleotides. In a further embodiment, said nucleic acid molecule comprises less than 30 further nucleotides. In one embodiment, the nucleic acid molecule used in the process is identical to a coding sequence of the sequences selected from the group consisting of SEQ ID NOs: 1, 3, 12, 38, 39, 40, 41, 42, 43, 44, 45, 46, 47, 48, 49, 50.

Polypeptides (=proteins), which still have the essential biological or enzymatic activity of the polypeptide of the present invention conferring an increased yield as compared to a corresponding non-transformed wild type plant cell, plant or part thereof i.e. whose activity is essentially not reduced, are polypeptides with at least 10% or 20%, by preference 30% or 40%, especially preferably 50% or 60%, very especially preferably 80% or 90 or more of the wild type biological activity or enzyme activity, advantageously, the activity is essentially not reduced in comparison with the activity of a polypeptide selected from the group consisting of SEQ ID NOs: 2, 4, 13, 51, 52, 53, 54, 55, 56, 57, 58, 59, 60, 61, 62, 63 expressed under identical conditions.

Homologues of table I, columns 5 and 7 or of the derived sequences selected from the group consisting of SEQ ID NOs: 2, 4, 13, 51, 52, 53, 54, 55, 56, 57, 58, 59, 60, 61, 62, 63 also mean truncated sequences, cDNA, single-stranded DNA or RNA of the coding and noncoding DNA sequence. Homologues of said sequences are also understood as meaning derivatives, which comprise noncoding regions such as, for example, UTRs, terminators, enhancers or promoter variants. The promoters upstream of the nucleotide sequences stated can be modified by one or more nucleotide substitution(s), insertion(s) and/or deletion(s) without, however, interfering with the functionality or activity either of the promoters, the open reading frame (=ORF) or with the 3'-regulatory region such as terminators or other 3'-regulatory regions, which are far away from the ORF. It is furthermore possible that the activity of the promoters is increased by modification of their sequence, or that they are replaced completely by more active promoters, even promoters from heterologous organisms. Appropriate promoters are known to the person skilled in the art and are mentioned herein below.

In addition to the nucleic acid molecules encoding the PRSs described above, another aspect of the invention pertains to negative regulators of the activity of a nucleic acid molecules selected from the group consisting of SEQ ID NOs: 1, 3, 12, 38, 39, 40, 41, 42, 43, 44, 45, 46, 47, 48, 49, 50. Antisense polynucleotides thereto are thought to inhibit the downregulating activity of those negative regulators by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a negative regulator of the activity of a nucleic acid molecules encoding a polypeptide having at least 80% sequence identity with the polypeptide selected from the group consisting of SEQ ID NOs: 2, 4, 13, 51, 52, 53, 54, 55, 56, 57, 58, 59, 60, 61, 62, 63.

The antisense nucleic acid can be complementary to an entire negative regulator strand, or to only a portion thereof. In an embodiment, the antisense nucleic acid molecule is antisense to a "noncoding region" of the coding strand of a nucleotide sequence encoding a PRS. The term "noncoding region" refers to 5' and 3' sequences that flank the coding region that are not translated into amino acids (i.e., also referred to as 5' and 3' untranslated regions). The antisense nucleic acid molecule can be complementary to only a portion of the noncoding region of PRS mRNA. For example, the antisense oligonucleotide can be complementary to the region surrounding the translation start site of PRS mRNA. An antisense oligonucleotide can be, for example, about 5, 10, 15, 20, 25, 30, 35, 40, 45 or 50 nucleotides in length. Typically, the antisense molecules of the present invention comprise an RNA having 60-100% sequence identity with at least 14 consecutive nucleotides of a noncoding region of one of the nucleic acid selected from the group consisting of SEQ ID NOs: 1, 3, 12, 38, 39, 40, 41, 42, 43, 44, 45, 46, 47, 48, 49, 50. Preferably, the sequence identity will be at least 70%, more preferably at least 75%, 80%, 85%, 90%, 95%, 98% and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)-uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyl uracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N2-carboxypropyl)-uracil, acp3 and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual b-units, the strands run parallel to each other (Gaultier et al., Nucleic Acids. Res. 15, 6625 (1987)). The antisense nucleic acid molecule can also comprise a 2'-o-methylribonucleotide (Inoue et al., Nucleic Acids Res. 15, 6131 (1987)) or a chimeric RNA-DNA analogue (Inoue et al., FEBS Lett. 215, 327 (1987)).

The antisense nucleic acid molecules of the invention are typically administered to a cell or generated in situ such that they hybridize with or bind to cellular mRNA and/or genomic DNA. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of a PRS polypeptide. By "ribozyme" is meant a catalytic RNA-based enzyme with ribonuclease activity which is capable of cleaving a single-stranded nucleic acid, such as an mRNA, to which it has a complementary region. Ribozymes (e.g., hammerhead ribozymes described in Haselhoff and Gerlach, Nature 334, 585 (1988)) can be used to catalytically cleave PRS mRNA transcripts to thereby inhibit translation of PRS mRNA. A ribozyme having specificity for a PRS-encoding nucleic acid can be designed based upon the nucleotide sequence of a PRS cDNA, as disclosed herein or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a PRS-encoding mRNA. See, e.g. U.S. Pat. Nos. 4,987,071 and 5,116,742 to Cech et al. Alternatively, PRS mRNA can be used to select a catalytic RNA having a specific ribonuclease activity from a pool of RNA molecules. See, e.g. Bartel D., and Szostak J. W., Science 261, 1411 (1993). In preferred embodiments, the ribozyme will contain a portion having at least 7, 8, 9, 10, 12, 14, 16, 18 or 20 nucleotides, and more preferably 7 or 8 nucleotides, that have 100% complementarity to a portion of the target RNA. Methods for making ribozymes are known to those skilled in the art. See, e.g. U.S. Pat. Nos. 6,025,167, 5,773,260 and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide selected from the group consisting of SEQ ID NOs: 2, 4, 13, 51, 52, 53, 54, 55, 56, 57, 58, 59, 60, 61, 62, 63 or a polypeptide having at least 70% sequence identity with a polypeptide selected from the group consisting of SEQ ID NOs: 2, 4, 13, 51, 52, 53, 54, 55, 56, 57, 58, 59, 60, 61, 62, 63. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides or ribonucleotide analogs, such as 2'-O-methyl ribosyl residues, or combinations thereof. See, e.g. U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g. U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., Science 238, 645 (1987), and Cooney et al., Science 241, 456 (1988)) and cosuppression (Napoli et al., The Plant Cell 2, 279, 1990,) are known in the art. Partial and full-length cDNAs have been used for the cosuppression of endogenous plant genes. See, e.g. U.S. Pat. Nos. 4,801,340, 5,034,323, 5,231,020, and 5,283,184; Van der Kroll et al., The Plant Cell 2, 291, (1990); Smith et al., Mol. Gen. Genetics 224, 477 (1990), and Napoli et al., The Plant Cell 2, 279 (1990).

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95% or more. The introduced sense polynucleotide need not be full length relative to the target gene or transcript. Preferably, the sense polynucleotide will have at least 65% sequence identity with at least 100 consecutive nucleotides of one of the nucleic acids selected from the group consisting of SEQ ID NOs: 1, 3, 12, 38, 39, 40, 41, 42, 43, 44, 45, 46, 47, 48, 49, 50. The regions of identity can comprise introns and/or exons and untranslated regions. The introduced sense polynucleotide may be present in the plant cell transiently, or may be stably integrated into a plant chromosome or extrachromosomal replicon.

Further, object of the invention is an expression vector comprising a nucleic acid molecule comprising a nucleic acid molecule selected from the group consisting of:

(a) a nucleic acid molecule encoding the polypeptide selected from the group consisting of SEQ ID NOs: 2, 4, 13, 51, 52, 53, 54, 55, 56, 57, 58, 59, 60, 61, 62, 63;

(b) a nucleic acid molecule selected from the group consisting of SEQ ID NOs: 1, 3, 12, 38, 39, 40, 41, 42, 43, 44, 45, 46, 47, 48, 49, 50;

(c) a nucleic acid molecule, which, as a result of the degeneracy of the genetic code, can be derived from a polypeptide sequence selected from the group consisting of SEQ ID NOs: 2, 4, 13, 51, 52, 53, 54, 55, 56, 57, 58, 59, 60, 61, 62, 63, and confers an increased yield as compared to a corresponding non-transformed wild type plant cell, a plant or a part thereof;

(d) a nucleic acid molecule having at least 30% identity, preferably at least 40%, 50%, 60%, 70%, 75%, 80%, 85%, 90%, 95%, 96%, 97%, 98%, 99%, 99.5% with the nucleic acid molecule sequence of a polynucleotide comprising the nucleic acid molecule selected from the group consisting of SEQ ID NOs: 1, 3, 12, 38, 39, 40, 41, 42, 43, 44, 45, 46, 47, 48, 49, 50, and confers an increased yield as compared to a corresponding non-transformed wild type plant cell, a plant or a part thereof;

(e) a nucleic acid molecule encoding a polypeptide having at least 30% identity, preferably at least 40%, 50%, 60%, 70%, 75%, 80%, 85%, 90%, 95%, 96%, 97%, 98%, 99%, 99.5%, with the amino acid sequence of the polypeptide encoded by the nucleic acid molecule of (a), (b), (c) or (d) and having the activity represented by a nucleic acid molecule comprising a polynucleotide selected from the group consisting of SEQ ID NOs: 1, 3, 12, 38, 39, 40, 41, 42, 43, 44, 45, 46, 47, 48, 49, 50, and confers an increased yield as compared to a corresponding non-transformed wild type plant cell, a plant or a part thereof;

(f) nucleic acid molecule which hybridizes with a nucleic acid molecule of (a), (b), (c), (d) or (e) under stringent hybridization conditions and confers an increased yield as compared to a corresponding non-transformed wild type plant cell, a plant or a part thereof;

(g) a nucleic acid molecule encoding a polypeptide which can be isolated with the aid of monoclonal or polyclonal antibodies made against a polypeptide encoded by one of the nucleic acid molecules of (a), (b), (c), (d), (e) or (f) and having the activity represented by the nucleic acid molecule comprising a polynucleotide selected from the group consisting of SEQ ID NOs: 1, 3, 12, 38, 39, 40, 41, 42, 43, 44, 45, 46, 47, 48, 49, 50;

(h) a nucleic acid molecule encoding a polypeptide comprising the polypeptide motif of the ADP binding site selected from the group consisting of SEQ ID NOs: 7, 8, 9, 10, 11, 14, 15, 16, 17, 18, or a polypeptide comprising a polypeptide according to the motif selected from the group consisting of SEQ ID No. 64, 65, 66, 67, 68, 69, 70, 71, 72, 73 and preferably having the activity represented by a nucleic acid molecule comprising a polynucleotide selected from the group consisting of SEQ ID NOs: 1, 3, 12, 38, 39, 40, 41, 42, 43, 44, 45, 46, 47, 48, 49, 50;

(i) a nucleic acid molecule encoding a polypeptide having the activity represented by a protein selected from the group consisting of SEQ ID NOs: 2, 4, 13, 51, 52, 53, 54, 55, 56, 57, 58, 59, 60, 61, 62, 63, and confers an increased yield as compared to a corresponding non-transformed wild type plant cell, a plant or a part thereof;

(j) nucleic acid molecule which comprises a polynucleotide, which is obtained by amplifying a cDNA library or a genomic library using the primers selected from the group consisting of SEQ ID NOs: 5, 6, which do not start at their 5'-end with the nucleotides ATA and preferably having the activity represented by a nucleic acid molecule comprising a polynucleotide as depicted in column 5 of table II or IV, application no. 1; and (k) a nucleic acid molecule which is obtainable by screening a suitable nucleic acid library, especially a cDNA library and/or a genomic library, under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt, 500 nt, 750 or 1000 nt of a nucleic acid molecule complementary to a nucleic acid molecule sequence characterized in (a) to (e) and encoding a polypeptide having the activity represented by a protein comprising a polypeptide selected from the group consisting of SEQ ID NOs: 2, 4, 13, 51, 52, 53, 54, 55, 56, 57, 58, 59, 60, 61, 62, 63.

The invention further provides an isolated recombinant expression vector comprising a PRS encoding nucleic acid as described above, wherein expression of the vector or PRS encoding nucleic acid, respectively in a host cell results in increased yield as compared to the corresponding non-transformed wild type of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Further types of vectors can be linearized nucleic acid sequences, such as transposons, which are pieces of DNA which can copy and insert themselves. There have been 2 types of transposons found: simple transposons, known as Insertion Sequences and composite transposons, which can have several genes as well as the genes that are required for transposition.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from Agrobacterium tumefaciens T-DNA such as the gene 3 known as octopine synthase of the Ti-plasmid pTiACH5 (Gielen et al., EMBO J. 3, 835 1(984)) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., Nucl. Acids Research 15, 8693 (1987)).

Plant gene expression has to be operably linked to an appropriate promoter conferring gene expression in a timely, cell or tissue specific manner. Preferred are promoters driving constitutive expression (Benfey et al., EMBO J. 8, 2195 (1989)) like those derived from plant viruses like the 35S CaMV (Franck et al., Cell 21, 285 (1980)), the 19S CaMV (see also U.S. Pat. No. 5,352,605 and PCT Application No. WO 84/02913) or plant promoters like those from Rubisco small subunit described in U.S. Pat. No. 4,962,028.

Additional advantageous regulatory sequences are, for example, included in the plant promoters such as CaMV/35S (Franck et al., Cell 21 285 (1980)), PRP1 (Ward et al., Plant. Mol. Biol. 22, 361 (1993)), SSU, OCS, lib4, usp, STLS1, B33, LEB4, nos, ubiquitin, napin or phaseolin promoter. Also advantageous in this connection are inducible promoters such as the promoters described in EP 388 186 (benzyl sulfonamide inducible), Gatz et al., Plant J. 2, 397 (1992) (tetracyclin inducible), EP-A-0 335 528 (abscisic acid inducible) or WO 93/21334 (ethanol or cyclohexenol inducible). Additional useful plant promoters are the cytoplasmic FBPase promotor or ST-LSI promoter of potato (Stockhaus et al., EMBO J. 8, 2445 (1989)), the phosphorybosyl phyrophoshate amido transferase promoter of *Glycine max* (gene bank accession No. U87999) or the noden specific promoter described in EP-A-0 249 676. Additional particularly advantageous promoters are seed specific promoters which can be used for monokotyledones or dikotyledones and are described in U.S. Pat. No. 5,608,152 (napin promoter from rapeseed), WO 98/45461 (phaseolin promoter from *Arobidopsis*), U.S. Pat. No. 5,504,200 (phaseolin promoter from *Phaseolus vulgaris*), WO 91/13980 (Bce4 promoter from *Brassica*) and Baeumlein et al., Plant J., 2 (2), 233 (1992) (LEB4 promoter from leguminosa). Said promoters are useful in dikotyledones. The following promoters are useful for example in monokotyledones lpt-2- or lpt-1-promoter from barley (WO 95/15389 and WO 95/23230) or hordein promoter from barley. Other useful promoters are described in WO 99/16890.

It is possible in principle to use all natural promoters with their regulatory sequences like those mentioned above for the novel process. It is also possible and advantageous in addition to use synthetic promoters.

The gene construct may also comprise further genes which are to be inserted into the organisms and which are for example involved in yield increase. It is possible and advantageous to insert and express in host organisms regulatory genes such as genes for inducers, repressors or enzymes which intervene by their enzymatic activity in the regulation, or one or more or all genes of a biosynthetic pathway. These genes can be heterologous or homologous in origin. The inserted genes may have their own promoter or else be under the control of same promoter as the sequences of the nucleic acid of table I or their homologs.

The gene construct advantageously comprises, for expression of the other genes present, additionally 3' and/or 5' terminal regulatory sequences to enhance expression, which are selected for optimal expression depending on the selected host organism and gene or genes.

These regulatory sequences are intended to make specific expression of the genes and protein expression possible as mentioned above. This may mean, depending on the host organism, for example that the gene is expressed or overexpressed only after induction, or that it is immediately expressed and/or overexpressed.

The regulatory sequences or factors may moreover preferably have a beneficial effect on expression of the introduced genes, and thus increase it. It is possible in this way for the regulatory elements to be enhanced advantageously at the transcription level by using strong transcription signals such as promoters and/or enhancers. However, in addition, it is also possible to enhance translation by, for example, improving the stability of the mRNA.

Other preferred sequences for use in plant gene expression cassettes are targeting-sequences necessary to direct the gene product in its appropriate cell compartment (for review see Kermode, Crit. Rev. Plant Sci. 15 (4), 285 (1996) and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, Annu. Rev. Plant Physiol. Plant Mol. Biol. 48, 89 (1997)). Chemically inducible promoters are especially suitable if gene expression is wanted to occur in a time specific manner.

Table IV lists several examples of promoters that may be used to regulate transcription of the nucleic acid coding sequences of the present invention.

TABLE IV

Examples of tissue-specific and inducible promoters in plants

| Expression | Reference |
|---|---|
| Cor78 - Cold, drought, salt, ABA, wounding-inducible | Ishitani, et al., Plant Cell 9, 1935 (1997), Yamaguchi-Shinozaki and Shinozaki, Plant Cell 6, 251 (1994) |
| Rci2A - Cold, dehydration-inducible | Capel et al., Plant Physiol 115, 569 (1997) |
| Rd22 - Drought, salt | Yamaguchi-Shinozaki and Shinozaki, Mol. Gen. Genet. 238, 17 (1993) |
| Cor15A - Cold, dehydration, ABA | Baker et al., Plant Mol. Biol. 24, 701 (1994) |
| GH3- Auxin inducible | Liu et al., Plant Cell 6, 645 (1994) |
| ARSK1-Root, salt inducible | Hwang and Goodman, Plant J. 8, 37 (1995) |
| PtxA - Root, salt inducible | GenBank accession X67427 |
| SbHRGP3 - Root specific | Ahn et al., Plant Cell 8, 1477 (1998). |
| KST1 - Guard cell specific | Plesch et al., Plant Journal. 28(4), 455- (2001) |
| KAT1 - Guard cell specific | Plesch et al., Gene 249, 83 (2000), Nakamura et al., Plant Physiol. 109, 371 (1995) |
| salicylic acid inducible | PCT Application No. WO 95/19443 |
| tetracycline inducible | Gatz et al., Plant J. 2, 397 (1992) |
| Ethanol inducible | PCT Application No. WO 93/21334 |
| Pathogen inducible PRP1 | Ward et al., Plant. Mol. Biol. 22, 361 -(1993) |
| Heat inducible hsp80 | U.S. Pat. No. 5,187,267 |
| Cold inducible alpha-amylase | PCT Application No. WO 96/12814 |
| Wound-inducible pinII | European Patent No. 375 091 |
| RD29A - salt-inducible | Yamaguchi-Shinozalei et al. Mol. Gen. Genet. 236, 331 (1993) |
| Plastid-specific viral RNA-polymerase | PCT Application No. WO 95/16783, PCT Application WO 97/06250 |

Other promoters, e.g. superpromotor (Ni et al., Plant Journal 7, 661 (1995)), Ubiquitin promoter (Callis et al., J. Biol. Chem., 265, 12486 (1990); U.S. Pat. No. 5,510,474; U.S. Pat. No. 6,020,190; Kawalleck et al., Plant. Molecular Biology, 21, 673 (1993)) or 34S promotor (GenBank Accession numbers M59930 and X16673) were similar useful for the present invention and are known to a person skilled in the art.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., BioEssays 10, 108 (1989). Examples of seed preferred promoters include, but are not limited to, cellulose synthase (celA), Cim1, gamma-zein, globulin-1, maize 19 kD zein (cZ19B1), and the like.

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, Cell 43, 729 (1985)).

The invention further provides a recombinant expression vector comprising a PRS DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a PRS mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub H. et al., Reviews—Trends in Genetics, Vol. 1(1), 23 (1986) and Mol et al., FEBS Letters 268, 427 (1990).

Another aspect of the invention pertains to isolated PRSs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of PRS in which the polypeptide is separated from some of the cellular components of the cells in which it is naturally or recombinantly produced. In one embodiment, the language "substantially free of cellular material" includes preparations of a PRS having less than about 30% (by dry weight) of non-PRS material (also referred to herein as a "contaminating polypeptide"), more preferably less than about 20% of non-PRS material, still more preferably less than about 10% of non-PRS material, and most preferably less than about 5% non-PRS material.

When the PRS or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of PRS in which the polypeptide is separated from chemical precursors or other chemicals that are involved in the synthesis of the polypeptide. In one embodiment, the language "substantially free of chemical precursors or other chemicals" includes preparations of a PRS having less than about 30% (by dry weight) of chemical precursors or non-PRS chemicals, more preferably less than about 20% chemical precursors or non-PRS chemicals, still more preferably less than about 10% chemical precursors or non-PRS chemicals, and most preferably less than about 5% chemical precursors or non-PRS chemicals. In preferred embodiments, isolated polypeptides, or biologically active portions thereof, lack contaminating polypeptides from the same organism from which the PRS is derived. Typically, such polypeptides are produced by recombinant expression of, for example, a *Saccharomyces cerevisiae, E. coli* or *Brassica napus, Glycine max, Zea mays* or *Oryza sativa* PRS, in an microorganism like *Saccharomyces cerevisiae, E. coli, C. glutamicum*, ciliates, algae, fungi or plants, provided that the polypeptide is recombinant expressed in an organism being different to the original organism.

The nucleic acid molecules, polypeptides, polypeptide homologs, fusion polypeptides, primers, vectors, and host cells described herein can be used in one or more of the following methods: identification of *Saccharomyces cerevisiae, E. coli* or *Brassica napus, Glycine max, Zea mays* or *Oryza sativa* and related organisms; mapping of genomes of organisms related to *Saccharomyces cerevisiae, E. coli*; identification and localization of *Saccharomyces cerevisiae, E. coli* or *Brassica napus, Glycine max, Zea mays* or *Oryza sativa* sequences of interest; evolutionary studies; determination of PRS regions required for function; modulation of a PRS activity; modulation of the metabolism of one or more cell functions; modulation of the transmembrane trans-port of one or more compounds; modulation of yield; and modulation of expression of PRS nucleic acids.

The PRS nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the PRS nucleic acid molecules of the invention may result in the production of PRSs having functional differences from the wild-type PRSs. These polypeptides may be improved in efficiency or activity, may be present in greater numbers in the cell than is usual, or may be decreased in efficiency or activity.

There are a number of mechanisms by which the alteration of a PRS of the invention may directly affect yield.

The effect of the genetic modification in plants regarding the yield increasing can be assessed by growing the modified plant under less than suitable conditions and then analyzing the growth characteristics and/or metabolism of the plant. Such analysis techniques are well known to one skilled in the art, and include dry weight, fresh weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, Vol. 17; Rehm et al., 1993 Biotechnology, Vol. 3, Chapter III: Product recovery and purification, page 469-714, VCH: Weinheim; Belter P. A. et al., 1988, Bioseparations: downstream processing for biotechnology, John Wiley and Sons; Kennedy J. F., and Cabral J. M. S., 1992, Recovery processes for biological materials, John Wiley and Sons; Shaeiwitz J. A. and Henry J. D., 1988, Biochemical separations, in Ulmann's Encyclopedia of Industrial Chemistry, Vol. B3, Chapter 11, page 1-27, VCH: Weinheim; and Dechow F. J., 1989, Separation and purification techniques in biotechnology, Noyes Publications).

For example, yeast expression vectors comprising the nucleic acids disclosed herein, or fragments thereof, can be constructed and transformed into *Saccharomyces* cerevisiae using standard protocols. The resulting transgenic cells can then be assayed for generation or alteration of yield. Similarly, plant expression vectors comprising the nucleic acids disclosed herein, or fragments thereof, can be constructed and transformed into an appropriate plant cell such as *Arabidopsis*, soy, rape, maize, cotton, rice, wheat, *Medicago truncatula*, etc., using standard protocols. The resulting transgenic cells and/or plants derived therefrom can then be assayed for generation or alteration of increased yield.

The engineering of one or more genes selected from the group consisting of SEQ ID NOs: 1, 3, 12, 38, 39, 40, 41, 42, 43, 44, 45, 46, 47, 48, 49, 50 and coding for the PRS selected from the group consisting of SEQ ID NOs: 2, 4, 13, 51, 52, 53, 54, 55, 56, 57, 58, 59, 60, 61, 62, 63 of the invention may also result in PRSs having altered activities which indirectly and/or directly impact the yield of plants.

Additionally, the sequences disclosed herein, or fragments thereof, can be used to generate knockout mutations in the genomes of various organisms, such as bacteria, mammalian cells, yeast cells, and plant cells (Girke, T., The Plant Journal 15, 39 (1998)). The resultant knockout cells can then be evaluated for their ability or capacity to increase yield and the effect on the phenotype and/or genotype of the mutation. For other methods of gene inactivation, see U.S. Pat. No. 6,004,804 and Puttaraju et al., Nature Biotechnology 17, 246 (1999).

The aforementioned mutagenesis strategies for PRSs resulting in enhanced increased yield are not meant to be limiting; variations on these strategies will be readily apparent to one skilled in the art. Using such strategies, and incorporating the mechanisms disclosed herein, the nucleic acid and polypeptide molecules of the invention may be utilized to generate algae, plants, fungi expressing mutated PRS nucleic acid and polypeptide molecules such that the yield is improved.

The present invention also provides antibodies that specifically bind to a PRS, or a portion thereof, as encoded by a nucleic acid described herein. Antibodies can be made by many well-known methods (see, e.g. Harlow and Lane, "Antibodies; A Laboratory Manual", Cold Spring Harbor Laboratory, Cold Spring Harbor, New York, (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. See, for example, Kelly et al., Bio/Technology 10, 163 (1992); Bebbington et al., Bio/Technology 10, 169 (1992).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual," Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane, "Antibodies, A Laboratory Manual," Cold Spring Harbor Publications, New York, (1988).

Gene expression in plants is regulated by the interaction of protein transcription factors with specific nucleotide sequences within the regulatory region of a gene. One example of transcription factors are polypeptides that contain zinc finger (ZF) motifs. Each ZF module is approximately 30 amino acids long folded around a zinc ion. The DNA recognition domain of a ZF protein is a α-helical structure that inserts into the major grove of the DNA double helix. The module contains three amino acids that bind to the DNA with each amino acid contacting a single base pair in the target DNA sequence. ZF motifs are arranged in a modular repeating fashion to form a set of fingers that recognize a contiguous DNA sequence. For example, a three-fingered ZF motif will recognize 9 bp of DNA. Hundreds of proteins have been shown to contain ZF motifs with between 2 and 37 ZF modules in each protein (Isalan M. et al., Biochemistry 37 (35), 12026 (1998); Moore M. et al., Proc. Natl. Acad. Sci. USA 98 (4), 1432 (2001) and Moore M. et al., Proc. Natl. Acad. Sci. USA 98 (4), 1437 (2001); U.S. Pat. No. 6,007,988 and U.S. Pat. No. 6,013,453).

The regulatory region of a plant gene contains many short DNA sequences (cis-acting elements) that serve as recognition domains for transcription factors, including ZF proteins. Similar recognition domains in different genes allow the coordinate expression of several genes encoding enzymes in a metabolic pathway by common transcription factors. Variation in the recognition domains among members of a gene family facilitates differences in gene expression within the same gene family, for example, among tissues and stages of development and in response to environmental conditions.

Typical ZF proteins contain not only a DNA recognition domain but also a functional domain that enables the ZF protein to activate or repress transcription of a specific gene. Experimentally, an activation domain has been used to activate transcription of the target gene (U.S. Pat. No. 5,789,538 and patent application WO 95/19431), but it is also possible to link a transcription repressor domain to the ZF and thereby inhibit transcription (patent applications WO 00/47754 and WO 01/002019). It has been reported that an enzymatic function such as nucleic acid cleavage can be linked to the ZF (patent application WO 00/20622).

The invention provides a method that allows one skilled in the art to isolate the regulatory region of one or more PRS encoding genes from the genome of a plant cell and to design zinc finger transcription factors linked to a functional domain that will interact with the regulatory region of the gene. The interaction of the zinc finger protein with the plant gene can be designed in such a manner as to alter expression of the gene and preferably thereby to confer increased yield.

In particular, the invention provides a method of producing a transgenic plant with a PRS coding nucleic acid, wherein expression of the nucleic acid(s) in the plant results in increased yield as compared to a wild type plant comprising: (a) transforming a plant cell with an expression vector comprising a PRS encoding nucleic acid, and (b) generating from the plant cell a transgenic plant with increased yield as compared to a wild type plant. For such plant transformation, binary vectors such as pBinAR can be used (Höfgen and Willmitzer, Plant Science 66, 221 (1990)). Moreover suitable binary vectors are for example pBIN19, pBI101, pGPTV or pPZP (Hajukiewicz P. et al., Plant Mol. Biol., 25, 989 (1994)).

Construction of the binary vectors can be performed by ligation of the cDNA into the T-DNA. 5' to the cDNA a plant promoter activates transcription of the cDNA. A polyadenylation sequence is located 3' to the cDNA. Tissue-specific expression can be achieved by using a tissue specific promoter as listed above. Also, any other promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, Crit. Rev. Plant Sci. 4 (15), 285 (1996)). The signal peptide is cloned 5' in frame to the cDNA to archive subcellular localization of the fusion protein. One skilled in the art will recognize that the promoter used should be operatively linked to the nucleic acid such that the promoter causes transcription of the nucleic acid which results in the synthesis of a mRNA which encodes a polypeptide.

Alternate methods of transfection include the direct transfer of DNA into developing flowers via electroporation or *Agrobacterium* mediated gene transfer. *Agrobacterium* mediated plant transformation can be performed using for example the GV3101(pMP90) (Koncz and Schell, Mol. Gen. Genet. 204, 383 (1986)) or LBA4404 (Ooms et al., Plasmid, 7, 15

(1982); Hoekema et al., Nature, 303, 179 (1983)) *Agrobacterium tumefaciens* strain. Transformation can be performed by standard transformation and regeneration techniques (Deblaere et al., Nucl. Acids. Res. 13, 4777 (1994); Gelvin and Schilperoort, Plant Molecular Biology Manual, 2$^{nd}$ Ed.—Dordrecht: Kluwer Academic Publ., 1995.—in Sect., Ringbuc Zentrale Signatur: BT11-P ISBN 0-7923-2731-4; Glick B. R. and Thompson J. E., Methods in Plant Molecular Biology and Biotechnology, Boca Raton: CRC Press, 1993.-360 S., ISBN 0-8493-5164-2). For example, rapeseed can be transformed via cotyledon or hypocotyl transformation (Moloney et al., Plant Cell Reports 8, 238 (1989); De Block et al., Plant Physiol. 91, 694 (1989)). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., Plant Cell Report 13, 282 (1994)). Additionally, transformation of soybean can be performed using for example a technique described in European Patent No. 424 047, U.S. Pat. No. 5,322,783, European Patent No. 397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique (see, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

Growing the modified plants under defined N-conditions, and then screening and analyzing the growth characteristics and/or metabolic activity assess the effect of the genetic modification in plants on increased yield. Such analysis techniques are well known to one skilled in the art. They include beneath to screening (Römpp Lexikon Biotechnologie, Stuttgart/New York: Georg Thieme Verlag 1992, "screening" p. 701) dry weight, fresh weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, Vol. 17; Rehm et al., 1993 Biotechnology, Vol. 3, Chapter III: Product recovery and purification, page 469-714, VCH: Weinheim; Belter, P. A. et al., 1988 Bioseparations: downstream processing for biotechnology, John Wiley and Sons; Kennedy J. F. and Cabral J. M. S., 1992 Recovery processes for biological materials, John Wiley and Sons; Shaeiwitz J. A. and Henry J. D., 1988 Biochemical separations, in: Ullmann's Encyclopedia of Industrial Chemistry, Vol. B3, Chapter 11, page 1-27, VCH: Weinheim; and Dechow F. J. (1989) Separation and purification techniques in biotechnology, Noyes Publications).

In one embodiment, the present invention relates to a method for the identification of a gene product conferring increased yield as compared to a corresponding non-transformed wild type cell in a cell of an organism for example plant, comprising the following steps:

(a) contacting, e.g. hybridizing, some or all nucleic acid molecules of a sample, e.g. cells, tissues, plants or microorganisms or a nucleic acid library, which can contain a candidate gene encoding a gene product conferring increased yield, with a nucleic acid molecule selected from the group consisting of SEQ ID NOs: 1, 3, 12, 38, 39, 40, 41, 42, 43, 44, 45, 46, 47, 48, 49, 50, or a functional homologue thereof;

(b) identifying the nucleic acid molecules, which hybridize under relaxed stringent conditions with said nucleic acid molecule, in particular to the nucleic acid molecule sequence selected from the group consisting of SEQ ID NOs: 1, 3, 12, 38, 39, 40, 41, 42, 43, 44, 45, 46, 47, 48, 49, 50, and, optionally, isolating the full length cDNA clone or complete genomic clone;

(c) identifying the candidate nucleic acid molecules or a fragment thereof in host cells, preferably in a plant cell;

(d) increasing the expressing of the identified nucleic acid molecules in the host cells for which increased yield are desired;

(e) assaying the level of increased yield of the host cells; and (f) identifying the nucleic acid molecule and its gene product which increased expression confers increased yield in the host cell compared to the wild type.

Relaxed hybridization conditions are: After standard hybridization procedures washing steps can be performed at low to medium stringency conditions usually with washing conditions of 40'-55° C. and salt conditions between 2×SSC and 0.2×SSC with 0.1% SDS in comparison to stringent washing conditions as e.g. 60° to 68° C. with 0.1% SDS. Further examples can be found in the references listed above for the stringend hybridization conditions. Usually washing steps are repeated with increasing stringency and length until a useful signal to noise ratio is detected and depend on many factors as the target, e.g. its purity, GC-content, size etc, the probe, e.g. its length, is it a RNA or a DNA probe, salt conditions, washing or hybridization temperature, washing or hybridization time etc.

In another embodiment, the present invention relates to a method for the identification of a gene product the expression of which confers an increased yield in a cell, comprising the following steps:

(a) identifying a nucleic acid molecule in an organism, which is at least 20%, preferably 25%, more preferably 30%, even more preferred are 35%. 40% or 50%, even more preferred are 60%, 70% or 80%, most preferred are 90% or 95% or more homolog to the nucleic acid molecule encoding a protein comprising the polypeptide molecule selected from the group consisting of SEQ ID NOs: 2, 4, 13, 51, 52, 53, 54, 55, 56, 57, 58, 59, 60, 61, 62, 63, or comprising a nucleic acid molecule encoding a polypeptide comprising the polypeptide motif of the ADP binding site selected from the group consisting of SEQ ID NOs: 7, 8, 9, 10, 11, 14, 15, 16, 17, 18, or comprising a polypeptide according to the motif selected from the group consisting of SEQ ID No. 64, 65, 66, 67, 68, 69, 70, 71, 72, 73 and preferably having the activity represented by a nucleic acid molecule comprising a polynucleotide selected from the group consisting of SEQ ID NOs: 1, 3, 12, 38, 39, 40, 41, 42, 43, 44, 45, 46, 47, 48, 49, 50, or being encoded by a nucleic acid molecule comprising a polynucleotide selected from the group consisting of SEQ ID NOs: 1, 3, 12, 38, 39, 40, 41, 42, 43, 44, 45, 46, 47, 48, 49, 50, or a homologue thereof as described herein, for example via homology search in a data bank;

(b) enhancing the expression of the identified nucleic acid molecules in the host cells;

(c) assaying the level of increased yield in the host cells; and (d) identifying the host cell, in which the enhanced expression confers increased yield in the host cell compared to a wild type.

Further, the nucleic acid molecule disclosed herein, in particular the nucleic acid molecule selected from the group consisting of SEQ ID NOs: 1, 3, 12, 38, 39, 40, 41, 42, 43, 44, 45, 46, 47, 48, 49, 50, may be sufficiently homologous to the sequences of related species such that these nucleic acid molecules may serve as markers for the construction of a genomic map in related organism or for association mapping. Furthermore natural variation in the genomic regions corresponding to nucleic acids disclosed herein, in particular the nucleic acid molecule selected from the group consisting of SEQ ID NOs: 1, 3, 12, 38, 39, 40, 41, 42, 43, 44, 45, 46, 47, 48, 49, 50, or homologous thereof may lead to variation in the activity of the proteins disclosed herein, in particular the proteins comprising polypeptides selected from the group consisting of SEQ ID NOs: 2, 4, 13, 51, 52, 53, 54, 55, 56, 57, 58, 59, 60, 61, 62, 63, or comprising the a nucleic acid molecule encoding a polypeptide comprising the polypeptide motif of the ADP binding site selected from the group consisting of SEQ ID NOs: 7, 8, 9, 10, 11, 14, 15, 16, 17, 18, or comprising a polypeptide according to the motif selected from the group consisting of SEQ ID No. 64, 65, 66, 67, 68, 69, 70, 71, 72, 73 and preferably having the activity represented by a nucleic acid molecule comprising a polynucleotide selected from the group consisting of SEQ ID NOs: 1, 3, 12, 38, 39, 40, 41, 42, 43, 44, 45, 46, 47, 48, 49, 50 and their homolgous and in consequence in a natural variation of yield.

In consequence natural variation eventually also exists in form of more active allelic variants leading already to a relative increase in the enhancement of yield. Different variants of the nucleic acids molecule disclosed herein, in particular the nucleic acid comprising the nucleic acid molecule selected from the group consisting of SEQ ID NOs: 1, 3, 12, 38, 39, 40, 41, 42, 43, 44, 45, 46, 47, 48, 49, 50, which corresponds to different enhancement yield levels can be identified and used for marker assisted breeding for increased yield.

Accordingly, the present invention relates to a method for breeding plants with increased yield, comprising
(a) selecting a first plant variety with increased yield based on increased expression of a nucleic acid of the invention as disclosed herein, in particular of a nucleic acid molecule comprising a nucleic acid molecule selected from the group consisting of SEQ ID NOs: 1, 3, 12, 38, 39, 40, 41, 42, 43, 44, 45, 46, 47, 48, 49, 50, or a polypeptide comprising a polypeptide selected from the group consisting of SEQ ID NOs: 2, 4, 13, 51, 52, 53, 54, 55, 56, 57, 58, 59, 60, 61, 62, 63, or comprising a a nucleic acid molecule encoding a polypeptide comprising the polypeptide motif of the ADP binding site selected from the group consisting of SEQ ID NOs: 7, 8, 9, 10, 11, 14, 15, 16, 17, 18, or comprising a polypeptide according to the motif selected from the group consisting of SEQ ID No. 64, 65, 66, 67, 68, 69, 70, 71, 72, 73 and preferably having the activity represented by a nucleic acid molecule comprising a polynucleotide selected from the group consisting of SEQ ID NOs: 1, 3, 12, 38, 39, 40, 41, 42, 43, 44, 45, 46, 47, 48, 49, 50, or a homologue thereof as described herein;
(b) associating the level of enhancement of yield with the expression level or the genomic structure of a gene encoding said polypeptide or said nucleic acid molecule;
(c) crossing the first plant variety with a second plant variety, which significantly differs in its level of enhancement of yield; and
(d) identifying, which of the offspring varieties has got increased levels of enhanced yield by the expression level of said polypeptide or nucleic acid molecule or the genomic structure of the genes encoding said polypeptide or nucleic acid molecule of the invention.

In one embodiment, the expression level of the gene according to step (b) is increased.

Yet another embodiment of the invention relates to a process for the identification of a compound conferring increased yield as compared to a corresponding non-transformed wild type plant cell, a plant or a part thereof in a plant cell, a plant or a part thereof, a plant or a part thereof, comprising the steps:
(a) culturing a plant cell; a plant or a part thereof maintaining a plant expressing the polypeptide selected from the group consisting of SEQ ID NOs: 2, 4, 13, 51, 52, 53, 54, 55, 56, 57, 58, 59, 60, 61, 62, 63, or being encoded by a nucleic acid molecule comprising a polynucleotide selected from the group consisting of SEQ ID NOs: 1, 3, 12, 38, 39, 40, 41, 42, 43, 44, 45, 46, 47, 48, 49, 50, or a homologue thereof as described herein or a polynucleotide encoding said polypeptide and conferring an increased yield as compared to a corresponding non-transformed wild type plant cell, a plant or a part thereof; a non-transformed wild type plant or a part thereof and providing a readout system capable of interacting with the polypeptide under suitable conditions which permit the interaction of the polypeptide with this readout system in the presence of a chemical compound or a sample comprising a plurality of chemical compounds and capable of providing a detectable signal in response to the binding of a chemical compound to said polypeptide under conditions which permit the expression of said readout system and of the protein selected from the group consisting of SEQ ID NOs: 2, 4, 13, 51, 52, 53, 54, 55, 56, 57, 58, 59, 60, 61, 62, 63, or being encoded by a nucleic acid molecule comprising a polynucleotide selected from the group consisting of SEQ ID NOs: 1, 3, 12, 38, 39, 40, 41, 42, 43, 44, 45, 46, 47, 48, 49, 50, or a homologue thereof as described herein; and
(b) identifying if the chemical compound is an effective agonist by detecting the presence or absence or decrease or increase of a signal produced by said readout system.

Said compound may be chemically synthesized or microbiologically produced and/or comprised in, for example, samples, e.g., cell extracts from, e.g., plants, animals or microorganisms, e.g. pathogens. Furthermore, said compound(s) may be known in the art but hitherto not known to be capable of suppressing the polypeptide of the present invention. The reaction mixture may be a cell free extract or may comprise a cell or tissue culture. Suitable set ups for the process for identification of a compound of the invention are known to the person skilled in the art and are, for example, generally described in Alberts et al., Molecular Biology of the Cell, third edition (1994), in particular Chapter 17. The compounds may be, e.g., added to the reaction mixture, culture medium, injected into the cell or sprayed onto the plant.

If a sample containing a compound is identified in the process, then it is either possible to isolate the compound from the original sample identified as containing the compound capable of activating or enhancing the increased yield as compared to a corresponding non-transformed wild type, or one can further subdivide the original sample, for exampie, if it consists of a plurality of different compounds, so as to reduce the number of different substances per sample and repeat the method with the subdivisions of the original sample. Depending on the complexity of the samples, the steps described above can be performed several times, preferably until the sample identified according to the said process only comprises a limited number of or only one substance(s). Preferably said sample comprises substances of similar chemical and/or physical properties, and most preferably said substances are identical. Preferably, the compound identified according to the described method above or its derivative is further formulated in a form suitable for the application in plant breeding or plant cell and tissue culture.

The compounds which can be tested and identified according to said process may be expression libraries, e.g., cDNA expression libraries, peptides, proteins, nucleic acids, antibodies, small organic compounds, hormones, peptidomimetics, PNAs or the like (Milner, Nature Medicine 1, 879 (1995); Hupp, Cell 83, 237 (1995); Gibbs, Cell 79, 193 (1994), and references cited supra). Said compounds can also be functional derivatives or analogues of known inhibitors or activators. Methods for the preparation of chemical derivatives and analogues are well known to those skilled in the art and are described in, for example, Beilstein, Handbook of Organic Chemistry, Springer, N.Y. Inc., 175 Fifth Avenue, New York, N.Y. 10010 U.S.A. and Organic Synthesis, Wiley, New York, USA. Furthermore, said derivatives and analogues can be tested for their effects according to methods known in the art. Furthermore, peptidomimetics and/or computer aided design of appropriate derivatives and analogues can be used, for example, according to the methods described above. The cell or tissue that may be employed in the process preferably is a host cell, plant cell or plant tissue of the invention described in the embodiments hereinbefore.

Thus, in a further embodiment the invention relates to a compound obtained or identified according to the method for identifying an agonist of the invention said compound being an antagonist of the polypeptide of the present invention.

Accordingly, in one embodiment, the present invention further relates to a compound identified by the method for identifying a compound of the present invention.

In one embodiment, the invention relates to an antibody specifically recognizing the compound or agonist of the present invention.

The invention also relates to a diagnostic composition comprising at least one of the aforementioned nucleic acid molecules, antisense nucleic acid molecule, RNAi, snRNA, dsRNA, siRNA, miRNA, ta-siRNA, cosuppression molecule, ribozyme, vectors, proteins, antibodies or compounds of the invention and optionally suitable means for detection.

The diagnostic composition of the present invention is suitable for the isolation of mRNA from a cell and contacting the mRNA so obtained with a probe comprising a nucleic acid probe as described above under hybridizing conditions, detecting the presence of mRNA hybridized to the probe, and thereby detecting the expression of the protein in the cell. Further methods of detecting the presence of a protein according to the present invention comprise immunotechniques well known in the art, for example enzyme linked immunoadsorbent assay. Furthermore, it is possible to use the nucleic acid molecules according to the invention as molecular markers or primers in plant breeding. Suitable means for detection are well known to a person skilled in the art, e.g. buffers and solutions for hydridization assays, e.g. the aforementioned solutions and buffers, further and means for Southern-, Western-, Northern- etc.-blots, as e.g. described in Sambrook et al. are known. In one embodiment diagnostic composition contain PCR primers designed to specifically detect the presense or the expression level of the nucleic acid molecule to be reduced in the process of the invention, e.g. of the nucleic acid molecule of the invention, or to descriminate between different variants or alleles of the nucleic acid molecule of the invention or which activity is to be reduced in the process of the invention.

In another embodiment, the present invention relates to a kit comprising the nucleic acid molecule, the vector, the host cell, the polypeptide, or the antisense, RNAi, snRNA, dsRNA, siRNA, miRNA, ta-siRNA, cosuppression molecule, or ribozyme molecule, or the viral nucleic acid molecule, the antibody, plant cell, the plant or plant tissue, the harvestable part, the propagation material and/or the compound and/or agonist identified according to the method of the invention.

The compounds of the kit of the present invention may be packaged in containers such as vials, optionally with/in buffers and/or solution. If appropriate, one or more of said components might be packaged in one and the same container. Additionally or alternatively, one or more of said components might be adsorbed to a solid support as, e.g. a nitrocellulose filter, a glass plate, a chip, or a nylon membrane or to the well of a micro titerplate. The kit can be used for any of the herein described methods and embodiments, e.g. for the production of the host cells, transgenic plants, pharmaceutical compositions, detection of homologous sequences, identification of antagonists or agonists, as food or feed or as a supplement thereof or as supplement for the treating of plants, etc.

Further, the kit can comprise instructions for the use of the kit for any of said embodiments.

In one embodiment said kit comprises further a nucleic acid molecule encoding one or more of the aforementioned protein, and/or an antibody, a vector, a host cell, an antisense nucleic acid, a plant cell or plant tissue or a plant. In another embodiment said kit comprises PCR primers to detect and discrimante the nucleic acid molecule to be reduced in the process of the invention, e.g. of the nucleic acid molecule of the invention.

In a further embodiment, the present invention relates to a method for the production of an agricultural composition providing the nucleic acid molecule for the use according to the process of the invention, the nucleic acid molecule of the invention, the vector of the invention, the antisense, RNAi, snRNA, dsRNA, siRNA, miRNA, ta-siRNA, cosuppression molecule, ribozyme, or antibody of the invention, the viral nucleic acid molecule of the invention, or the polypeptide of the invention or comprising the steps of the method according to the invention for the identification of said compound or agonist; and formulating the nucleic acid molecule, the vector or the polypeptide of the invention or the agonist, or compound identified according to the methods or processes of the present invention or with use of the subject matters of the present invention in a form applicable as plant agricultural composition.

In another embodiment, the present invention relates to a method for the production of the plant culture composition comprising the steps of the method of the present invention; and formulating the compound identified in a form acceptable as agricultural composition.

Under "acceptable as agricultural composition" is understood, that such a composition is in agreement with the laws regulating the content of fungicides, plant nutrients, herbizides, etc. Preferably such a composition is without any harm for the protected plants and the animals (humans included) fed therewith.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes and variations may be made therein without departing from the scope of the invention. The invention is further illustrated by the following examples, which are not to be construed in any way as limiting. On the contrary, it is to be clearly understood that various other embodiments, modifications and equivalents thereof, which, after reading the description herein, may suggest themselves to those skilled in the art without departing from the spirit of the present invention and/or the scope of the claims.

The invention will be described in more detail below with reference to the examples:

General Methods

Unless otherwise specified, all chemicals were from Fluka (Buchs), Merck (Darmstadt), Roth (Karlsruhe), Serva (Heidelberg) and Sigma (Deisenhofen). Restriction enzymes, DNA-modifying enzymes and molecular biological kits were from Amersham-Pharmacia (Freiburg), Biometra (Gottingen), Roche (Mannheim), New England Biolabs (Schwalbach), Novagen (Madison, Wis., USA), Perkin Elmer (Weiterstadt), Qiagen (Hilden), Stratagen (Amsterdam, Netherlands), Invitrogen (Karlsruhe) and Ambion (Cambridgeshire, United Kingdom). The reagents used were employed in accordance with the manufacturer's instructions.

For example, oligonucleotides can be synthesized chemically in the known manner using the phosphoamidite method (Voet, Voet, 2nd edition, Wiley Press New York, pages 896-897). The cloning steps carried out for the purposes of the present invention such as, for example, restriction cleavages, agarose gel electrophoreses, purification of DNA fragments, transfer of nucleic acids to nitrocellulose and nylon membranes, linking DNA fragments, transformation of $E.\ coli$ cells, bacterial cultures, multiplication of phages and sequence analysis of recombinant DNA, are carried out as described by Sambrook et al. (1989) Cold Spring Harbor Laboratory Press; ISBN 0-87969-309-6. Recombinant DNA molecules were sequenced using an ABI laser fluorescence DNA sequencer following the method of Sanger (Sanger et al. (1977) Proc Natl Acad Sci USA 74:5463-5467).

Plant Growth

The $A.\ thaliana$ seedling culture was performed according to Scheible et al. (2004). Arabidopsis seeds (100-120) were surface sterilised and imbibed at 5° C. in complete darkness for 3 d. Seeds were transferred and grown in sterile liquid culture (250 ml Erlenmeyer glass flasks) on orbital shakers with constant, uniform fluorescent light (approximate photon flux density 50 µmol*m-2*s-1 in the flask) and constant temperature (22° C.), in 30 ml of media. The sterile full nutrition media contained: 2 mM $KNO_3$, 1 mM $NH_4NO_3$, 1 mM Gln, 3 mM $KH_2PO_4/K_2HPO_4$ at pH 5.8, 4 mM $CaCl_2$, 1 mM $MgSO_4$, 2 mM $K_2SO_4$, 3 mM 2-[N-Morpholino]ethanesulfonic acid (MES) at pH 5.8 (KOH), 0.5% (w/v) sucrose, 50 mg I-1 kanamycin, 40 µM $Na_2FeEDTA$, 60 µM $H_3BO_3$, 14 µM $MnSO_4$, 1 µM $ZnSO_4$, 0.6 µM $CuSO_4$, 0.4 µM $NiCl_2$, 0.3 µM $HMoO_4$, 20 nM $CoCl_2$. Shaker speed was low (30 rpm) during the first 3 d and then increased to 80 rpm. Seedlings were harvested after 7 d by quickly freezing in liquid nitrogen. The $A.\ thaliana$ plant culture on soil was performed as follows: Seeds were surface sterilised and aseptically grown on media containing ½ strength Murashige and Skoog salts (micro and macro elements including vitamins), 0.25 mM 2-[N-Morpholino]ethanesulfonic acid (MES) pH 5.8 (KOH), 50 mg*I-1 kanamycin, 0.5% (w/v) sucrose and 0.8% (w/v) agar. Seeds were imbibed at 5° C. in complete darkness for 3 d and grown in a 12 hours photoperiod (photon flux density, 150 µmol*m-2*s-1, 22° C. light, 18° C. dark). After two weeks plants were transferred on soil in pots of 6 cm in diameter. For the adequate nutrients condition pots were filled with a 2:1 (v/v) mix of GS90 soil (composition: peat, clay, coconut fiber, 2 g/l salt, 160 mg/l N, 190 mg/l P2O5, 230 mg/l K2O, pH 6, supplied by Werner Tantau GmbH & Co. KG, Germany) and vermiculite (Gebrüder Patzer, Germany) and grown under short day conditions (8 h light, 16 h dark) at a light intensity of 145 µmol*m-2*s-1, 60% relative humidity, and temperatures of 20° C. (day) and 18° C. (night). For the limiting nutrients condition the GS90 soil was replaced by a 1:10 (v/v) mix of GS90 soil and "Null-soil" (composition: peat, clay, coconut fiber, 0.8 g/l salt, 50 mg/l N, 80 mg/l P2O5, 80 mg/l K2O, pH 6, supplied by Werner Tantau GmbH & Co. KG). Plants were grown under the same conditions as for adequate nutrients conditions.

For expression analysis and seed production and analysis plants were grown in high nitrogen conditions under long day (16 h light, 8 h dark) at a light intensity of 145 µmol* m-2*s-1, and 80% relative humidity, at temperatures of 20° C. (day) and 18° C. (night, 50% relative humidity).

The $Nicotiana\ tabacum$ seedling culture was performed identically to the $Arabidopsis$ seedling culture but seedlings were harvested after 8 d and a different type of nutrient solution was applied. The tobacco full nutrition media contained: Murashige and Skoog salts (micro and macro elements including vitamins), 0.25 mM 2-[N-Morpholino] ethanesulfonic acid (MES) pH 5.8 (KOH), 50 mg*I-1 kanamycin, 0.5% (w/v) sucrose. The $Nicotiana\ tabacum$ plant culture was performed as follows: Seeds were surface sterilised and aseptically grown on media containing Murashige and Skoog salts (micro and macro elements including vitamins), 0.25 mM 2-[N-Morpholino]ethanesulfonic acid (MES) pH 5.8 (KOH), 50 mg*I-1 kanamycin, 0.5% (w/v) sucrose and 0.8% (w/v) agar.

Seeds were imbibed at 5° C. in complete darkness for 3 d and grown in a 12 hours photoperiod (photon flux density, 150 µmol*m-2*s-1, 22° C.). After four weeks plants were transferred either on soil in pots of 20 cm in diameter filled with a 2:1 (v/v) mix of GS90 soil and sand in a greenhouse in a 16 hours photoperiod (photon flux density 200 µmol*m-2*s-1, 25° C. light, 8 hours night at 20° C., and 60% relative humidity). Plants were watered continuously by dropping 100-250 ml fertiliser enriched water (Hakaphos spezial (16% N, 8% P, 22% K, 3% Mg) at a concentration of 1 g*I-1) to each pot per day. Or after four weeks in tissue culture plants were transferred on sand in pots of 16 cm in diameter in a climate chamber in a 12 hours photoperiod (photon flux density 350 µmol*m-2*s-1, 23° C. light, 20° C. dark and 60% relative humidity) on quartz sand (1:1 mix of particles with a size of 0.3-0.8 and 0.6-1.2 mm; Dorsolit). Pots were watered after approximately 3 h of illumination each day, filling the pot with nutrient solution and allowing it to run out, leaving the fluid retained between the sand grains (field capacity). The nutrient solution contained: 4 mM $KNO_3$, 4 mM $Mg(NO_3)_2$, 3 mM $KH_2PO_4/K_2HPO_4$ at pH 5.8, 2 mM $MgSO_4$, 1 mM NaCl, 40 µM $Na_2FeEDTA$, 90 µM $H_3BO_3$, 20 µM $MnSO_4$, 1.5 µM $ZnSO_4$, 0.9 µM $CuSO_4$, 0.6 µM $NiCl_2$, 0.45 µM $HMoO_4$, 30 nM $CoCl_2$.

Cloning Procedures and Plasmid Construction $Escherichia\ coli$ strain XL-1 Blue and $Agrobacterium\ tumefaciens$ strain C58C1 containing pGV2260 were cultivated using standard procedures (Sambrock and Russel, 2001). Sequenz primers AgPRSv (GGA TCC AAT ATG TCG TCC AAT) and AgPRSh (GGA TCC TAC ATG ACA GCG) were used to amplify the wildtype PRS from plasmid pJRAgprs1486 and the mutant PRS from pJRAgprs1404 (mutant) using standard procedures. Subcloning into pCR Script (Stratagene) was in accordance with the protocol provided by the supplier. Clones were confirmed by sequence analysis. The 965 bp BamHI fragments encoding the full length proteins were cloned into the BamHI restricted binary vector pBinAR (Höfgen and Willmitzer, 1990). Sense direction of the insertion was checked by SalI digestion and PCR analysis using the primers 35Shv (TAT AGA GGA AGG GTC TTG CG) and AgPRSh. Definite plasmids to be transformed into plants were finally verified by sequence analysis.

Plant Transformation and Expression Analysis

*Agrobacterium*-mediated gene transfer was performed as by Rosahl et al. (1989) for tobacco plants and as by Bent and Clough (1998) for *Arabidopsis*. Expression of the transgene was analysed by Northern hybridisation as in Giermann et al. (2002) using the full length wildtype PRS as a probe.

Metabolite Analysis

In liquid nitrogen frozen plant material was ground to a powder using a ball mill (Retsch). Carbohydrates, amino acids and nucleotides were extracted and measured as in Schröder et al. 2005. Fatty acids were extracted according to the method of Bligh and Dyer (1959), and the lipid content was measured by GC of fatty acid methyl esters using pentadecanoic acid as internal standard (Benning and Somerville, 1992).

Enzyme Activity

Frozen plant material was ground to a powder in liquid nitrogen using a ball mill. Aliquots of 10 to 20 mg fresh weight were extracted by vigorous vortexing with 500 to 1000 µL of extraction buffer. The composition of the extraction buffer was 50 mM KH2PO4/K2HPO4 at pH 7.5, 10% (v/v) glycerol, 0.1% (v/v) Triton X-100, 5 mM MgCl2, 1 mM EDTA, 1 mM EGTA, 1 mM phenylmethylsulfonyl fluoride, and 5 mM DTT. The extract was centrifuged at 16,000*g for 10 min at 4° C. Measurement was performed in microplates by mixing 10 µl of supernatant of the enzyme extract with 100 to 200 µl of measuring buffer (KH2PO4/K2HPO4 at pH 7.5, 5 mM MgCl2, 3.75 mM ribose-5-phosphate, 2 mM ATP, 3.75 mM phosphoenolpyruvate, 0.2 mM NADH, 1.5 U myokinase, 3 U pyruvate kinase, 1.5 U lactate dehydrogenase). Soluble protein content of the supernatant was determined using the dye-binding assay (Bradford, 1976).

EXAMPLE 1

To clone the wild-type PRS gene (PRS) and the mutated PRS gene (PRSM; Leu133Ile, His 196Glu) from *Ashbya gossypii* into plant expression vectors, full-length cDNA sequences were employed in a PCR reaction with the oligonucleotide primers AgPRSv and AgPRSh.

```
Sequence primer AgPRSv:
5'-5'-GGA TCC AAT ATG TCG TCC AAT-3'  (SEQ ID NO 5)

Sequence primer AgPRSh:
5'-5'-GGA TCC TAC ATG ACA GCG-3'     (SEQ ID NO 6)
```

Composition of the PCR reaction (50 µl):
 5.00 µl 10 ng plasmid DNA
 5.00 µl 10× buffer (Pfu polymerase)
 5.00 µl 2 mM dNTP
 1.25 µl each primer (10 pmol/µL)
 0.50 µl Pfu polymerase
 The Pfu polymerase employed was from Stratagene.

PCR Program:
Initial denaturation for 2 min at 95° C., then 35 cycles of 45 sec at 95° C., 45 sec at 55° C. and 2 min at 72° C. Final extension for 5 min at 72° C.

The PCR products were cloned into the pCR Script (Stratagene) following the manufacturer's instructions, resulting in the vectors pCR-PRS and pCR-PRPM, and the sequence was verified by sequencing.

Cloning into the agro transformation vector pBIN involved incubating 0.5 µg of the vectors pCR-PRS and pCR-PRSM with the restriction enzyme BamHI (New England Biolabs) for 2 hours and separating the DNA fragments by gel electrophoresis. The respective 971 bp fragment of the PRS sequence was excized from the gel, purified with the "Gel Purification" kit from Qiagen following the manufacturer's instructions and eluted with 50 µl of elution buffer. 0.1 µg of the vector pBIN19 was first digested for 1 hour with the restriction enzyme BamHI and then separated using gel electrophoresis, purified with the "Gel Purification" kit from Qiagen following the manufacturer's instructions and eluted with 50 µl of elution buffer. The corresponding DNA fragments were then cloned into the binary vector pBIN behind the 35S terminator and the plastidic signal sequence of the small subunit of the ribulose-bisphosphate carboxylase. 10 µl in each case of the eluates of the PRS fragments and 10 ng of the treated pBIN19 vector were ligated overnight at 16° C. (T4 ligase, New England Biolabs). The ligation products were then transformed into TOP10 cells (Stratagene) following the manufacturer's instructions and suitably selected, resulting in the vectors pBIN-PRS and pBIN-PRSM. Positive clones are verified by sequencing and PCR using the primers AgPRSv and AgPRSh.

EXAMPLE 2

Plasmids for the Transformation of Plants

Binary vectors such as pBIN19 can be used for the transformation of plants (Höfgen und Willmitzer (1990) Plant Science 66: 221-230). The binary vectors can be constructed by ligating the cDNA into T-DNA in sense and antisense orientation. 5' of the cDNA, a plant promoter activates the transcription of the cDNA. A polyadenylation sequence is located 3' of the cDNA.

Tissue-specific expression can be achieved using a tissue-specific promoter. For example, seed-specific expression can be achieved by cloning in the napin or the LeB4 or the USP promoter 5' of the cDNA. Any other seed-specific promoter element can also be used. The CaMV 35S promoter can be used for constitutive expression in the whole plant.

The subcellular localization of gene products (proteins) is determined by various amino acid sequence motives at the end of or within the protein sequence. Thus, for example, a plastidic localization of the PRS synthase is achieved by cloning the PRS gene sequence behind the 5' area of the large subunit of ribulose 1,5-bisphosphate carboxylate which codes for the plastidic signal sequence.

A further example of a binary vector is the vector pSUN-USP and pGPTV-napin. The vector pSUN-USP contains the USP promoter and the OCS terminator. The vector pGPTV-napin contains a truncated version of the napin promoter, and the NOS terminator.

The fragments of Example 1 are cloned into the multiple cloning site of the vector pBIN19 behind the 35S promoter and the plastidic signal sequences of the ribulose 1,5-bisphosphate carboxylase, to make possible the seed-specific expression of the PRS gene and a plastidic localization of the gene product.

EXAMPLE 3

Transformation of *Agrobacterium*

*Agrobacterium*-mediated plant transformation can be carried out for example using the *Agrobacterium tumefaciens* strains GV3101 (pMP90) (Koncz und Schell (1986) Mol Gen Genet. 204: 383-396) or LBA4404 (Clontech). Standard transformation techniques may be used for the transformation (Deblaere et al. (1984) Nucl Acids Res 13:4777-4788).

EXAMPLE 4

Transformation of Plants

*Agrobacterium*-mediated plant transformation can be effected using standard transformation and regeneration techniques (Gelvin, Stanton B., Schilperoort, Robert A., Plant Molecular Biology Manual, 2nd ed., Dordrecht: Kluwer Academic Publ., 1995, in Sect., Ringbuch Zentrale Signatur: BT11-P ISBN 0-7923-2731-4; Glick, Bernard R., Thompson, John E., Methods in Plant Molecular Biology and Biotechnology, Boca Raton: CRC Press, 1993, 360 pp., ISBN 0-8493-5164-2).

The transformation of *Arabidopsis thaliana* by means of *Agrobacterium* was carried out by the method of Bechthold et al., 1993 (C.R. Acad. Sci. Ser. III Sci. Vie., 316, 1194-1199).

For example, oilseed rape can be transformed by cotyledon or hypocotyl transformation (Moloney et al. (1989) Plant Cell Report 8:238-242; De Block et al. (1989) Plant Physiol 91: 694-701). The use of antibiotics for the selection of *agrobacteria* and plants depends on the binary vector used for the transformation and the agrobacterial strain. The selection of oilseed rape is usually carried out using kanamycin as selectable plant marker.

*Agrobacterium*-mediated gene transfer into linseed (*Linum usitatissimum*) can be carried out for example using a technique described by Mlynarova et al. (1994) Plant Cell Report 13:282-285.

Soya can be transformed for example using a technique described in EP-A-0 0424 047 (Pioneer Hi-Bred International) or in EP-A-0 0397 687, U.S. Pat. No. 5,376,543, U.S. Pat. No. 5,169,770 (University of Toledo).

The transformation of plants using particle bombardment, polyethylene glycol mediated DNA uptake or via the silicon carbonate fiber technique is described, for example, by Freeling and Walbot "The Maize Handbook" (1993) ISBN 3-540-97826-7, Springer Verlag New York).

EXAMPLE 5

Studying the Expression of a Recombinant Gene Product in a Transformed Organism

A suitable method for determining the level of transcription of the gene (which indicates the amount of RNA available for translating the gene product) is to carry out a Northern blot as described hereinbelow (for reference see Ausubel et al. (1988) Current Protocols in Molecular Biology, Wiley: New York, or the above examples section), where a primer which is designed such that it binds to the gene of interest is labeled with a detectable label (usually a radiolabel or chemiluminescent label) so that, when the total RNA of a culture of the organism is extracted, separated on a gel, transferred to a stable matrix and incubated with this probe, binding and the extent of binding of the probe indicates the presence and the amount of mRNA for this gene. This information indicates the degree of transcription of the transformed gene. Cellular total RNA can be prepared from cells, tissues or organs using several methods, all of which are known in the art, for example the method Bormann, E. R., et al. (1992) Mol. Microbiol. 6:317-326.

Northern Hybridization:

To carry out the RNA hybridization, 20 µg of total RNA or 1 µg of poly(A)+ RNA were separated by means of gel electrophoresis in 1.25% strength agarose gels using formaldehyde and following the method described by Amasino (1986, Anal. Biochem. 152, 304), transferred to positively charged nylon membranes (Hybond N+, Amersham, Brunswick) by capillary force using 10×SSC, immobilized by UV light and prehybridized for 3 hours at 68° C. using hybridization buffer (10% dextran sulfate w/v, 1 M NaCl, 1% SDS, 100 mg herring sperm DNA). The DNA probe was labeled with the Highprime DNA labeling kit (Roche, Mannheim, Germany) during the prehybridization step, using alpha-32P-dCTP (Amersham Pharmacia, Brunswick, Germany). Hybridization was carried out overnight at 68° C. after addition of the labeled DNA probe in the same buffer. The wash steps were carried out twice for 15 minutes using 2×SSC and twice for 30 minutes using 1×SSC, 1% SDS, at 68° C. The sealed filters were exposed at −70° C. for a period of 1 to 14 days.

To study the presence or the relative amount of protein translated from this mRNA, standard techniques such as a Western blot may be employed (see, for example, Ausubel et al. (1988) Current Protocols in Molecular Biology, Wiley: New York). In this method, the cellular total proteins are extracted, separated by means of gel electrophoresis, transferred to a matrix like nitrocellulose and incubated with a probe such as an antibody which binds specifically to the desired protein. This probe is usually provided with a chemiluminescent or calorimetric label which can be detected readily. The presence and the amount of the label observed indicates the presence and the amount of the desired mutated protein which is present in the cell.

EXAMPLE 6

Analysis of the Effect of the Recombinant Proteins on the Production of the Desired Product The effect of genetic modification in plants, fungi, algae, ciliates or on the production of a desired compound (such as a fatty acid) can be determined by growing the modified microorganisms or the modified plant under suitable conditions (as described above) and examining the medium and/or the cellular components for increased production of the desired product (i.e. lipids or a fatty acid). These analytical techniques are known to the skilled worker and comprise spectroscopy, thin-layer chromatography, various staining methods, enzymatic and microbiological methods, and analytical chromatography such as high-performance liquid chromatography (see, for example, Ullmann, Encyclopedia of Industrial Chemistry, vol. A2, pp. 89-90 and pp. 443-613, VCH: Weinheim (1985); Fallon A et al. (1987) "Applications of HPLC in Biochemistry" in: Laboratory Techniques in Biochemistry and Molecular Biology, vol. 17; Rehm et al. (1993) Biotechnology, vol. 3, chapter III: "Product recovery and purification", pp. 469-714, VCH: Weinheim; Belter P A et al. (1988) Bioseparations: downstream processing for Biotechnology, John Wiley and Sons; Kennedy J. F. und Cabral J. M. S. (1992) Recovery processes for biological Materials, John Wiley and Sons; Shaeiwitz J. A. and Henry J. D. (1988) Biochemical Separations, in: Ullmann's Encyclopedia of Industrial Chemistry, vol. B3; chapter 11, p. 1-27, VCH: Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935-12940, and Browse et al. (1986) Analytic Biochemistry 152:141-145.

Qualitative and quantitative lipid or fatty acid analysis is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research, Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for producing the desired compound, such as intermediates and secondary products, in order to determine the overall efficacy of the production of the compound. The analytical methods encompass measurements of the nutrient quantities in the medium (for example sugars, carbohydrates, nitrogen sources, phosphate and other ions), measurements of the biomass compositions and of the growth, analysis of the production of customary metabolites of biosynthetic pathways, and measurements of gases produced during fermentation. Standard methods for these measurements are described in Applied Microbial Physiology; A Practical Approach, P. M. Rhodes and P. F. Stanbury, ed., IRL Press, pp. 103-129; 131-163 and 165-192 (ISBN: 0199635773) and references cited therein.

One example is the analysis of fatty acids (abbreviations: FAME, fatty acid methyl esters; GC-MS, gas-liquid chromatography/mass spectrometry; TAG, triacylglycerol; TLC, thin-layer chromatography).

Unambiguous proof for the presence of fatty acid products can be obtained by analyzing recombinant organisms by analytical standard methods: GC, GC-MS or TLC, as described variously by Christie and the references cited therein (1997, in: Advances on Lipid Methodology, fourth edition: Christie, Oily Press, Dundee, 119-169; 1998, Gaschromatographie-Massenspektrometrie-Verfahren [gas-chromatographic/mass-spectrometric methods], Lipide 33:343-353).

The material to be analyzed can be disrupted by sonication, milling in the glass mill, liquid nitrogen and milling or other applicable methods. After disruption, the material must be centrifuged. The sediment is resuspended in distilled water, heated for 10 minutes at 100° C., cooled on ice and recentrifuged, followed by extraction in 0.5 M sulfuric acid in methanol with 2% dimethoxypropane for 1 hour at 90° C., which gives hydrolyzed oil and lipid compounds, which give transmethylated lipids. These fatty acid methyl esters are extracted in petroleum ether and finally subjected to GC analysis using a capillary column (Chrompack, WCOT Fused Silica, CP-Wax-52 CB, 25 mm, 0.32 mm) at a temperature gradient of between 170° C. and 240° C. for 20 minutes and for 5 minutes at 240° C. The identity of the fatty acid methyl esters obtained must be defined using standards which are available from commercial sources (i.e. Sigma).

The following protocol was used for the quantitative oil analysis of the Arabidopsis plants transformed with the PRS gene:

Lipid extraction from the seeds is carried out by the method of Bligh & Dyer (1959) Can J Biochem Physiol 37:911. To this end, 10 Arabidopsis seeds are counted into 1.2 ml Qiagen microtubes (Qiagen, Hilden).

The seed material is then homogenized for extraction with 500 µl chloroform/methanol (2:1; contains mono-C17-glycerol from Sigma as internal standard) in an MM300 Retsch mill from Retsch (Haan) and incubated for 20 minutes at RT. The phases were separated after addition of 500 µl 50 mM potassium phosphate buffer pH 7.5. The organic phase is concentrated to dryness and, for transmethylation of the fatty acids, 2 ml of methanolic sulfuric acid (1 N) and 2% (v/v) of dimethoxypropane are added and the mixture is incubated at 80° C. for 30 min. 2×2 ml of hexane are then added to the cooled samples, and the samples are vortexed. The organic upper phases in question are combined in a new test tube and purified 1× with in each case 2 ml of 100 mM sodium bicarbonate solution and 2 ml of distilled water. Under argon, the organic upper phase obtained is concentrated to dryness, and the fatty acid methyl esters obtained in this manner are dissolved in a defined volume of hexane.

2 µl of the fatty acid methyl ester solution are finally separated by gas chromatography (HP 6890, Agilent Technologies) on a capillary column (Chrompack, WCOT Fused Silica, CP-Wax-52 CB, 25 m, 0.32 mm) and analyzed using a flame ionization detector. The oil was quantified by comparing the signal strengths of the derivatized fatty acids with those of the internal standard.

The respective oil contents are then determined by relation of the total fatty acids to the seed weight or the seed.

FIG. 1 shows, in an exemplary manner, the results for the quantitative determination of the oil contents (based on the seed weight in T3 seeds of 4 independent transgenic Arbidopsis lines (Mp2, Mp12, Mp14 and Mp15 and also Pp11, Pp13, Pp15 and Pp19) which had been transformed with the expression constructs pBIN19—PRSM and pBIN-PRS, respectively. Also listed are the seed weights of the control plants V72 and V75.

From each line, using 3 plants, in each case 3 independent extractions were carried out using in each case 10 seeds, and the extracts were measured independently. For the three independent measurements, the mean and the standard deviation were calculated. Based on the seed weight, the lipid content in the two control plants V7-2 and V7-5 was 21 and 23%, respectively. The lipid content in the lines Pp, which had been transformed with the construct pBIN-PRS and which expressed the wild-type sequence of the PRS, was from 28 to 33%. This corresponds to an increase in the oil content in the transgenic lines of from 28 to 52%. The lipid content in the lines Mp, which had been transformed with the construct pBIN-PRSM and which expressed the mutated sequence of the PRS, was between 38 and 50%. This corresponds to an increase in the oil content in the transgenic lines of from 75 to 132%.

Figure 2:
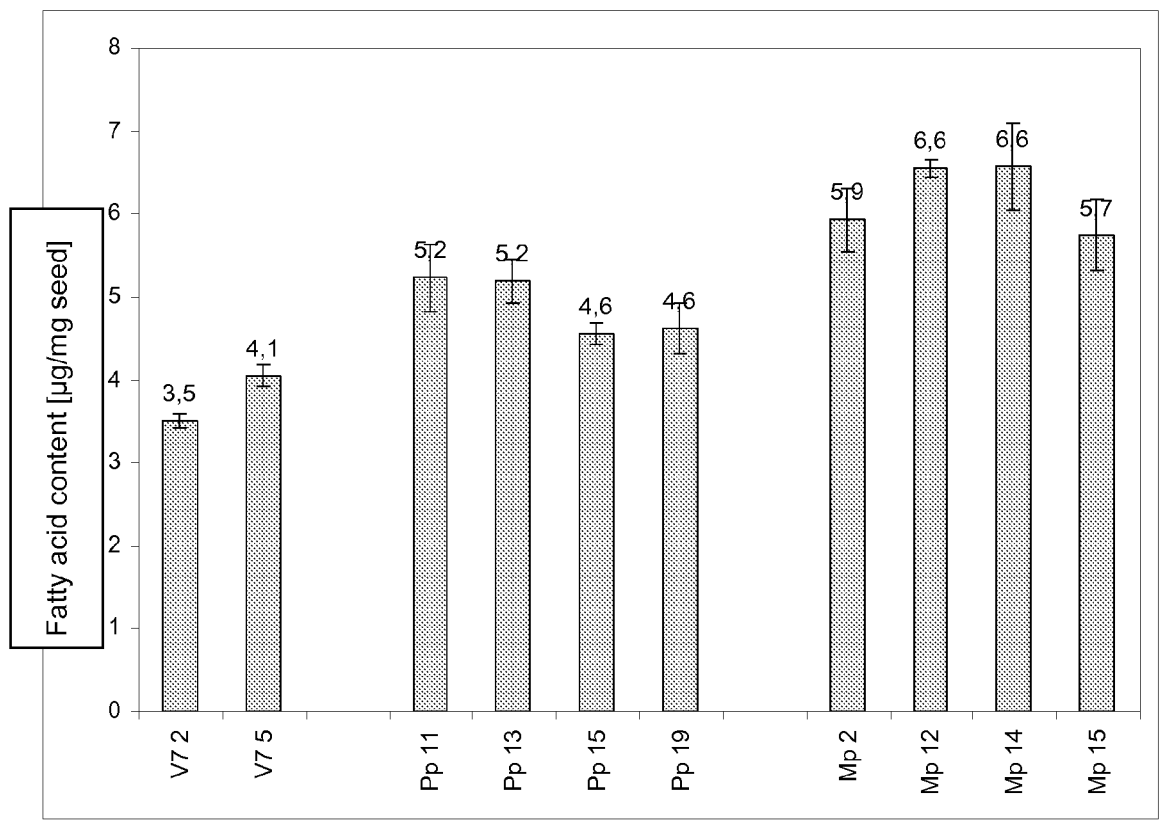
FIG. 2 shows the results of the quantitative determination of the oil contents (based on the seed) in T3 seed of 4 independent transgenic Arabidopsis lines (Mp2, Mp12, Mp14 and Mp15 and also Pp11, Pp13, Pp15 and Pp19) which had been transformed with the expression constructs pBIN19-PRSM and pBIN-PRS, respectively. Also listed are the seed weights of the control plants V72 and V75.

In an exemplary manner, FIG. 2 shows the results of the quantitative determination of the oil contents (based on the seed) in T3 seed of 4 independent transgenic Arabidopsis lines (Mp2, Mp12, Mp14 and Mp15 and also Pp11, Pp13, Pp15 and Pp19) which had been transformed with the expression constructs pBIN19-PRSM and pBIN-PRS, respectively. Also listed are the seed weights of the control plants V72 and V75. In the two control plants V7-2 and V7-5, the lipid content, based on the seed, was 3.5 and 4.1 µg, respectively. The lipid content in the lines Pp, which had been transformed with the construct pBIN-PRS and which expressed the wild-type sequence of the PRS, was from 4.6 to 5.2 µg. This corresponds to an increase in the oil content in the transgenic lines of from 20 to 38%. The lipid content in the lines Mp, which had been transformed with the construct pBIN-PRSM and which expressed the mutated sequence of the PRS, was between 5.7 and 6.6 µg. This corresponds to an increase in the oil content in the transgenic lines of from 50 to 74%.

The results clearly show that overexpression of phosphoribosyl pyrophosphate synthase results in a significant increase in the oil content. A further increase is achieved by overexpression of the mutated phosphoribosyl pyrophosphate synthase which is no longer subject to allosteric inhibition by ADP.

EXAMPLE 7

Determination of the Seed Weight

To determine the seed weight, from in each case 3 plants of each transgenic line or control line 3×100 seeds were collected, and the mean of the results was calculated.

Figure 3:
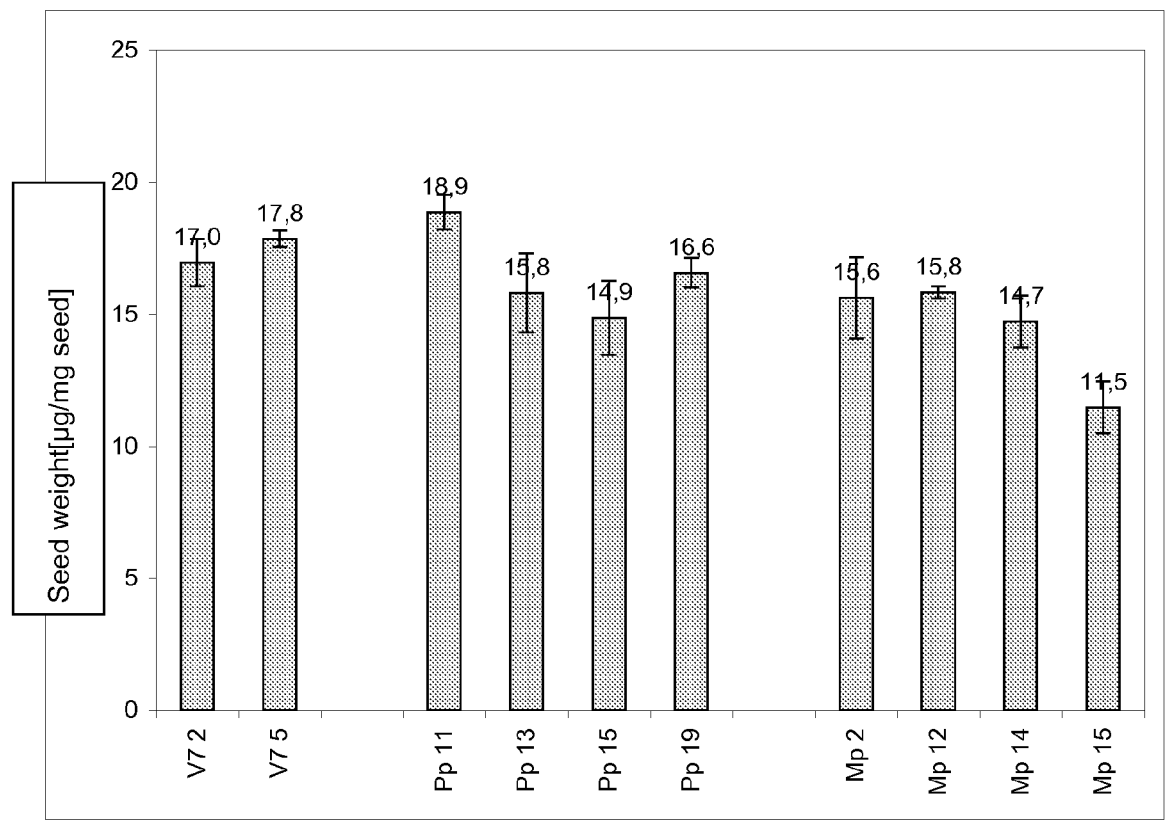
FIG. 3 shows the results for the determination of the weights of the T3 seeds in the transgenic lines Mp2, Mp12, Mp14 and Mp15 and the transgenic lines Pp11, Pp13, Pp15 and Pp19 which had been transformed with the expression constructs pBIN19-PRSM and pBIN-PRS, respectively. Also listed are the seed weights of the control plants V72 and V75.

FIG. 3 shows the results for the determination of the weights of the T3 seeds in the transgenic lines Mp2, Mp12, Mp14 and Mp15 and the transgenic lines Pp11, Pp13, Pp15 and Pp19 which had been transformed with the expression constructs pBIN19-PRSM and pBIN-PRS, respectively. Also listed are the seed weights of the control plants V72 and V75.

EXAMPLE 8

Growth Analysis of *Arabidopsis* Seedlings

To analyze the growth of *Arabidopsis* seedlings, T4 seedlings are cultivated for 8 days in liquid culture (2 mM $KNO_3$, 1 mM $NH_4NO_3$, 3 mM $K_2HPO_4$, 4 mM $CaCl_2$, 1 mM $MgSO_4$, 2 mM $K_2SO_4$, 3 mM MES, oligoelements, 0.5% sucrose, 1 mM glutamine, 10 mg/l kanamycin) under permanent light (150 µE). The fresh weight is then determined by weighing. In total, in each case 3 cultures with in each case 100 seedlings were analyzed of the control plants and each of the 4 transgenic lines which overexpressed the wild-type and mutated PRS without plastidic targeting.

Figure 4:
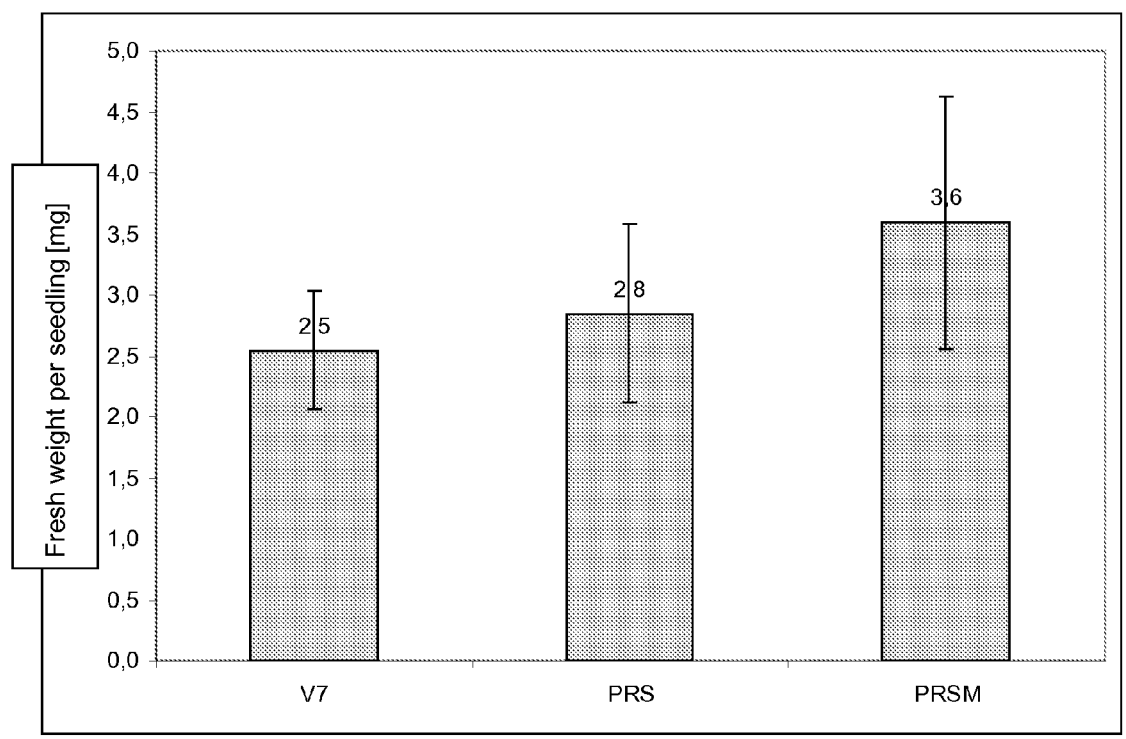
FIG. 4 shows the results of the growth analysis.

FIG. 4 shows the results of the growth analysis. After 8 days in the growth culture, the control seedlings had an average fresh weight of 2.5 mg. In contrast, the transgenic plants had a fresh weight of 2.8 mg (PRS) and 3.6 mg (PRSM), respectively. This corresponds to an increase in fresh weight of 12% (PRS) and 41%, respectively.

EXAMPLE 9

Production and Selection of Transgenic Plants with Expression of a Phosphoribosylpyrophosphate Synthetase Gene (PRS) of *Ashbya gossypii*

Two different PRS genes of fungal origin were used for the expression in plants. One encodes the wildtype PRS class I activity of *A. gossypii* ATCC 10895 (AGR371Cp) and the other represents a mutant form. The mutant variant carries three point mutations leading to the exchange of leucine 133 to isoleucine, and histidine 196 to glutamine.

Figure 5:
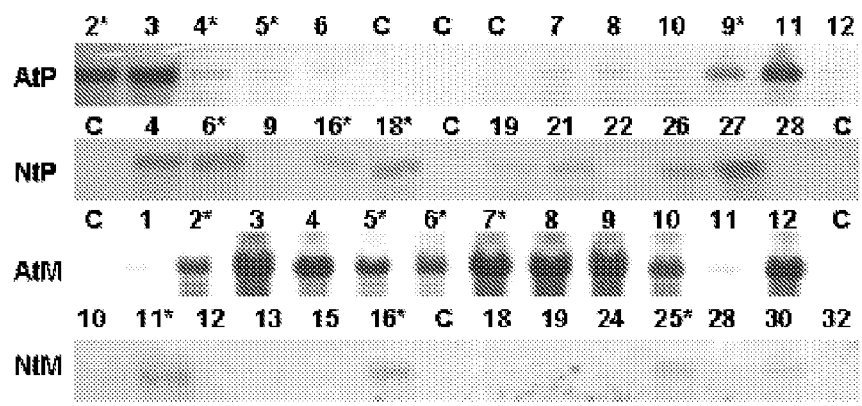
FIG. 5 shows expression of the *Ashbya gossypii* PRS gene in leaves of *Arabidopsis thaliana* and *Nicotiana tabacum* transformants.

Therefore this mutant form of the *A. gossypii* PRS protein resembles a protein of PRS class II activity. *A. gossypii* PRS genes were chosen because both variants of the gene were available that are highly heterologous to the plant genes. All constructs used to transform either *Nicotiana tabacum* or *Arabidopsis thaliana* plants were made with the binary vector pBinAR (Höfgen and Willmitzer, 1990), a derivative of the pBin19 vector containing the 35S promoter of the cauliflower mosaic virus for constitutive expression of the target gene and the octopine synthase polyadenylation signal. Primary transformants (T1) were grown on selection media containing 50 mg*I-1 kanamycin. Kanamycin resistant plantlets were transferred to soil and grown in growth chambers under standard cultivation conditions. For each transformation about 30 of the plants that survived the selection process were regenerated and further analysed. Leaves of these plants were analysed for the expression of the transgene three to five weeks after the transfer (FIG. 5). Seeds were collected, and the T2 offspring grown again on selection medium. Resistant plants of the T2 generation were selected when about one fourth of the offspring was not able to survive the selection process. These plants were transferred on soil into growth chambers and further grown under optimum conditions and seeds were harvested (T3). The T3 seeds were again put on selection plates, to identify sets of seed where all plants are kanamycin resistant and can be regarded as homozygous for at least one functional insertion of the T-DNA. All experiments were carried out with seed from the T3 or T4 generation that passed this selection process. Three to four lines originating from different individual primary transformants were chosen for each experiment. All experiments were carried out together with control plants that have passed the same selection criteria after transformation with an empty vector.

FIG. 5: Expression of the *Ashbya gossypii* PRS gene in leaves of *Arabidopsis thaliana* and *Nicotiana tabacum* transformants.

Plants were grown on selection media and resistant plantlets were transferred to soil and grown under standard cultivation conditions. Leaves of these plants were analysed three to five weeks after the transfer for steady-state PRS mRNA levels using the full-length cDNA coding for PRS as hybridisation probe. Same amounts of RNA were analysed. AtP: *A. thaliana* transformed with a construct to express the wildtype PRS gene of *A. gossypii*; NtP: *N. tabacum* transformed with a construct to express the wildtype PRS gene of *A. gossypii*; AtM: *A. thaliana* transformed with a construct to express a mutant form of the PRS gene of *A. gossypii*; NtM: *N. tabacum* transformed with a construct to express a mutant form of the PRS gene of *A. gossypii*; Numbers indicate the identity of the individual primary transformant; Asterisks indicate the lines that were further selected; C: control plants transformed with an empty vector.

EXAMPLE 10

PRS Expression Leads to Significant Increase in Extractable PRS Activity

It was confirmed that the expression of the PRS gene resulted in an increase in enzyme activity by assaying PRS activity using a standardised enzyme coupled spectrophotometric determination procedure.

Figure 6:
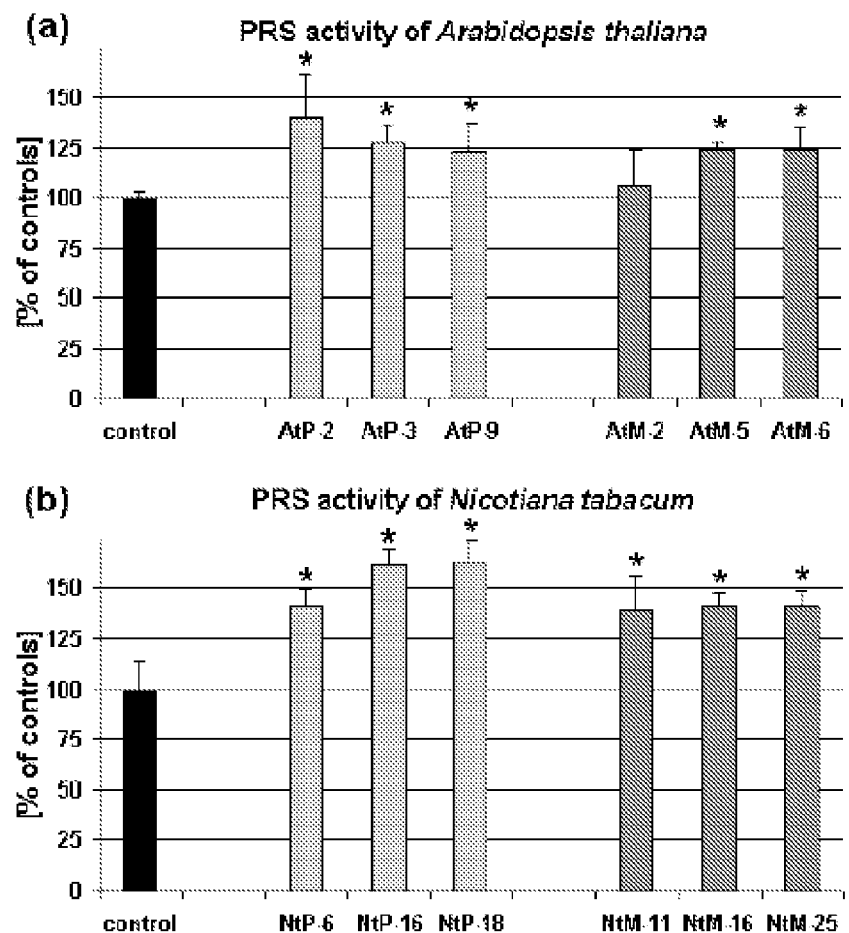
FIG. 6 shows PRS activities of *Arabidopsis thaliana* and *Nicotiana tabacum* seedlings.

Total PRS activity was assayed in soluble protein extracts of *A. thaliana* and *N. tabacum* seedlings grown in liquid culture after 7 or 8 days of growth in the respective growth media (FIG. 6). All data were calculated on a plant fresh weight basis as percentage of the respective control transformants (*N. tabacum*, 2.17±0.31 µmol·min$^{-1}$·(g fresh weight)$^{-1}$; *A. thaliana*, 2.83±0.14 µmol·min$^{-1}$·(g fresh weight)$^{-1}$.

The results show that expression of the wildtype PRS gene significantly increased PRS activity 1.2-1.4-fold in *Arabidopsis* and 1.4-1.6-fold in *Nicotiana*.

Expression of the mutated PRS gene increased the PRS activity 1.3-fold in *Arabidopsis* and 1.4-fold in *Nicotiana*. With exception of AtM-2 all values show no strong variation between the individual seed batches analysed and are significantly higher when compared to the respective control transformants.

FIG. 6: PRS activities of *Arabidopsis thaliana* and *Nicotiana tabacum* seedlings.

Plants were grown in liquid seedling culture for 7 or 8 days in the respective growth media. The experiments were carried out with plants of the T4 generation. Values are the means±standard deviation of three to four lines originating from different individual primary transformants. Data are given as percentage of the respective control transformants, with *N. tabacum* at 2.17±0.31 μmol*min-1*(g fresh weight)-1 and *A. thaliana* at 2.83±0.14 μmol*min-1*(g fresh weight)-1. Unpaired two-tailed t-tests were used. Significantly different values (P<0.05) are labelled with an asterisk.
(a) PRS activity of *Arabidopsis*. AtP: *A. thaliana* expressing the wildtype PRS gene; AtM: *A. thaliana* expressing a mutant form of the PRS gene; Numbers indicate the identity of the individual primary transformant.
(b) PRS activity of *Nicotiana*. NtP: *N. tabacum* expressing the wildtype PRS gene; NtM: *N. tabacum* expressing a mutant form of the PRS gene; Numbers indicate the identity of the individual primary transformant.

EXAMPLE 11

Metabolite Analysis Reveals a Negative Correlation of Sucrose Content with Biomass Accumulation Extracts of the seedlings were analysed for carbohydrate, nucleotide and amino acid content and composition. Metabolite levels were always calculated both on a fresh weight basis to analyse differences in concentrations and on a total seedling basis to summarise productivity.

Significant changes could be found for the individual sugar levels. Hexose concentrations were increased in *A. thaliana* or *N. tabacum* seedlings.

As the fresh weight accumulation of the seedlings with additional PRS activity after growth in liquid culture is increased, higher amounts of total carbohydrate content on a seedling basis are present in either *A. thaliana* or *N. tabacum* seedlings (data not shown).

Other important precursors needed for cell division and growth are nucleotides and amino acids. Therefore these intermediates were determined in *A. thaliana* and *N. tabacum* seedling cultures. Only the data of the *A. thaliana* seedlings were shown (FIG. 7) as significant changes correlating with the increased PRS activity could only be found in this species, while *N. tabacum* seedlings mostly show comparable but insignificant tendencies.

Analysis of nucleotide concentrations revealed an increase of UDP-glucose (FIG. 7a) and free nucleotides (FIG. 7b) in *A. thaliana* seedlings with increasing PRS activity, while only some of the UDP-glucose values are significantly different to the controls.

Additionally in some of the *A. thaliana* seedlings the ATP/ADP ratio was significantly increased (FIG. 7c), while this ratio was decreased in the *N. tabacum* seedlings with increasing PRS activity (data not shown).

These results suggest that an increase of the overall nucleotide pools is not the main reason for the increased rate of growth in plants that over express PRS.

Analysis of total amino acid concentrations revealed an increase in *A. thaliana* seedlings that correlates well with increasing PRS activity (FIG. 7d), while only some of the values are significantly different to the controls. A more detailed analysis of amino acid composition revealed identical behaviour in *A. thaliana* and *N. tabacum* seedlings but again only some results from *A. thaliana* were leading to significant changes. While the total amount of amino acids was increased in all seedlings with increased PRS activity, the proportion of minor amino acids decreased (FIG. 7e)

Other changes included an increase in the major amino acids serine and glycine (data not shown), and a correlating decrease in the proportion of the branched chain amino acids (BCAA) in *A. thaliana* seedlings with increased PRS activity (FIG. 7f). At this point it is supposed that these changes in the proportion of specific classes of amino acids in relation to the total amino acid pool are due to their coordinated regulation within individual amino acid biosynthesis pathways.

Figure 7:
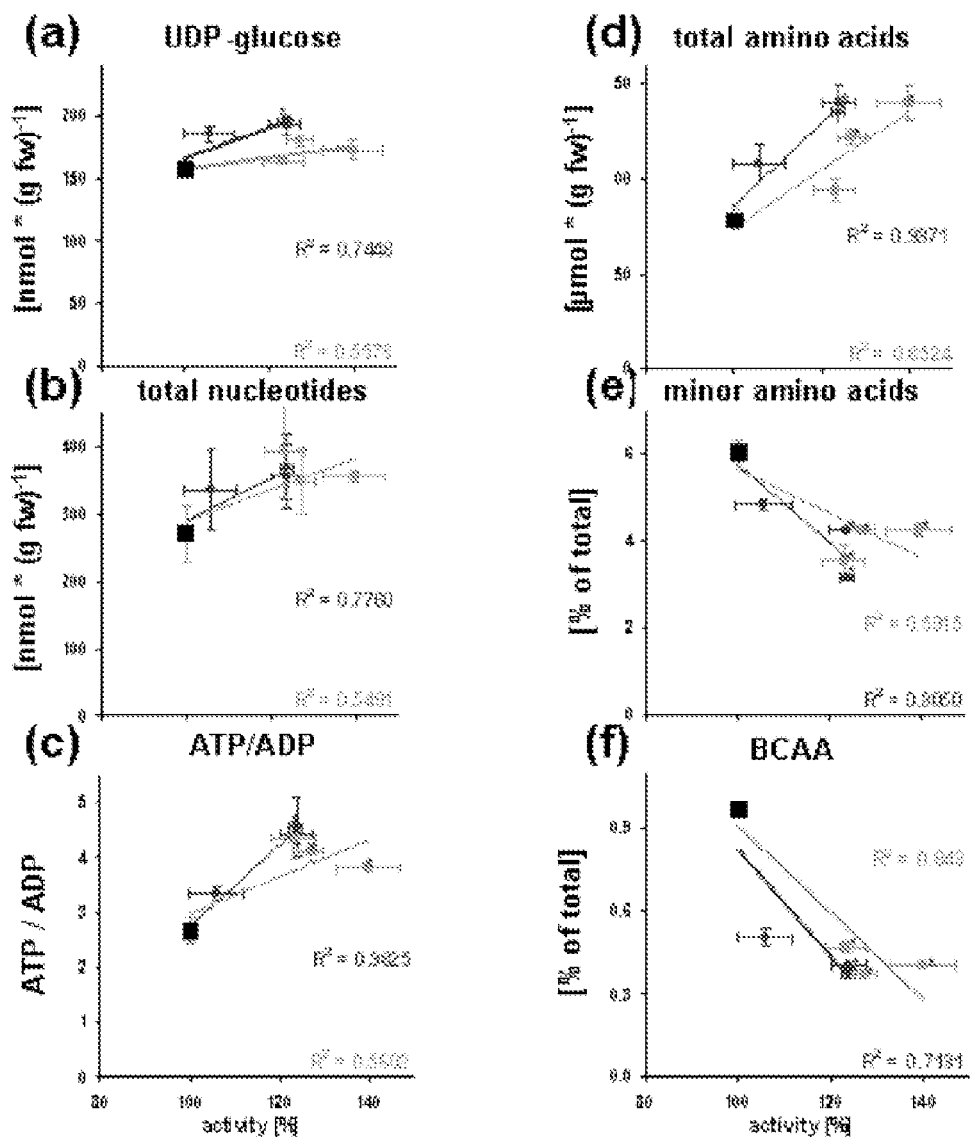
FIG. 7 shows metabolite analyses of Arabidopsis thaliana seedlings.

FIG. 7: Metabolite Analyses of *Arabidopsis thaliana* Seedlings.

Plants were grown in liquid seedling culture for 7 days as in FIG. 2. Values are given as means and standard error of three to four replicates. Unpaired two-tailed t-tests were used. Significantly different values (P<0.05) are labelled with a red asterisk. Linear correlation analysis was performed and the respective correlation coefficients were given. Total nucleotides: AMP, ADP, UDP, GDP, UTP, ATP, and GTP. Total amino acids: All L-α-amino acids without proline and cystein, including β-alanine, γ-aminobutyric acid, citrulline, and ornithine. Minor amino acids: arginine, histidine, isoleucine, leucine, lysine, methionine, phenylalanine, tryptophan, tyrosine, and valine. BCAA: branched chain amino acids: isoleucine, leucine, and valine.
(a)-(c) Relationship of PRS activity and nucleotide accumulation. Grey: *A. thaliana* expressing the wildtype PRS gene; black: *A. thaliana* expressing the mutant form; black square: empty vector controls.
(d)-(f) Relationship of PRS activity and amino acid accumulation. Grey: *A. thaliana* expressing the wildtype PRS gene; black: *A. thaliana* expressing the mutant form; black square: empty vector controls.

EXAMPLE 12

Figure 8:
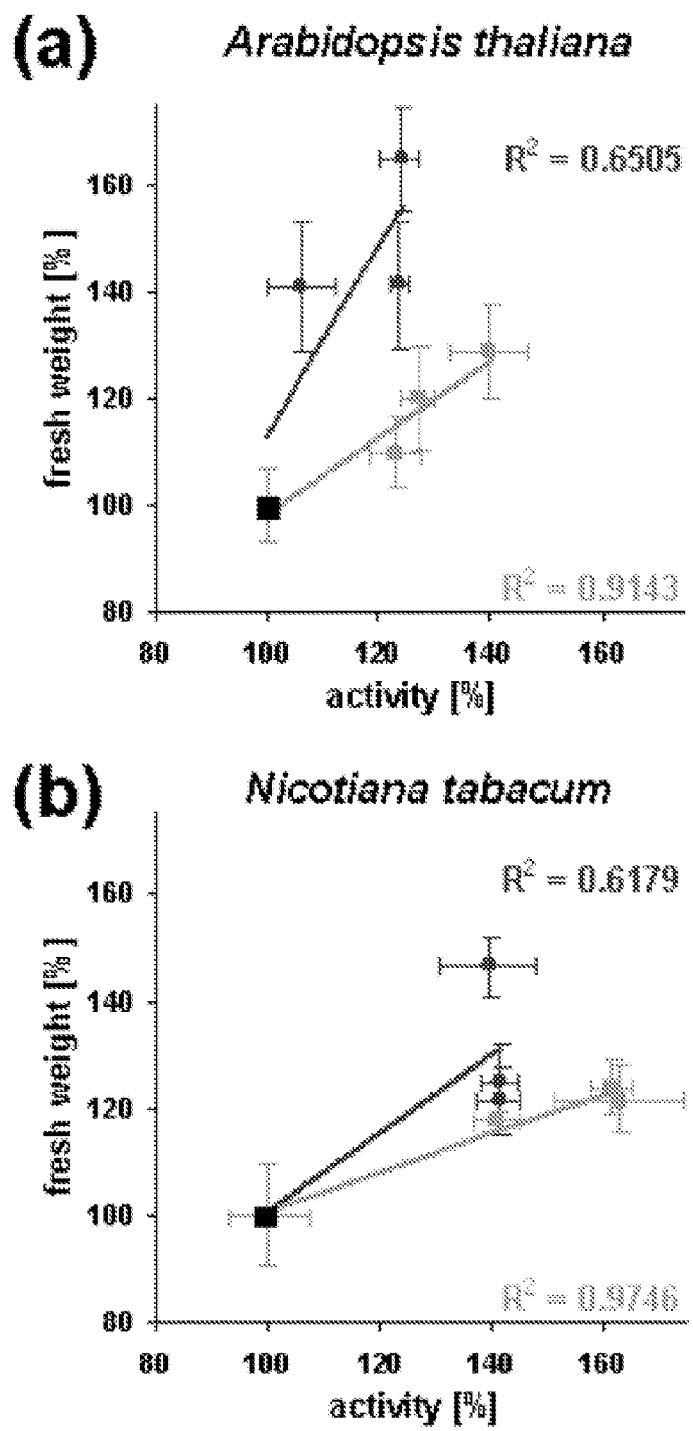
FIG. 8 shows correlation of PRS activity and fresh weight accumulation.

Higher Biomass Accumulation is Also Evident Under Different Standardised Growth Conditions Increased PRS activity increases growth of *A. thaliana* and *N. tabacum* seedlings under optimised conditions in liquid culture (FIG. 8).

FIG. 8: Correlation of PRS Activity and Fresh Weight Accumulation.

Plants were grown in liquid seedling cultures for 7 or 8 days in the respective growth media as in FIG. 6. Values are the means+/− standard error of three to four lines originating from different individual primary transformants. Data are given as percentage of the respective control transformants, with *N. tabacum* at 49.6±9.03 mg*seedling-1 and *A. thaliana* at 2.7±0.48 mg*seedling-1. Unpaired two-tailed t-tests were used. All fresh weight values are significantly different from the controls (P<0.05) except AtP-9. Linear correlation analysis was performed and the respective correlation coefficients were given.
(a) Relationship of PRS activity and fresh weight accumulation of *Arabidopsis*. grey: *A. thaliana* expressing the wildtype PRS gene; black: *A. thaliana* expressing the mutant form; black square: empty vector controls.
(b) Relationship of PRS activity and fresh weight accumulation of *Nicotiana*. grey: *N. tabacum* expressing the wildtype PRS gene; black: *N. tabacum* expressing the mutant form; black square: empty vector controls.

Further experiments were performed to investigate whether growth enhancement is also present in *A. thaliana* and *N. tabacum* plants grown under more natural and less optimised conditions.

*A. thaliana* plants were grown in growth chambers on soil with two different nutrient regimes and *N. tabacum* plants were grown either in growth chambers on quartz sand watered with nutrient solution at medium light intensities or in the greenhouse on soil with low light intensities. Expression of the PRS gene and also expression of the mutant form in either *A. thaliana* (FIG. 9) or *N. tabacum* (FIG. 10) led to an increase in growth at all tested growth conditions. At both high and low nutrient availability, *A. thaliana* plants expressing the PRS genes showed a bigger rosette diameter (data not shown) and higher rosette fresh weight when compared to the respective controls (FIG. 9), whereas leaf number was not altered (data not shown). *N. tabacum* plants expressing the PRS genes also showed increased biomass accumulation on a fresh and on a dry weight basis (FIG. 10) and increased leaf area (data not shown). Fresh weight accumulation of roots and shoots was analysed separately, but no significant change in root to shoot ratio could be found (data not shown). Again this indicates that growth increases in both organs in parallel. At any of the analysed growth conditions randomised *N. tabacum* plants expressing the PRS genes could be easily distinguished from the control transformants because of their increase of plant height. In summary all these approaches show that increased PRS activity increases plant biomass accumulation under a variety of growth conditions.

Figure 9:
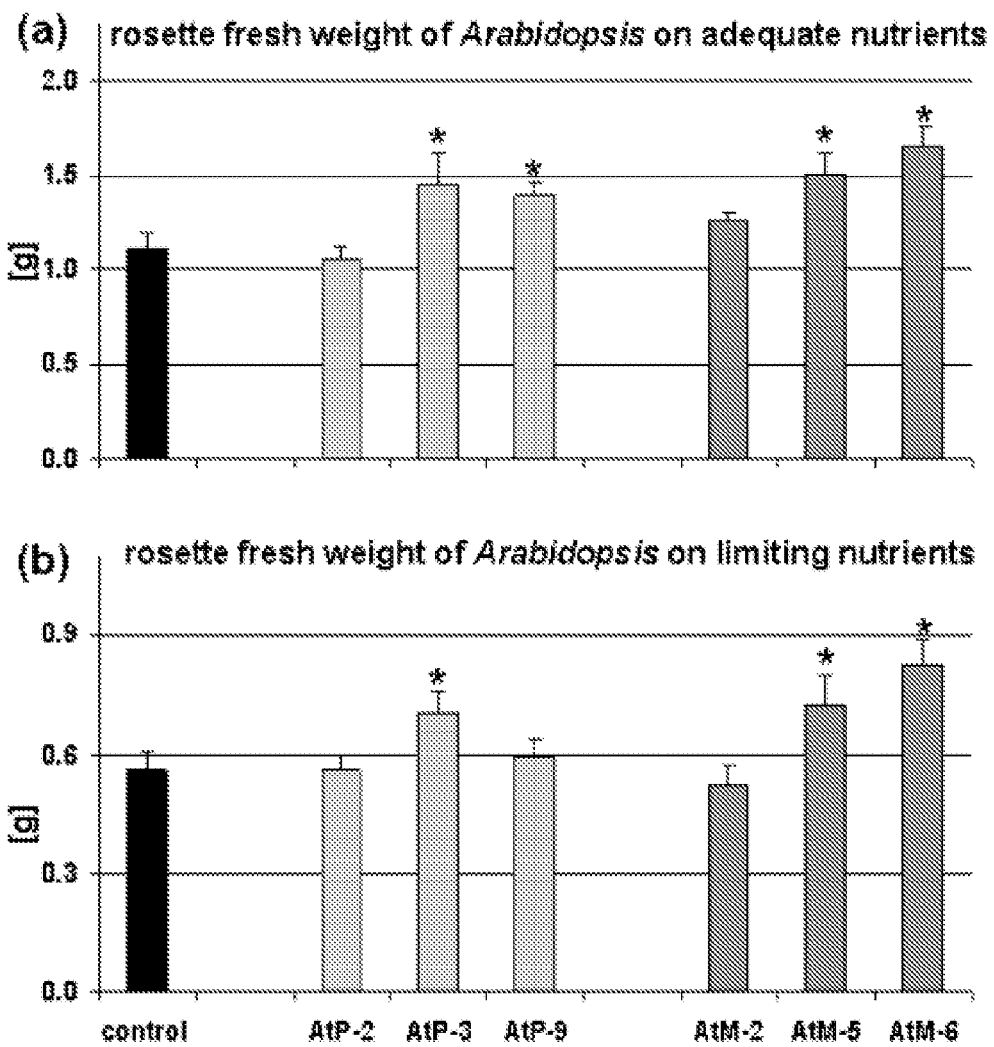
FIG. 9 shows growth analyses of *Arabidopsis thaliana* plants.

FIG. 9 Growth Analyses of *Arabidopsis thaliana* Plants.

Plants were grown at different conditions as indicated. The experiments were carried out with plants of the T4 generation. Values are the means+/− standard error of three biological replicates with six to twelve samples each. Unpaired two-tailed t-tests were used. Significantly different values ($P<0.05$) are labelled with an asterisk. AtP: *A. thaliana* expressing the wildtype PRS gene; AtM: *A. thaliana* expressing a mutant form of the PRS gene; Numbers indicate the identity of the individual primary transformant.

(a) Rosette fresh weight of *Arabidopsis* plants grown with adequate nutrients. Plants were grown in growth chambers with 8 h day at 145pE, 20° C., 60% relative humidity, and with 16 h night at 18° C. in pots of 6 cm in diameter filled with a substrate containing high nutrient concentrations. Plants were harvested 5 weeks after transfer on soil.

(b) Rosette fresh weight of *Arabidopsis* plants grown with limiting nutrients. Plants were grown at the same growth conditions and in parallel with plants in (a), but the substrate mixture containing low nutrient concentrations as described in the experimental procedures. Plants were harvested 5 weeks after transfer on soil.

Figure 10:
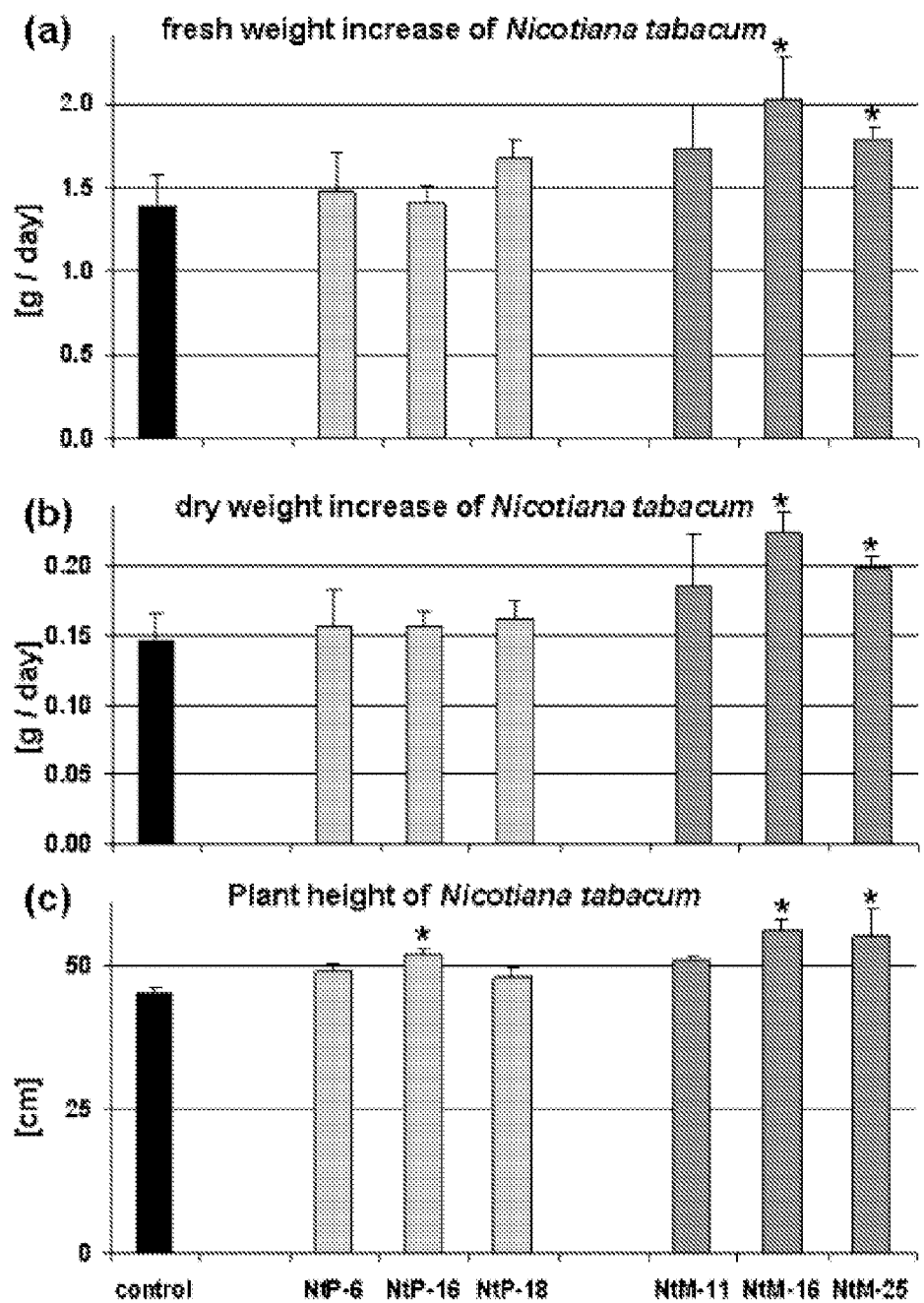
FIG. 10 shows growth analyses of *Nicotiana tabacum* plants.

FIG. 10: Growth Analyses of *Nicotiana tabacum* Plants.

The experiments were carried out with plants of the T4 generation. Values are the means+/− standard error of three biological replicates with four samples each. Unpaired two-tailed t-tests were used. Significantly different values ($P<0.05$) are labelled with an asterisk. NtP: *N. tabacum* expressing the wildtype PRS gene; NtM: *N. tabacum* expressing a mutant form of the PRS gene; Numbers indicate the identity of the individual primary transformant.

(a) Fresh weight increase. Plants were grown in growth chambers with 12 h day at 350 µE, 23° C., and 12 h night at 20° C. and 60% relative humidity in pots of 16 cm in diameter in quartz sand culture and watered daily with nutrient solution. Plants were harvested after 3 and 4 weeks after transfer on sand culture and growth rates per day were calculated from these measurements.

(b) Dry weight increase of *Nicotiana* plants grown as described in (a).

(c) Height of *Nicotiana* plants. Plants were grown in a greenhouse with 16 h day at 200 µE, 25° C., and 8 h night at 20° C., and 60% relative humidity in pots of 20 cm in diameter filled with soil. Plants were measured 5 weeks after transfer on soil.

EXAMPLE 13

Engineering Alfalfa Plants with Increased Biomass Production by Over-Expressing Phosphoribosyl Pyrophosphate Synthase A regenerating clone of alfalfa (*Medicago sativa*) is transformed using state of the art methods (e.g. McKersie et al., Plant Physiol 119, 839 (1999)). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D. C. W. and Atanassov A. (Plant Cell Tissue Organ Culture 4, 111 (1985)). Alternatively, the RA3 variety (University of Wisconsin) is selected for use in tissue culture (Walker et al., Am. J. Bot. 65, 654 (1978)).

Petiole explants are cocultivated with an overnight culture of *Agrobacterium tumefaciens* C58C1 pMP90 (McKersie et al., Plant Physiol 119, 839 (1999)) or LBA4404 containing a binary vector. Many different binary vector systems have been described for plant transformation (e.g. An G., in *Agrobacterium* Protocols, Methods in Molecular Biology, Vol 44, pp 47-62, Gartland K. M. A. and Davey M. R. eds. Humana Press, Totowa, N.J.). Many are based on the vector pBIN19 described by Bevan (Nucleic Acid Research. 12, 8711 (1984)) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 5,7673,666 and 6,225,105). Similarly, various promoters can be used to regulate the trait gene that provides constitutive, developmental, tissue or environmental regulation of gene transcription. In this example, the 34S promoter (GenBank Accession numbers M59930 and X16673) is used to provide constitutive expression of the trait gene.

The explants are cocultivated for 3 days in the dark on SH induction medium containing 288 mg/L Pro, 53 mg/L thioproline, 4.35 g/L $K_2SO_4$, and 100 µm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings are transplanted into pots and grown in a greenhouse.

T1 or T2 generation plants are produced and analyzed as described above.

EXAMPLE 14

Engineering Ryegrass Plants with Increased Biomass Production by Over-Expressing Phosphoribosyl Pyrophosphate Synthase Seeds of several different ryegrass varieties may be used as explant sources for transformation, including the commercial variety Gunne available from Svalöf Weibull seed company or the variety Affinity. Seeds are surface-sterilized sequentially with 1% Tween-20 for 1 minute, 100% bleach for 60 minutes, 3 rinses with 5 minutes each with deionized and distilled $H_2O$, and then germinated for 3-4 days on moist, sterile filter paper in the dark. Seedlings are further sterilized for 1 minute with 1% Tween-20, 5 minutes with 75% bleach, and rinsed 3 times with dd $H_2O$, 5 min each.

Surface-sterilized seeds are placed on the callus induction medium containing Murashige and Skoog basal salts and vitamins, 20 g/L sucrose, 150 mg/L asparagine, 500 mg/L casein hydrolysate, 3 g/L Phytagel, 10 mg/L BAP, and 5 mg/L dicamba. Plates are incubated in the dark at 25° C. for 4 weeks for seed germination and embryogenic callus induction.

After 4 weeks on the callus induction medium, the shoots and roots of the seedlings are trimmed away, the callus is transferred to fresh media, maintained in culture for another 4 weeks, and then transferred to MSO medium in light for 2 weeks. Several pieces of callus (11-17 weeks old) are either strained through a 10 mesh sieve and put onto callus induction medium, or cultured in 100 ml of liquid ryegrass callus induction media (same medium as for callus induction with agar) in a 250 ml flask. The flask is wrapped in foil and shaken at 175 rpm in the dark at 23° C. for 1 week. Sieving the liquid culture with a 40-mesh sieve collected the cells. The fraction collected on the sieve is plated and cultured on solid ryegrass callus induction medium for 1 week in the dark at 25° C. The callus is then transferred to and cultured on MS medium containing 1% sucrose for 2 weeks.

Transformation can be accomplished with either *Agrobacterium* of with particle bombardment methods. An expression vector is created containing a constitutive plant promoter and the cDNA of the gene in a pUC vector. The plasmid DNA is prepared from *E. coli* cells using with Qiagen kit according to manufacturer's instruction. Approximately 2 g of embryogenic callus is spread in the center of a sterile filter paper in a Petri dish. An aliquot of liquid MSO with 10 g/L sucrose is added to the filter paper. Gold particles (1.0 µm in size) are coated with plasmid DNA according to method of Sanford et al., 1993 and delivered to the embryogenic callus with the following parameters: 500 µg particles and 2 µg DNA per shot, 1300 psi and a target distance of 8.5 cm from stopping plate to plate of callus and 1 shot per plate of callus.

After the bombardment, calli are transferred back to the fresh callus development medium and maintained in the dark at room temperature for a 1-week period. The callus is then transferred to growth conditions in the light at 25° C. to initiate embryo differentiation with the appropriate selection agent, e.g. 250 nM Arsenal, 5 mg/L PPT or 50 mg/L kanamycin. Shoots resistant to the selection agent are appearing and once rotted are transferred to soil.

Samples of the primary transgenic plants (TO) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

Transgenic TO ryegrass plants are propagated vegetatively by excising tillers. The transplanted tillers are maintained in the greenhouse for 2 months until well established. The shoots are defoliated and allowed to grow for 2 weeks.

T1 or T2 generation plants are produced and analyzed as described.

EXAMPLE 15

Engineering Soybean Plants with Increased Biomass Production by Overexpressing Phosphoribosyl Pyrophosphate Synthase Soybean is transformed according to the following modification of the method described in the Texas A&M U.S. Pat. No. 5,164,310. Several commercial soybean varieties are amenable to transformation by this method. The cultivar Jack (available from the Illinois Seed Foundation) is a commonly used for transformation. Seeds are sterilized by immersion in 70% (v/v) ethanol for 6 min and in 25% commercial bleach (NaOCl) supplemented with 0.1% (v/v) Tween for 20 min, followed by rinsing 4 times with sterile double distilled water. Seven-day seedlings are propagated by removing the radicle, hypocotyl and one cotyledon from each seedling. Then, the epicotyl with one cotyledon is transferred to fresh germination media in petri dishes and incubated at 25° C. under a 16-h photoperiod (approx. 100 µmol/m$^2$s) for three weeks. Axillary nodes (approx. 4 mm in length) were cut from 3-4 week-old plants. Axillary nodes are excised and incubated in *Agrobacterium* LBA4404 culture.

Many different binary vector systems have been described for plant transformation (e.g. An G., in *Agrobacterium* Protocols. Methods in Molecular Biology Vol. 44, p. 47-62, Gartland K. M. A. and Davey M. R. eds. Humana Press, Totowa, N.J.). Many are based on the vector pBIN19 described by Bevan (Nucleic Acid Research. 12, 8711 (1984)) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 5,7673,666 and 6,225,105). Similarly, various promoters can be used to regulate the trait gene to provide constitutive, developmental, tissue or environmental regulation of gene transcription. In this example, the 34S promoter (GenBank Accession numbers M59930 and X16673) can be used to provide constitutive expression of the trait gene.

After the co-cultivation treatment, the explants are washed and transferred to selection media supplemented with 500 mg/L timentin. Shoots are excised and placed on a shoot elongation medium. Shoots longer than 1 cm are placed on rooting medium for two to four weeks prior to transplanting to soil.

The primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

T1 or T2 generation plants are produced analyted as described above.

EXAMPLE 16

Engineering Rapeseed/Canola Plants with Increased Biomass Production by Over-Expressing Phosphoribosyl Pyrophosphate Synthase Cotyledonary petioles and hypocotyls of 5-6 day-old young seedlings are used as explants for tissue culture and transformed according to Babic et al. (Plant Cell Rep 17, 183 (1998)). The commercial cultivar Westar (Agriculture Canada) is the standard variety used for transformation, but other varieties can be used.

*Agrobacterium tumefaciens* LBA4404 containing a binary vector can be used for canola transformation. Many different binary vector systems have been described for plant transformation (e.g. An G., in *Agrobacterium* Protocols. Methods in Molecular Biology Vol. 44, p. 47-62, Gartland K. M. A. and Davey M. R. eds. Humana Press, Totowa, N.J.). Many are based on the vector pBIN19 described by Bevan (Nucleic Acid Research. 12, 8711 (1984)) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 5,7673,666 and 6,225,105). Similarly, various promoters can be used to regulate the trait gene to provide constitutive, developmental, tissue or environmental regulation of gene transcription. In this example, the 34S promoter (GenBank Accession numbers M59930 and X16673) can be used to provide constitutive expression of the trait gene.

Canola seeds are surface-sterilized in 70% ethanol for 2 min., and then in 30% Clorox with a drop of Tween-20 for 10 min, followed by three rinses with sterilized distilled water. Seeds are then germinated in vitro 5 days on half strength MS medium without hormones, 1% sucrose, 0.7% Phytagar at 23° C., 16 h light. The cotyledon petiole explants with the cotyledon attached are excised from the in vitro seedlings, and inoculated with *Agrobacterium* by dipping the cut end of the petiole explant into the bacterial suspension. The explants are then cultured for 2 days on MSBAP-3 medium containing 3 mg/L BAP, 3% sucrose, 0.7% Phytagar at 23° C., 16 h light. After two days of co-cultivation with *Agrobacterium*, the petiole explants are transferred to MSBAP-3 medium containing 3 mg/L BAP, cefotaxime, carbenicillin, or timentin (300 mg/L) for 7 days, and then cultured on MSBAP-3 medium with cefotaxime, carbenicillin, or timentin and selection agent until shoot regeneration. When the shoots were 5-10 mm in length, they are cut and transferred to shoot elongation medium (MSBAP-0.5, containing 0.5 mg/L BAP). Shoots of about 2 cm in length are transferred to the rooting medium (MSO) for root induction.

Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

T1 or T2 generation plants are produced and analyzed as described above.

EXAMPLE 17

Engineering Corn Plants with Increased Biomass Production by Over-Expressing Phosphoribosyl Pyrophosphate Synthase Transformation of maize (*Zea Mays* L.) is performed with a modification of the method described by Ishida et al. (Nature Biotech 14745 (1996)). Transformation is genotype-dependent in corn and only specific genotypes are amenable to transformation and regeneration. The inbred line A188 (University of Minnesota) or hybrids with A188 as a parent are good sources of donor material for transformation (Fromm et al. Biotech 8, 833 (1990)), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system of Japan Tobacco is described in WO patents WO 94/00977 and WO 95/06722. Vectors were constructed as described. Various selection marker genes can be used including the maize gene encoding a mutated acetohydroxy acid synthase (AHAS) enzyme (U.S. Pat. No. 6,025,541). Similarly, various promoters can be used to regulate the trait gene to provide constitutive, developmental, tissue or environmental regulation of gene transcription. In this example, the 34S promoter (GenBank Accession numbers M59930 and X16673) was used to provide constitutive expression of the trait gene.

Excised embryos are grown on callus induction medium, then maize regeneration medium, containing imidazolinone as a selection agent. The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

The T1 transgenic plants are then evaluated for their enhanced stress tolerance, like tolerance to low temperature, and/or increased biomass production according to the method described in Example 1. The T1 generation of single locus insertions of the T-DNA will segregate for the transgene in a 3:1 ratio. Those progeny containing one or two copies of the transgene are tolerant regarding the imidazolinone herbicide, and exhibit an enhancement of stress tolerance, like tolerance to low temperature, and/or increased biomass production than those progeny lacking the transgenes.

T1 or T2 generation plants are produced and analyzed as described above.

Homozygous T2 plants exhibited similar phenotypes. Hybrid plants (F1 progeny) of homozygous transgenic plants and non-transgenic plants also exhibited the trait.

EXAMPLE 18

Engineering Wheat Plants with Increased Biomass Production by Over-Expressing Phosphoribosyl Pyrophosphate Synthase Transformation of wheat is performed with the method described by Ishida et al. (Nature Biotech. 14745 (1996)). The cultivar Bobwhite (available from CYMMIT, Mexico) is commonly used in transformation. Immature embryos are co-cultivated with Agrobacterium tumefaciens that carry "super binary" vectors, and transgenic plants are recovered through organogenesis. The super binary vector system of Japan Tobacco is described in WO patents WO 94/00977 and WO 95/06722. Vectors were constructed as described. Various selection marker genes can be used including the maize gene encoding a mutated acetohydroxy acid synthase (AHAS) enzyme (U.S. Pat. No. 6,025,541). Similarly, various promoters can be used to regulate the trait gene to provide constitutive, developmental, tissue or environmental regulation of gene transcription. In this example, the 34S promoter (GenBank Accession numbers M59930 and X16673) was used to provide constitutive expression of the trait gene.

After incubation with *Agrobacterium*, the embryos are grown on callus induction medium, then regeneration medium, containing imidazolinone as a selection agent. The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

The T1 transgenic plants are then evaluated for their increased biomass production according to the method described above. The T1 generation of single locus insertions of the T-DNA will segregate for the transgene in a 3:1 ratio. Those progeny containing one or two copies of the transgene are tolerant regarding the imidazolinone herbicide, and exhibit an increased biomass production compared to the progeny lacking the transgenes. Homozygous T2 plants exhibit similar phenotypes.

EXAMPLE 19

Identification of Identical and Heterologous Genes

Gene sequences can be used to identify identical or heterologous genes from cDNA or genomic libraries. Identical genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution, hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially identical or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homology (or sequence identity/similarity) only in a distinct domain of (for example 10-20 amino acids) can be carried out by using synthetic radio labeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide Hybridization Solution:
6×SSC
0.01 M sodium phosphate
1 mM EDTA (pH 8)
0.5% SDS
100 µg/ml denatured salmon sperm DNA
0.1% nonfat dried milk During hybridization, temperature is lowered stepwise to 5-10° C. below the estimated oligonucleotide $T_m$ or down to room temperature followed by washing steps and autoradiography. Washing is performed with low stringency such as 3 washing steps using 4×SSC. Further details are described by Sambrook J. et al., 1989, "Molecular Cloning: A Laboratory Manual," Cold Spring Harbor Laboratory Press or Ausubel F. M. et al., 1994, "Current Protocols in Molecular Biology," John Wiley & Sons.

EXAMPLE 20

Identification of Identical Genes by Screening Expression Libraries with Antibodies c-DNA clones can be used to produce recombinant polypeptide for example in *E. coli* (e.g. Qiagen QIAexpress pQE system). Recombinant polypeptides are then normally affinity purified via Ni-NTA affinity chromatography (Qiagen). Recombinant polypeptides are then used to produce specific antibodies for example by using standard techniques for rabbit immunization. Antibodies are affinity purified using a Ni-NTA column saturated with the recombinant antigen as described by Gu et al., BioTechniques 17, 257 (1994). The antibody can than be used to screen expression cDNA libraries to identify identical or heterologous genes via an immunological screening (Sambrook, J. et al., 1989, "Molecular Cloning: A Laboratory Manual," Cold Spring Harbor Laboratory Press or Ausubel, F. M. et al., 1994, "Current Protocols in Molecular Biology", John Wiley & Sons).

EXAMPLE 21

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp W. D., DNA repair mechanisms, in: *Escherichia coli* and *Salmonella*, p. 2277-2294, ASM, 1996, Washington.) Such strains are well known to those skilled in the art. The use of such strains is illustrated, for example, in Greener A. and Callahan M., Strategies 7, 32 (1994). Transfer of mutated DNA molecules into plants is preferably done after selection and testing in microorganisms. Transgenic plants are generated according to various examples within the exemplification of this document.

EXAMPLE 22

Engineering *Arabidopsis* Plants with Increased Biomass Production by Overexpressing PRS Encoding Genes for Example from *Brassica napus*, *Glycine Max*, *Zea mays* or *Oryza sativa* Using Tissue-Specific or Stress-Inducible Promoters Transgenic *Arabidopsis* plants over-expressing low temperature resistance and/or tolerance related protein encoding genes from for example *Brassica napus*, *Glycine max*, *Zea mays* and *Oryza sativa* are created as described in example 1 to express the PRS protein encoding transgenes under the control of a tissue-specific or stress-inducible promoter. T2 generation plants show increased biomass production and/or dry matter production and/or seed yield when compared to non-transgenic wild type plants.

EXAMPLE 23

Engineering Alfalfa Plants with Increased Biomass Production by Over-Expressing PRS Genes for Example from *Brassica napus*, *Glycine Max*, *Zea Mays* or *Oryza sativa* for Example A regenerating clone of alfalfa (*Medicago sativa*) is transformed using the method of McKersie et al., (Plant Physiol.

119, 839 (1999)). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown and Atanassov (Plant Cell Tissue Organ Culture 4, 111 (1985)). Alternatively, the RA3 variety (University of Wisconsin) has been selected for use in tissue culture (Walker et al., Am. J. Bot. 65, 54 (1978)).

Petiole explants are cocultivated with an overnight culture of *Agrobacterium* tumefaciens C58C1 pMP90 (McKersie et al., Plant Physiol 119, 839 (1999)) or LBA4404 containing a binary vector. Many different binary vector systems have been described for plant transformation (e.g. An G., in *Agrobacterium* Protocols. Methods in Molecular Biology Vol. 44, p. 47-62, Gartland K. M. A. and Davey M. R. eds. Humana Press, Totowa, N.J.). Many are based on the vector pBIN19 described by Bevan (Nucleic Acid Research. 12, 8711 (1984)) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 5,7673,666 and 6,225,105). Similarly, various promoters can be used to regulate the trait gene that provides constitutive, developmental, tissue or environmental regulation of gene transcription. In this example, the 34S promoter (GenBank Accession numbers M59930 and X16673) was used to provide constitutive expression of the trait gene.

The explants are cocultivated for 3 days in the dark on SH induction medium containing 288 mg/L Pro, 53 mg/L thioproline, 4.35 g/L $K_2SO_4$, and 100 μm acetosyringinone. The explants were washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings are transplanted into pots and grown in a greenhouse.

The T0 transgenic plants are propagated by node cuttings and rooted in Turface growth medium. T1 or T2 generation plants are analyzed as described in previous examples. Plants have increased biomass production and/or dry matter production and/or seed yield when compared to non-transgenic wild type plants.

EXAMPLE 24

Engineering Ryegrass Plants with Increased Biomass Production by Overexpressing PRS Genes for Example from *Brassica napus, Glycine max, Zea mays* or *Oryza sativa*

Seeds of several different ryegrass varieties may be used as explant sources for transformation, including the commercial variety Gunne available from Svalöf Weibull seed company or the variety Affinity. Seeds are surface-sterilized sequentially with 1% Tween-20 for 1 minute, 100% bleach for 60 minutes, 3 rinses of 5 minutes each with deionized and distilled $H_2O$, and then germinated for 3-4 days on moist, sterile filter paper in the dark. Seedlings are further sterilized for 1 minute with 1% Tween-20, 5 minutes with 75% bleach, and rinsed 3 times with double destilled $H_2O$, 5 min each.

Surface-sterilized seeds are placed on the callus induction medium containing Murashige and Skoog basal salts and vitamins, 20 g/L sucrose, 150 mg/L asparagine, 500 mg/L casein hydrolysate, 3 g/L Phytagel, 10 mg/L BAP, and 5 mg/L dicamba. Plates are incubated in the dark at 25° C. for 4 weeks for seed germination and embryogenic callus induction.

After 4 weeks on the callus induction medium, the shoots and roots of the seedlings are trimmed away, the callus is transferred to fresh media, maintained in culture for another 4 weeks, and then transferred to MSO medium in light for 2 weeks. Several pieces of callus (11-17 weeks old) are either strained through a 10 mesh sieve and put onto callus induction medium, or cultured in 100 ml of liquid ryegrass callus induction media (same medium as for callus induction with agar) in a 250 ml flask. The flask is wrapped in foil and shaken at 175 rpm in the dark at 23° C. for 1 week. Sieving the liquid culture with a 40-mesh sieve collect the cells. The fraction collected on the sieve is plated and cultured on solid ryegrass callus induction medium for 1 week in the dark at 25° C. The callus is then transferred to and cultured on MS medium containing 1% sucrose for 2 weeks.

Transformation can be accomplished with either *Agrobacterium* of with particle bombardment methods. An expression vector is created containing a constitutive plant promoter and the cDNA of the gene in a pUC vector. The plasmid DNA is prepared from *E. coli* cells using with Qiagen kit according to manufacturer's instruction. Approximately 2 g of embryogenic callus is spread in the center of a sterile filter paper in a Petri dish. An aliquot of liquid MSO with 10 g/l sucrose is added to the filter paper. Gold particles (1.0 μm in size) are coated with plasmid DNA according to method of Sanford et al., 1993 and delivered to the embryogenic callus with the following parameters: 500 μg particles and 2 μg DNA per shot, 1300 psi and a target distance of 8.5 cm from stopping plate to plate of callus and 1 shot per plate of callus.

After the bombardment, calli are transferred back to the fresh callus development medium and maintained in the dark at room temperature for a 1-week period. The callus is then transferred to growth conditions in the light at 25° C. to initiate embryo differentiation with the appropriate selection agent, e.g. 250 nM Arsenal, 5 mg/L PPT or 50 mg/L kanamycin. Shoots resistant to the selection agent appeared and once rooted are transferred to soil.

Samples of the primary transgenic plants (TO) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

Transgenic T0 ryegrass plants are propagated vegetatively by excising tillers. The transplanted tillers are maintained in the greenhouse for 2 months until well established. T1 or T2 generation plants are produced and analyzed as described above

EXAMPLE 25

Engineering Soybean Plants with Increased Biomass Production by Overexpressing PRS Genes for Example from *Brassica napus, Glycine max, Zea mays* or *Oryza sativa*

Soybean is transformed according to the following modification of the method described in the Texas A&M U.S. Pat.

No. 5,164,310. Several commercial soybean varieties are amenable to transformation by this method. The cultivar Jack (available from the Illinois Seed Foundation) is a commonly used for transformation. Seeds are sterilized by immersion in 70% (v/v) ethanol for 6 min and in 25% commercial bleach (NaOCl) supplemented with 0.1% (v/v) Tween for 20 min, followed by rinsing 4 times with sterile double distilled water. Seven-day old seedlings are propagated by removing the radicle, hypocotyl and one cotyledon from each seedling. Then, the epicotyl with one cotyledon is transferred to fresh germination media in petri dishes and incubated at 25° C. under a 16 h photoperiod (approx. 100 µmol/ms) for three weeks. Axillary nodes (approx. 4 mm in length) are cut from 3-4 week-old plants. Axillary nodes are excised and incubated in *Agrobacterium* LBA4404 culture.

Many different binary vector systems have been described for plant transformation (e.g. An G., in *Agrobacterium* Protocols. Methods in Molecular Biology Vol 44, p. 47-62, Gartland K. M. A. and Davey M. R. eds. Humana Press, Totowa, N.J.). Many are based on the vector pBIN19 described by Bevan (Nucleic Acid Research. 12, 8711 (1984)) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 5,7673,666 and 6,225,105). Similarly, various promoters can be used to regulate the trait gene to provide constitutive, developmental, tissue or environmental regulation of gene transcription. In this example, the 34S promoter (GenBank Accession numbers M59930 and X16673) is used to provide constitutive expression of the trait gene.

After the co-cultivation treatment, the explants are washed and transferred to selection media supplemented with 500 mg/L timentin. Shoots are excised and placed on a shoot elongation medium. Shoots longer than 1 cm are placed on rooting medium for two to four weeks prior to transplanting to soil.

The primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

Soybean plants over-expressing low temperature resistance and/or tolerance related genes from *Brassica napus, Glycine max, Zea mays* or *Oryza sativa*, for example, have higher seed yields.

T1 or T2 generation plants are produced and analyzed as described dry matter production and/or seed yield is compared to non-transgenic wild type plants.

EXAMPLE 26

Engineering Rapeseed/Canola Plants with Increased Biomass Production by Overexpressing PRS Genes for Example from *Brassica napus, Glycine max, Zea mays* or *Oryza sativa*

Cotyledonary petioles and hypocotyls of 5-6 day-old young seedlings are used as explants for tissue culture and transformed according to Babic et al. (Plant Cell Rep 17, 183 (1998)). The commercial cultivar Westar (Agriculture Canada) is the standard variety used for transformation, but other varieties can be used.

*Agrobacterium tumefaciens* LBA4404 containing a binary vector is used for canola transformation. Many different binary vector systems have been described for plant transformation (e.g. An G., in *Agrobacterium* Protocols. Methods in Molecular Biology Vol. 44, p. 47-62, Gartland K. M. A. and Davey M. R. eds. Humana Press, Totowa, N.J.). Many are based on the vector pBIN19 described by Bevan (Nucleic Acid Research. 12, 8711 (1984)) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 5,7673,666 and 6,225,105). Similarly, various promoters can be used to regulate the trait gene to provide constitutive, developmental, tissue or environmental regulation of gene transcription. In this example, the 34S promoter (GenBank Accession numbers M59930 and X16673) is used to provide constitutive expression of the trait gene.

Canola seeds are surface-sterilized in 70% ethanol for 2 min., and then in 30% Clorox with a drop of Tween-20 for 10 min, followed by three rinses with sterilized distilled water. Seeds are then germinated in vitro 5 days on half strength MS medium without hormones, 1% sucrose, 0.7% Phytagar at 23° C., 16 h light. The cotyledon petiole explants with the cotyledon attached are excised from the in vitro seedlings, and inoculated with *Agrobacterium* by dipping the cut end of the petiole explant into the bacterial suspension. The explants are then cultured for 2 days on MSBAP-3 medium containing 3 mg/L BAP, 3% sucrose, 0.7% Phytagar at 23° C., 16 h light. After two days of co-cultivation with *Agrobacterium*, the petiole explants are transferred to MSBAP-3 medium containing 3 mg/l BAP, cefotaxime, carbenicillin, or timentin (300 mg/L) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/L BAP). Shoots of about 2 cm in length are transferred to the rooting medium (MSO) for root induction.

Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then evaluated for their increased biomass production according to the method described above. It is found that transgenic rapeseed/canola over-expressing PRS genes from *Brassica napus, Glycine max, Zea mays* or *Oryza sativa* for example show an increased biomass production compared to non-transgenic control plants.

EXAMPLE 27

Engineering Corn Plants with Increased Biomass Production by Over-Expressing PRS Genes for Example from *Brassica napus, Glycine max, Zea mays* or *Oryza sativa*

Transformation of corn (*Zea mays* L.) is performed with a modification of the method described by Ishida et al. (Nature Biotech 14745 (1996)). Transformation is genotype-dependent in corn and only specific genotypes are amenable to transformation and regeneration. The inbred line A188 (University of Minnesota) or hybrids with A188 as a parent are good sources of donor material for transformation (Fromm et al. Biotech 8, 833 (1990), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system of Japan Tobacco is described in WO patents WO 94/00977 and WO 95/06722. Vectors are constructed as described. Various selection marker genes can be used including the corn gene encoding a mutated acetohydroxy acid synthase (AHAS) enzyme (U.S. Pat. No. 6,025,541). Similarly, various promoters can be used to regulate the trait gene to provide constitutive, developmental, tissue or environmental regulation of gene transcription. In this example, the 34S promoter (GenBank Accession numbers M59930 and X16673) is used to provide constitutive expression of the trait gene.

Excised embryos are grown on callus induction medium, then corn regeneration medium, containing imidazolinone as a selection agent. The Petri plates were incubated in the light at 25° C. for 2-3 weeks, or until shoots develop. The green shoots from each embryo are transferred to corn rooting medium and incubated at 25° C. for 2-3 weeks, until roots develop. The rooted shoots are transplanted to soil in the greenhouse. T1 seeds are produced from plants that exhibit tolerance to the imidazolinone herbicides and are PCR positive for the transgenes.

The T1 transgenic plants are then evaluated for increased biomass production according to the methods described above. The T1 generation of single locus insertions of the T-DNA will segregate for the transgene in a 1:2:1 ratio. Those progeny containing one or two copies of the transgene (3/4 of the progeny) are tolerant regarding the imidazolinone herbicide, and exhibit increased biomass production compared to those progeny lacking the transgenes. These plants have higher seed yields. Homozygous T2 plants exhibited similar phenotypes. Hybrid plants (F1 progeny) of homozygous transgenic plants and non-transgenic plants also exhibited increased biomass production.

EXAMPLE 28

Engineering Wheat Plants with Increased Biomass Production by Over-Expressing PRS Genes for Example from *Brassica napus, Glycine max, Zea mays* or *Oryza sativa*

Transformation of wheat is performed with the method described by Ishida et al. (Nature Biotech. 14745 (1996)). The cultivar Bobwhite (available from CYMMIT, Mexico) is commonly used in transformation. Immature embryos are co-cultivated with Agrobacterium tumefaciens that carry "super binary" vectors, and transgenic plants are recovered through organogenesis. The super binary vector system of Japan Tobacco is described in WO patents WO 94/00977 and WO 95/06722. Vectors are constructed as described. Various selection marker genes can be used including the maize gene encoding a mutated acetohydroxy acid synthase (AHAS) enzyme (U.S. Pat. No. 6,025,541). Similarly, various promoters can be used to regulate the trait gene to provide constitutive, developmental, tissue or environmental regulation of gene transcription. In this example, the 34S promoter (GenBank Accession numbers M59930 and X16673) is used to provide constitutive expression of the trait gene.

After incubation with *Agrobacterium*, the embryos are grown on callus induction medium, then regeneration medium, containing imidazolinone as a selection agent. The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

The T1 transgenic plants are then evaluated for their increased biomass production according to the method described above. The T1 generation of single locus insertions of the T-DNA will segregate for the transgene in a 1:2:1 ratio. Those progeny containing one or two copies of the transgene (3/4 of the progeny exhibit increased biomass production compared to those progeny lacking the transgenes.

EXAMPLE 29

Engineering Rice Plants with Increased Biomass Production by Over-Expressing PRS Genes Rice Transformation The *Agrobacterium* containing the expression vector is used to transform *Oryza sativa* plants. Mature dry seeds of the rice japonica cultivar Nipponbare are dehusked. Sterilization is carried out by incubating for one minute in 70% ethanol, followed by 30 minutes in 0.2% HgCl2, followed by a 6 times 15 minutes wash with sterile distilled water. The sterile seeds are then germinated on a medium containing 2,4-D (callus induction medium). After incubation in the dark for four weeks, embryogenic, scutellum-derived calli are excised and propagated on the same medium. After two weeks, the calli are multiplied or propagated by subculture on the same medium for another 2 weeks. Embryogenic callus pieces are sub-cultured on fresh medium 3 days before co-cultivation (to boost cell division activity).

*Agrobacterium* strain LBA4404 containing the expression vector is used for co-cultivation. *Agrobacterium* is inoculated on AB medium with the appropriate antibiotics and cultured for 3 days at 28° C. The bacteria are then collected and suspended in liquid co-cultivation medium to a density (OD600) of about 1. The suspension is then transferred to a Petri dish and the calli immersed in the suspension for 15 minutes. The callus tissues are then blotted dry on a filter paper and transferred to solidified, co-cultivation medium and incubated for 3 days in the dark at 25° C. Co-cultivated calli are grown on 2,4-D-containing medium for 4 weeks in the dark at 28° C. in the presence of a selection agent. During this period, rapidly growing resistant callus islands develop. After transfer of this material to a regeneration medium and incubation in the light, the embryogenic potential is released and shoots develop in the next four to five weeks. Shoots are excised from the calli and incubated for 2 to 3 weeks on an auxin-containing medium from which they are transferred to soil. Hardened shoots are grown under high humidity and short days in a greenhouse.

Approximately 35 independent T0 rice transformants are generated for each construct. The primary transformants are transferred from a tissue culture chamber to a greenhouse. After a quantitative PCR analysis to verify copy number of the T-DNA insert, only single copy transgenic plants that exhibit tolerance to the selection agent are kept for harvest of T1 seed. Seeds are then harvested three to five months after transplanting. The method yields single locus transformants at a rate of over 50% (Aldemita and Hodges 1996, Chan et al. 1993, Hiei et al. 1994).

Rice Phenotypic Evaluation Procedure

1. Evaluation Setup

Five to eight events, of which the T1 progeny segregates 3:1 for presence/absence of the transgene, are retained. For each of these events, approximately 10 T1 seedlings containing the transgene (hetero- and homo-zygotes) and approximately 10 T1 seedlings lacking the transgene (nullizygotes) are selected by monitoring visual marker expression. The transgenic plants and the corresponding nullizygotes are grown side-by-side at random positions. Greenhouse conditions are of shorts days (12 hours light), 28° C. in the light and 22° C. in the dark, and a relative humidity of 70%.

From the stage of sowing until the stage of maturity the plants are passed several times through a digital imaging cabinet. At each time point digital images (2048×1536 pixels, 16 million colours) are taken of each plant from at least 6 different angles.

2. Statistical Analysis: F-Test

A two factor ANOVA (analysis of variants) is used as a statistical model for the overall evaluation of plant phenotypic characteristics. An F-test is carried out on all the parameters measured of all the plants of all the events transformed with the gene of the present invention. The F-test is carried out to check for an effect of the gene over all the transformation events and to verify for an overall effect of the gene, also known as a global gene effect. The threshold for significance for a true global gene effect is set at a 5% probability level for the F-test. A significant F-test value points to a gene effect, meaning that it is not only the mere presence or position of the gene that is causing the differences in phenotype.

3. Parameters Measured 3.1 Biomass-Related Parameter Measurement

From the stage of sowing until the stage of maturity the plants are passed several times through a digital imaging cabinet. At each time point digital images (2048×1536 pixels, 16 million colours) are taken of each plant from at least 6 different angles.

The plant aboveground area (or leafy biomass) is determined by counting the total number of pixels on the digital images from aboveground plant parts discriminated from the background. This value is averaged for the pictures taken on the same time point from the different angles and is converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

3.2 Seed-Related Parameter Measurements

The mature primary panicles are harvested, counted, bagged, barcode-labelled and then dried for three days in an oven at 37° C. The panicles are then threshed and all the seeds are collected and counted. The filled husks are separated from the empty ones using an air-blowing device. The empty husks are discarded and the remaining fraction is counted again. The filled husks are weighed on an analytical balance. The number of filled seeds is determined by counting the number of filled husks that remain after the separation step. The total seed weight per plant is measured by weighing all filled husks harvested from one plant. Total seed number per plant is measured by counting the number of husks harvested from a plant. Thousand Kernel Weight (TKW) is extrapolated from the number of filled seeds counted and their total weight. The Harvest Index (HI) in the present invention is defined as the ratio between the total seed weight per plant and the above ground area (mm$^2$), multiplied by a factor 106. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

---

The invention claimed is:

1. A method for producing a transgenic plant cell, plant, or part thereof with increased yield as compared to a corresponding non-transformed wild type plant cell, plant, or part thereof comprising:
   a) introducing a nucleic acid sequence encoding a phosphoribosyl pyrophosphate synthase into a plant cell, plant, or part thereof, such that the phosphoribosyl pyrophosphate synthase is expressed; and
   b) selecting a plant cell, plant, or part thereof with increased yield as compared to a corresponding non-transformed wild type plant cell, plant, or part thereof.

2. The method of claim 1, wherein the phosphoribosyl pyrophosphate synthase comprises:
   (i) a polypeptide, a consensus sequence, or at least one polypeptide motif selected from the group consisting of SEQ ID NO: 2, 4, 13, 51, 52, 53, 54, 55, 56, 57, 58, 59, 60, 61, 62, 63, 7, 8, 9, 10, 11, 14, 15, 16, 17, 18, 64, 65, 66, 67, 68, 69, 70, 71, 72, and 73;
   (ii) an expression product of a nucleic acid molecule comprising the polynucleotide of SEQ ID NO: 1, 3, 12, 38, 39, 40, 41, 42, 43, 44, 45, 46, 47, 48, 49, or 50; or
   (iii) a polypeptide having at least 75% sequence identity to the amino acid sequence of SEQ ID NO: 2, 4, 13, 51, 52, 53, 54, 55, 56, 57, 58, 59, 60, 61, 62, or 63, and having the activity of the amino acid sequence of SEQ ID NO: 2, 4, 13, 51, 52, 53, 54, 55, 56, 57, 58, 59, 60, 61, 62, or 63.

3. The method of claim 1, wherein the nucleic acid sequence comprises:
   (a) a nucleic acid molecule encoding a polypeptide comprising an amino acid sequence selected from the group consisting of SEQ ID NO: 2, 4, 13, 51, 52, 53, 54, 55, 56, 57, 58, 59, 60, 61, 62, and 63;
   (b) a nucleic acid molecule selected from the group consisting of SEQ ID NO: 1, 3, and 12;
   (c) a nucleic acid molecule that has at least 75% sequence identity with the nucleic acid molecule of SEQ ID NO: 1, 3, or 12 and that confers an increased yield to a plant cell, plant, or part thereof as compared to a corresponding non-transformed wild type plant cell, plant, or part thereof;
   (d) a nucleic acid molecule encoding a polypeptide comprising an amino acid sequence having at least 75% sequence identity with the amino acid sequence encoded by the nucleic acid molecule of (a) or (b), wherein said polypeptide has the activity of the polypeptide of SEQ ID NO: 2, 4, 13, 51, 52, 53, 54, 55, 56, 57, 58, 59, 60, 61, 62, or 63 and confers an increased yield to a plant cell, plant, or part thereof as compared to a corresponding non-transformed wild type plant cell, plant, or part thereof;

(e) a nucleic acid molecule which hybridizes with the nucleic acid molecule of (a) or (b) under stringent hybridization conditions and confers an increased yield to a plant cell, plant, or part thereof as compared to a corresponding non-transformed wild type plant cell, plant, or part thereof, wherein said stringent hybridization conditions are selected from the group consisting of:
  i) hybridization in 6×SSC at approximately 45° C.;
  ii) hybridization in 4×SSC at 65° C.; and
  iii) hybridization in 50% formamide, 4×SSC at 42° C.;
(f) a nucleic acid molecule encoding a polypeptide which can be isolated with the aid of a monoclonal or polyclonal antibody made against a polypeptide encoded by one of the nucleic acid molecules of (a) or (b) and having the activity of a phosphoribosyl pyrophosphate synthase, wherein said nucleic acid molecule comprises a polynucleotide selected from the group consisting of SEQ ID NO: 1, 3, 12, 38, 39, 40, 41, 42, 43, 44, 45, 46, 47, 48, 49, and 50;
(g) a nucleic acid molecule encoding a polypeptide comprising a consensus sequence or one or more polypeptide motifs selected from the group consisting of SEQ ID NO: 7, 8, 9, 10, 11, 14, 15, 16, 17, 18, 64, 65, 66, 67, 68, 69, 70, 71, 72, and 73 and having the activity of a phosphoribosyl pyrophosphate synthase, wherein said phosphoribosyl pyrophosphate synthase comprises a polypeptide selected from the group consisting of SEQ ID NO: 2, 4, 7, 8, 9, 10, 11, 13, 14, 15, 16, 17, 18, 64, 65, 66, 67, 68, 69, 70, 71, 72, and 73;
(h) a nucleic acid molecule that encodes a polypeptide having the activity of a phosphoribosyl pyrophosphate synthase and confers increased yield to a plant cell, plant, or part thereof as compared to a corresponding non-transformed wild type plant cell, plant, or part thereof, wherein said phosphoribosyl pyrophosphate synthase comprises a protein selected from the group consisting of SEQ ID NO: 2, 4, 13, 51, 52, 53, 54, 55, 56, 57, 58, 59, 60, 61, 62, and 63;
(i) a nucleic acid molecule which comprises a polynucleotide which is obtained by amplifying a cDNA library or a genomic library using primers selected from the group consisting of SEQ ID NO: 5 and 6, wherein said polynucleotide encodes a polypeptide having the activity of a phosphoribosyl pyrophosphate synthase, and comprises a polynucleotide selected from the group consisting of SEQ ID NO: 1, 3, 12, 38, 39, 40, 41, 42, 43, 44, 45, 46, 47, 48, 49, and 50; or
(j) a nucleic acid molecule obtained by screening a suitable nucleic acid library under stringent hybridization conditions with a probe comprising a complementary sequence of a nucleic acid molecule of (a) or (b) or with a fragment thereof, having at least 15 nt of a nucleic acid molecule complementary to a nucleic acid molecule sequence characterized in (a) to (d) and encoding a polypeptide having the activity of a phosphoribosyl pyrophosphate synthase comprising a polypeptide selected from the group consisting of SEQ ID NO: 2, 4, 13, 51, 52, 53, 54, 55, 56, 57, 58, 59, 60, 61, 62, and 63, wherein said stringent hybridization conditions are selected from the group consisting of:
  i) hybridization in 6×SSC at approximately 45° C.;
  ii) hybridization in 4×SSC at 65° C.; and
  iii) hybridization in 50% formamide, 4×SSC at 42° C.

4. The method of claim 1, wherein the nucleic acid sequence coding for the phosphoribosyl pyrophosphate synthase originates from a fungus selected from the group of Ascomycetes, filamentous fungi, fungi from the genera Aspergillus, Trichoderma, Ashbya, Eremothecium, Neurospora, Fusarium, Beauveria, Mortierella, Saprolegnia, Pythium.

5. The method of claim 1, wherein the total oil content in the transformed plant cell, plant, or part thereof is increased as compared to a corresponding non-transformed wild type plant cell, plant, or part thereof.

6. The method of claim 1, wherein the total oil content in seeds of the transformed plant is increased as compared to a corresponding non-transformed wild type plant.

7. The method of claim 1, wherein the biomass of the transformed plant cell, plant, or part thereof is increased as compared to a corresponding non-transformed wild type plant cell, plant, or part thereof.

8. The method of claim 7, wherein the transformed plant cell, plant, or part thereof is harvested after cultivation and the oil present in the transformed plant cell, plant, or part thereof is isolated.

9. The method of claim 1, wherein a monocotyledonous crop plant is transformed.

10. The method of claim 9, wherein the monocotyledonous crop plant is from the family Gramineae.

11. The method of claim 1, wherein a dicotyledonous crop plant is transformed.

12. The method of claim 11, wherein the transformed plant cell, plant, or part thereof is harvested after cultivation and the biomass present in the transformed plant cell, plant, or part thereof is isolated.

13. A transgenic plant cell, plant, or part thereof with increased yield as compared to a corresponding non-transformed wild type plant cell, plant, or part thereof produced by the method of claim 1.

14. A seed produced by the transgenic plant of claim 13, wherein the seed is genetically homozygous for the transgene conferring increased yield as compared to a corresponding non-transformed wild type plant cell, plant, or part thereof.

15. A transformed host cell comprising at least one nucleic acid molecule comprising:
  (a) a nucleic acid molecule encoding a polypeptide comprising an amino acid sequence selected from the group consisting of SEQ ID NO: 2, 4, 13, 51, 52, 53, 54, 55, 56, 57, 58, 59, 60, 61, 62, and 63;
  (b) a nucleic acid molecule selected from the group consisting of SEQ ID NO: 1, 3, and 12;
  (c) a nucleic acid molecule that has at least 75% sequence identity with the nucleic acid molecule of SEQ ID NO: 1, 3, or 12 and that confers an increased yield to a plant cell, plant, or part thereof as compared to a corresponding non-transformed wild type plant cell, plant, or part thereof;
  (d) a nucleic acid molecule encoding a polypeptide comprising an amino acid sequence having at least 75% sequence identity with the amino acid sequence encoded by the nucleic acid molecule of (a) or (b), wherein said polypeptide has the activity of the polypeptide of SEQ ID NO: 2, 4, 13, 51, 52, 53, 54, 55, 56, 57, 58, 59, 60, 61, 62, or 63 and confers an increased yield to a plant cell, plant, or part thereof as compared to a corresponding non-transformed wild type plant cell, plant, or part thereof;
  (e) a nucleic acid molecule which hybridizes with the nucleic acid molecule of (a) or (b) under stringent hybridization conditions and confers an increased yield to a plant cell, plant, or part thereof as compared to a corresponding non-transformed wild type plant cell, plant, or part thereof, wherein said stringent hybridization conditions are selected from the group consisting of:
  i) hybridization in 6×SSC at approximately 45° C.;
  ii) hybridization in 4×SSC at 65° C.; and
  iii) hybridization in 50% formamide, 4×SSC at 42° C.;
(f) a nucleic acid molecule encoding a polypeptide which can be isolated with the aid of a monoclonal or polyclonal antibody made against a polypeptide encoded by one of the nucleic acid molecules of (a) or (b) and having the activity of a phosphoribosyl pyrophosphate synthase, wherein said nucleic acid molecule comprises a polynucleotide selected from the group consisting of SEQ ID NO: 1, 3, 12, 38, 39, 40, 41, 42, 43, 44, 45, 46, 47, 48, 49, and 50;
(g) a nucleic acid molecule encoding a polypeptide comprising a consensus sequence or one or more polypeptide motifs selected from the group consisting of SEQ ID NO: 7, 8, 9, 10, 11, 14, 15, 16, 17, 18, 64, 65, 66, 67, 68, 69, 70, 71, 72, and 73 and having the activity of a phosphoribosyl pyrophosphate synthase, wherein said phosphoribosyl pyrophosphate synthase comprises a polypeptide selected from the group consisting of SEQ ID NO: NO: 2, 4, 7, 8, 9, 10, 11, 13, 14, 15, 16, 17, 18, 64, 65, 66, 67, 68, 69, 70, 71, 72, and 73;
(h) a nucleic acid molecule that encodes a polypeptide having the activity of a phosphoribosyl pyrophosphate synthase and confers increased yield to a plant cell, plant, or part thereof as compared to a corresponding non-transformed wild type plant cell, plant, or part thereof, wherein said phosphoribosyl pyrophosphate synthase comprises a protein selected from the group consisting of SEQ ID NO: 2, 4, 13, 51, 52, 53, 54, 55, 56, 57, 58, 59, 60, 61, 62, and 63;
(i) a nucleic acid molecule which comprises a polynucleotide which is obtained by amplifying a cDNA library or a genomic library using primers selected from the group consisting of SEQ ID NOs: 5 and 6, wherein said polynucleotide encodes a polypeptide having the activity of a phosphoribosyl pyrophosphate synthase, and comprises a polynucleotide selected from the group consisting of SEQ ID NO: 1, 3, 12, 38, 39, 40, 41, 42, 43, 44, 45, 46, 47, 48, 49, and 50; or
(j) a nucleic acid molecule obtained by screening a suitable nucleic acid library under stringent hybridization conditions with a probe comprising a complementary sequence of a nucleic acid molecule of (a) or (b) or with a fragment thereof, having at least 15 nt of a nucleic acid molecule complementary to a nucleic acid molecule sequence characterized in (a) to (d) and encoding a polypeptide having the activity of a phosphoribosyl pyrophosphate synthase comprising a polypeptide selected from the group consisting of SEQ ID NO: 2, 4, 13, 51, 52, 53, 54, 55, 56, 57, 58, 59, 60, 61, 62, and 63, wherein said stringent hybridization conditions are selected from the group consisting of:
  i) hybridization in 6×SSC at approximately 45° C.;
  ii) hybridization in 4×SSC at 65° C.; and
  iii) hybridization in 50% formamide, 4×SSC at 42° C.

16. A plant tissue, propagation material, harvested material, or plant comprising the host cell of claim 15.

17. A method for selecting a plant or plant cell with an increased yield as compared to a corresponding non-transformed wild type plant or plant cell comprising utilizing a nucleic acid molecule as a marker for selecting a plant or plant cell with an increased yield as compared to a corresponding non-transformed wild type plant or plant cell, wherein the nucleic acid molecule comprises:
(a) a nucleic acid molecule encoding a polypeptide comprising an amino acid sequence selected from the group consisting of SEQ ID NO: 2, 4, 13, 51, 52, 53, 54, 55, 56, 57, 58, 59, 60, 61, 62, and 63;
(b) a nucleic acid molecule selected from the group consisting of SEQ ID NO: 1, 3, and 12;
(c) a nucleic acid molecule that has at least 75% sequence identity with the nucleic acid molecule of SEQ ID NO: 1, 3, or 12 and that confers an increased yield to a plant cell, plant, or part thereof as compared to a corresponding non-transformed wild type plant cell, plant, or part thereof;
(d) a nucleic acid molecule encoding a polypeptide comprising an amino acid sequence having at least 75% sequence identity with the amino acid sequence encoded by the nucleic acid molecule of (a) or (b), wherein said polypeptide has the activity of the polypeptide of SEQ ID NO: 2, 4, 13, 51, 52, 53, 54, 55, 56, 57, 58, 59, 60, 61, 62, or 63 and confers an increased yield to a plant cell, plant, or part thereof as compared to a corresponding non-transformed wild type plant cell, plant, or part thereof;
(e) a nucleic acid molecule which hybridizes with the nucleic acid molecule of (a) or (b) under stringent hybridization conditions and confers an increased yield to a plant cell, plant, or part thereof as compared to a corresponding non-transformed wild type plant cell, plant, or part thereof, wherein said stringent hybridization conditions are selected from the group consisting of:
  i) hybridization in 6×SSC at approximately 45° C.;
  ii) hybridization in 4×SSC at 65° C.; and
  iii) hybridization in 50% formamide, 4×SSC at 42° C.;
(f) a nucleic acid molecule encoding a polypeptide which can be isolated with the aid of a monoclonal or polyclonal antibody made against a polypeptide encoded by one of the nucleic acid molecules of (a) or (b) and having the activity of a phosphoribosyl pyrophosphate synthase, wherein said nucleic acid molecule comprises a polynucleotide selected from the group consisting of SEQ ID NO: 1, 3, 12, 38, 39, 40, 41, 42, 43, 44, 45, 46, 47, 48, 49, and 50;
(g) a nucleic acid molecule encoding a polypeptide comprising a consensus sequence or one or more polypeptide motifs selected from the group consisting of SEQ ID NO: 7, 8, 9, 10, 11, 14, 15, 16, 17, 18, 64, 65, 66, 67, 68, 69, 70, 71, 72, and 73 and having the activity of a phosphoribosyl pyrophosphate synthase, wherein said phosphoribosyl pyrophosphate synthase comprises a polypeptide selected from the group consisting of SEQ ID NO: 2, 4, 7, 8, 9, 10, 11, 13, 14, 15, 16, 17, 18, 64, 65, 66, 67, 68, 69, 70, 71, 72, and 73;
(h) a nucleic acid molecule that encodes a polypeptide having the activity of a phosphoribosyl pyrophosphate synthase and confers increased yield to a plant cell, plant, or part thereof as compared to a corresponding non-transformed wild type plant cell, plant, or part thereof, wherein said phosphoribosyl pyrophosphate synthase comprises a protein selected from the group consisting of SEQ ID NO: 2, 4, 13, 51, 52, 53, 54, 55, 56, 57, 58, 59, 60, 61, 62, and 63;
(i) a nucleic acid molecule which comprises a polynucleotide which is obtained by amplifying a cDNA library or a genomic library using primers selected from the group consisting of SEQ ID NO: 5 and 6, wherein said polynucleotide encodes a polypeptide having the activity of a phosphoribosyl pyrophosphate synthase, and comprises a polynucleotide selected from the group consisting of SEQ ID NO: 1, 3, 12, 38, 39, 40, 41, 42, 43, 44, 45, 46, 47, 48, 49, and 50; or (j) a nucleic acid molecule obtained by screening a suitable nucleic acid library under stringent hybridization conditions with a probe comprising a complementary sequence of a nucleic acid molecule of (a) or (b) or with a fragment thereof, having at least 15 nt of a nucleic acid molecule complementary to a nucleic acid molecule sequence characterized in (a) to (d) and encoding a polypeptide having the activity of a phosphoribosyl pyrophosphate synthase comprising a polypeptide selected from the group consisting of SEQ ID NO: 2, 4, 13, 51, 52, 53, 54, 55, 56, 57, 58, 59, 60, 61, 62, and 63.

* * * * *

SEQUENCE LISTING

```
<160> NUMBER OF SEQ ID NOS: 73

<210> SEQ ID NO 1
<211> LENGTH: 957
<212> TYPE: DNA
<213> ORGANISM: Ashbya gossypii
<220> FEATURE:
<221> NAME/KEY: CDS
<222> LOCATION: (1)..(957)

<400> SEQUENCE: 1 atg tcg tcc aat agc ata aag ctg cta gca ggt aac tcg cac ccg gac      48
Met Ser Ser Asn Ser Ile Lys Leu Leu Ala Gly Asn Ser His Pro Asp
1               5                   10                  15 cta gct gag aag gtc tcc gtt cgc cta ggt gta cca ctt tcg aag att      96
Leu Ala Glu Lys Val Ser Val Arg Leu Gly Val Pro Leu Ser Lys Ile
            20                  25                  30 gga gtg tat cac tac tct aac aaa gag acg tca gtt act atc ggc gaa     144
Gly Val Tyr His Tyr Ser Asn Lys Glu Thr Ser Val Thr Ile Gly Glu
        35                  40                  45 agt atc cgt gat gaa gat gtc tac atc atc cag aca gga acg ggg gag     192
```

```
Ser Ile Arg Asp Glu Asp Val Tyr Ile Ile Gln Thr Gly Thr Gly Glu
     50                  55                  60 cag gaa atc aac gac ttc ctc atg gaa ctg ctc atc atg atc cat gcc        240
Gln Glu Ile Asn Asp Phe Leu Met Glu Leu Leu Ile Met Ile His Ala
 65                  70                  75                  80 tgc cgg tca gcc tct gcg cgg aag atc aca gcg gtt ata cca aac ttc        288
Cys Arg Ser Ala Ser Ala Arg Lys Ile Thr Ala Val Ile Pro Asn Phe
                 85                  90                  95 cct tac gca aga caa gac aaa aag gac aag tcg cga gca ccg ata act        336
Pro Tyr Ala Arg Gln Asp Lys Lys Asp Lys Ser Arg Ala Pro Ile Thr
            100                 105                 110 gcc aag ctg gtg gcc aag atg cta gag acc gcg ggg tgc aac cac gtt        384
Ala Lys Leu Val Ala Lys Met Leu Glu Thr Ala Gly Cys Asn His Val
        115                 120                 125 atc acg atg gat ttg cac gcg tct caa att cag ggt ttc ttc cac att        432
Ile Thr Met Asp Leu His Ala Ser Gln Ile Gln Gly Phe Phe His Ile
    130                 135                 140 cca gtg gac aac cta tat gca gag ccg aac atc ctg cac tac atc caa        480
Pro Val Asp Asn Leu Tyr Ala Glu Pro Asn Ile Leu His Tyr Ile Gln
145                 150                 155                 160 cat aat gtg gac ttc cag aat agt atg ttg gtc gcg cca gac gcg ggg        528
His Asn Val Asp Phe Gln Asn Ser Met Leu Val Ala Pro Asp Ala Gly
                165                 170                 175 tcg gcg aag cgc acg tcg acg ctt tcg gac aag ctg aat ctc aac ttc        576
Ser Ala Lys Arg Thr Ser Thr Leu Ser Asp Lys Leu Asn Leu Asn Phe
            180                 185                 190 gcg ttg atc cac aaa gaa cgg cag aag gcg aac gag gtc tcg cgg atg        624
Ala Leu Ile His Lys Glu Arg Gln Lys Ala Asn Glu Val Ser Arg Met
        195                 200                 205 gtg ttg gtg ggt gat gtc gcc gac aag tcc tgt att att gta gac gac        672
Val Leu Val Gly Asp Val Ala Asp Lys Ser Cys Ile Ile Val Asp Asp
    210                 215                 220 atg gcg gac acg tgc gga acg cta gtg aag gcc act gac acg ctg atc        720
Met Ala Asp Thr Cys Gly Thr Leu Val Lys Ala Thr Asp Thr Leu Ile
225                 230                 235                 240 gaa aat ggg gcg aaa gaa gtg att gcc att gtg aca cac ggt ata ttt        768
Glu Asn Gly Ala Lys Glu Val Ile Ala Ile Val Thr His Gly Ile Phe
                245                 250                 255 tct ggc ggc gcc cgc gag aag ttg cgc aac agc aag ctg gca cgg atc        816
Ser Gly Gly Ala Arg Glu Lys Leu Arg Asn Ser Lys Leu Ala Arg Ile
            260                 265                 270 gta agc aca aat acg gtg cca gtg gac ctc aat cta gat atc tac cac        864
Val Ser Thr Asn Thr Val Pro Val Asp Leu Asn Leu Asp Ile Tyr His
        275                 280                 285 caa att gac att agt gcc att ttg gcc gag gca att aga agg ctt cac        912
Gln Ile Asp Ile Ser Ala Ile Leu Ala Glu Ala Ile Arg Arg Leu His
    290                 295                 300 aac ggg gaa agt gtg tcg tac ctg ttc aat aac gct gtc atg tag            957
Asn Gly Glu Ser Val Ser Tyr Leu Phe Asn Asn Ala Val Met
305                 310                 315

<210> SEQ ID NO 2
<211> LENGTH: 318
<212> TYPE: PRT
<213> ORGANISM: Ashbya gossypii

<400> SEQUENCE: 2

Met Ser Ser Asn Ser Ile Lys Leu Leu Ala Gly Asn Ser His Pro Asp
 1               5                  10                  15

Leu Ala Glu Lys Val Ser Val Arg Leu Gly Val Pro Leu Ser Lys Ile
             20                  25                  30
```

```
Gly Val Tyr His Tyr Ser Asn Lys Glu Thr Ser Val Thr Ile Gly Glu
            35                  40                  45

Ser Ile Arg Asp Glu Asp Val Tyr Ile Ile Gln Thr Gly Thr Gly Glu
     50                  55                  60

Gln Glu Ile Asn Asp Phe Leu Met Glu Leu Leu Ile Met Ile His Ala
 65                  70                  75                  80

Cys Arg Ser Ala Ser Ala Arg Lys Ile Thr Ala Val Ile Pro Asn Phe
                 85                  90                  95

Pro Tyr Ala Arg Gln Asp Lys Lys Asp Lys Ser Arg Ala Pro Ile Thr
            100                 105                 110

Ala Lys Leu Val Ala Lys Met Leu Glu Thr Ala Gly Cys Asn His Val
        115                 120                 125

Ile Thr Met Asp Leu His Ala Ser Gln Ile Gln Gly Phe Phe His Ile
    130                 135                 140

Pro Val Asp Asn Leu Tyr Ala Glu Pro Asn Ile Leu His Tyr Ile Gln
145                 150                 155                 160

His Asn Val Asp Phe Gln Asn Ser Met Leu Val Ala Pro Asp Ala Gly
                165                 170                 175

Ser Ala Lys Arg Thr Ser Thr Leu Ser Asp Lys Leu Asn Leu Asn Phe
            180                 185                 190

Ala Leu Ile His Lys Glu Arg Gln Lys Ala Asn Glu Val Ser Arg Met
        195                 200                 205

Val Leu Val Gly Asp Val Ala Asp Lys Ser Cys Ile Ile Val Asp Asp
    210                 215                 220

Met Ala Asp Thr Cys Gly Thr Leu Val Lys Ala Thr Asp Thr Leu Ile
225                 230                 235                 240

Glu Asn Gly Ala Lys Glu Val Ile Ala Ile Val Thr His Gly Ile Phe
                245                 250                 255

Ser Gly Gly Ala Arg Glu Lys Leu Arg Asn Ser Lys Leu Ala Arg Ile
            260                 265                 270

Val Ser Thr Asn Thr Val Pro Val Asp Leu Asn Leu Asp Ile Tyr His
        275                 280                 285

Gln Ile Asp Ile Ser Ala Ile Leu Ala Glu Ala Ile Arg Arg Leu His
    290                 295                 300

Asn Gly Glu Ser Val Ser Tyr Leu Phe Asn Asn Ala Val Met
305                 310                 315

<210> SEQ ID NO 3
<211> LENGTH: 957
<212> TYPE: DNA
<213> ORGANISM: Artificial Sequence
<220> FEATURE:
<223> OTHER INFORMATION: PRS with point mutation
<220> FEATURE:
<221> NAME/KEY: CDS
<222> LOCATION: (1)..(957)

<400> SEQUENCE: 3 atg tcg tcc aat agc ata aag ctg cta gca ggt aac tcg cac ccg gac      48
Met Ser Ser Asn Ser Ile Lys Leu Leu Ala Gly Asn Ser His Pro Asp
 1               5                  10                  15 cta gct gag aag gtc tcc gtt cgc cta ggt gta cca ctt tcg aag att      96
Leu Ala Glu Lys Val Ser Val Arg Leu Gly Val Pro Leu Ser Lys Ile
            20                  25                  30 gga gtg tat cac tac tct aac aaa gag acg tca gtt act atc ggc gaa     144
Gly Val Tyr His Tyr Ser Asn Lys Glu Thr Ser Val Thr Ile Gly Glu
        35                  40                  45
```

```
agt atc cgt gat gaa gat gtc tac atc atc cag aca gga acg ggg gag    192
Ser Ile Arg Asp Glu Asp Val Tyr Ile Ile Gln Thr Gly Thr Gly Glu
 50                  55                  60 cag gaa atc aac gac ttc ctc atg gaa ctg ctc atc atg atc cat gcc    240
Gln Glu Ile Asn Asp Phe Leu Met Glu Leu Leu Ile Met Ile His Ala
 65              70                  75                  80 tgc cgg tca gcc tct gcg cgg aag atc aca gcg gtt ata cca aac ttc    288
Cys Arg Ser Ala Ser Ala Arg Lys Ile Thr Ala Val Ile Pro Asn Phe
             85                  90                  95 cct tac gca aga caa gac aaa aag gac aag tcg cga gca ccg ata act    336
Pro Tyr Ala Arg Gln Asp Lys Lys Asp Lys Ser Arg Ala Pro Ile Thr
        100                 105                 110 gcc aag ctg gtg gcc aag atg cta gag acc gcg ggg tgc aac cac gtt    384
Ala Lys Leu Val Ala Lys Met Leu Glu Thr Ala Gly Cys Asn His Val
            115                 120                 125 atc acg atg gat atc cac gcg tct caa att cag ggt ttc ttc cac att    432
Ile Thr Met Asp Ile His Ala Ser Gln Ile Gln Gly Phe Phe His Ile
130                 135                 140 cca gtg gac aac cta tat gca gag ccg aac atc ctg cac tac atc caa    480
Pro Val Asp Asn Leu Tyr Ala Glu Pro Asn Ile Leu His Tyr Ile Gln
145                 150                 155                 160 cat aat gtg gac ttc cag aat agt atg ttg gtc gcg cca gac gcg ggg    528
His Asn Val Asp Phe Gln Asn Ser Met Leu Val Ala Pro Asp Ala Gly
                165                 170                 175 tcg gcg aag cgc acg tcg acg ctt tcg gac aag ctg aat ctc aac ttc    576
Ser Ala Lys Arg Thr Ser Thr Leu Ser Asp Lys Leu Asn Leu Asn Phe
            180                 185                 190 gcg ttg atc cag aaa gaa cgg cag aag gcg aac gag gtc tcg cgg atg    624
Ala Leu Ile Gln Lys Glu Arg Gln Lys Ala Asn Glu Val Ser Arg Met
        195                 200                 205 gtg ttg gtg ggt gat gtc gcc gac aag tcc tgt att att gta gac gac    672
Val Leu Val Gly Asp Val Ala Asp Lys Ser Cys Ile Ile Val Asp Asp
    210                 215                 220 atg gcg gac acg tgc gga acg cta gtg aag gcc act gac acg ctg atc    720
Met Ala Asp Thr Cys Gly Thr Leu Val Lys Ala Thr Asp Thr Leu Ile
225                 230                 235                 240 gaa aat ggg gcg aaa gaa gtg att gcc att gtg aca cac ggt ata ttt    768
Glu Asn Gly Ala Lys Glu Val Ile Ala Ile Val Thr His Gly Ile Phe
                245                 250                 255 tct ggc ggc gcc cgc gag aag ttg cgc aac agc aag ctg gca cgg atc    816
Ser Gly Gly Ala Arg Glu Lys Leu Arg Asn Ser Lys Leu Ala Arg Ile
            260                 265                 270 gta agc aca aat acg gtg cca gtg gac ctc aat cta gat atc tac cac    864
Val Ser Thr Asn Thr Val Pro Val Asp Leu Asn Leu Asp Ile Tyr His
        275                 280                 285 caa att gac att agt gcc att ttg gcc gag gca att aga agg ctt cac    912
Gln Ile Asp Ile Ser Ala Ile Leu Ala Glu Ala Ile Arg Arg Leu His
    290                 295                 300 aac ggg gaa agt gtg tcg tac ctg ttc aat aac gct gtc atg tag        957
Asn Gly Glu Ser Val Ser Tyr Leu Phe Asn Asn Ala Val Met
305                 310                 315

<210> SEQ ID NO 4
<211> LENGTH: 318
<212> TYPE: PRT
<213> ORGANISM: Artificial Sequence
<220> FEATURE:
<223> OTHER INFORMATION: Synthetic Construct

<400> SEQUENCE: 4

Met Ser Ser Asn Ser Ile Lys Leu Leu Ala Gly Asn Ser His Pro Asp
1               5                   10                  15
```

-continued

Leu Ala Glu Lys Val Ser Val Arg Leu Gly Val Pro Leu Ser Lys Ile
            20                  25                  30

Gly Val Tyr His Tyr Ser Asn Lys Glu Thr Ser Val Thr Ile Gly Glu
        35                  40                  45

Ser Ile Arg Asp Glu Asp Val Tyr Ile Ile Gln Thr Gly Thr Gly Glu
    50                  55                  60

Gln Glu Ile Asn Asp Phe Leu Met Glu Leu Leu Ile Met Ile His Ala
65                  70                  75                  80

Cys Arg Ser Ala Ser Ala Arg Lys Ile Thr Ala Val Ile Pro Asn Phe
                85                  90                  95

Pro Tyr Ala Arg Gln Asp Lys Lys Asp Lys Ser Arg Ala Pro Ile Thr
            100                 105                 110

Ala Lys Leu Val Ala Lys Met Leu Glu Thr Ala Gly Cys Asn His Val
        115                 120                 125

Ile Thr Met Asp Ile His Ala Ser Gln Ile Gln Gly Phe Phe His Ile
    130                 135                 140

Pro Val Asp Asn Leu Tyr Ala Glu Pro Asn Ile Leu His Tyr Ile Gln
145                 150                 155                 160

His Asn Val Asp Phe Gln Asn Ser Met Leu Val Ala Pro Asp Ala Gly
                165                 170                 175

Ser Ala Lys Arg Thr Ser Thr Leu Ser Asp Lys Leu Asn Leu Asn Phe
            180                 185                 190

Ala Leu Ile Gln Lys Glu Arg Gln Lys Ala Asn Glu Val Ser Arg Met
        195                 200                 205

Val Leu Val Gly Asp Val Ala Asp Lys Ser Cys Ile Ile Val Asp Asp
    210                 215                 220

Met Ala Asp Thr Cys Gly Thr Leu Val Lys Ala Thr Asp Thr Leu Ile
225                 230                 235                 240

Glu Asn Gly Ala Lys Glu Val Ile Ala Ile Val Thr His Gly Ile Phe
                245                 250                 255

Ser Gly Gly Ala Arg Glu Lys Leu Arg Asn Ser Lys Leu Ala Arg Ile
            260                 265                 270

Val Ser Thr Asn Thr Val Pro Val Asp Leu Asn Leu Asp Ile Tyr His
        275                 280                 285

Gln Ile Asp Ile Ser Ala Ile Leu Ala Glu Ala Ile Arg Arg Leu His
    290                 295                 300

Asn Gly Glu Ser Val Ser Tyr Leu Phe Asn Asn Ala Val Met
305                 310                 315

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ggatccaata tgtcgtccaa t                                          21

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6

-continued ggatcctaca tgacagcg                                            18

<210> SEQ ID NO 7
<211> LENGTH: 64
<212> TYPE: PRT
<213> ORGANISM: Ashbya gossypii

<400> SEQUENCE: 7

Leu His Ala Ser Gln Ile Gln Gly Phe Phe His Ile Pro Val Asp Asn
1               5                   10                  15

Leu Tyr Ala Glu Pro Asn Ile Leu His Tyr Ile Gln His Asn Val Asp
            20                  25                  30

Phe Gln Asn Ser Met Leu Val Ala Pro Asp Ala Gly Ser Ala Lys Arg
        35                  40                  45

Thr Ser Thr Leu Ser Asp Lys Leu Asn Leu Asn Phe Ala Leu Ile His
    50                  55                  60

<210> SEQ ID NO 8
<211> LENGTH: 81
<212> TYPE: PRT
<213> ORGANISM: Ashbya gossypii

<400> SEQUENCE: 8

Thr Met Asp Leu His Ala Ser Gln Ile Gln Gly Phe Phe His Ile Pro
1               5                   10                  15

Val Asp Asn Leu Tyr Ala Glu Pro Asn Ile Leu His Tyr Ile Gln His
            20                  25                  30

Asn Val Asp Phe Gln Asn Ser Met Leu Val Ala Pro Asp Ala Gly Ser
        35                  40                  45

Ala Lys Arg Thr Ser Thr Leu Ser Asp Lys Leu Asn Leu Asn Phe Ala
    50                  55                  60

Leu Ile His Lys Glu Arg Gln Lys Ala Asn Glu Val Ser Arg Met Val
65                  70                  75                  80

Leu

<210> SEQ ID NO 9
<211> LENGTH: 91
<212> TYPE: PRT
<213> ORGANISM: Ashbya gossypii

<400> SEQUENCE: 9

Leu Glu Thr Ala Gly Cys Asn His Val Ile Thr Met Asp Leu His Ala
1               5                   10                  15

Ser Gln Ile Gln Gly Phe Phe His Ile Pro Val Asp Asn Leu Tyr Ala
            20                  25                  30

Glu Pro Asn Ile Leu His Tyr Ile Gln His Asn Val Asp Phe Gln Asn
        35                  40                  45

Ser Met Leu Val Ala Pro Asp Ala Gly Ser Ala Lys Arg Thr Ser Thr
    50                  55                  60

Leu Ser Asp Lys Leu Asn Leu Asn Phe Ala Leu Ile His Lys Glu Arg
65                  70                  75                  80

Gln Lys Ala Asn Glu Val Ser Arg Met Val Leu
            85                  90

<210> SEQ ID NO 10
<211> LENGTH: 111
<212> TYPE: PRT
<213> ORGANISM: Ashbya gossypii

<400> SEQUENCE: 10

```
Pro Ile Thr Ala Lys Leu Val Ala Lys Met Leu Glu Thr Ala Gly Cys
1               5                   10                  15

Asn His Val Ile Thr Met Asp Leu His Ala Ser Gln Ile Gln Gly Phe
            20                  25                  30

Phe His Ile Pro Val Asp Asn Leu Tyr Ala Glu Pro Asn Ile Leu His
        35                  40                  45

Tyr Ile Gln His Asn Val Asp Phe Gln Asn Ser Met Leu Val Ala Pro
    50                  55                  60

Asp Ala Gly Ser Ala Lys Arg Thr Ser Thr Leu Ser Asp Lys Leu Asn
65                  70                  75                  80

Leu Asn Phe Ala Leu Ile His Lys Glu Arg Gln Lys Ala Asn Glu Val
                85                  90                  95

Ser Arg Met Val Leu Val Gly Asp Val Ala Asp Lys Ser Cys Ile
            100                 105                 110
```

<210> SEQ ID NO 11
<211> LENGTH: 131
<212> TYPE: PRT
<213> ORGANISM: Ashbya gossypii

<400> SEQUENCE: 11

```
Arg Gln Asp Lys Lys Asp Lys Ser Arg Ala Pro Ile Thr Ala Lys Leu
1               5                   10                  15

Val Ala Lys Met Leu Glu Thr Ala Gly Cys Asn His Val Ile Thr Met
            20                  25                  30

Asp Leu His Ala Ser Gln Ile Gln Gly Phe Phe His Ile Pro Val Asp
        35                  40                  45

Asn Leu Tyr Ala Glu Pro Asn Ile Leu His Tyr Ile Gln His Asn Val
    50                  55                  60

Asp Phe Gln Asn Ser Met Leu Val Ala Pro Ala Gly Ser Ala Lys
65                  70                  75                  80

Arg Thr Ser Thr Leu Ser Asp Lys Leu Asn Leu Asn Phe Ala Leu Ile
                85                  90                  95

His Lys Glu Arg Gln Lys Ala Asn Glu Val Ser Arg Met Val Leu Val
            100                 105                 110

Gly Asp Val Ala Asp Lys Ser Cys Ile Ile Val Asp Asp Met Ala Asp
        115                 120                 125

Thr Cys Gly
    130
```

<210> SEQ ID NO 12
<211> LENGTH: 1456
<212> TYPE: DNA
<213> ORGANISM: Zea mays
<220> FEATURE:
<221> NAME/KEY: CDS
<222> LOCATION: (79)..(1278)

<400> SEQUENCE: 12

```
ttcgtataga ccggattaaa accctaggcc ctagccaccg cccaccgtcg cctcagcaaa    60
tcctcctccc gtttcacc atg ccg ccc tgc tgc tcc ccc acc acc tcc gcc    111
                    Met Pro Pro Cys Cys Ser Pro Thr Thr Ser Ala
                    1               5                   10 gtc acc gct gcg gcg gca tct ccc ggc gcc tcg cgc agc ggg ggc ctc    159
Val Thr Ala Ala Ala Ala Ser Pro Gly Ala Ser Arg Ser Gly Gly Leu
            15                  20                  25 ctg cgc cgc tcg cgc cca gcc ccc gcc gcc gtg aat tgt aaa aag att    207
Leu Arg Arg Ser Arg Pro Ala Pro Ala Ala Val Asn Cys Lys Lys Ile
```

```
                30                    35                    40
gat tct ctg agg tca atc aat gga gca cca cct tgc att ccg gtg tcc    255
Asp Ser Leu Arg Ser Ile Asn Gly Ala Pro Pro Cys Ile Pro Val Ser
 45                  50                  55 aac agg tcg tta ttg act cct gta acc ttg cca gtt ttc cgg gat cca    303
Asn Arg Ser Leu Leu Thr Pro Val Thr Leu Pro Val Phe Arg Asp Pro
 60                  65                  70                  75 aac atg agg aac gac acg agg ctg cgc atc ttc tca ggc aca gcc aat    351
Asn Met Arg Asn Asp Thr Arg Leu Arg Ile Phe Ser Gly Thr Ala Asn
                 80                  85                  90 cct tcc ctt tcc cag gag ata gca agt tac ttg ggg cta gaa ctt ggg    399
Pro Ser Leu Ser Gln Glu Ile Ala Ser Tyr Leu Gly Leu Glu Leu Gly
         95                 100                 105 aag ata acc ata aag agg ttt gct gat ggt gaa ata tat gtt cag ttg    447
Lys Ile Thr Ile Lys Arg Phe Ala Asp Gly Glu Ile Tyr Val Gln Leu
            110                 115                 120 caa gaa agt gta cgg ggc tgt gat gtt ttc ctt gtg caa ccg tcg tgt    495
Gln Glu Ser Val Arg Gly Cys Asp Val Phe Leu Val Gln Pro Ser Cys
    125                 130                 135 cct cca gca aat gaa aat ctt atg gag ctt ctg atc atg att gat gcc    543
Pro Pro Ala Asn Glu Asn Leu Met Glu Leu Leu Ile Met Ile Asp Ala
140                 145                 150                 155 tgt agg aga gca tct gct aag aat atc act gca gtt atc cct tat ttt    591
Cys Arg Arg Ala Ser Ala Lys Asn Ile Thr Ala Val Ile Pro Tyr Phe
                160                 165                 170 ggt tat gca agg gct gac agg aag tcc cag ggc agg gaa tct ata gct    639
Gly Tyr Ala Arg Ala Asp Arg Lys Ser Gln Gly Arg Glu Ser Ile Ala
        175                 180                 185 gca aaa ctt gta gct aat atg att acc gaa gct ggt gcc aac cgt gtc    687
Ala Lys Leu Val Ala Asn Met Ile Thr Glu Ala Gly Ala Asn Arg Val
            190                 195                 200 ctt gtt tgt gat ctt cat tct agt caa gca atg gga tac ttt gac atc    735
Leu Val Cys Asp Leu His Ser Ser Gln Ala Met Gly Tyr Phe Asp Ile
    205                 210                 215 cca gta gat cac gtt tat ggc cag cct gtt att ctt gat tat ctc gcc    783
Pro Val Asp His Val Tyr Gly Gln Pro Val Ile Leu Asp Tyr Leu Ala
220                 225                 230                 235 agc aag aca ata tgt tca gat gac ttg gta gtt gta tct cct gat gtt    831
Ser Lys Thr Ile Cys Ser Asp Asp Leu Val Val Val Ser Pro Asp Val
                240                 245                 250 gga ggt gtt gcc agg gca cgt gcc ttt gcc aaa aag ctg tca gat gca    879
Gly Gly Val Ala Arg Ala Arg Ala Phe Ala Lys Lys Leu Ser Asp Ala
        255                 260                 265 cct cta gct att gta gat aaa aga agg caa gga cat aat gtc gct gag    927
Pro Leu Ala Ile Val Asp Lys Arg Arg Gln Gly His Asn Val Ala Glu
            270                 275                 280 gtg atg aat ctt att gga gac gtg aga gga aaa gtg gct gtt atg atg    975
Val Met Asn Leu Ile Gly Asp Val Arg Gly Lys Val Ala Val Met Met
    285                 290                 295 gat gat atg atc gac aca gca ggt acc att tcc aaa gga gct gag cta   1023
Asp Asp Met Ile Asp Thr Ala Gly Thr Ile Ser Lys Gly Ala Glu Leu
300                 305                 310                 315 ctg cac cag gaa ggc gcc cga gaa gta tat gct tgc tgc aca cat ggt   1071
Leu His Gln Glu Gly Ala Arg Glu Val Tyr Ala Cys Cys Thr His Gly
                320                 325                 330 gtt ttt agc cca ccc gcc atc gaa agg cta tca agt gga ttg ttc caa   1119
Val Phe Ser Pro Pro Ala Ile Glu Arg Leu Ser Ser Gly Leu Phe Gln
        335                 340                 345 gaa gta atc atc aca aac acc atc cct ctg aag gag gag aag agt ttt   1167
Glu Val Ile Ile Thr Asn Thr Ile Pro Leu Lys Glu Glu Lys Ser Phe
```

```
                   350              355                  360
ccg cag ctg act att ctt tcg gtt gct aac ctc ttg ggg gaa aca atc    1215
Pro Gln Leu Thr Ile Leu Ser Val Ala Asn Leu Leu Gly Glu Thr Ile
365                      370                 375 tgg cgc gtt cac gat gat tgc tcg gtt ggt cat gag cca tac tcc agc    1263
Trp Arg Val His Asp Asp Cys Ser Val Gly His Glu Pro Tyr Ser Ser
380                 385                 390                 395 ttg gat att gac tga tgcttaagga atagttgtgg cagctcgcaa ccttctcttt    1318
Leu Asp Ile Asp cttttctttt ggcctcggtt tttgtctgtg cgtgtaataa gcaatgtttt tgtggaattc    1378
tgttagcgca gaacctcagc cttgtatttg agtgacagca cataagatga cattccagat    1438
tcaaaaaaaa aaaaaaaa                                                  1456
```

<210> SEQ ID NO 13
<211> LENGTH: 399
<212> TYPE: PRT
<213> ORGANISM: Zea mays

<400> SEQUENCE: 13

Met Pro Pro Cys Cys Ser Pro Thr Thr Ser Ala Val Thr Ala Ala Ala
1               5                   10                  15

Ala Ser Pro Gly Ala Ser Arg Ser Gly Gly Leu Leu Arg Arg Ser Arg
            20                  25                  30

Pro Ala Pro Ala Ala Val Asn Cys Lys Lys Ile Asp Ser Leu Arg Ser
        35                  40                  45

Ile Asn Gly Ala Pro Pro Cys Ile Pro Val Ser Asn Arg Ser Leu Leu
    50                  55                  60

Thr Pro Val Thr Leu Pro Val Phe Arg Asp Pro Asn Met Arg Asn Asp
65                  70                  75                  80

Thr Arg Leu Arg Ile Phe Ser Gly Thr Ala Asn Pro Ser Leu Ser Gln
                85                  90                  95

Glu Ile Ala Ser Tyr Leu Gly Leu Glu Leu Gly Lys Ile Thr Ile Lys
            100                 105                 110

Arg Phe Ala Asp Gly Glu Ile Tyr Val Gln Leu Gln Glu Ser Val Arg
        115                 120                 125

Gly Cys Asp Val Phe Leu Val Gln Pro Ser Cys Pro Pro Ala Asn Glu
    130                 135                 140

Asn Leu Met Glu Leu Leu Ile Met Ile Asp Ala Cys Arg Arg Ala Ser
145                 150                 155                 160

Ala Lys Asn Ile Thr Ala Val Ile Pro Tyr Phe Gly Tyr Ala Arg Ala
                165                 170                 175

Asp Arg Lys Ser Gln Gly Arg Glu Ser Ile Ala Ala Lys Leu Val Ala
            180                 185                 190

Asn Met Ile Thr Glu Ala Gly Ala Asn Arg Val Leu Val Cys Asp Leu
        195                 200                 205

His Ser Ser Gln Ala Met Gly Tyr Phe Asp Ile Pro Val Asp His Val
    210                 215                 220

Tyr Gly Gln Pro Val Ile Leu Asp Tyr Leu Ala Ser Lys Thr Ile Cys
225                 230                 235                 240

Ser Asp Asp Leu Val Val Val Ser Pro Asp Val Gly Gly Val Ala Arg
                245                 250                 255

Ala Arg Ala Phe Ala Lys Lys Leu Ser Asp Ala Pro Leu Ala Ile Val
            260                 265                 270

Asp Lys Arg Arg Gln Gly His Asn Val Ala Glu Val Met Asn Leu Ile
        275                 280                 285

```
Gly Asp Val Arg Gly Lys Val Ala Val Met Met Asp Asp Met Ile Asp
    290                 295                 300

Thr Ala Gly Thr Ile Ser Lys Gly Ala Glu Leu Leu His Gln Glu Gly
305                 310                 315                 320

Ala Arg Glu Val Tyr Ala Cys Cys Thr His Gly Val Phe Ser Pro Pro
                325                 330                 335

Ala Ile Glu Arg Leu Ser Ser Gly Leu Phe Gln Glu Val Ile Ile Thr
                340                 345                 350

Asn Thr Ile Pro Leu Lys Glu Glu Lys Ser Phe Pro Gln Leu Thr Ile
            355                 360                 365

Leu Ser Val Ala Asn Leu Leu Gly Glu Thr Ile Trp Arg Val His Asp
    370                 375                 380

Asp Cys Ser Val Gly His Glu Pro Tyr Ser Ser Leu Asp Ile Asp
385                 390                 395

<210> SEQ ID NO 14
<211> LENGTH: 64
<212> TYPE: PRT
<213> ORGANISM: Artificial Sequence
<220> FEATURE:
<223> OTHER INFORMATION: ADP binding site from PRS with point mutation

<400> SEQUENCE: 14

Ile His Ala Ser Gln Ile Gln Gly Phe Phe His Ile Pro Val Asp Asn
1               5                   10                  15

Leu Tyr Ala Glu Pro Asn Ile Leu His Tyr Ile Gln His Asn Val Asp
            20                  25                  30

Phe Gln Asn Ser Met Leu Val Ala Pro Asp Ala Gly Ser Ala Lys Arg
        35                  40                  45

Thr Ser Thr Leu Ser Asp Lys Leu Asn Leu Asn Phe Ala Leu Ile Gln
    50                  55                  60

<210> SEQ ID NO 15
<211> LENGTH: 81
<212> TYPE: PRT
<213> ORGANISM: Artificial Sequence
<220> FEATURE:
<223> OTHER INFORMATION: ADP binding site from PRS with point mutation

<400> SEQUENCE: 15

Thr Met Asp Ile His Ala Ser Gln Ile Gln Gly Phe Phe His Ile Pro
1               5                   10                  15

Val Asp Asn Leu Tyr Ala Glu Pro Asn Ile Leu His Tyr Ile Gln His
            20                  25                  30

Asn Val Asp Phe Gln Asn Ser Met Leu Val Ala Pro Asp Ala Gly Ser
        35                  40                  45

Ala Lys Arg Thr Ser Thr Leu Ser Asp Lys Leu Asn Leu Asn Phe Ala
    50                  55                  60

Leu Ile Gln Lys Glu Arg Gln Lys Ala Asn Glu Val Ser Arg Met Val
65                  70                  75                  80

Leu

<210> SEQ ID NO 16
<211> LENGTH: 91
<212> TYPE: PRT
<213> ORGANISM: Artificial Sequence
<220> FEATURE:
<223> OTHER INFORMATION: ADP binding site from PRS with point mutation

<400> SEQUENCE: 16
```

Leu Glu Thr Ala Gly Cys Asn His Val Ile Thr Met Asp Ile His Ala
1               5                   10                  15

Ser Gln Ile Gln Gly Phe Phe His Ile Pro Val Asp Asn Leu Tyr Ala
            20                  25                  30

Glu Pro Asn Ile Leu His Tyr Ile Gln His Asn Val Asp Phe Gln Asn
        35                  40                  45

Ser Met Leu Val Ala Pro Asp Ala Gly Ser Ala Lys Arg Thr Ser Thr
    50                  55                  60

Leu Ser Asp Lys Leu Asn Leu Asn Phe Ala Leu Ile Gln Lys Glu Arg
65                  70                  75                  80

Gln Lys Ala Asn Glu Val Ser Arg Met Val Leu
                85                  90

<210> SEQ ID NO 17
<211> LENGTH: 111
<212> TYPE: PRT
<213> ORGANISM: Artificial Sequence
<220> FEATURE:
<223> OTHER INFORMATION: ADP binding site from PRS with point mutation

<400> SEQUENCE: 17

Pro Ile Thr Ala Lys Leu Val Ala Lys Met Leu Glu Thr Ala Gly Cys
1               5                   10                  15

Asn His Val Ile Thr Met Asp Ile His Ala Ser Gln Ile Gln Gly Phe
            20                  25                  30

Phe His Ile Pro Val Asp Asn Leu Tyr Ala Glu Pro Asn Ile Leu His
        35                  40                  45

Tyr Ile Gln His Asn Val Asp Phe Gln Asn Ser Met Leu Val Ala Pro
    50                  55                  60

Asp Ala Gly Ser Ala Lys Arg Thr Ser Thr Leu Ser Asp Lys Leu Asn
65                  70                  75                  80

Leu Asn Phe Ala Leu Ile Gln Lys Glu Arg Gln Lys Ala Asn Glu Val
                85                  90                  95

Ser Arg Met Val Leu Val Gly Asp Val Ala Asp Lys Ser Cys Ile
            100                 105                 110

<210> SEQ ID NO 18
<211> LENGTH: 131
<212> TYPE: PRT
<213> ORGANISM: Artificial Sequence
<220> FEATURE:
<223> OTHER INFORMATION: ADP binding site from PRS with point mutation

<400> SEQUENCE: 18

Arg Gln Asp Lys Lys Asp Lys Ser Arg Ala Pro Ile Thr Ala Lys Leu
1               5                   10                  15

Val Ala Lys Met Leu Glu Thr Ala Gly Cys Asn His Val Ile Thr Met
            20                  25                  30

Asp Ile His Ala Ser Gln Ile Gln Gly Phe Phe His Ile Pro Val Asp
        35                  40                  45

Asn Leu Tyr Ala Glu Pro Asn Ile Leu His Tyr Ile Gln His Asn Val
    50                  55                  60

Asp Phe Gln Asn Ser Met Leu Val Ala Pro Asp Ala Gly Ser Ala Lys
65                  70                  75                  80

Arg Thr Ser Thr Leu Ser Asp Lys Leu Asn Leu Asn Phe Ala Leu Ile
                85                  90                  95

Gln Lys Glu Arg Gln Lys Ala Asn Glu Val Ser Arg Met Val Leu Val
            100                 105                 110

-continued

Gly Asp Val Ala Asp Lys Ser Cys Ile Ile Val Asp Asp Met Ala Asp
            115                 120                 125

Thr Cys Gly
    130

<210> SEQ ID NO 19
<211> LENGTH: 62
<212> TYPE: PRT
<213> ORGANISM: Acetabularia mediterranea

<400> SEQUENCE: 19

Met Ala Ser Ile Met Met Asn Lys Ser Val Val Leu Ser Lys Glu Cys
1               5                   10                  15

Ala Lys Pro Leu Ala Thr Pro Lys Val Thr Leu Asn Lys Arg Gly Phe
            20                  25                  30

Ala Thr Thr Ile Ala Thr Lys Asn Arg Glu Met Met Val Trp Gln Pro
        35                  40                  45

Phe Asn Asn Lys Met Phe Glu Thr Phe Ser Phe Leu Pro Pro
    50                  55                  60

<210> SEQ ID NO 20
<211> LENGTH: 90
<212> TYPE: PRT
<213> ORGANISM: Arabidopsis thaliana

<400> SEQUENCE: 20

Met Ala Ala Ser Leu Gln Ser Thr Ala Thr Phe Leu Gln Ser Ala Lys
1               5                   10                  15

Ile Ala Thr Ala Pro Ser Arg Gly Ser Ser His Leu Arg Ser Thr Gln
            20                  25                  30

Ala Val Gly Lys Ser Phe Gly Leu Glu Thr Ser Ser Ala Arg Leu Thr
        35                  40                  45

Cys Ser Phe Gln Ser Asp Phe Lys Asp Phe Thr Gly Lys Cys Ser Asp
    50                  55                  60

Ala Val Lys Ile Ala Gly Phe Ala Leu Ala Thr Ser Ala Leu Val Val
65                  70                  75                  80

Ser Gly Ala Ser Ala Glu Gly Ala Pro Lys
                85                  90

<210> SEQ ID NO 21
<211> LENGTH: 96
<212> TYPE: PRT
<213> ORGANISM: Arabidopsis thaliana

<400> SEQUENCE: 21

Met Ala Gln Val Ser Arg Ile Cys Asn Gly Val Gln Asn Pro Ser Leu
1               5                   10                  15

Ile Cys Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Glu Lys Ala Ser Glu
65                  70                  75                  80

Ile Val Leu Gln Pro Ile Arg Glu Ile Ser Gly Leu Ile Lys Leu Pro
                85                  90                  95

<210> SEQ ID NO 22
<211> LENGTH: 100
<212> TYPE: PRT
<213> ORGANISM: Arabidopsis thaliana

<400> SEQUENCE: 22

Met Ala Ala Ala Thr Thr Thr Thr Thr Ser Ser Ile Ser Phe
1               5                   10                  15

Ser Thr Lys Pro Ser Pro Ser Ser Lys Ser Pro Leu Pro Ile Ser
                20                  25                  30

Arg Phe Ser Leu Pro Phe Ser Leu Asn Pro Asn Lys Ser Ser Ser
                35                  40                  45

Ser Arg Arg Arg Gly Ile Lys Ser Ser Ser Pro Ser Ser Ile Ser Ala
        50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala
            100

<210> SEQ ID NO 23
<211> LENGTH: 46
<212> TYPE: PRT
<213> ORGANISM: Arabidopsis thaliana

<400> SEQUENCE: 23

Met Ile Thr Ser Ser Leu Thr Cys Ser Leu Gln Ala Leu Lys Leu Ser
1               5                   10                  15

Ser Pro Phe Ala His Gly Ser Thr Pro Leu Ser Ser Leu Ser Lys Pro
                20                  25                  30

Asn Ser Phe Pro Asn His Arg Met Pro Ala Leu Val Pro Val
                35                  40                  45

<210> SEQ ID NO 24
<211> LENGTH: 93
<212> TYPE: PRT
<213> ORGANISM: Arabidopsis thaliana

<400> SEQUENCE: 24

Met Ala Ser Leu Leu Gly Thr Ser Ser Ala Ile Trp Ala Ser Pro
1               5                   10                  15

Ser Leu Ser Ser Pro Ser Ser Lys Pro Ser Ser Ser Pro Ile Cys Phe
                20                  25                  30

Arg Pro Gly Lys Leu Phe Gly Ser Lys Leu Asn Ala Gly Ile Gln Ile
                35                  40                  45

Arg Pro Lys Lys Asn Arg Ser Arg Tyr His Val Ser Val Met Asn Val
        50                  55                  60

Ala Thr Glu Ile Asn Ser Thr Glu Gln Val Val Gly Lys Phe Asp Ser
65                  70                  75                  80

Lys Lys Ser Ala Arg Pro Val Tyr Pro Phe Ala Ala Ile
                85                  90

<210> SEQ ID NO 25
<211> LENGTH: 52
<212> TYPE: PRT
<213> ORGANISM: Arabidopsis thaliana

<400> SEQUENCE: 25

Met Ala Ser Thr Ala Leu Ser Ser Ala Ile Val Gly Thr Ser Phe Ile

```
                1               5                   10                  15
Arg Arg Ser Pro Ala Pro Ile Ser Leu Arg Ser Leu Pro Ser Ala Asn
                20                  25                  30

Thr Gln Ser Leu Phe Gly Leu Lys Ser Gly Thr Ala Arg Gly Gly Arg
            35                  40                  45

Val Val Ala Met
        50

<210> SEQ ID NO 26
<211> LENGTH: 39
<212> TYPE: PRT
<213> ORGANISM: Arabidopsis thaliana

<400> SEQUENCE: 26

Met Ala Ala Ser Thr Met Ala Leu Ser Ser Pro Ala Phe Ala Gly Lys
1               5                   10                  15

Ala Val Asn Leu Ser Pro Ala Ala Ser Glu Val Leu Gly Ser Gly Arg
                20                  25                  30

Val Thr Asn Arg Lys Thr Val
            35

<210> SEQ ID NO 27
<211> LENGTH: 92
<212> TYPE: PRT
<213> ORGANISM: Arabidopsis thaliana

<400> SEQUENCE: 27

Met Ala Ala Ile Thr Ser Ala Thr Val Thr Ile Pro Ser Phe Thr Gly
1               5                   10                  15

Leu Lys Leu Ala Val Ser Ser Lys Pro Lys Thr Leu Ser Thr Ile Ser
                20                  25                  30

Arg Ser Ser Ser Ala Thr Arg Ala Pro Pro Lys Leu Ala Leu Lys Ser
            35                  40                  45

Ser Leu Lys Asp Phe Gly Val Ile Ala Val Ala Thr Ala Ala Ser Ile
        50                  55                  60

Val Leu Ala Gly Asn Ala Met Ala Met Glu Val Leu Leu Gly Ser Asp
65                  70                  75                  80

Asp Gly Ser Leu Ala Phe Val Pro Ser Glu Phe Thr
                85                  90

<210> SEQ ID NO 28
<211> LENGTH: 85
<212> TYPE: PRT
<213> ORGANISM: Arabidopsis thaliana

<400> SEQUENCE: 28

Met Ala Ala Ala Val Ser Thr Val Gly Ala Ile Asn Arg Ala Pro Leu
1               5                   10                  15

Ser Leu Asn Gly Ser Gly Ser Gly Ala Val Ser Ala Pro Ala Ser Thr
                20                  25                  30

Phe Leu Gly Lys Lys Val Val Thr Val Ser Arg Phe Ala Gln Ser Asn
            35                  40                  45

Lys Lys Ser Asn Gly Ser Phe Lys Val Leu Ala Val Lys Glu Asp Lys
        50                  55                  60

Gln Thr Asp Gly Asp Arg Trp Arg Gly Leu Ala Tyr Asp Thr Ser Asp
65                  70                  75                  80

Asp Gln Ile Asp Ile
                85
```

-continued

<210> SEQ ID NO 29
<211> LENGTH: 54
<212> TYPE: PRT
<213> ORGANISM: Arabidopsis thaliana

<400> SEQUENCE: 29

Met Lys Ser Ser Met Leu Ser Ser Thr Ala Trp Thr Ser Pro Ala Gln
1               5                   10                  15

Ala Thr Met Val Ala Pro Phe Thr Gly Leu Lys Ser Ser Ala Ser Phe
            20                  25                  30

Pro Val Thr Arg Lys Ala Asn Asn Asp Ile Thr Ser Ile Thr Ser Asn
        35                  40                  45

Gly Gly Arg Val Ser Cys
        50

<210> SEQ ID NO 30
<211> LENGTH: 91
<212> TYPE: PRT
<213> ORGANISM: Arabidopsis thaliana

<400> SEQUENCE: 30

Met Ala Ala Ser Gly Thr Ser Ala Thr Phe Arg Ala Ser Val Ser Ser
1               5                   10                  15

Ala Pro Ser Ser Ser Gln Leu Thr His Leu Lys Ser Pro Phe Lys
            20                  25                  30

Ala Val Lys Tyr Thr Pro Leu Pro Ser Arg Ser Lys Ser Ser
            35                  40                  45

Phe Ser Val Ser Cys Thr Ile Ala Lys Asp Pro Pro Val Leu Met Ala
    50                  55                  60

Ala Gly Ser Asp Pro Ala Leu Trp Gln Arg Pro Asp Ser Phe Gly Arg
65                  70                  75                  80

Phe Gly Lys Phe Gly Gly Lys Tyr Val Pro Glu
            85                  90

<210> SEQ ID NO 31
<211> LENGTH: 80
<212> TYPE: PRT
<213> ORGANISM: Brassica campestris

<400> SEQUENCE: 31

Met Ser Thr Thr Phe Cys Ser Ser Val Cys Met Gln Ala Thr Ser Leu
1               5                   10                  15

Ala Ala Thr Thr Arg Ile Ser Phe Gln Lys Pro Ala Leu Val Ser Thr
            20                  25                  30

Thr Asn Leu Ser Phe Asn Leu Arg Arg Ser Ile Pro Thr Arg Phe Ser
        35                  40                  45

Ile Ser Cys Ala Ala Lys Pro Glu Thr Val Glu Lys Val Ser Lys Ile
    50                  55                  60

Val Lys Lys Gln Leu Ser Leu Lys Asp Asp Gln Lys Val Val Ala Glu
65                  70                  75                  80

<210> SEQ ID NO 32
<211> LENGTH: 51
<212> TYPE: PRT
<213> ORGANISM: Brassica napus

<400> SEQUENCE: 32

Met Ala Thr Thr Phe Ser Ala Ser Val Ser Met Gln Ala Thr Ser Leu
1               5                   10                  15

```
Ala Thr Thr Thr Arg Ile Ser Phe Gln Lys Pro Val Leu Val Ser Asn
            20                  25                  30

His Gly Arg Thr Asn Leu Ser Phe Asn Leu Ser Arg Thr Arg Leu Ser
            35                  40                  45

Ile Ser Cys
    50

<210> SEQ ID NO 33
<211> LENGTH: 44
<212> TYPE: PRT
<213> ORGANISM: Chlamydomonas reinhardtii

<400> SEQUENCE: 33

Met Gln Ala Leu Ser Ser Arg Val Asn Ile Ala Ala Lys Pro Gln Arg
1               5                   10                  15

Ala Gln Arg Leu Val Val Arg Ala Glu Glu Val Lys Ala Ala Pro Lys
            20                  25                  30

Lys Glu Val Gly Pro Lys Arg Gly Ser Leu Val Lys
            35                  40

<210> SEQ ID NO 34
<211> LENGTH: 51
<212> TYPE: PRT
<213> ORGANISM: Cucurbita moschata

<400> SEQUENCE: 34

Met Ala Glu Leu Ile Gln Asp Lys Ser Ala Gln Ser Ala Ala Ala Thr
1               5                   10                  15

Ala Ala Ala Ala Ser Ser Gly Tyr Glu Arg Arg Asn Glu Pro Ala His
            20                  25                  30

Ser Arg Lys Phe Leu Glu Val Arg Ser Glu Glu Glu Leu Leu Ser Cys
            35                  40                  45

Ile Lys Lys
    50

<210> SEQ ID NO 35
<211> LENGTH: 62
<212> TYPE: PRT
<213> ORGANISM: Spinacea oleracea

<400> SEQUENCE: 35

Met Ser Thr Ile Asn Gly Cys Leu Thr Ser Ile Ser Pro Ser Arg Thr
1               5                   10                  15

Gln Leu Lys Asn Thr Ser Thr Leu Arg Pro Thr Phe Ile Ala Asn Ser
            20                  25                  30

Arg Val Asn Pro Ser Ser Ser Val Pro Pro Ser Leu Ile Arg Asn Gln
            35                  40                  45

Pro Val Phe Ala Ala Pro Ala Pro Ile Ile Thr Pro Thr Leu
    50                  55                  60

<210> SEQ ID NO 36
<211> LENGTH: 75
<212> TYPE: PRT
<213> ORGANISM: Spinacea oleracea

<400> SEQUENCE: 36

Met Thr Thr Ala Val Thr Ala Ala Val Ser Phe Pro Ser Thr Lys Thr
1               5                   10                  15

Thr Ser Leu Ser Ala Arg Cys Ser Ser Val Ile Ser Pro Asp Lys Ile
            20                  25                  30
```

```
Ser Tyr Lys Lys Val Pro Leu Tyr Tyr Arg Asn Val Ser Ala Thr Gly
        35                  40                  45

Lys Met Gly Pro Ile Arg Ala Gln Ile Ala Ser Asp Val Glu Ala Pro
    50                  55                  60

Pro Pro Ala Pro Ala Lys Val Glu Lys Met Ser
65                  70                  75

<210> SEQ ID NO 37
<211> LENGTH: 55
<212> TYPE: PRT
<213> ORGANISM: Spinacea oleracea

<400> SEQUENCE: 37

Met Thr Thr Ala Val Thr Ala Ala Val Ser Phe Pro Ser Thr Lys Thr
1               5                   10                  15

Thr Ser Leu Ser Ala Arg Ser Ser Ser Val Ile Ser Pro Asp Lys Ile
            20                  25                  30

Ser Tyr Lys Lys Val Pro Leu Tyr Tyr Arg Asn Val Ser Ala Thr Gly
        35                  40                  45

Lys Met Gly Pro Ile Arg Ala
    50                  55

<210> SEQ ID NO 38
<211> LENGTH: 957
<212> TYPE: DNA
<213> ORGANISM: Ashbya gossypii
<220> FEATURE:
<223> OTHER INFORMATION: ATCC 10895

<400> SEQUENCE: 38
atgtcgtcca atagcataaa gctgctagca ggtaactcgc acccggacct agctgagaag      60
gtctccgttc gcctaggtgt accactttcg aagattggag tgtatcacta ctctaacaaa     120
gagacgtcag ttactatcgg cgaaagtatc cgtgatgaag atgtctacat catccagaca     180
ggaacggggg agcaggaaat caacgacttc ctcatggaac tgctcatcat gatccatgcc     240
tgccggtcag cctctgcgcg gaagatcaca gcggttatac caaacttccc ttacgcaaga     300
caagacaaaa aggacaagtc gcgagcaccg ataactgcca agctggtggc caagatgcta     360
gagaccgcgg ggtgcaacca cgttatcacg atggatttgc acgcgtctca aattcagggt     420
ttcttccaca ttccagtgga caacctatat gcagagccga acatcctgca ctacatccaa     480
cataatgtgg acttccagaa tagtatgttg gtcgcgccag acgcggggtc ggcgaagcgc     540
acgtcgacgc tttcggacaa gctgaatctc aacttcgcgt tgatccacaa agaacggcag     600
aaggcgaacg aggtctcgcg gatggtgttg gtgggtgatg tcgccgacaa gtcctgtatt     660
attgtagacg acatggcgga cacgtgcgga acgctagtga aggccactga cacgctgatc     720
gaaaatgggg cgaaagaagt gattgccatt gtgacacacg gtatattttc tggcggcgcc     780
cgcgagaagt tgcgcaacag caagctggca cggatcgtaa gcacaaatac ggtgccagtg     840
gacctcaatc tagatatcta ccaccaaatt gacattagtg ccattttggc cgaggcaatt     900
agaaggcttc acaacgggga aagtgtgtcg tacctgttca ataacgctgt catgtag        957

<210> SEQ ID NO 39
<211> LENGTH: 963
<212> TYPE: DNA
<213> ORGANISM: Aspergillus fumigatus
<220> FEATURE:
<223> OTHER INFORMATION: Af293

<400> SEQUENCE: 39
```

```
atggccacaa attcaatcaa gcttctgact ggtaacagtc accctgaact tgcgaatctc    60
gttgctgctc ggctcggcat cgagctgacc aagatcatgg tcctgcagta ttcgaattcg   120
gaaacaagtg tcacaattgg tgaaagtgta cgagacgagg atgtgttcat cttgcagtcc   180
acgaaaccga acgatatcaa tgacggatta atggagcttc ttatcatgat caacgcctgc   240
aagactgcct cggcccgccg catcacggct gtcattccca acttccccta cgcccgtcaa   300
gataagaaag acaagagccg tgcgccgatc accgcgaaat tgatggcgaa catgctccaa   360
accgctggtt gcaaccatgt catcacaatg gatcttcacg ccagtcagat tcagggcttc   420
tttaatgtcc ctgtagataa cttgtatgcc gagcctagca tgttgaagtg gatccgggaa   480
cacttggatg tgaagaattg cgtcatcgtc agtcccgatg ccggtggtgc gaagcgtgct   540
acggggattg cggaccgcct tgacctgcaa ttcgctctca ttcacaagga acgccctcgt   600
cctaacgagg tctcgcgcat ggttctcgtt ggaaacgtca aggacaagat tgcgatcatc   660
gttgacgaca tggctgatac atgcggtact ctcgtcaagg ccgctgacac tgtcatgcag   720
cacggtgcca aggaagtcaa cgccattgtc gtacacggca ttctctccgg caatgctatt   780
gagaacatca caacagttg cttaaaacgt ctcgtcgtga ctaacacagt gccccacaag   840
gagaagaagg agctttgtga caagattgac accattgata tcagccctac gttggcggag   900
gcttgcaggc gcacacacaa tggtgaatct gtcagtttcc tgttttcgca cgctgtcgcg   960
tag                                                                 963

<210> SEQ ID NO 40
<211> LENGTH: 963
<212> TYPE: DNA
<213> ORGANISM: Aspergillus niger

<400> SEQUENCE: 40
atggcttcga actcgatcaa gctcttgact ggtaacagtc accctgagct tgcaaacctc    60
gtggcagctc ggcttggcat tgaactgacc aagatcatgg tcctccaata ttcgaaccag   120
gaaacgagtg tcacaatcgg agagagtgta cgagatgagg atgttttcat cttgcagtcg   180
acgcggccca atgatatcaa cgatggactg atggagctgc tcatcatgat caatgcttgc   240
aagaccgcct ccgcaagacg tatcacggcc gtcattccca actttcccta tgcgcgccaa   300
gataagaagg ataagagccg tgctcctatc actgccaagc ttatggcaaa catgctccag   360
actgctggtt gcaaccacgt catcaccatg gacctccatg ccagccagat ccaaggcttc   420
ttcaacgttc ccgtcgataa cctgtatgcc gagcctagta tactgaagtg gattcgcgaa   480
cacctggatg tgagcaactg tatcattgtc agtcctgacg ctggtggtgc taagcgtgcc   540
actgccatcg ccgatcgcct cgatctccag tttcgcctca tccacaagga gcgcccccgc   600
cccaacgagg tctcgcgcat ggttctcgtt ggtagcgtca aggacaagat tgctatcatc   660
gttgacgaca tggctgatac ctgcggtact cttgtcaagg ccgccgatac tgtgatgcag   720
cacggagcta aggaagtcaa cgcgattgtt gtccacggta tcctttccgg caaggctact   780
cagaacatca caacagctg cttgagccgt gttgttgtga ccaacactgt tcctcacgaa   840
gacaagaagg agcagtgcga taagatcgag acgatcgaca tcagccccac ccttgcagag   900
gcctgcagac gtacgcacaa cggcgagtct gtgagcttcc tgttctcgca cgctgttgcc   960
taa                                                                 963

<210> SEQ ID NO 41
<211> LENGTH: 960
```

<212> TYPE: DNA
<213> ORGANISM: Candida glabrata
<220> FEATURE:
<223> OTHER INFORMATION: CBS138

<400> SEQUENCE: 41

| | | | | | |
|---|---|---|---|---|---|
| atgtctacaa | atagcattaa | actgttggca | ggtaactcgc | accctgagct | tgctgagctt | 60 |
| ttgtcgagaa | gactgggcat | tccattgtcg | aaggtcggtg | tgtatcagta | ctcgaacacc | 120 |
| gagacttcag | ttactattgg | tgaaagtata | cgtgatgagg | atgtgtacat | tatacagacg | 180 |
| ggtattggtg | cacaagaggt | gaacgatttt | ctgatggagc | tgctgattct | tatccatgct | 240 |
| tgcaaaaccg | catcagtgag | gagaatcaca | gcggttatcc | caaacttccc | ttacgctaga | 300 |
| caggacaaaa | aagataaatc | acgtgcgcca | attactgcca | agctaatcgc | taagatgttg | 360 |
| gagactgcag | gatgtgacca | tgtcatcacc | atggacctac | acgcctctca | gatacaaggt | 420 |
| ttcttccaca | tccctgtgga | taacctgtat | gcagagccaa | gtgtcctaaa | ttacataaga | 480 |
| actaagaccg | atttgaagaa | cactatactg | gtgtccccag | atgccggtgg | tgcgaagagg | 540 |
| gttgcttctc | ttgcagacaa | gctggacttg | aactttgctt | tgattcacaa | ggagaggcaa | 600 |
| aaggccaatg | aagtttccag | gatggtcctt | gtcggtgatg | ttcaaggtaa | atcatgtctc | 660 |
| ttgattgacg | atatggcgga | cacttgtggt | acattggtga | aggcttgtga | tactttactt | 720 |
| gaacacggtg | ccaaggaagt | tattgccatt | gtaacacatg | gtatattttc | tggttcagca | 780 |
| agagaaaagt | tagctaacag | taaactgtcc | aagatcgtat | gcacaaatac | agttcctgtg | 840 |
| gatatcgatc | ttccgattgt | agaccaagtt | gatataagtc | caactttagc | agaagccata | 900 |
| aaaagattac | ataacggtga | atccgtgtct | tatctttttca | ctcacgctcc | accagcctga | 960 |

<210> SEQ ID NO 42
<211> LENGTH: 963
<212> TYPE: DNA
<213> ORGANISM: Coccidioides immitis
<220> FEATURE:
<223> OTHER INFORMATION: Coccidioides immitis RS

<400> SEQUENCE: 42
atggctacga attctatcaa gctattgact ggaaacagtc acccggagct agcgcagctg 60
gttgccgata ggcttgggat cgagttgacg cgggtcatgg tttcgcagta ttcaaaccag 120
gagaccagcg tcactattgg agaaagtgtg agagatgaag atgtttttat tttacaatcg 180
acacgaccta atgatatcaa tgacggcctt atggaactcc ttattatgat aaacgcttgc 240
aaaactgctt ctgcgagacg catcactgct gtcattccca acttccccta tgctcgccaa 300
gacaaaaagg ataagagtcg cgcacccatc acagccaaac tcatggccaa tatgctccag 360
actgctgggt gcaatcacgt tatcaccatg gatctccatg ccagtcagat tcaaggattt 420
ttcaatgtgc ctgtggacaa cctctacgct gagccaagca tgttgcgatg gattcgtcag 480
aaccttgatg tatccaactg cgttatcgtc agtccagatg ctggtggtgc caaacgtgcc 540
actgccattg cagatcggct tgatctccag ttcgctctta ttcataagga acgaccacgg 600
ccaaatgagg tctctcgcat ggttcttgta ggcagcgtta aggataagat tgctattatt 660
gttgatgaca tggccgatac ttgcggtaca ctggtcaaag ctgctagcac cctcatcgac 720
aacggtgcga aggaagtcct cgctattgtg acacacggca ttcttagtgg gaaggccatt 780
gagacgctga ataccgggcg attgagtcgt attgtcgtta cgaatacagt gccgcatgag 840
gaaaagaagt tactctgtga taagatcgag actatcgaca tcagtcctgt gttggcggag 900
gcatgtcgac gaacgcataa cggggagtca gttagcttcc tgttttcgca tgcggtgtcc 960

```
taa                                                                963

<210> SEQ ID NO 43
<211> LENGTH: 972
<212> TYPE: DNA
<213> ORGANISM: Debaryomyces hansenii
<220> FEATURE:
<223> OTHER INFORMATION: CBS767

<400> SEQUENCE: 43
atgacagcat ctcagaacgc tataaagctc ttacacggta attctcaccc tgaacttgcc     60
aagttaattt cgaaaaaatt aggtataggt ttagctaagg tgggtgcttt ccaatataca    120
aataaagaga cagccgttgc agtaggagaa tccgtaagag atgaagacgt ttacattatc    180
caaacaggat gtggtgaagg agaaataaat gatttttaa tggaactact tattattata    240
aatgcttgta aaactgctag tgcaagaaga atcactgctg ttataccaaa tttcccttac    300
gccagacaag ataaaaaaga taaatcaaga gctcctatca ccgcaaaatt gatagcaaat    360
ctcttgcaaa cagcaggatg taaccatgtt ataacattag atttgcatgc atctcaaatt    420
caagggtttt tcagagtgcc ggttgataac ttgtatgctg aaccctccgt attaagacat    480
atcaaagata attatggtaa agaggactta attattgttt ctcctgatgc tggcggtgcc    540
aagagagttg catcgattgc tgataaatta gatgttaatt ttgctttgat tcataaagaa    600
agacaaaaag ccaatgaagt ttcaaaaatg gttctcgtag gtgatgtcac taataagtca    660
tgtttattaa ttgacgatat ggctgatact tgtggtactt tggttaaagc agctgatgtt    720
ttattaaaaa atggtgctaa gaaggtagtc gcaataatca cacacggtat attctcttcg    780
aatgcaattg aaaaacttaa taattcgaat ctcgataaaa tcatatgtac caattctatg    840
ccattagaga ataagttatc ccaatgtccc aaattagaga taatagatat aagtgctact    900
ttagctgagg ctattagaag gttacataac ggtgaaagtg tgtcttattt atttaacaac    960
gctcctgctt ga                                                        972

<210> SEQ ID NO 44
<211> LENGTH: 975
<212> TYPE: DNA
<213> ORGANISM: Kluyveromyces lactis

<400> SEQUENCE: 44
atggaaacga gtaaaagaat gagtaccaat agcatcaaat tattggctgg taactctcat     60
cccgagctag ctcagaatat tgctagaacc cttgggttgc gcttgtccaa catcggagtt    120
taccagtact ctaatcagga aacttctgtc actatcgggg agagtatacg tgatgaggac    180
gtgtacatta ttcaaactgg tacaggggag caagagatta acgatttctt gatggaatta    240
ttgattataa ttcatgcatg cagaacagct tctgctagaa gaatcactgc cgtgattccg    300
aattttccat atgcaagaca ggataaaaag gataaatctc gtgctccaat cacagcgaaa    360
ttagtagcac agatgttgga aactgctgga tgtgatcacg tcatcactat ggacctacat    420
gcttctcaaa ttcaaggttt cttccatatt cctgtggata atctttacgc cgaaccaagt    480
gttctaaaat atattcaaca taaaactgac atcggtaatg cgatccttgt atcgcctgat    540
gccggcggtg ctaagagagt tgcttctctg gcagataagc tagatttgaa cttcgcgtta    600
atccataagg aaagacaaaa ggctaacgag gtttctcgta tggtgcttgt gggtgatgtt    660
acagggaagt catgtctatt gatcgatgac atggctgata catgtggtac cttggttaag    720
gcgtcagata cactattaga gcatggtgct aaggaggtat tggccattgt cactcatggt    780
```

| | |
|---|---|
| atcttctctg gatctgcaga acagaaattg aagaatagta aactatcaag gatcgtgtgc | 840 |
| actaatacag ttcctgtcga cttggacgtt aatattctgg accaaattga tatcagccct | 900 |
| accctagcgg aggcgatcag aagattgcat aatggggaaa gtgtgtcata tctatttaca | 960 |
| catgcggcta tatag | 975 |

<210> SEQ ID NO 45
<211> LENGTH: 969
<212> TYPE: DNA
<213> ORGANISM: Lodderomyces elongisporus
<220> FEATURE:
<223> OTHER INFORMATION: NRRL YB-4239

<400> SEQUENCE: 45

| | |
|---|---|
| atgcatcaac gattaccaaa ctcaatcaag attctagctg ggaactcgca tatagattta | 60 |
| tgtgaaaaaa ttgcaaagag attaggtata aacatagcaa gggttggtgc ctttcaatac | 120 |
| acaaacacag agacagccat cgctatcggt gaatctgttc gagatgagga cgtttacatt | 180 |
| gttcaaaccg gatgtggcga aatcaacgat ttttaatgg aattactatt catgatcaat | 240 |
| gcttgtagaa ctgcaagtgc tcgaaggata actgcagtta taccaaattt ccctatgcg | 300 |
| agacaagaca aaaggacaa gtcaagagca ccaattactg caaaattgat tgcaaacttg | 360 |
| ttacaaacgg caggatgcga tcatgtgatt acgatggact tgcatgcgag tcagatccaa | 420 |
| gggttcttta gagtccctgt cgataacttg tatgctgaac cgattgtatt gaggtatatt | 480 |
| cgcgaaaatt tcaacaaaga cgatattatc atggtgagcc ccgatgcagg aggagctaaa | 540 |
| agggttgcga gtctagcaga taaattggat gtccagtttg cattgatcca taagaaaga | 600 |
| caaaaggcca acgaaatctc aagaatggtg ctcgttggtg atgtcaagga caaaatctgt | 660 |
| atactagttg acgacattgc tgatacttgt ggtactctat gtaaagctgc cgatatccta | 720 |
| cttgataacg gcgccaaaaa cgttgtttgc atggtgacac atgcaatctt ttctgggaat | 780 |
| gctattgaac gactcaacaa ctcgagattg gatagagtag ttgctacaaa ctcgttgcct | 840 |
| attgaggata aacttgcaaa gtgcaagaaa ttggaaatct tggacatcag cccgacatta | 900 |
| gctgaggcca taaggagatt gcataatggt gaaagtgtca gctacttgtt caacaatgtg | 960 |
| cctgaataa | 969 |

<210> SEQ ID NO 46
<211> LENGTH: 963
<212> TYPE: DNA
<213> ORGANISM: Neosartorya fischeri
<220> FEATURE:
<223> OTHER INFORMATION: NRRL 181

<400> SEQUENCE: 46

| | |
|---|---|
| atggccacaa attcgatcaa acttctgact ggtaacagtc accctgaact tgcgaacctc | 60 |
| gttgctgctc ggctcggcat cgagttgacc aagatcatgg tcctgcagta ttcgaattct | 120 |
| gaaacaagtg tcacaattgg tgaaagtgta cgagacgagg atgtgttcat cttgcagtcc | 180 |
| acgaaaccga acgatatcaa tgacggattg atggagcttc ttatcatgat caacgcttgc | 240 |
| aagactgcct cggcccgtcg catcacggct gtcatcccca acttccccta cgcccgtcaa | 300 |
| gataagaaag acaagagccg tgcgccgatc accgcgaaat tgatggcgaa catgctccaa | 360 |
| accgctggct gcaaccatgt cattacaatg gatctccacg ccagtcagat tcagggtttc | 420 |
| tttaatgtcc ctgtagataa cttgtatgcc gagcctagca tgttgaagtg gatccgggaa | 480 |
| cacttggatg tgaagaactg cgtcatcgtc agtcccgatg ccggtggtgc gaagcgtgct | 540 |

```
acggggattg cggaccgtct tgacctgcaa ttcgctctca ttcacaagga acgccctcgt    600
cccaacgagg tctcgcgcat ggttctcgtt ggaaacgtca aggacaagat tgcgatcatc    660
gttgacgaca tggctgatac atgtggtact ctcgtcaagg ccgccgacac tgtcatgcag    720
cacggtgcca aggaagtcaa cgccattgtc gtacacggca ttctctccgg caatgccatt    780
gagaacatca acaacagttg cttaaaccgt ctcgtcgtga ccaacacagt gccccataag    840
gagaagaagg agatgtgtga caagattgac accattgata tcagccctac gttggcggag    900
gcttgcagac gcacacacaa tggtgaatct gtcagtttcc tgttctcaca cgctgtcgcg    960
tag                                                                  963

<210> SEQ ID NO 47
<211> LENGTH: 972
<212> TYPE: DNA
<213> ORGANISM: Pichia stipitis
<220> FEATURE:
<223> OTHER INFORMATION: CBS 6054

<400> SEQUENCE: 47
atgcctgcta cacccaactc catcaagttg ataggcggga actcgcaccc tgagttgtgt     60
gaaaaggtgt ccaagaaact tggtctaagt ttggccaagg taggagcttt ccagtacacc    120
aataaggaaa cagctgtagc agtaggagaa tctgtcagag atgaagatgt ctatattatc    180
cagactggat gtggagaaca agacatcaac gactttgtca tggagctctt gatcataatc    240
aatgcctgta aaatagccag tgccagaaga atcacagcag tggttcccaa ctttccctat    300
gctagacaag acaagaagga taagctgaga gcacccatta cggccaagtt gatggcgaac    360
ttgttgcaaa cggccggttg taaccatgtt atcaccatgg atttacacgc ttcacagatt    420
cagggctttt tccgtgtccc cgtagacaac ttgtatgctg aacctctggt gttgagatat    480
atcaccaaca actttgacaa aaaggactta attatcgtat caccagatgc gggaggagcc    540
aaaagagtag cgtccatagc tgacaagttg gatgtccagt ttgctttgat ccacaaggaa    600
aggcagaaag ccaacgaagt gtcaagaatg gtgcttgtgg agacgtctc agacaaggtg    660 tgtatcttga tagatgatat ggccgatacc tgtggaacat tatgtaaggc tgcagacatc    720
ttgctcgaca atggtgctca gaaggttgta gccatggtca cacacggtat catgtcgtca    780
aatgctacag aaaagttgaa caactccaag ttggaccgga tcgtatgtac taattcccta    840
ccattgaatg ataagcttgc ccagtgtccc aagctagaag tgattgatat cgctcctact    900
ttggctgagg ctatcaggag acttcacaac ggtgaaagtg tcagctattt attcaacaac    960
atccccgagt ag                                                        972

<210> SEQ ID NO 48
<211> LENGTH: 1065
<212> TYPE: DNA
<213> ORGANISM: Saccharomyces cerevisiae

<400> SEQUENCE: 48
atggtcatcg accttgagca tgtggtagac tacataatgc acatagactc tcagcttcaa     60
ctcaaaaagg cttctccagc aaaaatgaat tcagagtctc gagaagatat ggctataaat    120
agtatcaaat tgctagcggg aaactcccat cctgatttgg ctgaacaaat atcgaaaaag    180
ttaggtattc cactttccaa agttggtgtg taccagtatt ctaataaaga aacctctgtc    240
accataggtg agagccttcg cgacgaagat gtgtatatta tccaaactgg aataggtgaa    300
caagaaatta tgattttctt gatggaatta ttaatttttaa ttcatgcttg caaaattgca    360
```

-continued

```
tctgcaagaa agatcactac tgtaataccc aattttccat atgcaagaca agacaagaaa    420
gataaatccc gggcgcccat taccgcaaag ttggttgcca atttattgca aactgctggt    480
gctgatcatg tcatcacaat ggatctccat gcctcccaaa ttcaagggtt tttccatatc    540
ccggttgaca acctatatgc agaaccaagt gttttaaatt atattagaac gaaaacagat    600
ttcgacaatg ctattttggt gtcgcctgat gcaggtggtg ctaagagagt agctgctttg    660
gctgacaagt tagatttaaa ttttgctttg attcacaaag agaggcaaaa agctaacgag    720
gtttcaaaaa tggtgcttgt tggtgatgtt accaataaat catgtttatt agttgatgat    780
atggcggata cttgtggtac gttggtaaaa gcttgtgata cgttgatgga gcatggtgcc    840
aaagaagtta tagctattgt tacacacggt attttctccg gttcagcaag agaaaagcta    900
agaaatagta gattgtctag aattgtttgc acaaataccg ttccggtaga tttggattta    960
cctattgctg accagatcga tattagtccc acgttcgctg aagctataag aagactacac   1020
aatggtgaat ccgtgtcata tttgttcacc catgctccag tatag                   1065
```

<210> SEQ ID NO 49
<211> LENGTH: 966
<212> TYPE: DNA
<213> ORGANISM: Sclerotinia sclerotiorum
<220> FEATURE:
<223> OTHER INFORMATION: Sclerotinia sclerotiorum 1980

<400> SEQUENCE: 49

```
atggcgacga attctattaa gttgcttacg ggcaatagcc acccgcaatt ggcgaagttg     60
gttgctgata gattgggtat tgaacttgca aagactatga gcttgaacta ttcaaatcaa    120
gaaaccagcg tcacagtggg agagagtgtc agagatgagg atgttttcat cctccaatcc    180
actgcacctg gcgatattaa cgatggactc atggaactgc tcatcatgat caatgcctgc    240
aaaaccgcat ccgcacgccg cattacagct gtcatcccca acttcccata cgcacgtcaa    300
gacaagaaag ataaatcccg cgctcctatc tcggctaaac ttatcgcgaa tatgttgcaa    360
actgccggtt gtaatcatgt tattactatg gatttacatg caagtcagat tcaagggttc    420
ttcaatgttc cagtggataa cttgtatgcg gagccaagta ctttgaggtg gattagagag    480
aacttggagg ttagcaagtg tgtggttgtt agtccggatg ccggtggtgc taagagagca    540
acctccatag ccgaccgtct cgatctcggt tttgccctca tccacaaaga gcgcgcccgc    600
cctaacgaag tatcccgcat ggtcctcgtc ggtgacgtcg tcgataaaat cgccatcctt    660
gtagacgaca tggccgatac ttgcggaacc ctcgtcaaag ctgccgagac agtcatggaa    720
cacggcgcta aagaagtcgt cgccatcgtc acccacggta tcctaagcgg agctgcaatc    780
gaaaccttaa acaagagtaa attgagcaga gtagtagtta caaacacagt accactcaga    840
ggaaaggagg aacaatgtgg gagattgagg gttatggata ttagtgctac gttagctgag    900
gcaattagga ggacgcataa tggcgagagt gtgagctttt tgtttacgca tgcacctatg    960
gactaa                                                               966
```

<210> SEQ ID NO 50
<211> LENGTH: 1020
<212> TYPE: DNA
<213> ORGANISM: Vanderwaltozyma polyspora
<220> FEATURE:
<223> OTHER INFORMATION: DSM 70294

<400> SEQUENCE: 50

```
atggatcata atttagaatt acagttacaa gaatccgatt taaaattacg tagtggtgaa     60
```

-continued

```
catatgtctt ctaatagtat caagctaatc tctgggaatt cccatccaga acttgctgag    120
ctaatatcta agaaattggc tatcccatta tcaaaagtgg gtgtatacca atattctaat    180
atggagactt ctgtcaccat cggtgaaagt attagagatg aagatgttta tcattcaa     240 actggtactg gtgaacagga attaacgat ttcctaatgg agttgttaat aatgatacat    300
gcttgtaaaa ctgcttctgt tagaagaatc actgcagtta tcccaagttt cccttatgca   360
agacaagata agaaggataa atcgcgtgcc ccaatcactg ccaagttgat tgcaaattta   420
ttggaaactg caggctgtga ccatgtcatc acaatggacc tacacgcttc tcaaattcaa   480
gggttcttcc atattccagt agacaattta tatgctgaac caagtgtatt aaactatatt   540
agaaatcata caaatctagc aaacgcaatt ctagtctcac cagatgctgg tggtgctaag   600
agagtagcct ctattgctga taagcttgat ttaaatttcg ctttgattca taggaaaga    660 caaaaggcaa acgaagtttc aagaatggtc ctggtcggtg atgtcaaggg gaaatcatgt   720
ttattgatcg atgacatggc tgacacttgt ggtactttag taaaagcttg tgatacttg    780 ttagatcacg gtgctgaaga agttattgca atcgttactc atggtatctt ctccggttct   840
gctagagaaa aattgaaaaa cagtagatta tcaaagatcg tttgtaccaa tacagtacca   900
atagacttag atttagatat tgtagatcaa gttgatatca gtccaacttt ggcagaagcc   960
ataaggagat tacataacgg tgaatcggtc tcctacttat ttactcacgc tccagtatga  1020
```

<210> SEQ ID NO 51
<211> LENGTH: 318
<212> TYPE: PRT
<213> ORGANISM: Ashbya gossypii
<220> FEATURE:
<223> OTHER INFORMATION: ATCC 10895

<400> SEQUENCE: 51

```
Met Ser Ser Asn Ser Ile Lys Leu Leu Ala Gly Asn Ser His Pro Asp
1               5                   10                  15

Leu Ala Glu Lys Val Ser Val Arg Leu Gly Val Pro Leu Ser Lys Ile
            20                  25                  30

Gly Val Tyr His Tyr Ser Asn Lys Glu Thr Ser Val Thr Ile Gly Glu
        35                  40                  45

Ser Ile Arg Asp Glu Asp Val Tyr Ile Ile Gln Thr Gly Thr Gly Glu
    50                  55                  60

Gln Glu Ile Asn Asp Phe Leu Met Glu Leu Leu Ile Met Ile His Ala
65                  70                  75                  80

Cys Arg Ser Ala Ser Ala Arg Lys Ile Thr Ala Val Ile Pro Asn Phe
                85                  90                  95

Pro Tyr Ala Arg Gln Asp Lys Lys Asp Lys Ser Arg Ala Pro Ile Thr
            100                 105                 110

Ala Lys Leu Val Ala Lys Met Leu Glu Thr Ala Gly Cys Asn His Val
        115                 120                 125

Ile Thr Met Asp Leu His Ala Ser Gln Ile Gln Gly Phe Phe His Ile
    130                 135                 140

Pro Val Asp Asn Leu Tyr Ala Glu Pro Asn Ile Leu His Tyr Ile Gln
145                 150                 155                 160

His Asn Val Asp Phe Gln Asn Ser Met Leu Val Pro Asp Ala Gly
                165                 170                 175

Ser Ala Lys Arg Thr Ser Thr Leu Ser Asp Lys Leu Asn Leu Asn Phe
            180                 185                 190

Ala Leu Ile His Lys Glu Arg Gln Lys Ala Asn Glu Val Ser Arg Met
```

```
                195                 200                 205
Val Leu Val Gly Asp Val Ala Asp Lys Ser Cys Ile Ile Val Asp Asp
210                 215                 220

Met Ala Asp Thr Cys Gly Thr Leu Val Lys Ala Thr Asp Thr Leu Ile
225                 230                 235                 240

Glu Asn Gly Ala Lys Glu Val Ile Ala Ile Val Thr His Gly Ile Phe
                    245                 250                 255

Ser Gly Gly Ala Arg Glu Lys Leu Arg Asn Ser Lys Leu Ala Arg Ile
                260                 265                 270

Val Ser Thr Asn Thr Val Pro Val Asp Leu Asn Leu Asp Ile Tyr His
                275                 280                 285

Gln Ile Asp Ile Ser Ala Ile Leu Ala Glu Ala Ile Arg Arg Leu His
290                 295                 300

Asn Gly Glu Ser Val Ser Tyr Leu Phe Asn Asn Ala Val Met
305                 310                 315

<210> SEQ ID NO 52
<211> LENGTH: 320
<212> TYPE: PRT
<213> ORGANISM: Aspergillus fumigatus
<220> FEATURE:
<223> OTHER INFORMATION: Af293

<400> SEQUENCE: 52

Met Ala Thr Asn Ser Ile Lys Leu Leu Thr Gly Asn Ser His Pro Glu
1               5                   10                  15

Leu Ala Asn Leu Val Ala Ala Arg Leu Gly Ile Glu Leu Thr Lys Ile
                20                  25                  30

Met Val Leu Gln Tyr Ser Asn Ser Glu Thr Ser Val Thr Ile Gly Glu
            35                  40                  45

Ser Val Arg Asp Glu Asp Val Phe Ile Leu Gln Ser Thr Lys Pro Asn
    50                  55                  60

Asp Ile Asn Asp Gly Leu Met Glu Leu Leu Ile Met Ile Asn Ala Cys
65                  70                  75                  80

Lys Thr Ala Ser Ala Arg Arg Ile Thr Ala Val Ile Pro Asn Phe Pro
                85                  90                  95

Tyr Ala Arg Gln Asp Lys Lys Asp Lys Ser Arg Ala Pro Ile Thr Ala
                100                 105                 110

Lys Leu Met Ala Asn Met Leu Gln Thr Ala Gly Cys Asn His Val Ile
            115                 120                 125

Thr Met Asp Leu His Ala Ser Gln Ile Gln Gly Phe Phe Asn Val Pro
130                 135                 140

Val Asp Asn Leu Tyr Ala Glu Pro Ser Met Leu Lys Trp Ile Arg Glu
145                 150                 155                 160

His Leu Asp Val Lys Asn Cys Val Ile Val Ser Pro Asp Ala Gly Gly
                165                 170                 175

Ala Lys Arg Ala Thr Gly Ile Ala Asp Arg Leu Asp Leu Gln Phe Ala
                180                 185                 190

Leu Ile His Lys Glu Arg Pro Arg Pro Asn Glu Val Ser Arg Met Val
            195                 200                 205

Leu Val Gly Asn Val Lys Asp Lys Ile Ala Ile Val Asp Asp Met
210                 215                 220

Ala Asp Thr Cys Gly Thr Leu Val Lys Ala Ala Asp Thr Val Met Gln
225                 230                 235                 240

His Gly Ala Lys Glu Val Asn Ala Ile Val Val His Gly Ile Leu Ser
                245                 250                 255
```

```
Gly Asn Ala Ile Glu Asn Ile Asn Asn Ser Cys Leu Lys Arg Leu Val
            260                 265                 270

Val Thr Asn Thr Val Pro His Lys Glu Lys Glu Leu Cys Asp Lys
275                 280                 285

Ile Asp Thr Ile Asp Ile Ser Pro Thr Leu Ala Glu Ala Cys Arg Arg
    290                 295                 300

Thr His Asn Gly Glu Ser Val Ser Phe Leu Phe Ser His Ala Val Ala
305                 310                 315                 320

<210> SEQ ID NO 53
<211> LENGTH: 320
<212> TYPE: PRT
<213> ORGANISM: Aspergillus niger

<400> SEQUENCE: 53

Met Ala Ser Asn Ser Ile Lys Leu Leu Thr Gly Asn Ser His Pro Glu
1               5                   10                  15

Leu Ala Asn Leu Val Ala Ala Arg Leu Gly Ile Glu Leu Thr Lys Ile
            20                  25                  30

Met Val Leu Gln Tyr Ser Asn Gln Glu Thr Ser Val Thr Ile Gly Glu
        35                  40                  45

Ser Val Arg Asp Glu Asp Val Phe Ile Leu Gln Ser Thr Arg Pro Asn
50                  55                  60

Asp Ile Asn Asp Gly Leu Met Glu Leu Leu Ile Met Ile Asn Ala Cys
65                  70                  75                  80

Lys Thr Ala Ser Ala Arg Arg Ile Thr Ala Val Ile Pro Asn Phe Pro
                85                  90                  95

Tyr Ala Arg Gln Asp Lys Lys Asp Lys Ser Arg Ala Pro Ile Thr Ala
            100                 105                 110

Lys Leu Met Ala Asn Met Leu Gln Thr Ala Gly Cys Asn His Val Ile
        115                 120                 125

Thr Met Asp Leu His Ala Ser Gln Ile Gln Gly Phe Phe Asn Val Pro
    130                 135                 140

Val Asp Asn Leu Tyr Ala Glu Pro Ser Ile Leu Lys Trp Ile Arg Glu
145                 150                 155                 160

His Leu Asp Val Ser Asn Cys Ile Ile Val Ser Pro Asp Ala Gly Gly
                165                 170                 175

Ala Lys Arg Ala Thr Ala Ile Ala Asp Arg Leu Asp Leu Gln Phe Ala
            180                 185                 190

Leu Ile His Lys Glu Arg Pro Arg Pro Asn Glu Val Ser Arg Met Val
        195                 200                 205

Leu Val Gly Ser Val Lys Asp Lys Ile Ala Ile Val Asp Asp Met
    210                 215                 220

Ala Asp Thr Cys Gly Thr Leu Val Lys Ala Ala Asp Thr Val Met Gln
225                 230                 235                 240

His Gly Ala Lys Glu Val Asn Ala Ile Val Val His Gly Ile Leu Ser
                245                 250                 255

Gly Lys Ala Thr Gln Asn Ile Asn Asn Ser Cys Leu Ser Arg Val Val
            260                 265                 270

Val Thr Asn Thr Val Pro His Glu Asp Lys Lys Glu Gln Cys Asp Lys
        275                 280                 285

Ile Glu Thr Ile Asp Ile Ser Pro Thr Leu Ala Glu Ala Cys Arg Arg
    290                 295                 300

Thr His Asn Gly Glu Ser Val Ser Phe Leu Phe Ser His Ala Val Ala
305                 310                 315                 320
```

<210> SEQ ID NO 54
<211> LENGTH: 319
<212> TYPE: PRT
<213> ORGANISM: Candida glabrata
<220> FEATURE:
<223> OTHER INFORMATION: CBS138

<400> SEQUENCE: 54

```
Met Ser Thr Asn Ser Ile Lys Leu Leu Ala Gly Asn Ser His Pro Glu
1               5                   10                  15

Leu Ala Glu Leu Leu Ser Arg Arg Leu Gly Ile Pro Leu Ser Lys Val
            20                  25                  30

Gly Val Tyr Gln Tyr Ser Asn Thr Glu Thr Ser Val Thr Ile Gly Glu
        35                  40                  45

Ser Ile Arg Asp Glu Asp Val Tyr Ile Ile Gln Thr Gly Ile Gly Ala
    50                  55                  60

Gln Glu Val Asn Asp Phe Leu Met Glu Leu Leu Ile Leu Ile His Ala
65                  70                  75                  80

Cys Lys Thr Ala Ser Val Arg Arg Ile Thr Ala Val Ile Pro Asn Phe
                85                  90                  95

Pro Tyr Ala Arg Gln Asp Lys Lys Asp Lys Ser Arg Ala Pro Ile Thr
            100                 105                 110

Ala Lys Leu Ile Ala Lys Met Leu Glu Thr Ala Gly Cys Asp His Val
        115                 120                 125

Ile Thr Met Asp Leu His Ala Ser Gln Ile Gln Gly Phe Phe His Ile
    130                 135                 140

Pro Val Asp Asn Leu Tyr Ala Glu Pro Ser Val Leu Asn Tyr Ile Arg
145                 150                 155                 160

Thr Lys Thr Asp Leu Lys Asn Thr Ile Leu Val Ser Pro Asp Ala Gly
                165                 170                 175

Gly Ala Lys Arg Val Ala Ser Leu Ala Asp Lys Leu Asp Leu Asn Phe
            180                 185                 190

Ala Leu Ile His Lys Glu Arg Gln Lys Ala Asn Glu Val Ser Arg Met
        195                 200                 205

Val Leu Val Gly Asp Val Gln Gly Lys Ser Cys Leu Leu Ile Asp Asp
    210                 215                 220

Met Ala Asp Thr Cys Gly Thr Leu Val Lys Ala Cys Asp Thr Leu Leu
225                 230                 235                 240

Glu His Gly Ala Lys Glu Val Ile Ala Ile Val Thr His Gly Ile Phe
                245                 250                 255

Ser Gly Ser Ala Arg Glu Lys Leu Ala Asn Ser Lys Leu Ser Lys Ile
            260                 265                 270

Val Cys Thr Asn Thr Val Pro Val Asp Ile Asp Leu Pro Ile Val Asp
        275                 280                 285

Gln Val Asp Ile Ser Pro Thr Leu Ala Glu Ala Ile Lys Arg Leu His
    290                 295                 300

Asn Gly Glu Ser Val Ser Tyr Leu Phe Thr His Ala Pro Pro Ala
305                 310                 315
```

<210> SEQ ID NO 55
<211> LENGTH: 320
<212> TYPE: PRT
<213> ORGANISM: Coccidioides immitis
<220> FEATURE:
<223> OTHER INFORMATION: Coccidioides immitis RS

<400> SEQUENCE: 55

Met Ala Thr Asn Ser Ile Lys Leu Leu Thr Gly Asn Ser His Pro Glu
1               5                   10                  15

Leu Ala Gln Leu Val Ala Asp Arg Leu Gly Ile Glu Leu Thr Arg Val
                20                  25                  30

Met Val Ser Gln Tyr Ser Asn Gln Glu Thr Ser Val Thr Ile Gly Glu
            35                  40                  45

Ser Val Arg Asp Glu Asp Val Phe Ile Leu Gln Ser Thr Arg Pro Asn
        50                  55                  60

Asp Ile Asn Asp Gly Leu Met Glu Leu Leu Ile Met Ile Asn Ala Cys
65                  70                  75                  80

Lys Thr Ala Ser Ala Arg Arg Ile Thr Ala Val Ile Pro Asn Phe Pro
                85                  90                  95

Tyr Ala Arg Gln Asp Lys Lys Asp Lys Ser Arg Ala Pro Ile Thr Ala
            100                 105                 110

Lys Leu Met Ala Asn Met Leu Gln Thr Ala Gly Cys Asn His Val Ile
        115                 120                 125

Thr Met Asp Leu His Ala Ser Gln Ile Gln Gly Phe Phe Asn Val Pro
130                 135                 140

Val Asp Asn Leu Tyr Ala Glu Pro Ser Met Leu Arg Trp Ile Arg Gln
145                 150                 155                 160

Asn Leu Asp Val Ser Asn Cys Val Ile Val Ser Pro Asp Ala Gly Gly
                165                 170                 175

Ala Lys Arg Ala Thr Ala Ile Ala Asp Arg Leu Asp Leu Gln Phe Ala
            180                 185                 190

Leu Ile His Lys Glu Arg Pro Arg Pro Asn Glu Val Ser Arg Met Val
        195                 200                 205

Leu Val Gly Ser Val Lys Asp Lys Ile Ala Ile Val Asp Asp Met
210                 215                 220

Ala Asp Thr Cys Gly Thr Leu Val Lys Ala Ala Ser Thr Leu Ile Asp
225                 230                 235                 240

Asn Gly Ala Lys Glu Val Leu Ala Ile Val Thr His Gly Ile Leu Ser
                245                 250                 255

Gly Lys Ala Ile Glu Thr Leu Asn Thr Gly Arg Leu Ser Arg Ile Val
            260                 265                 270

Val Thr Asn Thr Val Pro His Glu Glu Lys Lys Leu Leu Cys Asp Lys
        275                 280                 285

Ile Glu Thr Ile Asp Ile Ser Pro Val Leu Ala Glu Ala Cys Arg Arg
290                 295                 300

Thr His Asn Gly Glu Ser Val Ser Phe Leu Phe Ser His Ala Val Ser
305                 310                 315                 320

<210> SEQ ID NO 56
<211> LENGTH: 323
<212> TYPE: PRT
<213> ORGANISM: Debaryomyces hansenii
<220> FEATURE:
<223> OTHER INFORMATION: CBS767

<400> SEQUENCE: 56

Met Thr Ala Ser Gln Asn Ala Ile Lys Leu Leu His Gly Asn Ser His
1               5                   10                  15

Pro Glu Leu Ala Lys Leu Ile Ser Lys Leu Gly Ile Gly Leu Ala
                20                  25                  30

Lys Val Gly Ala Phe Gln Tyr Thr Asn Lys Glu Thr Ala Val Ala Val
            35                  40                  45

```
Gly Glu Ser Val Arg Asp Glu Asp Val Tyr Ile Ile Gln Thr Gly Cys
 50                  55                  60

Gly Glu Gly Glu Ile Asn Asp Phe Leu Met Glu Leu Leu Ile Ile Ile
 65                  70                  75                  80

Asn Ala Cys Lys Thr Ala Ser Ala Arg Arg Ile Thr Ala Val Ile Pro
                 85                  90                  95

Asn Phe Pro Tyr Ala Arg Gln Asp Lys Lys Asp Lys Ser Arg Ala Pro
                100                 105                 110

Ile Thr Ala Lys Leu Ile Ala Asn Leu Leu Gln Thr Ala Gly Cys Asn
            115                 120                 125

His Val Ile Thr Leu Asp Leu His Ala Ser Gln Ile Gln Gly Phe Phe
    130                 135                 140

Arg Val Pro Val Asp Asn Leu Tyr Ala Glu Pro Ser Val Leu Arg His
145                 150                 155                 160

Ile Lys Asp Asn Tyr Gly Lys Glu Asp Leu Ile Ile Val Ser Pro Asp
                165                 170                 175

Ala Gly Gly Ala Lys Arg Val Ala Ser Ile Ala Asp Lys Leu Asp Val
            180                 185                 190

Asn Phe Ala Leu Ile His Lys Glu Arg Gln Lys Ala Asn Glu Val Ser
        195                 200                 205

Lys Met Val Leu Val Gly Asp Val Thr Asn Lys Ser Cys Leu Leu Ile
210                 215                 220

Asp Asp Met Ala Asp Thr Cys Gly Thr Leu Val Lys Ala Ala Asp Val
225                 230                 235                 240

Leu Leu Lys Asn Gly Ala Lys Lys Val Ala Ile Ile Thr His Gly
                245                 250                 255

Ile Phe Ser Ser Asn Ala Ile Glu Lys Leu Asn Asn Ser Asn Leu Asp
            260                 265                 270

Lys Ile Ile Cys Thr Asn Ser Met Pro Leu Glu Asn Lys Leu Ser Gln
            275                 280                 285

Cys Pro Lys Leu Glu Ile Ile Asp Ile Ser Ala Thr Leu Ala Glu Ala
            290                 295                 300

Ile Arg Arg Leu His Asn Gly Glu Ser Val Ser Tyr Leu Phe Asn Asn
305                 310                 315                 320

Ala Pro Ala

<210> SEQ ID NO 57
<211> LENGTH: 324
<212> TYPE: PRT
<213> ORGANISM: Kluyveromyces lactis

<400> SEQUENCE: 57

Met Glu Thr Ser Lys Arg Met Ser Thr Asn Ser Ile Lys Leu Leu Ala
 1               5                  10                  15

Gly Asn Ser His Pro Glu Leu Ala Gln Asn Ile Ala Arg Thr Leu Gly
             20                  25                  30

Leu Arg Leu Ser Asn Ile Gly Val Tyr Gln Tyr Ser Asn Gln Glu Thr
         35                  40                  45

Ser Val Thr Ile Gly Glu Ser Ile Arg Asp Glu Asp Val Tyr Ile Ile
 50                  55                  60

Gln Thr Gly Thr Gly Glu Gln Glu Ile Asn Asp Phe Leu Met Glu Leu
 65                  70                  75                  80

Leu Ile Ile Ile His Ala Cys Arg Thr Ala Ser Ala Arg Arg Ile Thr
                 85                  90                  95

Ala Val Ile Pro Asn Phe Pro Tyr Ala Arg Gln Asp Lys Lys Asp Lys
```

```
                   100                 105                 110
Ser Arg Ala Pro Ile Thr Ala Lys Leu Val Ala Gln Met Leu Glu Thr
            115                 120                 125

Ala Gly Cys Asp His Val Ile Thr Met Asp Leu His Ala Ser Gln Ile
        130                 135                 140

Gln Gly Phe Phe His Ile Pro Val Asp Asn Leu Tyr Ala Glu Pro Ser
145                 150                 155                 160

Val Leu Lys Tyr Ile Gln His Lys Thr Asp Ile Gly Asn Ala Ile Leu
                165                 170                 175

Val Ser Pro Asp Ala Gly Gly Ala Lys Arg Val Ala Ser Leu Ala Asp
            180                 185                 190

Lys Leu Asp Leu Asn Phe Ala Leu Ile His Lys Glu Arg Gln Lys Ala
                195                 200                 205

Asn Glu Val Ser Arg Met Val Leu Val Gly Asp Val Thr Gly Lys Ser
            210                 215                 220

Cys Leu Leu Ile Asp Asp Met Ala Asp Thr Cys Gly Thr Leu Val Lys
225                 230                 235                 240

Ala Ser Asp Thr Leu Leu Glu His Gly Ala Lys Glu Val Leu Ala Ile
                245                 250                 255

Val Thr His Gly Ile Phe Ser Gly Ser Ala Glu Gln Lys Leu Lys Asn
            260                 265                 270

Ser Lys Leu Ser Arg Ile Val Cys Thr Asn Thr Val Pro Val Asp Leu
                275                 280                 285

Asp Val Asn Ile Leu Asp Gln Ile Asp Ile Ser Pro Thr Leu Ala Glu
            290                 295                 300

Ala Ile Arg Arg Leu His Asn Gly Glu Ser Val Ser Tyr Leu Phe Thr
305                 310                 315                 320

His Ala Ala Ile

<210> SEQ ID NO 58
<211> LENGTH: 322
<212> TYPE: PRT
<213> ORGANISM: Lodderomyces elongisporus
<220> FEATURE:
<223> OTHER INFORMATION: NRRL YB-4239

<400> SEQUENCE: 58

Met His Gln Arg Leu Pro Asn Ser Ile Lys Ile Leu Ala Gly Asn Ser
1               5                   10                  15

His Ile Asp Leu Cys Glu Lys Ile Ala Lys Arg Leu Gly Ile Asn Ile
            20                  25                  30

Ala Arg Val Gly Ala Phe Gln Tyr Thr Asn Thr Glu Thr Ala Ile Ala
        35                  40                  45

Ile Gly Glu Ser Val Arg Asp Glu Asp Val Tyr Ile Val Gln Thr Gly
    50                  55                  60

Cys Gly Glu Ile Asn Asp Phe Leu Met Glu Leu Leu Phe Met Ile Asn
65                  70                  75                  80

Ala Cys Arg Thr Ala Ser Ala Arg Arg Ile Thr Ala Val Ile Pro Asn
                85                  90                  95

Phe Pro Tyr Ala Arg Gln Asp Lys Lys Asp Lys Ser Arg Ala Pro Ile
            100                 105                 110

Thr Ala Lys Leu Ile Ala Asn Leu Leu Gln Thr Ala Gly Cys Asp His
        115                 120                 125

Val Ile Thr Met Asp Leu His Ala Ser Gln Ile Gln Gly Phe Phe Arg
    130                 135                 140
```

```
Val Pro Val Asp Asn Leu Tyr Ala Glu Pro Ile Val Leu Arg Tyr Ile
145                 150                 155                 160

Arg Glu Asn Phe Asn Lys Asp Asp Ile Ile Met Val Ser Pro Asp Ala
            165                 170                 175

Gly Gly Ala Lys Arg Val Ala Ser Leu Ala Asp Lys Leu Asp Val Gln
        180                 185                 190

Phe Ala Leu Ile His Lys Glu Arg Gln Lys Ala Asn Glu Ile Ser Arg
    195                 200                 205

Met Val Leu Val Gly Asp Val Lys Asp Lys Ile Cys Ile Leu Val Asp
210                 215                 220

Asp Ile Ala Asp Thr Cys Gly Thr Leu Cys Lys Ala Ala Asp Ile Leu
225                 230                 235                 240

Leu Asp Asn Gly Ala Lys Asn Val Val Cys Met Val Thr His Ala Ile
                245                 250                 255

Phe Ser Gly Asn Ala Ile Glu Arg Leu Asn Asn Ser Arg Leu Asp Arg
            260                 265                 270

Val Val Ala Thr Asn Ser Leu Pro Ile Glu Asp Lys Leu Ala Lys Cys
        275                 280                 285

Lys Lys Leu Glu Ile Leu Asp Ile Ser Pro Thr Leu Ala Glu Ala Ile
    290                 295                 300

Arg Arg Leu His Asn Gly Glu Ser Val Ser Tyr Leu Phe Asn Asn Val
305                 310                 315                 320

Pro Glu

<210> SEQ ID NO 59
<211> LENGTH: 320
<212> TYPE: PRT
<213> ORGANISM: Neosartorya fischeri
<220> FEATURE:
<223> OTHER INFORMATION: NRRL 181

<400> SEQUENCE: 59

Met Ala Thr Asn Ser Ile Lys Leu Leu Thr Gly Asn Ser His Pro Glu
1               5                   10                  15

Leu Ala Asn Leu Val Ala Ala Arg Leu Gly Ile Glu Leu Thr Lys Ile
            20                  25                  30

Met Val Leu Gln Tyr Ser Asn Ser Glu Thr Ser Val Thr Ile Gly Glu
        35                  40                  45

Ser Val Arg Asp Glu Asp Val Phe Ile Leu Gln Ser Thr Lys Pro Asn
    50                  55                  60

Asp Ile Asn Asp Gly Leu Met Glu Leu Leu Ile Met Ile Asn Ala Cys
65                  70                  75                  80

Lys Thr Ala Ser Ala Arg Arg Ile Thr Ala Val Ile Pro Asn Phe Pro
                85                  90                  95

Tyr Ala Arg Gln Asp Lys Lys Asp Lys Ser Arg Ala Pro Ile Thr Ala
            100                 105                 110

Lys Leu Met Ala Asn Met Leu Gln Thr Ala Gly Cys Asn His Val Ile
        115                 120                 125

Thr Met Asp Leu His Ala Ser Gln Ile Gln Gly Phe Phe Asn Val Pro
    130                 135                 140

Val Asp Asn Leu Tyr Ala Glu Pro Ser Met Leu Lys Trp Ile Arg Glu
145                 150                 155                 160

His Leu Asp Val Lys Asn Cys Val Ile Val Ser Pro Asp Ala Gly Gly
                165                 170                 175

Ala Lys Arg Ala Thr Gly Ile Ala Asp Arg Leu Asp Leu Gln Phe Ala
            180                 185                 190
```

Leu Ile His Lys Glu Arg Pro Arg Pro Asn Glu Val Ser Arg Met Val
        195                 200                 205

Leu Val Gly Asn Val Lys Asp Lys Ile Ala Ile Val Asp Asp Met
        210                 215                 220

Ala Asp Thr Cys Gly Thr Leu Val Lys Ala Asp Thr Val Met Gln
225                 230                 235                 240

His Gly Ala Lys Glu Val Asn Ala Ile Val His Gly Ile Leu Ser
                245                 250                 255

Gly Asn Ala Ile Glu Asn Ile Asn Asn Ser Cys Leu Asn Arg Leu Val
                260                 265                 270

Val Thr Asn Thr Val Pro His Lys Glu Lys Glu Met Cys Asp Lys
        275                 280                 285

Ile Asp Thr Ile Asp Ile Ser Pro Thr Leu Ala Glu Ala Cys Arg Arg
        290                 295                 300

Thr His Asn Gly Glu Ser Val Ser Phe Leu Phe Ser His Ala Val Ala
305                 310                 315                 320

<210> SEQ ID NO 60
<211> LENGTH: 323
<212> TYPE: PRT
<213> ORGANISM: Pichia stipitis
<220> FEATURE:
<223> OTHER INFORMATION: CBS 6054

<400> SEQUENCE: 60

Met Pro Ala Thr Pro Asn Ser Ile Lys Leu Ile Gly Gly Asn Ser His
1               5                   10                  15

Pro Glu Leu Cys Glu Lys Val Ser Lys Leu Gly Leu Ser Leu Ala
            20                  25                  30

Lys Val Gly Ala Phe Gln Tyr Thr Asn Lys Glu Thr Ala Val Ala Val
        35                  40                  45

Gly Glu Ser Val Arg Asp Glu Val Tyr Ile Gln Thr Gly Cys
            50                  55                  60

Gly Glu Gln Asp Ile Asn Asp Phe Val Met Glu Leu Ile Ile Ile
65                  70                  75                  80

Asn Ala Cys Lys Ile Ala Ser Ala Arg Arg Ile Thr Ala Val Val Pro
                85                  90                  95

Asn Phe Pro Tyr Ala Arg Gln Asp Lys Lys Asp Lys Ser Arg Ala Pro
                100                 105                 110

Ile Thr Ala Lys Leu Met Ala Asn Leu Leu Gln Thr Ala Gly Cys Asn
            115                 120                 125

His Val Ile Thr Met Asp Leu His Ala Ser Gln Ile Gln Gly Phe Phe
            130                 135                 140

Arg Val Pro Val Asp Asn Leu Tyr Ala Glu Pro Ser Val Leu Arg Tyr
145                 150                 155                 160

Ile Thr Asn Asn Phe Asp Lys Lys Asp Leu Ile Ile Val Ser Pro Asp
                165                 170                 175

Ala Gly Gly Ala Lys Arg Val Ala Ser Ile Ala Asp Lys Leu Asp Val
            180                 185                 190

Gln Phe Ala Leu Ile His Lys Glu Arg Gln Lys Ala Asn Glu Val Ser
            195                 200                 205

Arg Met Val Leu Val Gly Asp Val Ser Asp Lys Val Cys Ile Leu Ile
        210                 215                 220

Asp Asp Met Ala Asp Thr Cys Gly Thr Leu Cys Lys Ala Ala Asp Ile
225                 230                 235                 240

```
Leu Leu Asp Asn Gly Ala Gln Lys Val Val Ala Met Val Thr His Gly
                245                 250                 255

Ile Met Ser Ser Asn Ala Thr Glu Lys Leu Asn Asn Ser Lys Leu Asp
            260                 265                 270

Arg Ile Val Cys Thr Asn Ser Leu Pro Leu Asn Asp Lys Leu Ala Gln
        275                 280                 285

Cys Pro Lys Leu Glu Val Ile Asp Ile Ala Pro Thr Leu Ala Glu Ala
    290                 295                 300

Ile Arg Arg Leu His Asn Gly Glu Ser Val Ser Tyr Leu Phe Asn Asn
305                 310                 315                 320

Ile Pro Glu

<210> SEQ ID NO 61
<211> LENGTH: 354
<212> TYPE: PRT
<213> ORGANISM: Saccharomyces cerevisiae

<400> SEQUENCE: 61

Met Val Ile Asp Leu Glu His Val Val Asp Tyr Ile Met His Ile Asp
1               5                   10                  15

Ser Gln Leu Gln Leu Lys Lys Ala Ser Pro Ala Lys Met Asn Ser Glu
            20                  25                  30

Ser Arg Glu Asp Met Ala Ile Asn Ser Ile Lys Leu Leu Ala Gly Asn
        35                  40                  45

Ser His Pro Asp Leu Ala Glu Gln Ile Ser Lys Lys Leu Gly Ile Pro
    50                  55                  60

Leu Ser Lys Val Gly Val Tyr Gln Tyr Ser Asn Lys Glu Thr Ser Val
65                  70                  75                  80

Thr Ile Gly Glu Ser Leu Arg Asp Glu Asp Val Tyr Ile Ile Gln Thr
                85                  90                  95

Gly Ile Gly Glu Gln Glu Ile Asn Asp Phe Leu Met Glu Leu Leu Ile
            100                 105                 110

Leu Ile His Ala Cys Lys Ile Ala Ser Ala Arg Lys Ile Thr Thr Val
        115                 120                 125

Ile Pro Asn Phe Pro Tyr Ala Arg Gln Asp Lys Lys Asp Lys Ser Arg
    130                 135                 140

Ala Pro Ile Thr Ala Lys Leu Val Ala Asn Leu Leu Gln Thr Ala Gly
145                 150                 155                 160

Ala Asp His Val Ile Thr Met Asp Leu His Ala Ser Gln Ile Gln Gly
                165                 170                 175

Phe Phe His Ile Pro Val Asp Asn Leu Tyr Ala Glu Pro Ser Val Leu
            180                 185                 190

Asn Tyr Ile Arg Thr Lys Thr Asp Phe Asp Asn Ala Ile Leu Val Ser
        195                 200                 205

Pro Asp Ala Gly Gly Ala Lys Arg Val Ala Ala Leu Ala Asp Lys Leu
    210                 215                 220

Asp Leu Asn Phe Ala Leu Ile His Lys Glu Arg Gln Lys Ala Asn Glu
225                 230                 235                 240

Val Ser Lys Met Val Leu Val Gly Asp Val Thr Asn Lys Ser Cys Leu
                245                 250                 255

Leu Val Asp Asp Met Ala Asp Thr Cys Gly Thr Leu Val Lys Ala Cys
            260                 265                 270

Asp Thr Leu Met Glu His Gly Ala Lys Glu Val Ile Ala Ile Val Thr
        275                 280                 285

His Gly Ile Phe Ser Gly Ser Ala Arg Glu Lys Leu Arg Asn Ser Arg
```

```
              290                 295                 300
Leu Ser Arg Ile Val Cys Thr Asn Thr Val Pro Val Asp Leu Asp Leu
305                 310                 315                 320

Pro Ile Ala Asp Gln Ile Asp Ile Ser Pro Thr Phe Ala Glu Ala Ile
                325                 330                 335

Arg Arg Leu His Asn Gly Glu Ser Val Ser Tyr Leu Phe Thr His Ala
                340                 345                 350

Pro Val

<210> SEQ ID NO 62
<211> LENGTH: 321
<212> TYPE: PRT
<213> ORGANISM: Sclerotinia sclerotiorum
<220> FEATURE:
<223> OTHER INFORMATION: Sclerotinia sclerotiorum 1980

<400> SEQUENCE: 62

Met Ala Thr Asn Ser Ile Lys Leu Leu Thr Gly Asn Ser His Pro Gln
1               5                   10                  15

Leu Ala Lys Leu Val Ala Asp Arg Leu Gly Ile Glu Leu Ala Lys Thr
                20                  25                  30

Met Ser Leu Asn Tyr Ser Asn Gln Glu Thr Ser Val Thr Val Gly Glu
            35                  40                  45

Ser Val Arg Asp Glu Asp Val Phe Ile Leu Gln Ser Thr Ala Pro Gly
50                  55                  60

Asp Ile Asn Asp Gly Leu Met Glu Leu Leu Ile Met Ile Asn Ala Cys
65                  70                  75                  80

Lys Thr Ala Ser Ala Arg Arg Ile Thr Ala Val Ile Pro Asn Phe Pro
                85                  90                  95

Tyr Ala Arg Gln Asp Lys Lys Asp Lys Ser Arg Ala Pro Ile Ser Ala
                100                 105                 110

Lys Leu Ile Ala Asn Met Leu Gln Thr Ala Gly Cys Asn His Val Ile
            115                 120                 125

Thr Met Asp Leu His Ala Ser Gln Ile Gln Gly Phe Phe Asn Val Pro
130                 135                 140

Val Asp Asn Leu Tyr Ala Glu Pro Ser Thr Leu Arg Trp Ile Arg Glu
145                 150                 155                 160

Asn Leu Glu Val Ser Lys Cys Val Val Val Ser Pro Asp Ala Gly Gly
                165                 170                 175

Ala Lys Arg Ala Thr Ser Ile Ala Asp Arg Leu Asp Leu Gly Phe Ala
                180                 185                 190

Leu Ile His Lys Glu Arg Ala Arg Pro Asn Glu Val Ser Arg Met Val
            195                 200                 205

Leu Val Gly Asp Val Val Asp Lys Ile Ala Ile Leu Val Asp Asp Met
210                 215                 220

Ala Asp Thr Cys Gly Thr Leu Val Lys Ala Ala Glu Thr Val Met Glu
225                 230                 235                 240

His Gly Ala Lys Glu Val Val Ala Ile Val Thr His Gly Ile Leu Ser
                245                 250                 255

Gly Ala Ala Ile Glu Thr Leu Asn Lys Ser Lys Leu Ser Arg Val Val
                260                 265                 270

Val Thr Asn Thr Val Pro Leu Arg Gly Lys Glu Glu Gln Cys Gly Arg
            275                 280                 285

Leu Arg Val Met Asp Ile Ser Ala Thr Leu Ala Glu Ala Ile Arg Arg
290                 295                 300
```

-continued

Thr His Asn Gly Glu Ser Val Ser Phe Leu Phe Thr His Ala Pro Met
305                 310                 315                 320

Asp

<210> SEQ ID NO 63
<211> LENGTH: 339
<212> TYPE: PRT
<213> ORGANISM: Vanderwaltozyma polyspora
<220> FEATURE:
<223> OTHER INFORMATION: DSM 70294

<400> SEQUENCE: 63

Met Asp His Asn Leu Glu Leu Gln Leu Gln Ser Asp Leu Lys Leu
1               5                   10                  15

Arg Ser Gly Glu His Met Ser Ser Asn Ser Ile Lys Leu Ile Ser Gly
                20                  25                  30

Asn Ser His Pro Glu Leu Ala Glu Leu Ile Ser Lys Lys Leu Ala Ile
            35                  40                  45

Pro Leu Ser Lys Val Gly Val Tyr Gln Tyr Ser Asn Met Glu Thr Ser
    50                  55                  60

Val Thr Ile Gly Glu Ser Ile Arg Asp Glu Asp Val Tyr Ile Ile Gln
65                  70                  75                  80

Thr Gly Thr Gly Glu Gln Glu Ile Asn Asp Phe Leu Met Glu Leu Leu
                85                  90                  95

Ile Met Ile His Ala Cys Lys Thr Ala Ser Val Arg Arg Ile Thr Ala
                100                 105                 110

Val Ile Pro Ser Phe Pro Tyr Ala Arg Gln Asp Lys Lys Asp Lys Ser
            115                 120                 125

Arg Ala Pro Ile Thr Ala Lys Leu Ile Ala Asn Leu Leu Glu Thr Ala
130                 135                 140

Gly Cys Asp His Val Ile Thr Met Asp Leu His Ala Ser Gln Ile Gln
145                 150                 155                 160

Gly Phe Phe His Ile Pro Val Asp Asn Leu Tyr Ala Glu Pro Ser Val
                165                 170                 175

Leu Asn Tyr Ile Arg Asn His Thr Asn Leu Ala Asn Ala Ile Leu Val
            180                 185                 190

Ser Pro Asp Ala Gly Gly Ala Lys Arg Val Ala Ser Ile Ala Asp Lys
    195                 200                 205

Leu Asp Leu Asn Phe Ala Leu Ile His Lys Glu Arg Gln Lys Ala Asn
210                 215                 220

Glu Val Ser Arg Met Val Leu Val Gly Asp Val Lys Gly Lys Ser Cys
225                 230                 235                 240

Leu Leu Ile Asp Asp Met Ala Asp Thr Cys Gly Thr Leu Val Lys Ala
                245                 250                 255

Cys Asp Thr Leu Leu Asp His Gly Ala Glu Glu Val Ile Ala Ile Val
            260                 265                 270

Thr His Gly Ile Phe Ser Gly Ser Ala Arg Glu Lys Leu Lys Asn Ser
        275                 280                 285

Arg Leu Ser Lys Ile Val Cys Thr Asn Thr Val Pro Ile Asp Leu Asp
    290                 295                 300

Leu Asp Ile Val Asp Gln Val Asp Ile Ser Pro Thr Leu Ala Glu Ala
305                 310                 315                 320

Ile Arg Arg Leu His Asn Gly Glu Ser Val Ser Tyr Leu Phe Thr His
                325                 330                 335

Ala Pro Val

```
<210> SEQ ID NO 64
<211> LENGTH: 60
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid

<400> SEQUENCE: 64

Pro Xaa Phe Pro Tyr Ala Arg Gln Asp Lys Lys Asp Lys Ser Arg Ala
1               5                   10                  15

Pro Ile Xaa Ala Lys Leu Xaa Ala Xaa Xaa Leu Glx Thr Ala Gly Xaa
            20                  25                  30

Asx His Val Ile Thr Xaa Asp Leu His Ala Ser Gln Ile Gln Gly Phe
        35                  40                  45

Phe Xaa Xaa Pro Val Asp Asn Leu Tyr Ala Glu Pro
    50                  55                  60

<210> SEQ ID NO 65
<211> LENGTH: 25
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 65
```

```
Phe Ala Leu Ile His Lys Glu Arg Xaa Xaa Xaa Asn Glu Xaa Ser Xaa
1               5                   10                  15

Met Val Leu Val Gly Xaa Val Xaa Lys
            20                  25
```

<210> SEQ ID NO 66
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 66

```
Asp Asp Xaa Ala Asp Thr Cys Gly Thr Leu Xaa Lys Ala
1               5                   10
```

<210> SEQ ID NO 67
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 67

```
Gly Glu Ser Xaa Arg Asp Glu Asp Val Xaa Ile Xaa Gln
1               5                   10
```

<210> SEQ ID NO 68
<211> LENGTH: 17
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 68

```
Ala Glu Ala Xaa Xaa Arg Xaa His Asn Gly Glu Ser Val Ser Xaa Leu
1               5                   10                  15

Phe
```

```
<210> SEQ ID NO 69
<211> LENGTH: 16
<212> TYPE: PRT
<213> ORGANISM: Artificial Sequence
<220> FEATURE:
<223> OTHER INFORMATION: consensus sequence

<400> SEQUENCE: 69

Phe Pro Tyr Ala Arg Gln Asp Lys Lys Asp Lys Ser Arg Ala Pro Ile
1               5                   10                  15

<210> SEQ ID NO 70
<211> LENGTH: 11
<212> TYPE: PRT
<213> ORGANISM: Artificial Sequence
<220> FEATURE:
<223> OTHER INFORMATION: consensus sequence

<400> SEQUENCE: 70

Asp Leu His Ala Ser Gln Ile Gln Gly Phe Phe
1               5                   10

<210> SEQ ID NO 71
<211> LENGTH: 9
<212> TYPE: PRT
<213> ORGANISM: Artificial Sequence
<220> FEATURE:
<223> OTHER INFORMATION: consensus sequence

<400> SEQUENCE: 71

Pro Val Asp Asn Leu Tyr Ala Glu Pro
1               5

<210> SEQ ID NO 72
<211> LENGTH: 8
<212> TYPE: PRT
<213> ORGANISM: Artificial Sequence
<220> FEATURE:
<223> OTHER INFORMATION: consensus sequence

<400> SEQUENCE: 72

Phe Ala Leu Ile His Lys Glu Arg
1               5

<210> SEQ ID NO 73
<211> LENGTH: 352
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(43)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid
<220> FEATURE:
<221> NAME/KEY: misc_feature
<222> LOCATION: (51)..(57)
<223> OTHER INFORMATION: Xaa can be any naturally occurring amino acid
<220> FEATURE:
<221> NAME/KEY: misc_feature
```

```
<222> LOCATION: (59)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (75)..(78)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (92)..(99)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (114)..(115)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (150)..(151)
<223> OTHER INFORMATION: Xaa can be any naturally occurring amino acid
<220> FEATURE:
<221> NAME/KEY: misc_feature
```

```
<222> LOCATION: (157)..(157)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (175)..(176)
<223> OTHER INFORMATION: Xaa can be any naturally occurring amino acid
<220> FEATURE:
<221> NAME/KEY: misc_feature
<222> LOCATION: (186)..(187)
<223> OTHER INFORMATION: Xaa can be any naturally occurring amino acid
<220> FEATURE:
<221> NAME/KEY: misc_feature
<222> LOCATION: (189)..(190)
<223> OTHER INFORMATION: Xaa can be any naturally occurring amino acid
<220> FEATURE:
<221> NAME/KEY: misc_feature
<222> LOCATION: (192)..(202)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (213)..(217)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (222)..(223)
<223> OTHER INFORMATION: Xaa can be any naturally occurring amino acid
<220> FEATURE:
<221> NAME/KEY: misc_feature
<222> LOCATION: (232)..(234)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (249)..(253)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (267)..(273)
<223> OTHER INFORMATION: Xaa can be any naturally occurring amino acid
<220> FEATURE:
<221> NAME/KEY: misc_feature
```

```
<222> LOCATION: (276)..(277)
<223> OTHER INFORMATION: Xaa can be any naturally occurring amino acid
<220> FEATURE:
<221> NAME/KEY: misc_feature
<222> LOCATION: (279)..(283)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (289)..(290)
<223> OTHER INFORMATION: Xaa can be any naturally occurring amino acid
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (294)..(299)
<223> OTHER INFORMATION: Xaa can be any naturally occurring amino acid
<220> FEATURE:
<221> NAME/KEY: misc_feature
<222> LOCATION: (301)..(304)
<223> OTHER INFORMATION: Xaa can be any naturally occurring amino acid
<220> FEATURE:
<221> NAME/KEY: misc_feature
<222> LOCATION: (307)..(308)
<223> OTHER INFORMATION: Xaa can be any naturally occurring amino acid
<220> FEATURE:
<221> NAME/KEY: misc_feature
<222> LOCATION: (310)..(323)
<223> OTHER INFORMATION: Xaa can be any naturally occurring amino acid
<220> FEATURE:
<221> NAME/KEY: misc_feature
<222> LOCATION: (326)..(329)
<223> OTHER INFORMATION: Xaa can be any naturally occurring amino acid
<220> FEATURE:
<221> NAME/KEY: misc_feature
<222> LOCATION: (333)..(334)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (344)..(344)
<223> OTHER INFORMATION: Xaa can be any naturally occurring amino acid
<220> FEATURE:
<221> NAME/KEY: misc_feature
<222> LOCATION: (347)..(352)
<223> OTHER INFORMATION: Xaa can be any naturally occurring amino acid

<400> SEQUENCE: 73

Met Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Asn Xaa Ile Lys Xaa Xaa Xaa Gly Asn Ser His Xaa
        35                  40                  45

Xaa Leu Xaa Xaa Xaa Xaa Xaa Xaa Xaa Leu Xaa Xaa Xaa Xaa Xaa Xaa
    50                  55                  60

Xaa Xaa Xaa Xaa Tyr Xaa Asn Xaa Glu Thr Xaa Xaa Xaa Xaa Gly Glu
65                  70                  75                  80

Ser Xaa Arg Asp Glu Asp Val Xaa Ile Xaa Gln Xaa Xaa Xaa Xaa Xaa
                85                  90                  95

Xaa Xaa Xaa Asn Asp Xaa Xaa Met Glu Leu Leu Xaa Xaa Ile Xaa Ala
```

-continued

```
                        100                    105                     110
Cys Xaa Xaa Ala Ser Xaa Arg Xaa Ile Thr Xaa Val Xaa Pro Xaa Phe
            115                     120                 125

Pro Tyr Ala Arg Gln Asp Lys Lys Asp Lys Ser Arg Ala Pro Ile Xaa
            130                     135                 140

Ala Lys Leu Xaa Ala Xaa Xaa Leu Glx Thr Ala Gly Xaa Asx His Val
145                     150                     155                 160

Ile Thr Xaa Asp Leu His Ala Ser Gln Ile Gln Gly Phe Phe Xaa Xaa
                165                     170                 175

Pro Val Asp Asn Leu Tyr Ala Glu Pro Xaa Xaa Leu Xaa Xaa Ile Xaa
                180                     185                 190

Xaa Xaa Xaa Xaa Xaa Xaa Xaa Xaa Xaa Val Xaa Pro Asp Ala Gly
            195                     200                 205

Xaa Ala Lys Arg Xaa Xaa Xaa Xaa Asp Xaa Leu Asx Xaa Xaa Phe
            210                     215                 220

Ala Leu Ile His Lys Glu Arg Xaa Xaa Xaa Asn Glu Xaa Ser Xaa Met
225                     230                     235                 240

Val Leu Val Gly Xaa Val Xaa Lys Xaa Xaa Xaa Xaa Xaa Asp Asp Xaa
                245                     250                 255

Ala Asp Thr Cys Gly Thr Leu Xaa Lys Ala Xaa Xaa Xaa Xaa Xaa
                260                     265                 270

Xaa Gly Ala Xaa Xaa Val Xaa Xaa Xaa Xaa Xaa His Xaa Ile Xaa Ser
            275                     280                 285

Xaa Xaa Ala Xaa Glx Xaa Xaa Xaa Xaa Xaa Leu Xaa Xaa Xaa Xaa
            290                     295                 300

Thr Asn Xaa Xaa Pro Xaa Xaa Xaa Xaa Xaa Xaa Xaa Xaa Xaa Xaa
305                     310                     315                 320

Xaa Xaa Xaa Asp Ile Xaa Xaa Xaa Xaa Ala Glu Ala Xaa Xaa Arg Xaa
                325                     330                 335

His Asn Gly Glu Ser Val Ser Xaa Leu Phe Xaa Xaa Xaa Xaa Xaa Xaa
            340                     345                 350
```